United States Patent
Park et al.

(10) Patent No.: US 11,404,647 B2
(45) Date of Patent: Aug. 2, 2022

(54) ORGANIC COMPOUND FOR ORGANIC LIGHT EMITTING DIODE AND ORGANIC LIGHT EMITTING DIODE INCLUDING SAME

(71) Applicant: SFC CO., LTD., Cheongju-si (KR)

(72) Inventors: Sang-woo Park, Cheongju-si (KR); Seung-Soo Lee, Cheongju-si (KR); Tae Gyun Lee, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 284 days.

(21) Appl. No.: 16/900,474

(22) Filed: Jun. 12, 2020

(65) Prior Publication Data
US 2020/0403165 A1    Dec. 24, 2020

(30) Foreign Application Priority Data

Jun. 20, 2019 (KR) .......................... 10-2019-0073701

(51) Int. Cl.
*H01L 51/00* (2006.01)
*C07D 307/91* (2006.01)
(Continued)

(52) U.S. Cl.
CPC ........ *H01L 51/0073* (2013.01); *C07D 307/91* (2013.01); *C09K 11/06* (2013.01);
(Continued)

(58) Field of Classification Search
CPC ............. H01L 51/0073; H01L 51/0059; H01L 51/0072; H01L 51/0074
See application file for complete search history.

(56) References Cited

U.S. PATENT DOCUMENTS

2018/0013071 A1    1/2018   Cha et al.

FOREIGN PATENT DOCUMENTS

| CN | 106187963 A | 12/2016 |
|----|-------------|---------|
| EP | 3269790 A1  | 1/2018  |

(Continued)

*Primary Examiner* — Anthony Ho
(74) *Attorney, Agent, or Firm* — STIP Law Group, LLC

(57) ABSTRACT

Disclosed herein are an organic light emitting compound represented by [Chemical Formula 1] below and an organic light emitting diode comprising same. In [Chemical Formula 1], the substituents $R_1$ to $R_5$, $R_{11}$ to $R_{18}$, $R_{21}$ to $R_{22}$, and $R_{31}$ to $R_{40}$, the linkers $L_1$ to $L_3$, and $m_1$ and $m_2$ are as defined in the description:

(Continued)

[Chemical Formula 1]

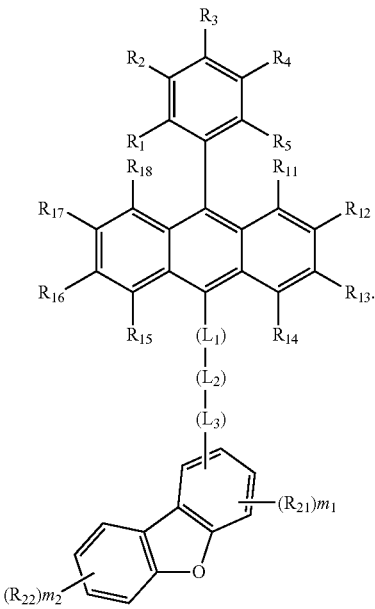

22 Claims, 1 Drawing Sheet

(51) Int. Cl.
*C09K 11/06* (2006.01)
*H01L 51/50* (2006.01)

(52) U.S. Cl.
CPC ...... *H01L 51/0059* (2013.01); *H01L 51/0072* (2013.01); *H01L 51/0074* (2013.01); *C09K 2211/1007* (2013.01); *C09K 2211/1018* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

FOREIGN PATENT DOCUMENTS

| | | |
|---|---|---|
| KR | 101068224 B1 | 9/2011 |
| KR | 101111406 B1 | 4/2012 |
| KR | 20140058290 A | 5/2014 |
| KR | 20160107669 A | 9/2016 |
| KR | 20170009714 A | 1/2017 |
| KR | 20190056338 A | 5/2019 |
| WO | WO2015009076 A1 | 1/2015 |

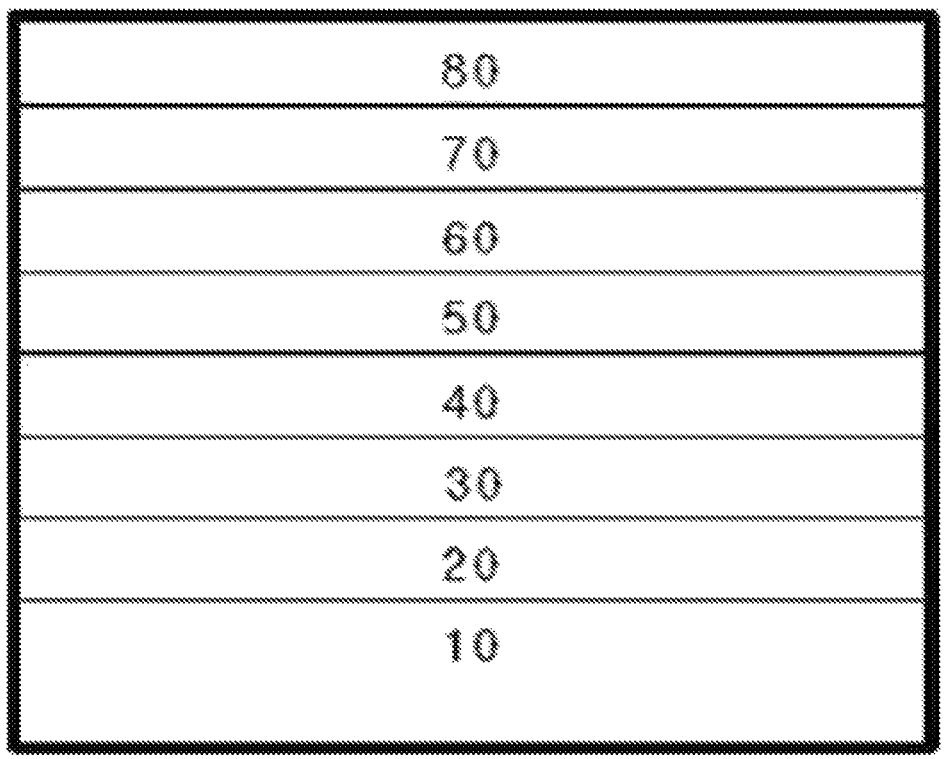

ORGANIC COMPOUND FOR ORGANIC LIGHT EMITTING DIODE AND ORGANIC LIGHT EMITTING DIODE INCLUDING SAME

CROSS-REFERENCE TO RELATED APPLICATIONS

This application claims the priority of the Korean Patent Applications NO 10-2019-0073701 filed on Jun. 20, 2019 and NO 10-2020-0061343 filed on May 22, 2020, in the Korean Intellectual Property Office, the disclosure of which is incorporated herein by reference.

BACKGROUND OF THE INVENTION

1. Field of the Invention

The present disclosure relates to a compound for an organic light emitting diode and an organic light emitting diode comprising the same. More particularly, the present disclosure relates to a compound for an organic light emitting diode, which has a specific deuterium-substituted anthracene derivative-based structure that provides an organic light emitting diode with high efficiency and long life span characteristics, and an organic light emitting diode comprising the same.

2. Description of the Prior Art

Organic light-emitting diodes, based on self-luminescence, exhibit the advantages of having a wide viewing angle, excellent contrast, fast response time, high brightness, excellent driving voltage and response rate characteristics, and of allowing for a polychromic display.

A typical organic light-emitting diode includes a positive electrode (anode) and a negative electrode (cathode), facing each other, with an organic emission layer disposed therebetween.

As to the general structure of the organic light-emitting diode, a hole transport layer, a light-emitting layer, an electron transport layer, and a cathode are formed in that order on an anode. Here, all of the hole transport layer, the light-emitting layer, and the electron transport layer are organic films comprising organic compounds.

An organic light-emitting diode having such a structure operates as follows: when a voltage is applied between the anode and the cathode, the anode injects holes which are then transferred to the light-emitting layer via the hole transport layer while electrons injected from the cathode move to the light-emitting layer via the electron transport layer. In the luminescent zone, the carriers such as holes and electrons recombine to produce an exciton. When the exciton returns to the ground state from the excited state, the molecule of the light-emitting layer emits light.

Materials used as the organic layers in organic light-emitting diodes may be divided according to functions into luminescent materials and charge carrier materials, for example, a hole injection material, a hole transport material, an electron injection material, and an electron transport material. The light-emitting mechanism forms the basis of classification of luminescent materials as fluorescent and phosphorescent materials, which use excitons in singlet and triplet states, respectively.

When a single material is employed as the luminescent material, intermolecular actions cause the maximum luminescence wavelength to shift toward a longer wavelength, resulting in a reduction in color purity and luminous efficiency due to light attenuation. In this regard, a host-dopant system may be used as a luminescent material so as to increase the color purity and the luminous efficiency through energy transfer. This is based on the principle whereby, when a dopant which is smaller in energy band gap than a host forming a light-emitting layer is added in a small amount to the light-emitting layer, excitons are generated from the light-emitting layer and transported to the dopant, emitting light at high efficiency. Here, light with desired wavelengths can be obtained depending on the kind of the dopant because the wavelength of the host moves to the wavelength range of the dopant.

Meanwhile, studies have been made to introduce a deuterium-substituted compound as a material in the light emitting layer in order to improve the longevity and stability of the organic light emitting diode.

Compounds substituted with deuterium are known to exhibit differences in thermodynamic behavior from those bonded with hydrogen because the atomic mass of deuterium is twice as great as that of hydrogen, which results in lower zero point energy and lower vibration energy level.

In addition, physicochemical properties involving deuterium, such as chemical bond lengths, etc., appear to be different from those involving hydrogen for hydrogen. In particular, the van der Waals radius of deuterium is smaller than that of hydrogen, because of the smaller stretching amplitude of the C-D bond compared to the C—H bond. Generally, the C-D bond is shorter and stronger than the C—H bond. Upon deuterium substitution, the ground state energy is lowered and a short bond length is formed between the carbon atom and the deuterium atom. Accordingly, the molecular hardcore volume becomes smaller, thereby reducing the electron polarizability can be reduced, and the thin film volume can be increased by weakening the intermolecular interaction.

As discussed above, deuterium substitution provides the effect of reducing the crystallinity of the thin film, that is, it makes the thin film amorphous. Generally, a compound having deuterium substitution may be advantageously used to increase the life span and driving characteristics of an OLED and further improve the thermal resistance.

With respect to related arts for organic light emitting compounds containing deuterium, reference may be made to Korean Patent Number 10-1111406, which discloses a low-voltage driving and long life span diode employing a deuterium-substituted, carbazole-containing compound or a mixture of deuterium-substituted compounds and to Korean Patent Number 10-1068224, which discloses the use of an anthracene derivative bearing a deuterium-substituted phenyl group as a host.

However, there is a continuing need for development of a compound useful in a light emitting layer of an organic light emitting diode that has a long life span and improved efficiency, despite efforts made to fabricate organic light emitting diodes exhibiting longevity characteristics.

RELATED ART DOCUMENT

Korean Patent Number 10-1111406 (Apr. 12, 2012)
Korean Patent Number 10-1068224 (Sep. 28, 2011)

SUMMARY OF THE INVENTION

In order to solve problems encountered in the conventional techniques, a purpose of the present disclosure is to provide an organic light-emitting compound as a host in a light emitting layer of an organic light emitting diode, the compound being based on a special structure of an anthracene derivative having an unsubstituted or deuterium-substituted phenyl group introduced into a specific position thereof, whereby high efficiency and further improved enhanced long life span characteristics can be imparted into the organic light emitting diode.

Another purpose of the present disclosure is to provide an organic light emitting diode comprising the organic light emitting compound as a host in a light emitting layer thereof.

The present disclosure provides an organic light-emitting compound represented by the following [Chemical Formula 1]:

[Chemical Formula 1]

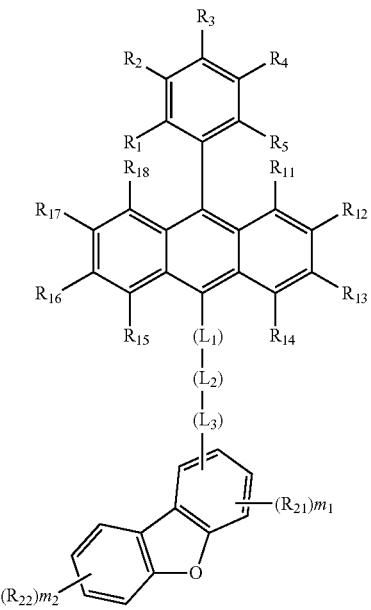

wherein, $R_1$ to $R_5$ and $R_{11}$ to $R_{18}$ may be the same or different and are each independently a hydrogen atom or a deuterium atom;

$R_{21}$ and $R_{22}$ may be the same or different and are each independently any one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heterong member, a cyano, a nitro, a halogen, a substituted or unsubstituted alkylsilyl of 1 to 30 carbon atoms, and a substituted or unsubstituted arylsilyl of 6 to 30 carbon atoms;

$m_1$ is an integer of 0-3 wherein when $m_1$ is 2 or greater, the corresponding $R_{21}$'s may be the same or different;

$m_2$ is an integer of 0-4 wherein when $m_2$ is 2 or greater, the corresponding $R_{22}$'s may be the same or different;

the carbon atoms of the aromatic rings in the dibenzofuran moiety are each bonded with a hydrogen atom or a deuterium atom when $R_{21}$ or $R_{22}$ is not bonded thereto;

$L_1$ to $L_3$ may be the same or different and are each independently a linker selected from a single bond, a substituted or unsubstituted arylene of 6 to 50 carbon atoms, and a substituted or unsubstituted heteroarylene of 2 to 50 carbon atoms, any two of the linkers $L_1$ to $L_3$ being the same or different and being each independently selected from the linker represented by the following Structural Formula 1 and a substituted or unsubstituted arylene of 6 to 50 carbon atoms:

[Structural Formula 1]

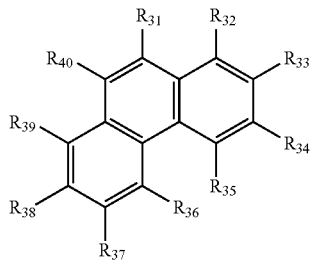

wherein, any two of the substituents $R_{31}$ to $R_{40}$ are each a single bond connected to the anthracenyl moiety, the linkers $L_1$ to $L_3$, or the dibenzofuran moiety in the compound represented by Chemical Formula 1, and the eight remaining substituents among $R_{31}$ to $R_{40}$, none of which is a single bond, may be the same or different and are each independently any one selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heterong member, a cyano, a nitro, a halogen, a substituted or unsubstituted alkylsilyl of 1 to 30 carbon atoms, and a substituted or unsubstituted arylsilyl of 6 to 30 carbon atoms.

In addition, the present disclosure provides an organic light-emitting diode comprising a first electrode; a second electrode facing the first electrode; and an organic layer interposed between the first electrode and the second electrode, wherein the organic layer comprises at least one of the organic light emitting compounds represented by [Chemical Formula 1].

BRIEF DESCRIPTION OF THE DRAWINGS

The above and other aspects, features and advantages of the present disclosure will be more apparent from the following detailed description taken in conjunction with the accompanying drawings, in which:

FIG. 1 is a schematic view of the structure of an organic light-emitting diode according to an embodiment of the present disclosure.

DETAILED DESCRIPTION OF THE EXEMPLARY EMBODIMENTS

Hereinafter, exemplary embodiments which can be easily implemented by those skilled in the art will be described with reference to the accompanying drawings.

In each drawing of the present disclosure, sizes or scales of components may be enlarged or reduced than their actual sizes or scales for better illustration, and known components are not depicted therein to clearly show features of the present disclosure. Therefore, the present disclosure is not limited to the drawings. When describing the principle of the embodiments of the present disclosure in detail, details of well-known functions and features may be omitted to avoid unnecessarily obscuring the presented embodiments.

In drawings, for convenience of description, sizes of components may be exaggerated for clarity. For example, since sizes and thicknesses of components in drawings are arbitrarily shown for convenience of description, the sizes and thicknesses are not limited thereto. Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between", may be used herein for ease of description to refer to the relative positioning.

Throughout the specification, unless explicitly described to the contrary, the word "comprise" and variations such as "comprises" or "comprising" will be understood to imply the inclusion of stated elements but not the exclusion of any other elements.

In order to endow an organic light emitting diode with high efficiency and a long life span, especially with a long life span, the present disclosure provides an organic light emitting compound for use as a host in a light emitting layer of the organic light emitting diode, which is based on an anthracene derivative in which a phenanthrylene group and an arylene group are adopted as linkers, an unsubstituted or deuterium-substituted phenyl group is introduced at a specific position of the anthracene derivative, and the anthracene moiety should be substituted with a hydrogen atom or a deuterium atom, except for the phenyl group and the linkers, thereby guaranteeing a long life span characteristics and further improved efficiency.

In greater detail, the present disclosure provides an organic light emitting compound represented by the following Chemical Formula 1:

[Chemical Formula 1]

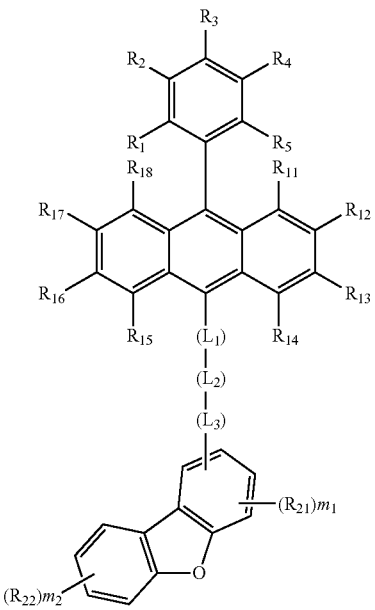

wherein, $R_1$ to $R_5$ and $R_{11}$ to $R_{18}$ may be the same or different and are each independently a hydrogen atom or a deuterium atom;

$R_{21}$ and $R_{22}$ may be the same or different and are each independently any one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heteroring member, a cyano, a nitro, a halogen, a substituted or unsubstituted alkylsilyl of 1 to 30 carbon atoms, and a substituted or unsubstituted arylsilyl of 6 to 30 carbon atoms;

$m_1$ is an integer of 0-3 wherein when $m_1$ is 2 or greater, the corresponding $R_{21}$'s may be the same or different;

$m_2$ is an integer of 0-4 wherein when $m_2$ is 2 or greater, the corresponding $R_{22}$'s may be the same or different;

the carbon atoms of the aromatic rings in the dibenzofuran moiety are each bonded with a hydrogen atom or a deuterium atom when $R_{21}$ or $R_{22}$ is not bonded thereto;

$L_1$ to $L_3$ may be the same or different and are each independently a linker selected from a single bond, a substituted or unsubstituted arylene of 6 to 50 carbon atoms, and a substituted or unsubstituted heteroarylene of 2 to 50 carbon atoms, any two of the linkers $L_1$ to $L_3$ being the same or different and being each independently selected from the linker represented by the following Structural Formula 1 and a substituted or unsubstituted arylene of 6 to 50 carbon atoms:

[Structural Formula 1]

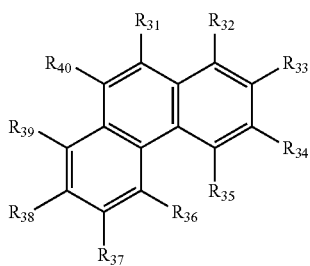

wherein, any two of the substituents $R_{31}$ to $R_{40}$ are each a single bond connected to the anthracenyl moiety, the linkers $L_1$ to $L_3$, or the dibenzofuran moiety in the compound represented by Chemical Formula 1, that is, any two of the substituents $R_{31}$ to $R_{40}$ are each a single bond and may be respectively connected to the anthracenyl moiety and the linker $L_2$, or may be respectively connected to the linkers $L_1$ and $L_3$, or may be respectively connected to the linker $L_2$ and the dibenzofuran moiety in the compound represented by Chemical Formula 1, and the eight remaining substituents among $R_{31}$ to $R_{40}$, none of which is a single bond, may be the same or different and are each independently any one selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heteroring member, a cyano, a nitro, a halogen, a substituted or unsubstituted alkylsilyl of 1 to 30 carbon atoms, and a substituted or unsubstituted arylsilyl of 6 to 30 carbon atoms, wherein the term "substituted" in the expression "substituted or unsubstituted" means having at least one substituent selected from the group consisting of a deuterium atom, a cyano, a halogen, a nitro, an alkyl of 1 to 24 carbon atoms, a cycloalkyl of 3 to 24 carbon atoms, a halogenated alkyl of 1 to 24 carbon atoms, an arylalkyl of 7 to 24 carbon atoms, an aryl of 6 to 24 carbon atoms, a heteroaryl of 2 to 24 carbon atoms, an alkoxy of 1 to 24 carbon atoms, an alkylsilyl of 1 to 24 carbon atoms, and an arylsilyl of 6 to 24 carbon atoms, an aryloxy of 6 to 24 carbon atoms.

The expression indicating the number of carbon atoms, such as "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system including a 5- to 7-membered ring, and preferably a 5- to 6-membered ring. Further, the aromatic system may include a fused ring that is formed by adjacent substituents on the aryl radical.

Examples of the aryl include phenyl, naphthyl, biphenyl, terphenyl, anthryl, indenyl, fluorenyl, phenanthryl, triperylenyl, pyrenyl, perylenyl, chrysenyl, naphthacenyl, and fluoranthenyl, but are not limited thereto.

At least one hydrogen atom of the aryl may be substituted by a deuterium atom, a halogen atom, a hydroxy, a nitro, a cyano, a silyl, an amino (—$NH_2$, —NH(R), —N(R')(R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The heteroaryl substituent used in the compound of the present disclosure refers to a hetero aromatic radical of 2 to 24 carbon atoms bearing 1 to 4 heteroatoms selected from among N, O, P, Se, Te, Si, Ge, and S. In the aromatic radical, two or more rings may be fused. One or more hydrogen atoms on the heteroaryl may be substituted by the same substituents as on the aryl.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the alkoxy substituent useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted by the same substituent as in the aryl.

As used herein, the wording "at least partially deuterium-substituted" means that when a plurality of hydrogen atoms is bonded to one or more carbon atoms in a compound, at least one of the hydrogen atoms (H) is replaced by a deuterium atom (D). For example, "at least partially deuterium-substituted aryl of 6 to 50 carbon atoms" refers to an aryl of 6 to 50 carbon atoms in which at least one hydrogen atom (H) bonded directly to one carbon atom of the aryl group is replaced by a deuterium atom.

According to an embodiment of the present disclosure, the organic light emitting compound represented by Chemical Formula 1 of the present disclosure is technically characterized by the structure in which the anthracene ring moiety has as hydrogen atoms or deuterium atoms as substituents on the carbon atoms thereof at all positions, except for the unsubstituted or deuterium-substituted phenyl moiety at position 10 and the serially bonded linkers ($L_1$, $L_2$, and $L_3$) or the dibenzofuran moiety at position 9 wherein any two of $L_1$ to $L_3$ may be the same or different and are each independently selected from a substituted or unsubstituted phenanthrylene group represented by Structural Formula 1 and a substituted or unsubstituted arylene of 6 to 50 carbon atoms, and the other linker is selected from a single bond, a substituted or unsubstituted arylene of 6 to 50 carbon atoms, and a substituted or unsubstituted heteroarylene of 2 to 50 carbon atoms, the linker $L_3$ being bonded to an carbon atom on the aromatic rings of the dibenzofuran moiety:

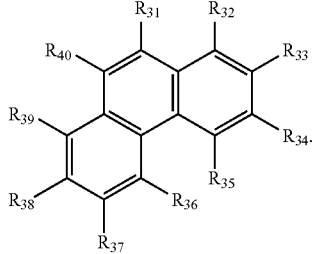

[Structural Formula 1]

In an embodiment of the present disclosure, the substituents $R_{21}$ and $R_{22}$ bonded to the dibenzofuran moiety may be the same or different and are each independently any one selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heteroring member, a cyano, a nitro, a halogen, a substituted or unsubstituted alkylsilyl of 1 to 30 carbon atoms, and a substituted or unsubstituted arylsilyl of 6 to 30 carbon atoms;

$m_2$ is an integer of 0-3 wherein when $m_2$ is 2 or greater, the corresponding $R_{21}$'s may be the same or different;

$m_2$ is an integer of 0-4 wherein when $m_2$ is 2 or greater, the corresponding $R_{22}$'s may be the same or different; and the carbon atoms of the aromatic rings in the dibenzofuran moiety are each bonded with a hydrogen atom or a deuterium atom when $R_{21}$ or $R_{22}$ is not bonded thereto.

Given the organic light emitting compound represented by [Chemical Formula 1] in a light emitting layer thereof, a light emitting diode can exhibit improved luminous efficiency as well as longevity.

In an embodiment, the organic compound represented by [Chemical Formula 1] according to the present disclosure may have a structure in which $R_1$ to $R_5$ are each a deuterium atom, such that the perdeuteriophenyl group is the anthracene ring at position 10.

In an embodiment of the present disclosure, one of the linkers $L_1$ to $L_3$ may be a substituted or unsubstituted arylene of 6 to 50 carbon atoms, particularly a substituted or unsubstituted arylene of 6 to 20 carbon atoms, and more particularly a substituted or unsubstituted arylene of 6 to 16 carbon atoms. Concrete examples of the groups for one of the linkers $L_1$ to $L_3$ include a substituted or unsubstituted phenylene, a substituted or unsubstituted naphthylene, and a substituted or unsubstituted phenanthrylene.

In an embodiment of the present disclosure, one of the linkers $L_1$ to $L_3$ may be a substituted or unsubstituted heteroarylene of 2 to 50 carbon atoms, particularly a substituted or unsubstituted heteroarylene of 2 to 20 carbon atoms, and more particularly a substituted or unsubstituted heteroarylene of 3 to 16 carbon atoms.

In an embodiment of the present disclosure, the one of the linkers $L_1$ to $L_3$, which is neither the linker represented by Structural Formula 1, nor a substituted or unsubstituted arylene of 6 to 50 carbon atoms, in the organic light emitting compound represented by Chemical Formula 1 may be a single bond. In this context, concrete examples of the substituted or unsubstituted arylene of 6 to 50 carbon atoms for one of $L_1$ to $L_3$, which is neither represented by Structural Formula 1, nor a single bond, include phenylene, naphthylene and phenanthrylene.

In another embodiment of the present disclosure, any two of the linkers $L_1$ to $L_3$ in Chemical Formula 1 may be the same or different and are each independently a substituted or unsubstituted arylene of 6 to 50 carbon atoms; the other one of $L_1$ to $L_3$, which is not the substituted or unsubstituted arylene of 6 to 50 carbon atoms, may be the linker represented by Structural Formula 1. In this regard, the two linkers of $L_1$ to $L_3$, which are a substituted or unsubstituted arylene of 6 to 50 carbon atoms, may be the same or different and are each selected from a phenylene, a naphthylene and a phenanthrylene.

In the organic light emitting compound represented by [Chemical Formula 1] according to the present disclosure, the eight substituents of $R_{31}$ to $R_{40}$ in Structural Formula 1, which are not a single bond, may be the same or different and may each be independently a hydrogen atom or a deuterium atom.

Furthermore, the substituents $R_{21}$ and $R_{22}$ in the organic light emitting compound represented by [Chemical Formula 1] may be the same or different and may each be independently a hydrogen atom, a deuterium atom, or an unsubstituted or at least partially deuterium-substituted aryl of 6 to 50 carbon atoms. In a particular embodiment, the substituents $R_{21}$ and $R_{22}$ may be the same or different, or may each be independently an unsubstituted or at least partially deuterium-substituted aryl of 6 to 50 carbon atoms. In a more particular embodiment, the substituents $R_{21}$ and $R_{22}$ may be the same or different, or may each be independently an unsubstituted or at least partially deuterium-substituted aryl of 6 to 20.

In the organic light emitting compound represented by [Chemical Formula 1] according to the present disclosure, $m_2$ may be 0 and $m_2$ may be 1 or 2, or $m_2$ may be 1 or 2 and $m_2$ may be 0 wherein the corresponding $R_{21}$ or $R_{22}$ is boned to only one of the two aromatic rings in the dibenzofuran moiety, with one or two substituents present on each aromatic ring in the dibenzofuran moiety.

In the organic light emitting compound represented by Chemical Formula 1 according to the present disclosure, the two single bonds in Structural Formula 1 may be selected from $R_{31}$, $R_{34}$, $R_{36}$, and $R_{38}$, through which the linker of Structural Formula 1 is respectively connected to the anthracenyl moiety, or the dibenzofuran moiety, or any one among $L_1$ to $L_3$ which is not Structural Formula 1.

That is, the two single bonds in Structural Formula 1 may be selected from $R_{31}$, $R_{34}$, $R_{36}$, and $R_{38}$, through which the linker of Structural Formula 1 is respectively connected to the anthracenyl moiety and the linker $L_2$ when being $L_1$, to the linkers $L_1$ and $L_3$ when being $L_2$, or to the linker $L_2$ and the dibenzofuran moiety when being $L_3$. In this regard, the two single bonds in Structural Formula 1 may be particularly selected from $R_{31}$, $R_{34}$, and $R_{21}$; or from $R_{31}$ and $R_{21}$.

In the organic light emitting compound represented by Chemical Formula 1 according to the present disclosure, when the two single bonds in Structural Formula 1 may be selected from $R_{31}$, $R_{34}$, $R_{36}$, and $R_{38}$, through which the linker of Structural Formula 1 is connected to the anthracenyl moiety, or the dibenzofuran moiety, or any one of $L_1$ to $L_3$ which is not Structural Formula 1, the substituent $R_{31}$ in Structural Formula 1 is a single bond connected to the anthracenyl moiety or is a single bond connected to any one of $L_1$ to $L_3$ which is not Structural Formula 1; and $R_{34}$ or $R_{38}$ is a single bond connected to any one of $L_1$ to $L_3$, which is not Structural Formula 1, or is a single bond connected to the dibenzofuran moiety.

In the organic light emitting compound represented by Chemical Formula 1 according to the present disclosure, when the two single bonds in Structural Formula 1 may be selected from $R_{31}$, $R_{34}$, $R_{36}$, and $R_{38}$, through which the linker of Structural Formula 1 is connected to the anthracenyl moiety, or the dibenzofuran moiety, or any one of $L_1$ to $L_3$ which is not Structural Formula 1, the substituent $R_{31}$ may be selected from among the single bond connected to the anthracenyl moiety and a single bond connected to any one of $L_1$ to $L_3$ which is not Structural Formula 1; and $R_{36}$ may be selected from among the single bond connected to the dibenzofuran moiety and the single bond connected to any one of $L_1$ to $L_3$ which is not Structural Formula 1.

In the organic light emitting compound represented by Chemical Formula 1 according to the present disclosure, when the two single bonds in Structural Formula 1 may be selected from $R_{31}$, $R_{34}$, $R_{36}$, and $R_{38}$, through which the linker of Structural Formula 1 is connected to the anthracenyl moiety, or the dibenzofuran moiety, or any one of $L_1$ to $L_3$ which is not Structural Formula 1, the substituent $R_{38}$ is selected from among the single bond connected to the anthracenyl moiety and the single bond connected to any one of $L_1$ to $L_3$ which is not Structural Formula 1; and the substituent $R_{31}$ is selected from the single bond connected to the dibenzofuran moiety and the single bond connected to any one of $L_1$ to $L_3$ which is not Structural Formula 1.

The compound represented by Chemical Formula 1 having a preferable bonding structure between the dibenzofuran moiety and the linker $L_3$ according to the present disclosure may be the organic light emitting compound represented by the following Chemical Formula 1-1 or Chemical Formula 1-2:

[Chemical Formula 1-1]

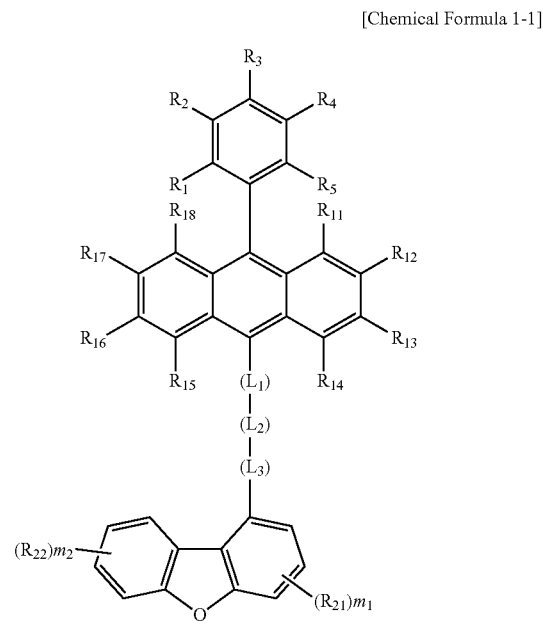

[Chemical Formula 1-2]

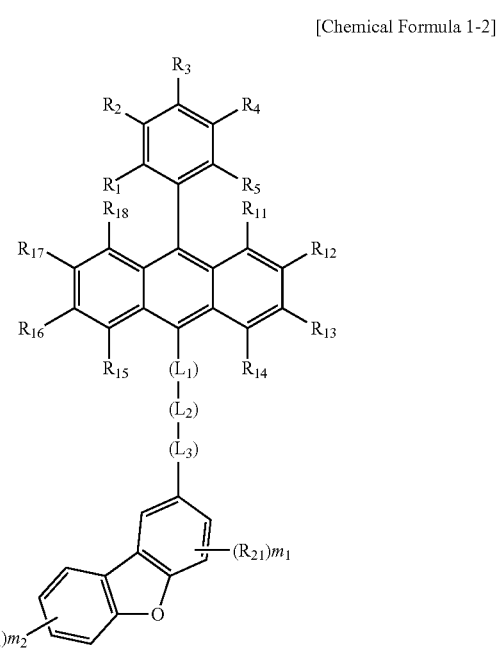

wherein, $R_1$ to $R_5$, $R_{11}$ to $R_{15}$, $L_1$ to $L_3$, $R_{21}$, $R_{22}$, $m_1$, and $m_2$ are as defined above.

More particularly, the organic light emitting compound represented by Chemical Formula 1 may be any one of <Compound 1> to <Compound 24>, but is not limited thereto:

<Compound 1>
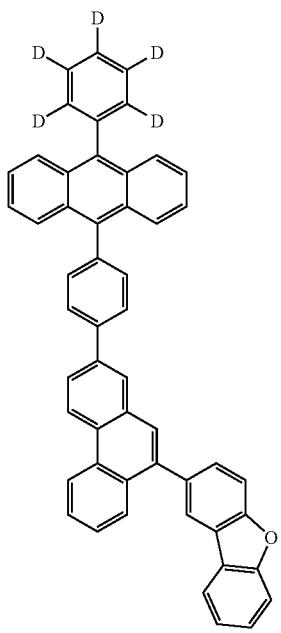
<Compound 3>
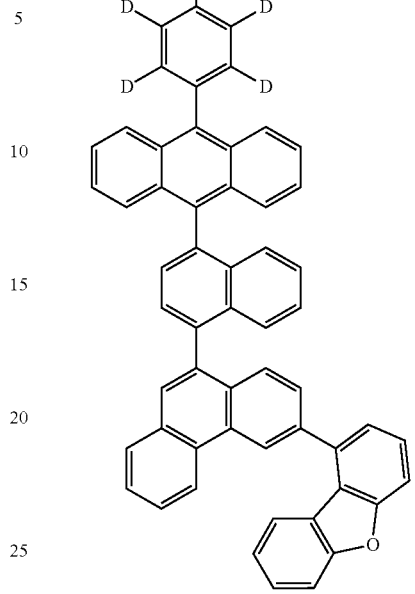
<Compound 2>
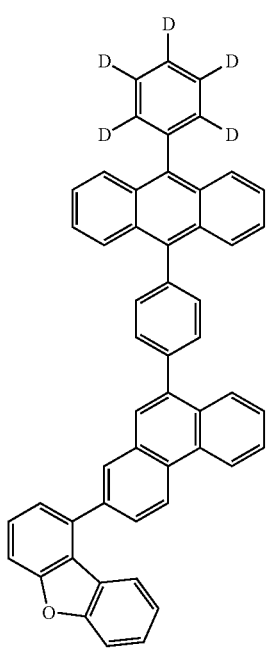
<Compound 4>

<Compound 5>
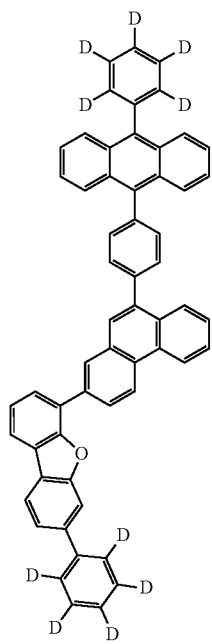
<Compound 6>
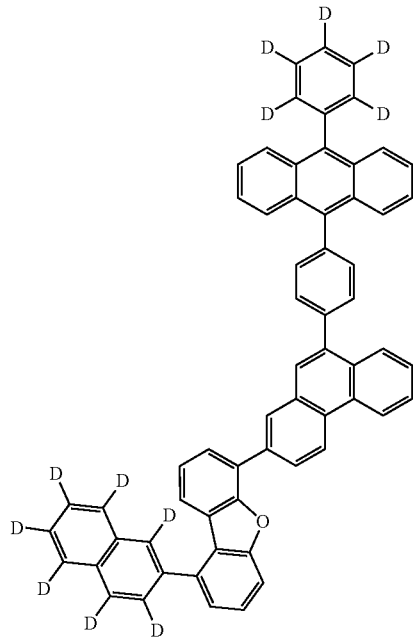
<Compound 7>
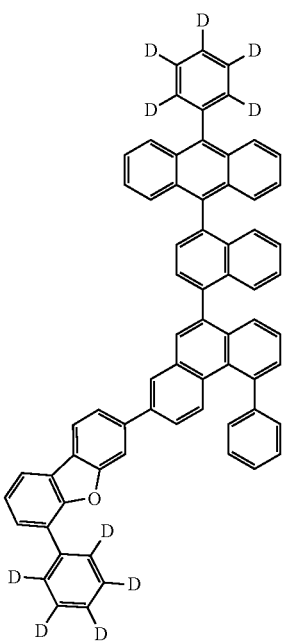
<Compound 8>
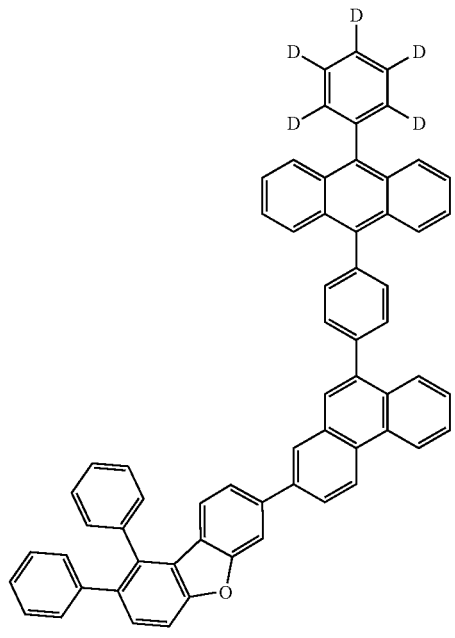

<Compound 9>
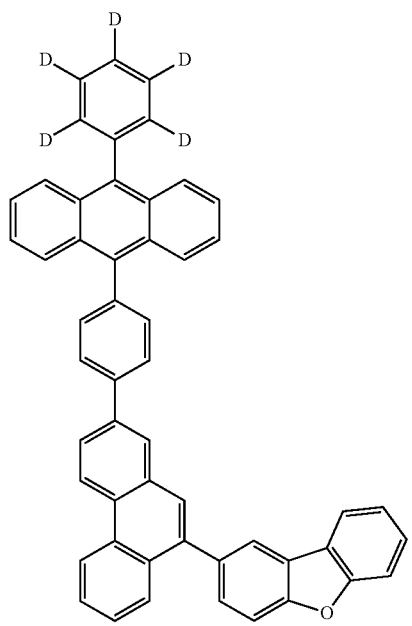
<Compound 10>
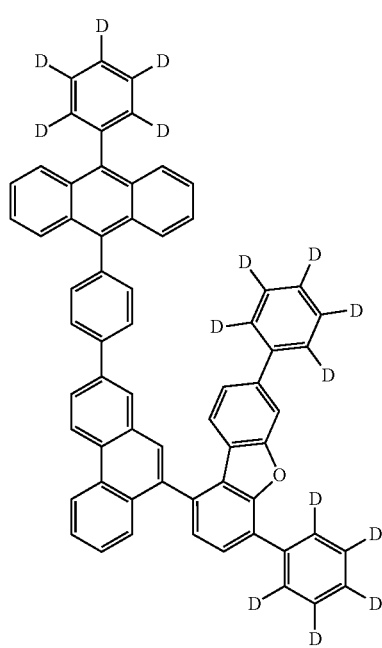
<Compound 11>
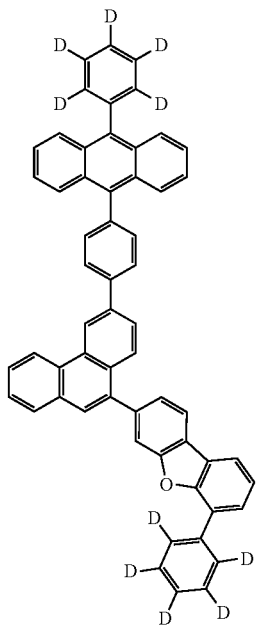
<Compound 12>
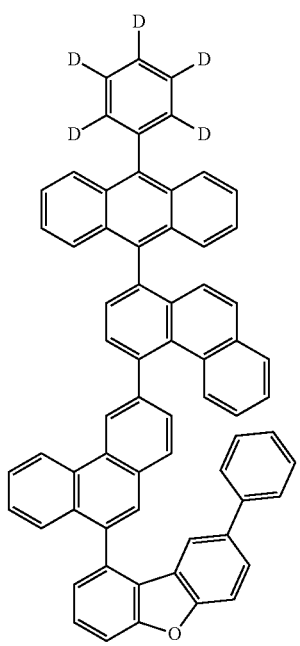

<Compound 13>
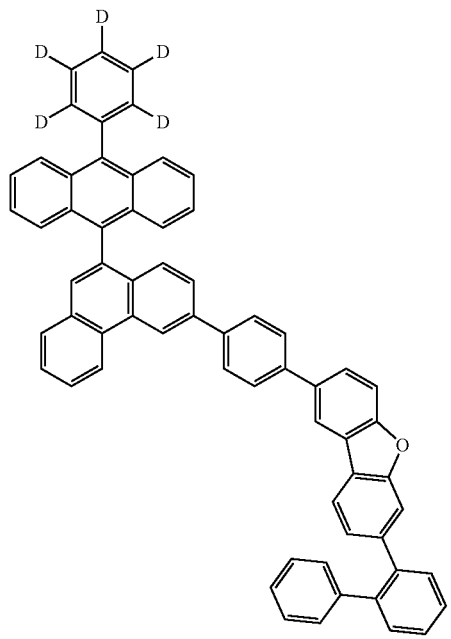
<Compound 14>
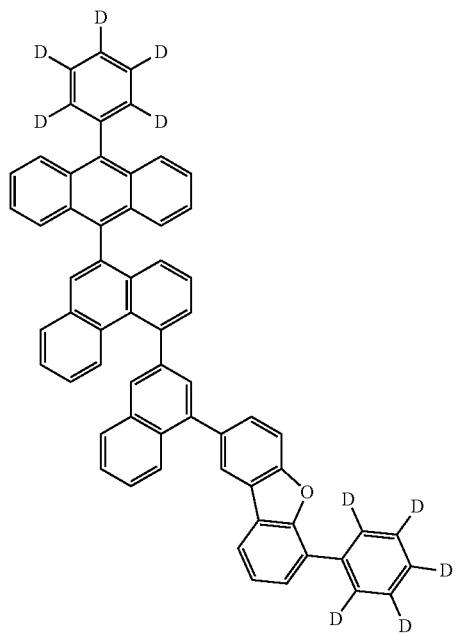
<Compound 15>
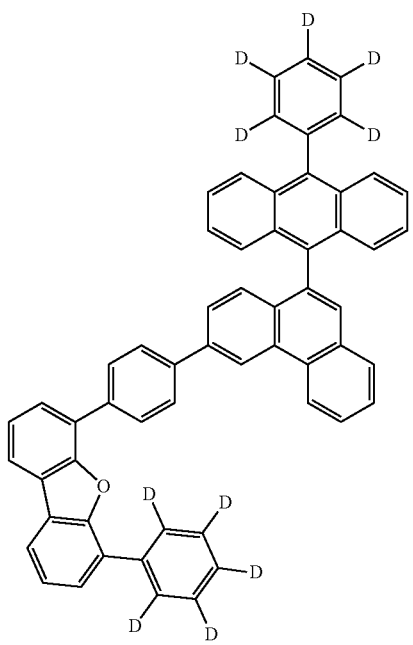
<Compound 16>
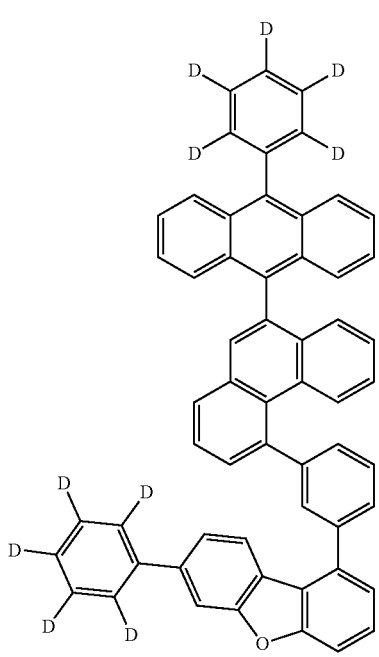

<Compound 17>
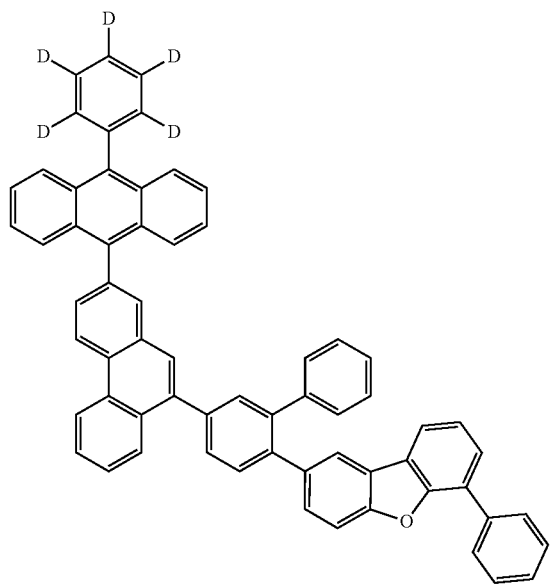
<Compound 19>
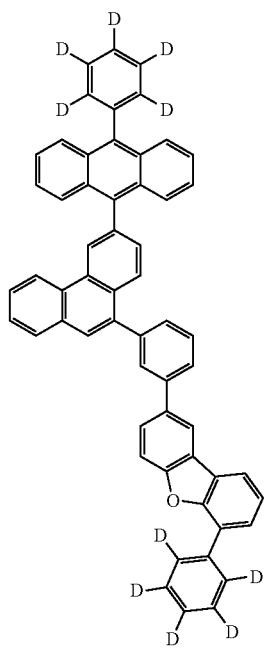
<Compound 18>
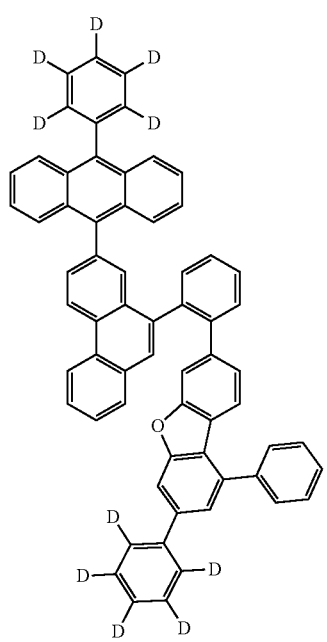
<Compound 20>
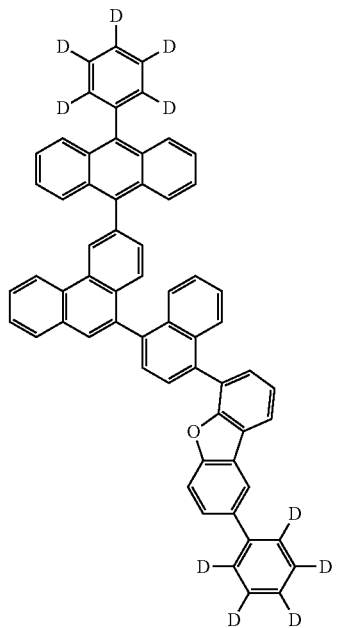

<Compound 21>

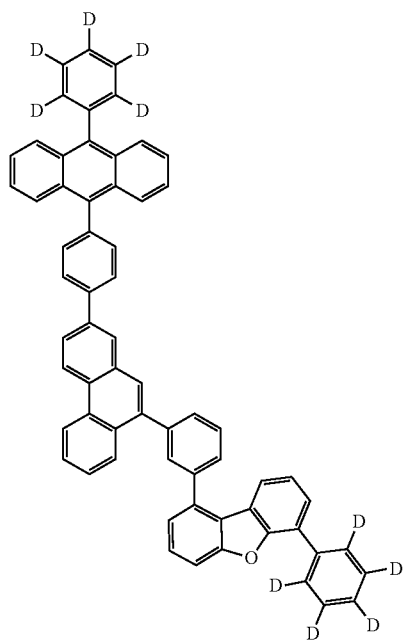

<Compound 22>

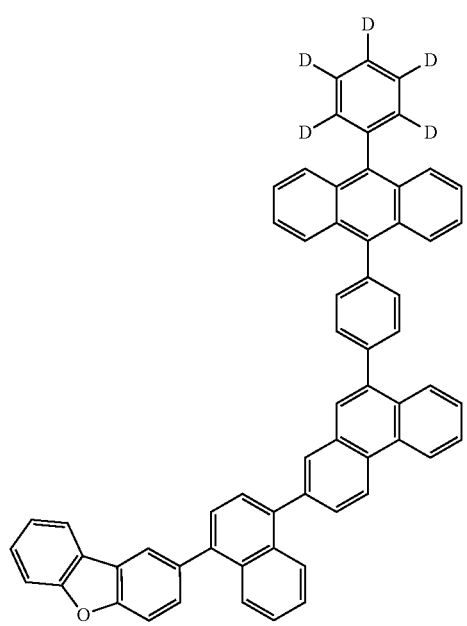

<Compound 23>

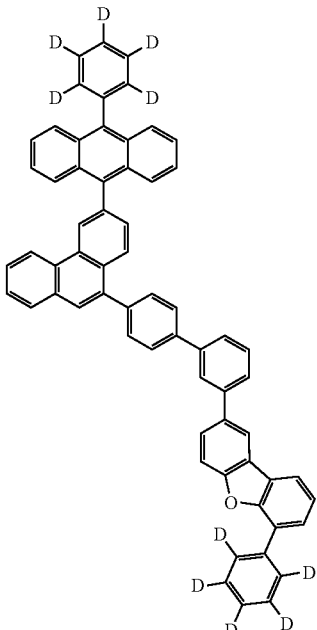

<Compound 24>

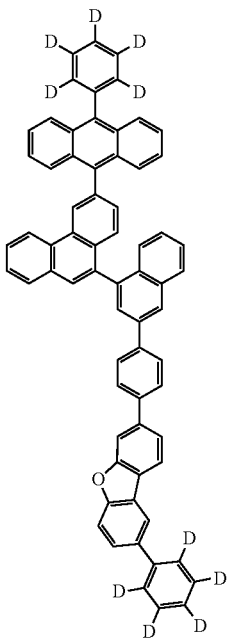

In addition, the present disclosure provides an organic light emitting diode comprising the organic light emitting compound represented by Chemical Formula 1.

In a preferable embodiment, the organic light emitting diode comprises: a first electrode; a second electrode facing the first electrode; and an organic layer interposed between the first electrode and the second electrode, wherein the organic layer comprises at least one of the organic light emitting compounds of the present disclosure.

In this regard, the organic layer in the organic light emitting diode may include at least one of a hole injection layer, a hole transport layer, a functional layer capable of both hole injection and hole transport, an electron transport layer, and an electron injection layer, in addition to the light-emitting layer.

Moreover, when the organic layer interposed between the first electrode and the second electrode is a light emitting layer, the light emitting layer contains a host and a dopant wherein the organic light emitting compound according to the present disclosure may serve as the host.

FIG. 1 is a schematic view of the structure of an organic light-emitting diode according to some embodiments of the present disclosure.

As shown in FIG. 1, the organic light-emitting diode according to the present disclosure comprises an anode 20, a hole transport layer 40, an organic light-emitting layer 50, an electron transport layer 60, and a cathode 80, and optionally a hole injection layer 30 and an electron injection layer 70. In addition, one or two intermediate layers may be further formed in the organic light-emitting diode.

Here, the organic light emitting compound represented by Chemical Formula 1 can be used as a host in the light emitting layer.

Reference is made to FIG. 1 with regard to the organic light-emitting diode of the present disclosure and the fabrication thereof. First, a substrate 10 is coated with an anode electrode material to form an anode 20. So long as it is used in a typical organic light-emitting diode, any substrate may be used as the substrate 10.

Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imparted to the hole injection layer material, as long as it is one that is typically used in the art. For example, mention may be made of 2-TNATA [4,4',4''-tris(2-naphthylphenyl-phenylamino)-triphenylamine], NPD [N,N'-di(1-naphthyl)-N,N'-diphenylbenzidine], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine], but the present disclosure is not limited thereby.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenyl-benzidine (a-NPD).

Then, an organic light-emitting layer 50 containing a host and a dopant is deposited on the hole transport layer 40 by deposition in a vacuum or by spin coating. In some embodiments of the present disclosure, the light-emitting layer particularly ranges in thickness from 50 to 2,000 Å. Here, an electron density control layer (not shown) may be further formed on the organic light emitting layer 50, as necessary.

On the other hand, the light emitting layer may contain a dopant material as well as the host including the organic light emitting compound according to the present disclosure. In the case where the light-emitting layer contains a host and a dopant, the content of the dopant may range from about 0.01 to 20 parts by weight, based on 100 parts by weight of the host, but is not limited thereto.

In addition, the organic light emitting compound represented by Chemical Formula 1 may be used as a host, alone or in combination with a well-known host When used in combination with a well-known host, an available host may be at least one of the compounds represented by Chemical Formula B, below:

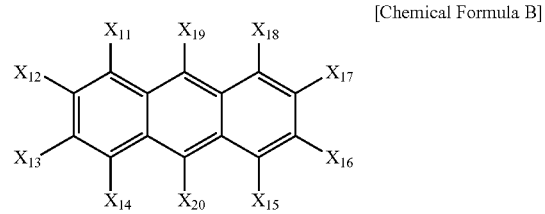

[Chemical Formula B]

wherein, $X_{11}$ to $X_{20}$, which may be the same or different, are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 5 to 50 carbon atoms, a substituted or unsubstituted heteroaryl of 3 to 50 carbon atoms bearing O, N, or S as a heteroatom, a substituted or unsubstituted silicone, a substituted or unsubstituted boron, a substituted or unsubstituted silane, a carbonyl, a phosphoryl, an amino, a nitrile, a halogen, an amide, and an ester, wherein adjacent radicals may form an aliphatic, an aromatic, an aliphatic hetero, or an aromatic hetero fused ring.

More particularly, concrete examples of the host compound represented by Chemical Formula B include, but are not limited to, compounds of [Chemical Formula 1] to [Chemical Formula 196]:

[Chemical Formula 1]

[Chemical Formula 2]

[Chemical Formula 3]

[Chemical Formula 4]

[Chemical Formula 5]

[Chemical Formula 6]

[Chemical Formula 7]

[Chemical Formula 8]
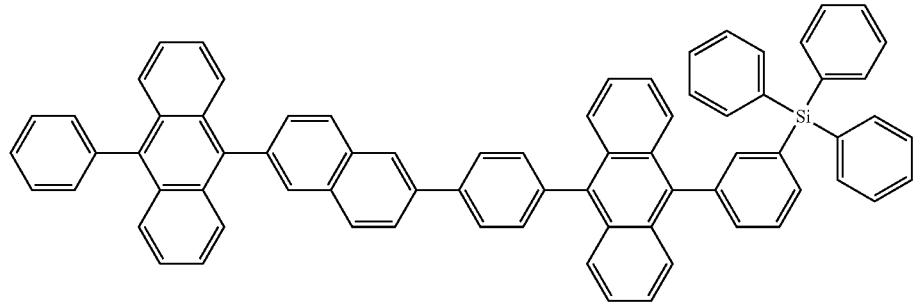
[Chemical Formula9]
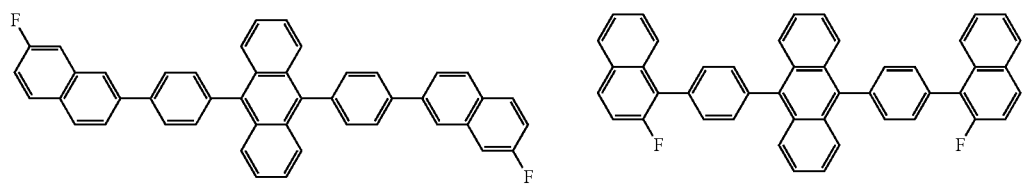
[Chemical Formula10]
[Chemical Formula11]
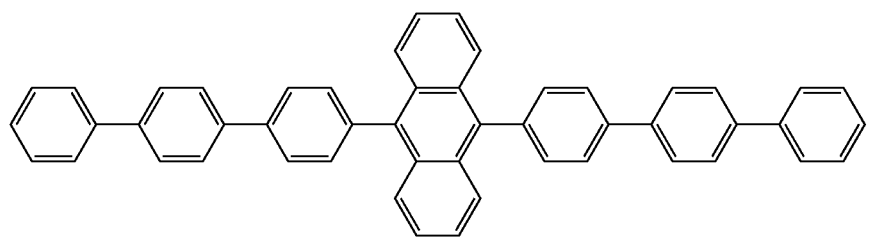
[Chemical Formula12]
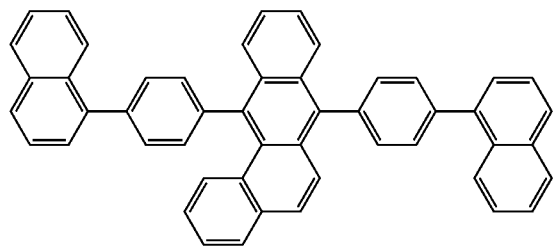
[Chemical Formula13]
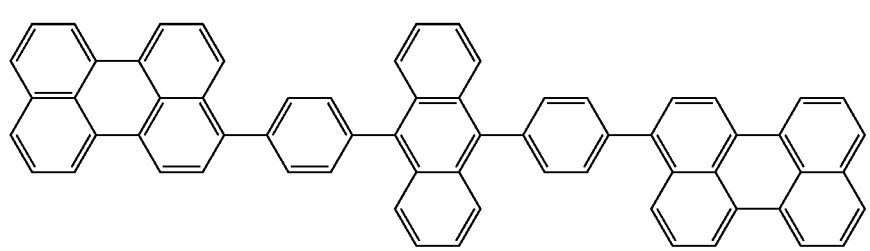
[Chemical Formula14]
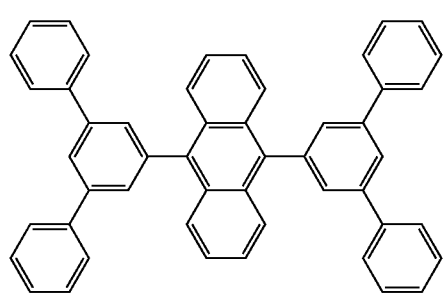
[Chemical Formula15]
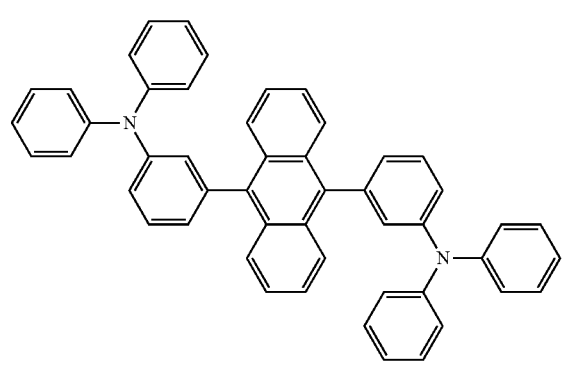

[Chemical Formula16]
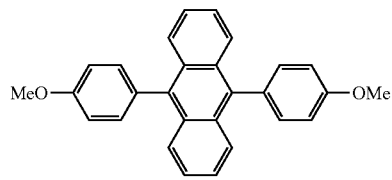
[Chemical Formula17]
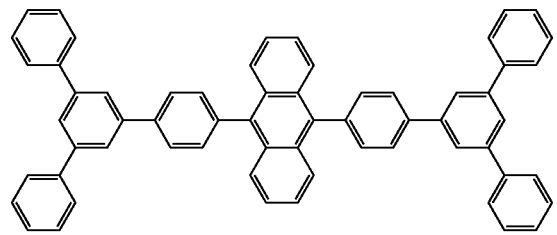
[Chemical Formula18]
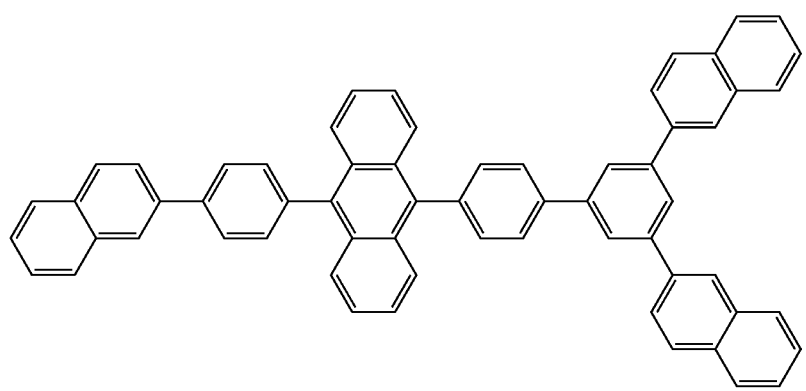
[Chemical Formula19]
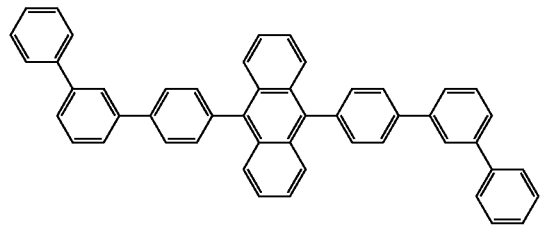
[Chemical Formula20]
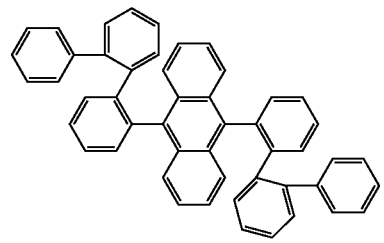
[Chemical Formula21]
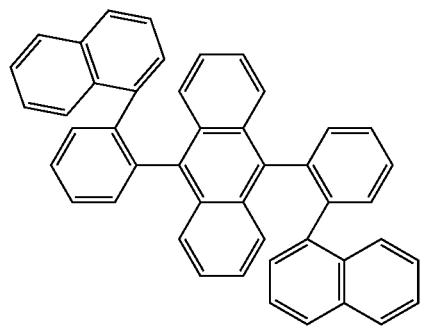
[Chemical Formula22]
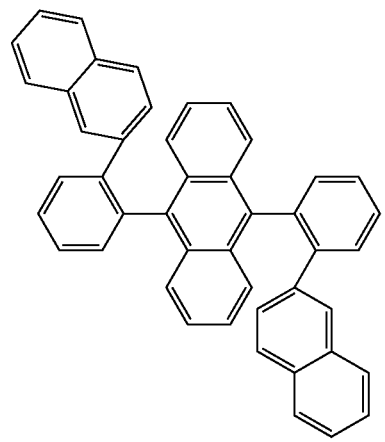

-continued
[Chemical Formula23]
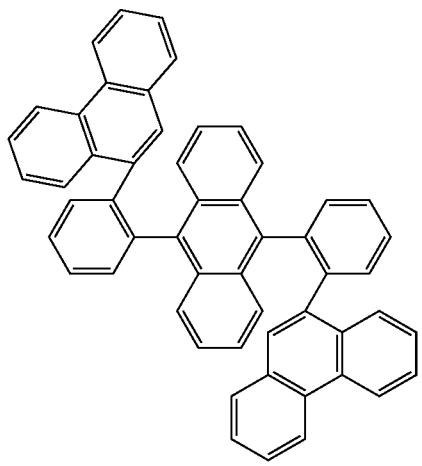
[Chemical Formula24]
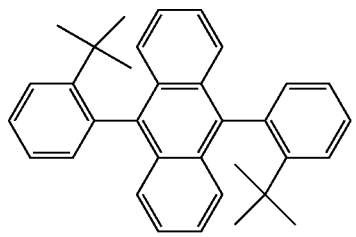
[Chemical Formula25]
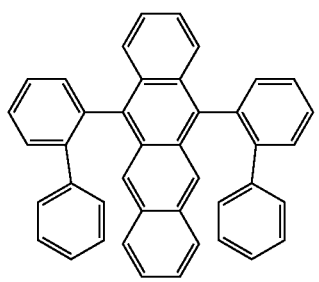
[Chemical Formula26]
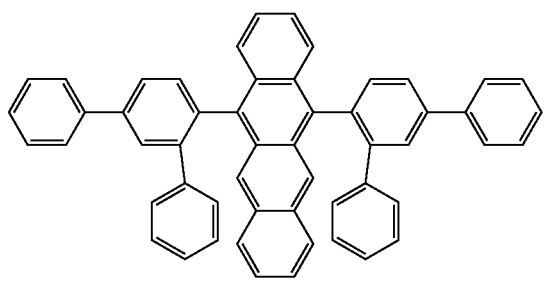
[Chemical Formula27]
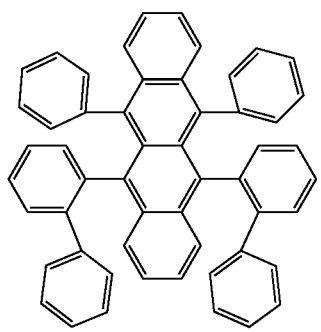
[Chemical Formula28]
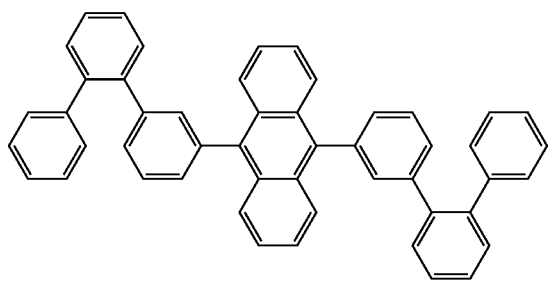
[Chemical Formula29]
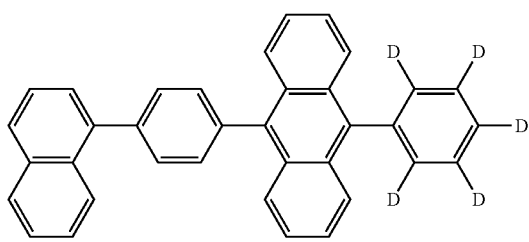
[Chemical Formula30]
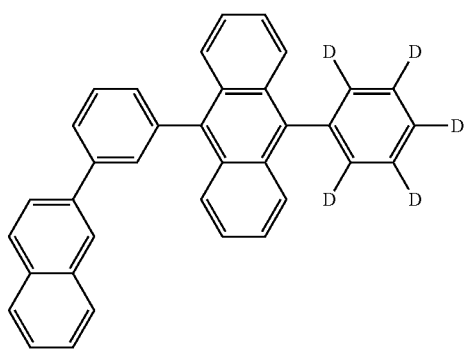

[Chemical Formula31]
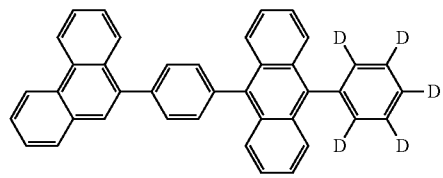
[Chemical Formula32]
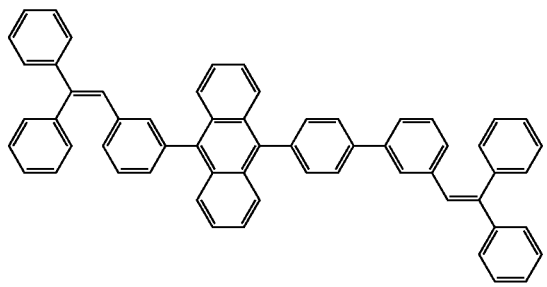
[Chemical Formula33]
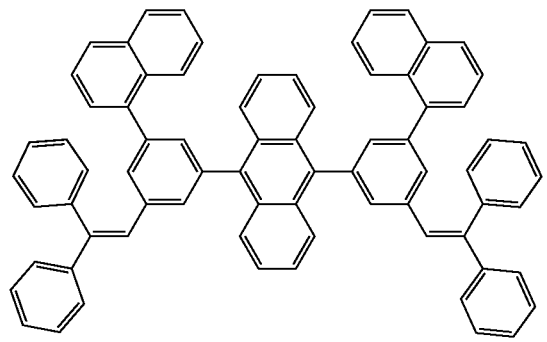
[Chemical Formula34]
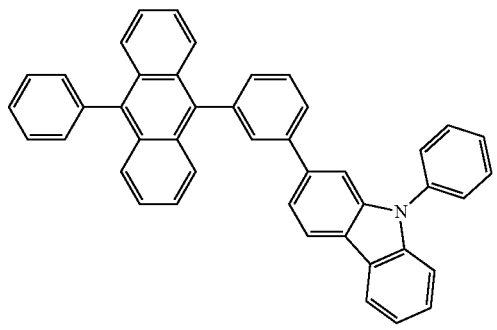
[Chemical Formula35]
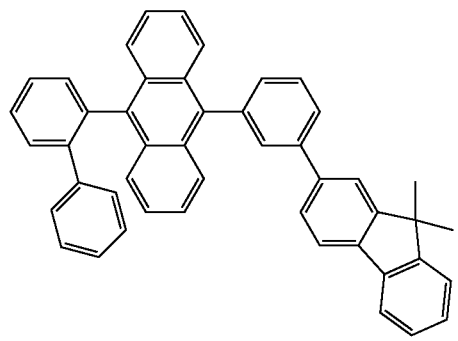
[Chemical Formula36]
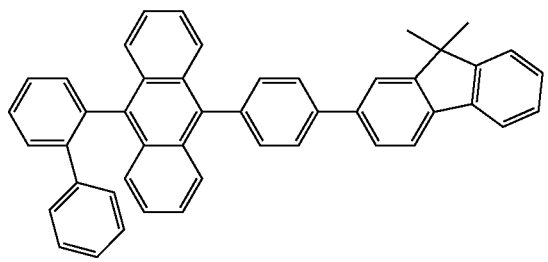
[Chemical Formula37]
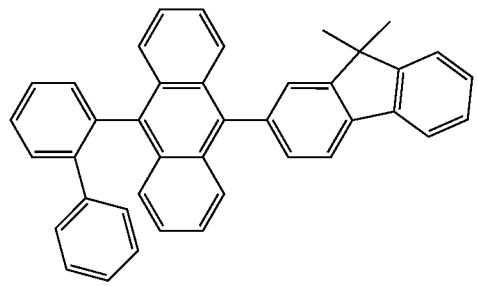
[Chemical Formula38]
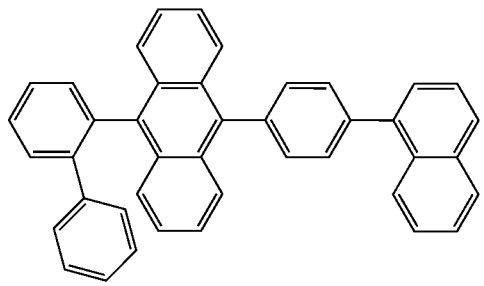
[Chemical Formula39]
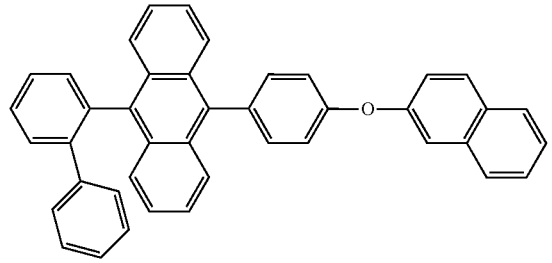
[Chemical Formula40]
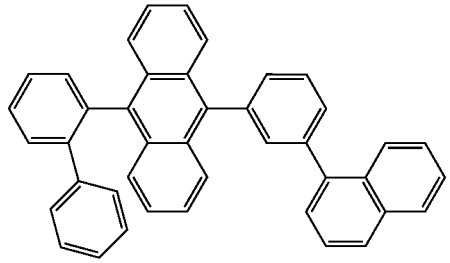

-continued
[Chemical Formula41]
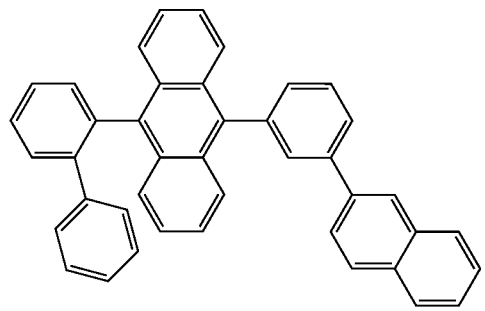
[Chemical Formula42]
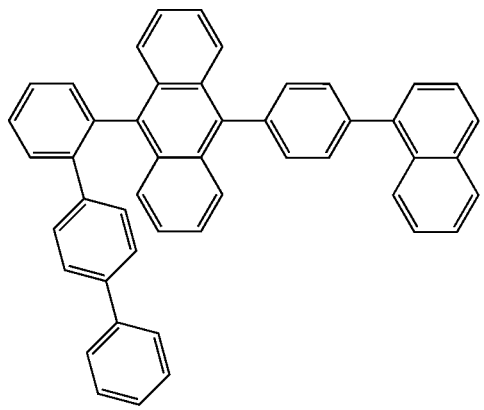
[Chemical Formula43]
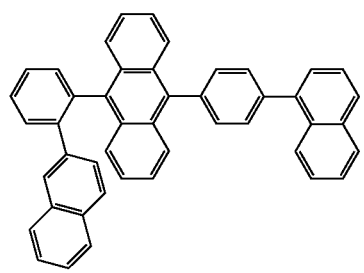
[Chemical Formula44]
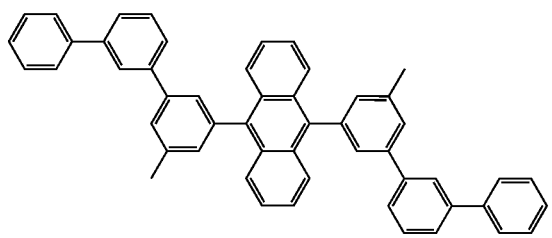
[Chemical Formula45]
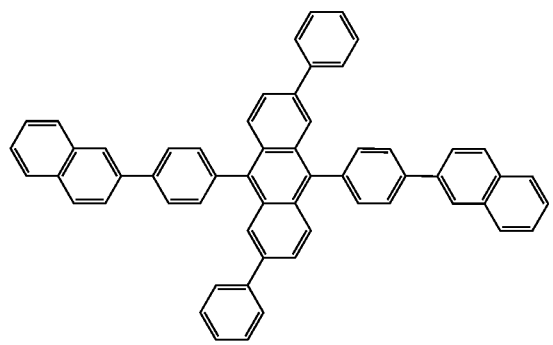
[Chemical Formula46]
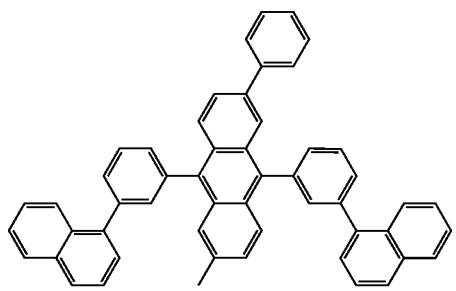
[Chemical Formula47]
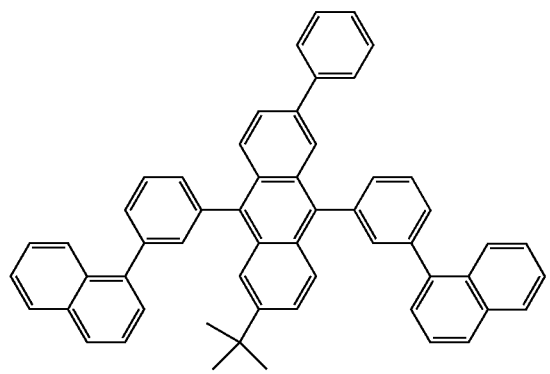
[Chemical Formula48]
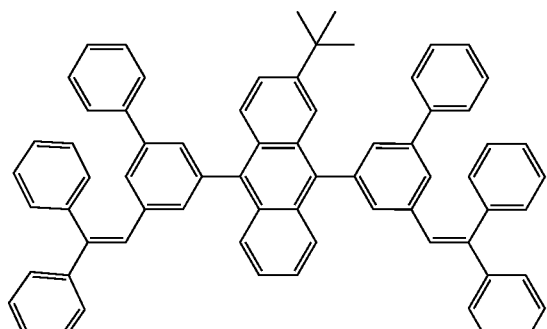

[Chemical Formula49]
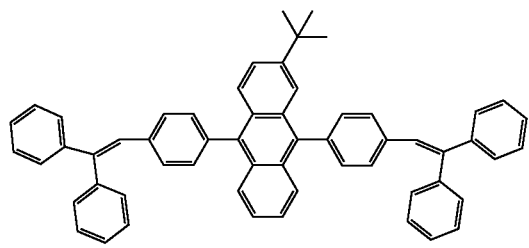
[Chemical Formula50]
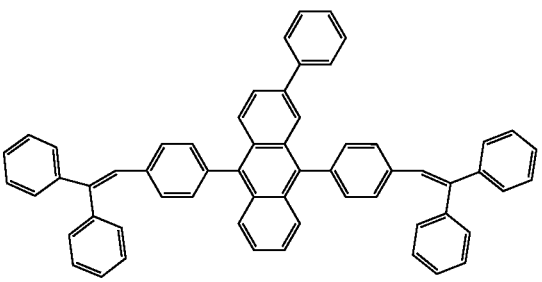
[Chemical Formula51]
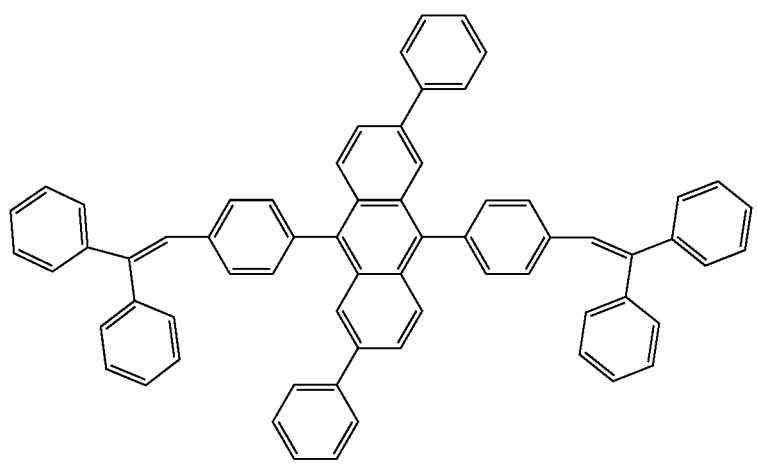
[Chemical Formula52]
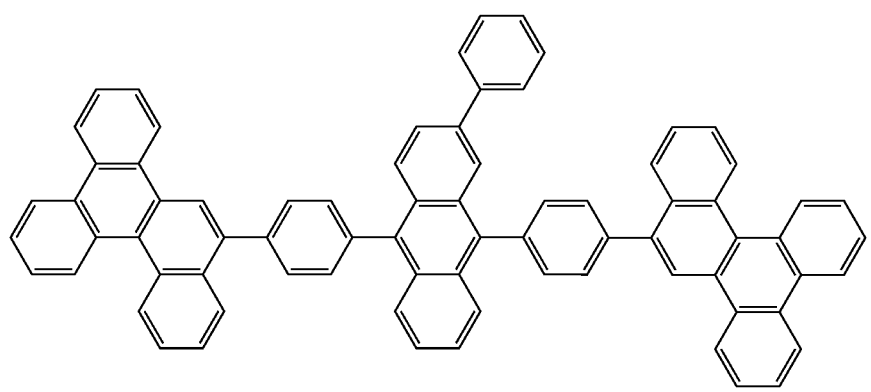
[Chemical Formula53]
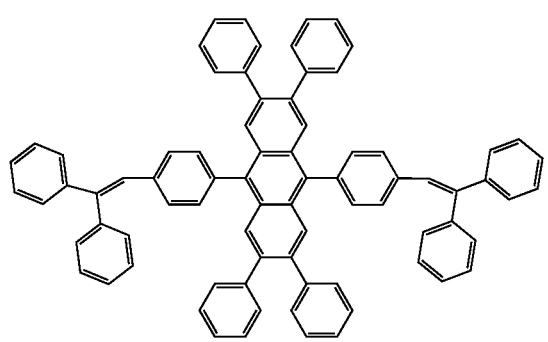
[Chemical Formula54]
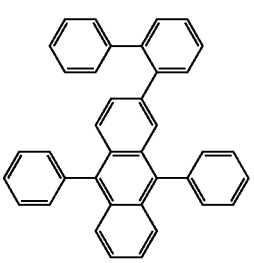

-continued
[Chemical Formula55]
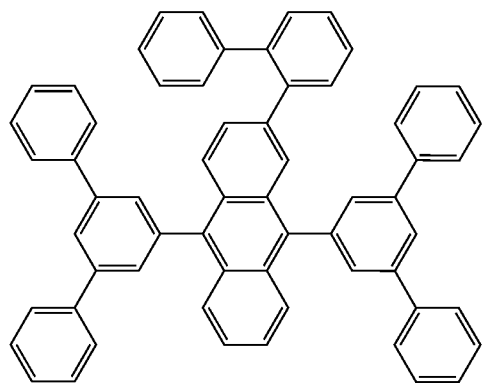
[Chemical Formula56]
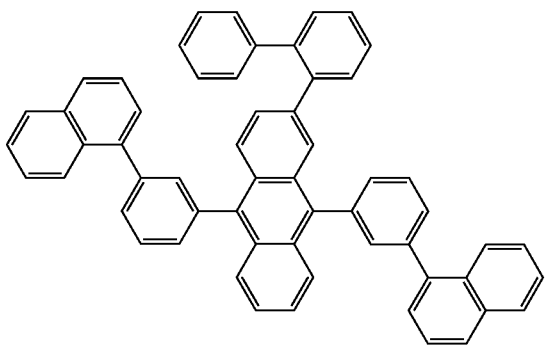
[Chemical Formula57]
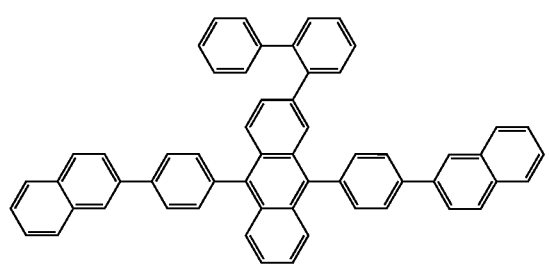
[Chemical Formula58]
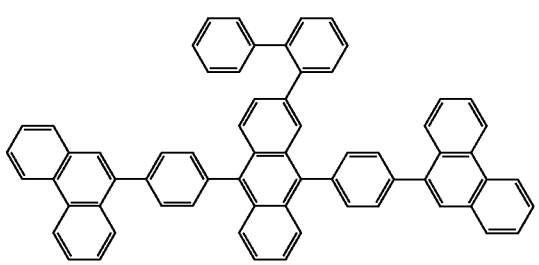
[Chemical Formula59]
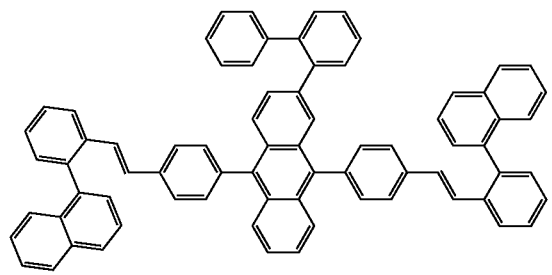
[Chemical Formula60]
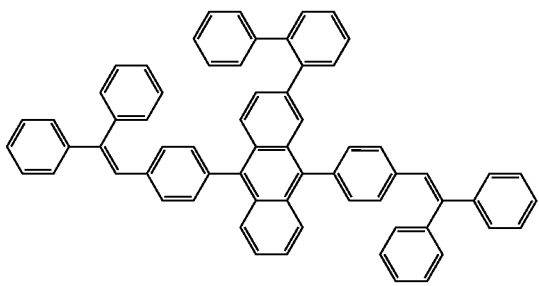
[Chemical Formula61]
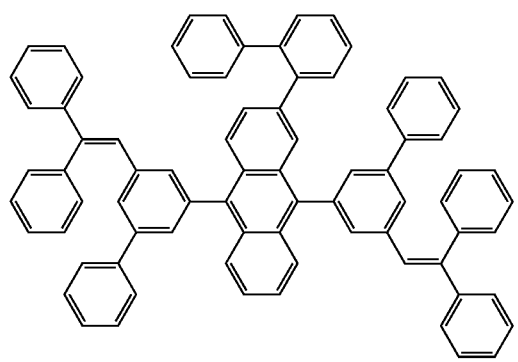
[Chemical Formula62]
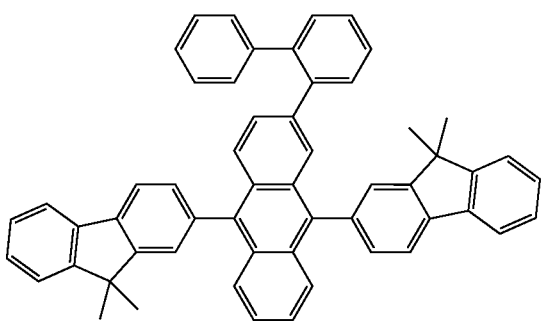

-continued
[Chemical Formula63]
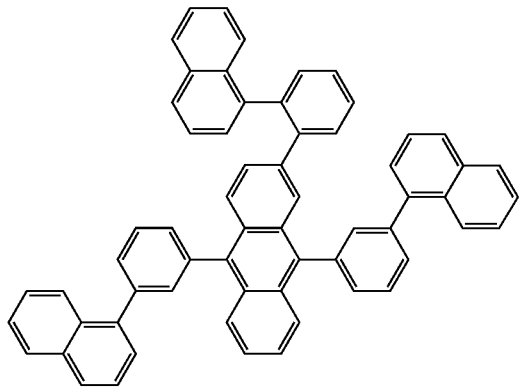
[Chemical Formula64]
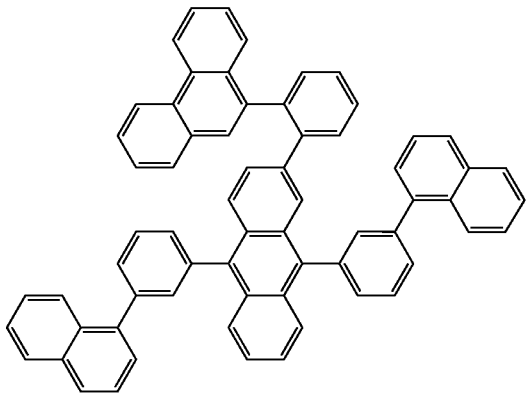
[Chemical Formula65]
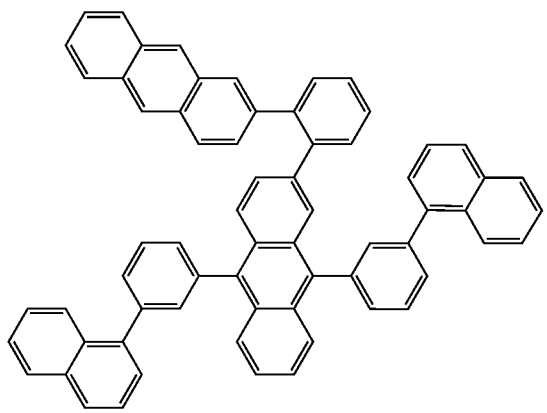
[Chemical Formula66]
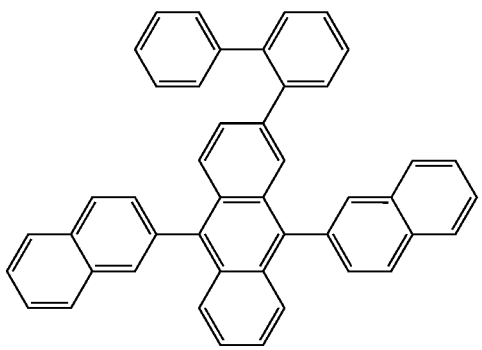
[Chemical Formula67]
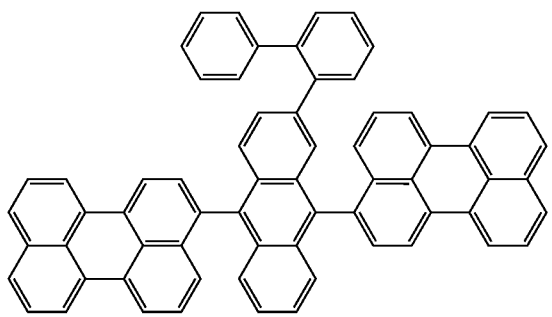
[Chemical Formula68]
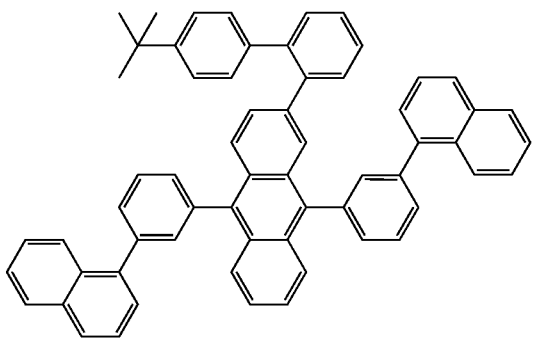
[Chemical Formula69]
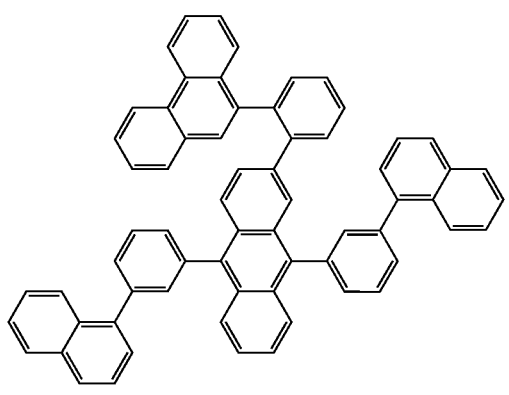
[Chemical Formula70]
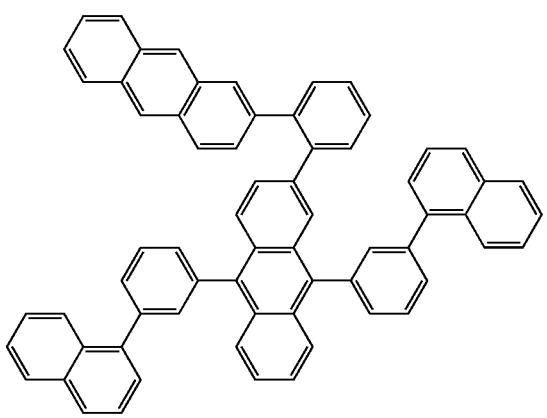

-continued

[Chemical Formula71]

[Chemical Formula72]

[Chemical Formula73]

[Chemical Formula74]

[Chemical Formula75]

[Chemical Formula76]

[Chemical Formula77]

[Chemical Formula78]

[Chemical Formula79]
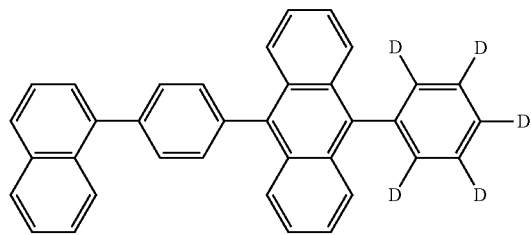
[Chemical Formula80]
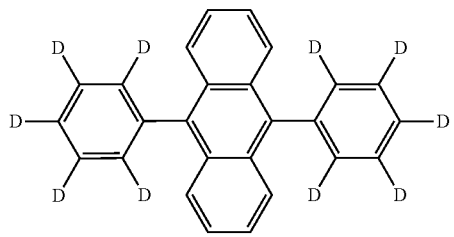
[Chemical Formula81]
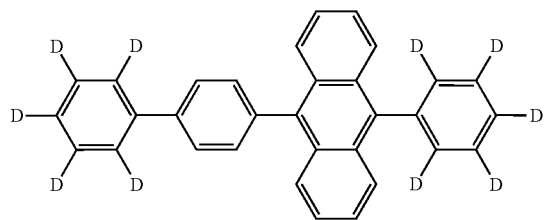
[Chemical Formula82]
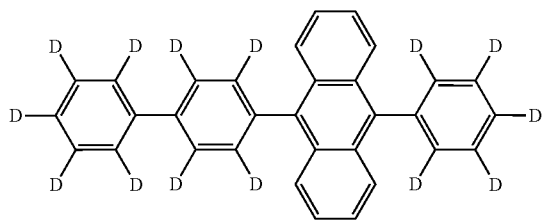
[Chemical Formula83]
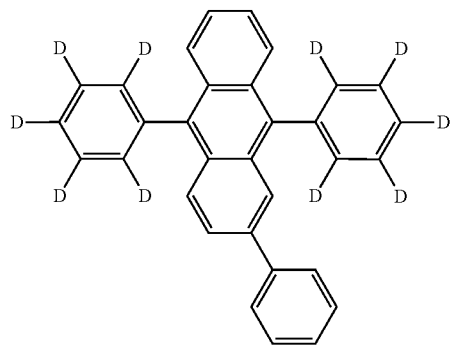
[Chemical Formula84]
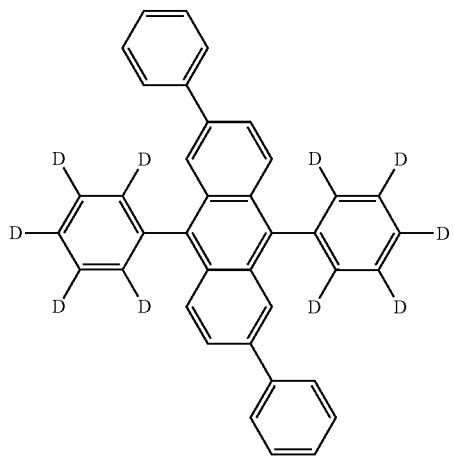
[Chemical Formula85]
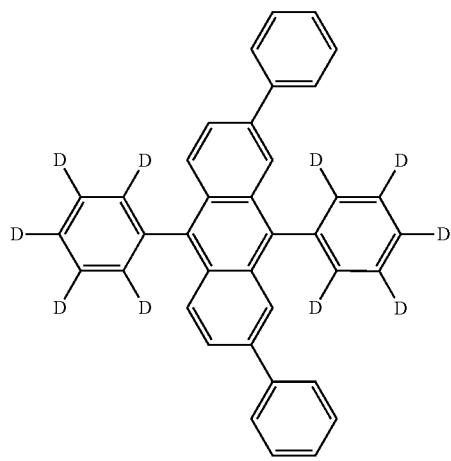
[Chemical Formula86]
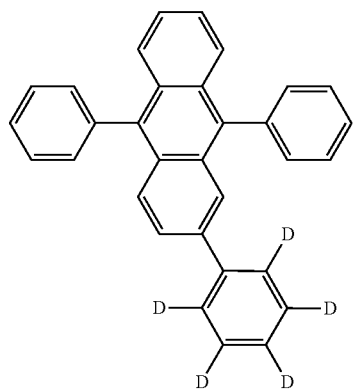

-continued
[Chemical Formula87]
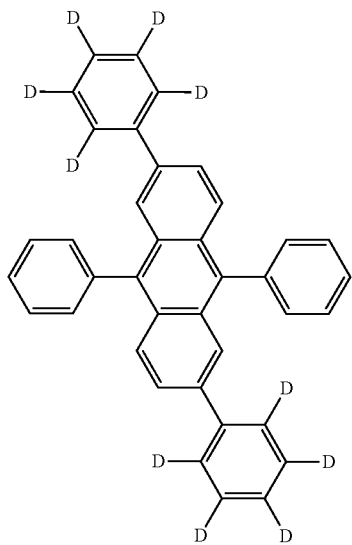
[Chemical Formula88]
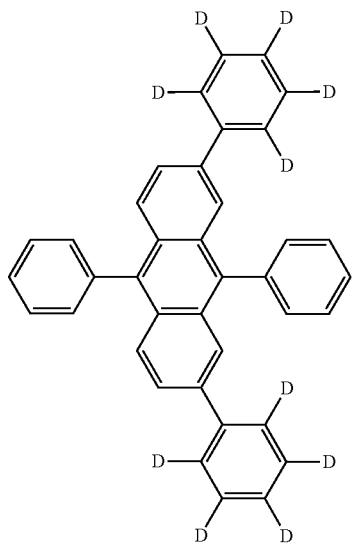
[Chemical Formula89]
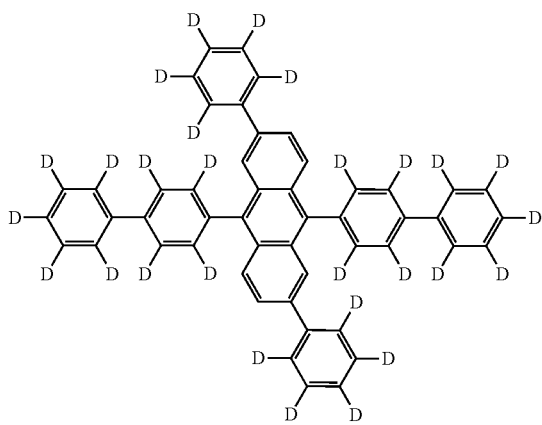
[Chemical Formula90]
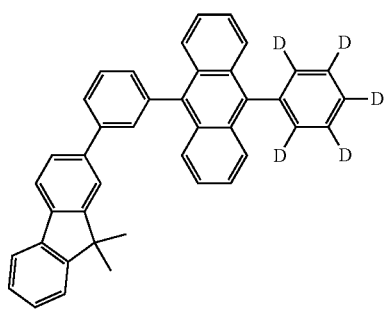
[Chemical Formula91]
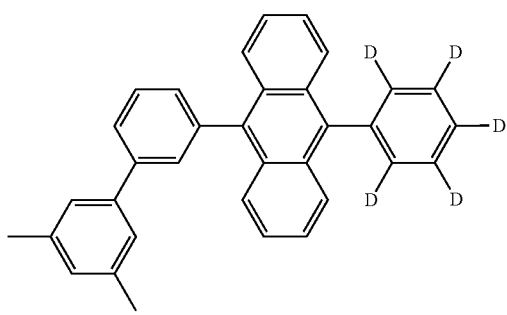
[Chemical Formula92]
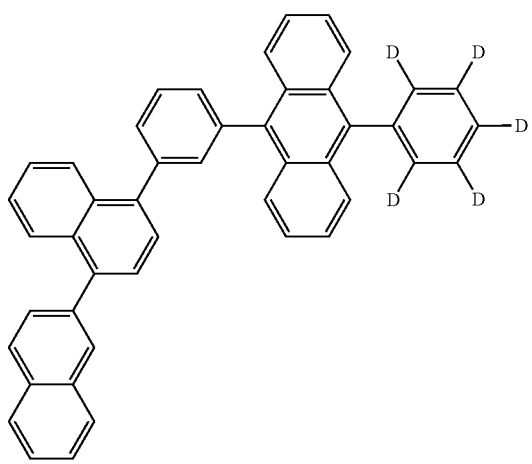

[Chemical Formula93]
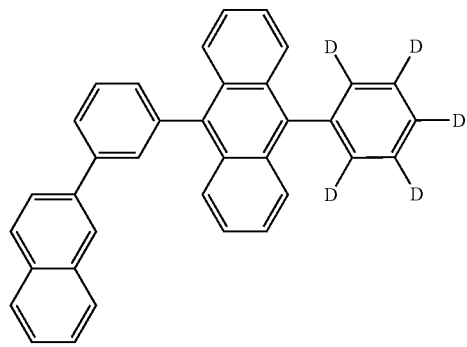
[Chemical Formula94]
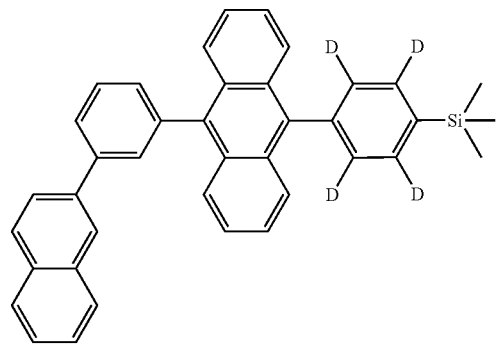
[Chemical Formula95]
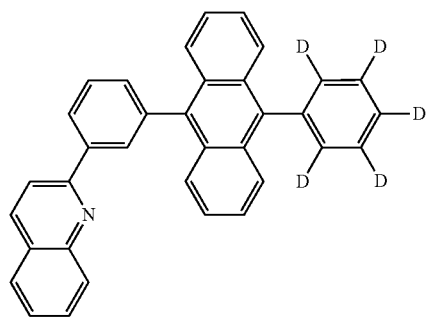
[Chemical Formula96]
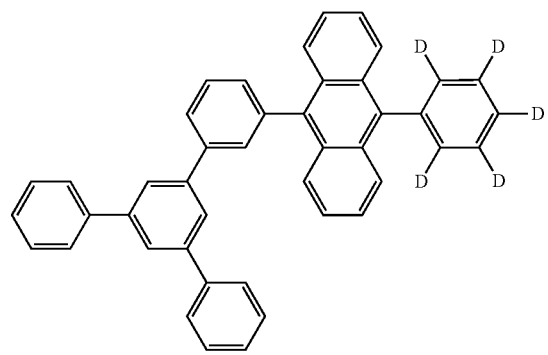
[Chemical Formula97]
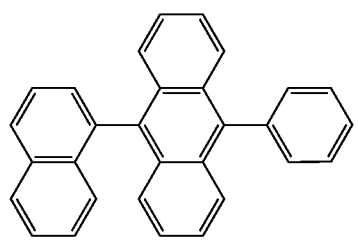
[Chemical Formula98]
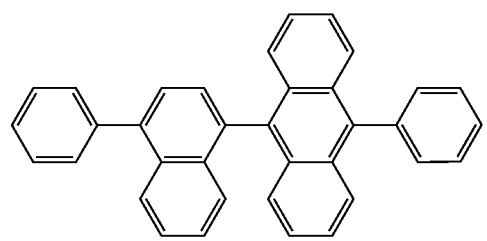
[Chemical Formula99]
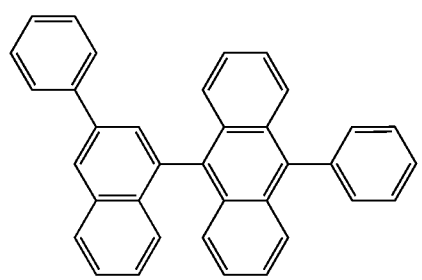
[Chemical Formula100]
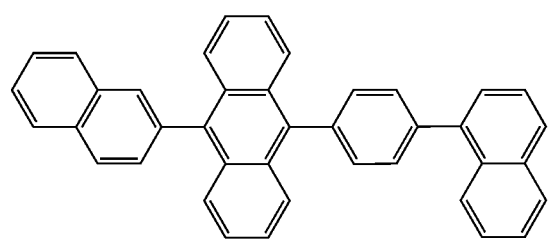
[Chemical Formula101]
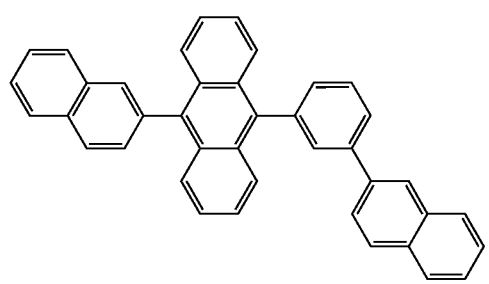
[Chemical Formula102]
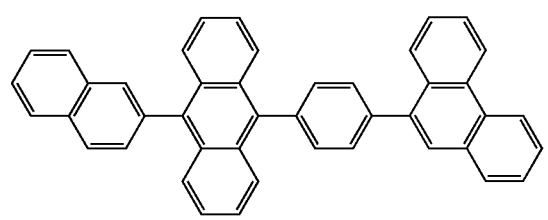

-continued
[Chemical Formula103]
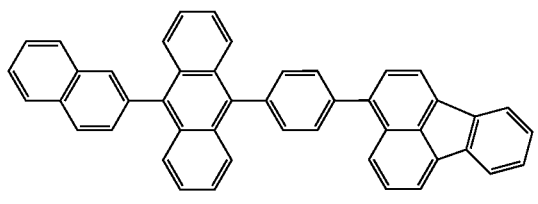
[Chemical Formula104]
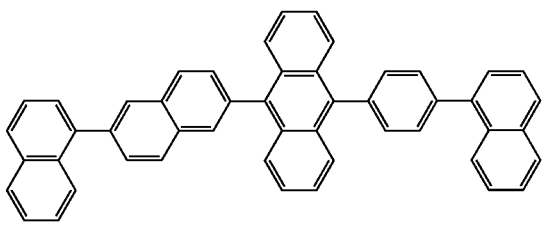
[Chemical Formula105]
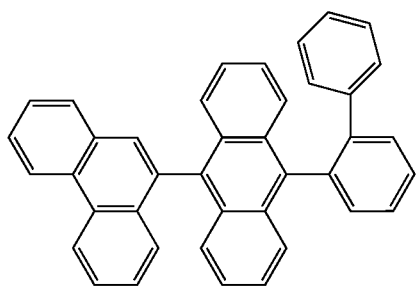
[Chemical Formula106]
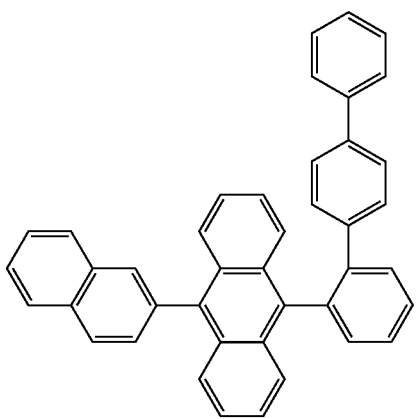
[Chemical Formula107]
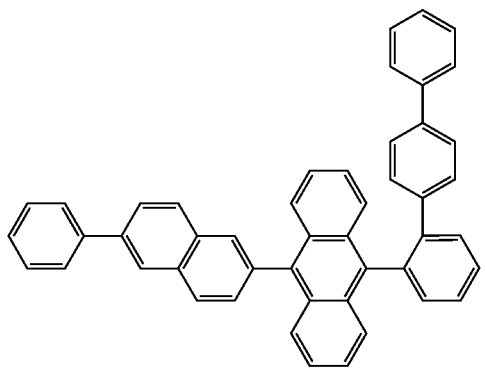
[Chemical Formula108]
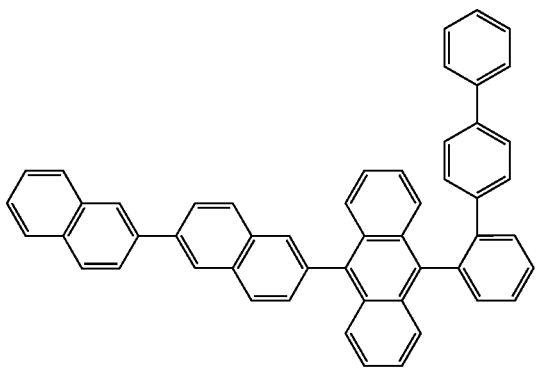
[Chemical Formula109]
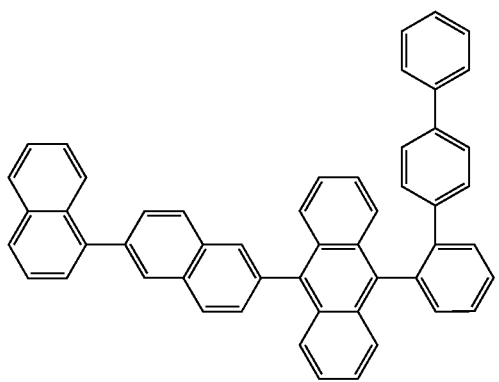
[Chemical Formula110]
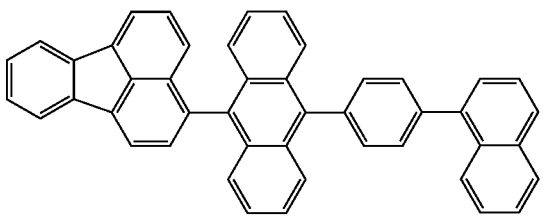

-continued
[Chemical Formula111]
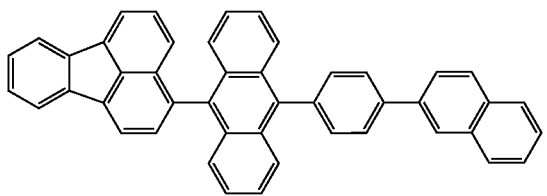
[Chemical Formula112]
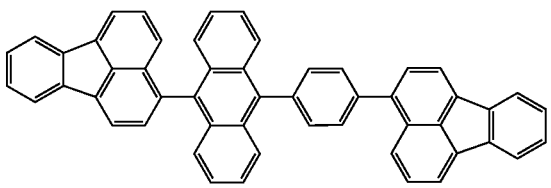
[Chemical Formula113]
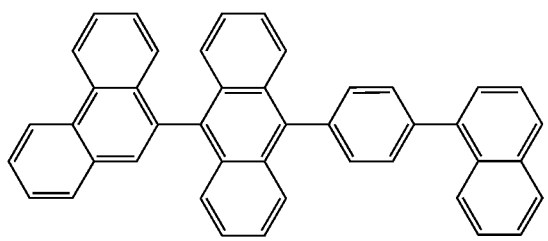
[Chemical Formula114]
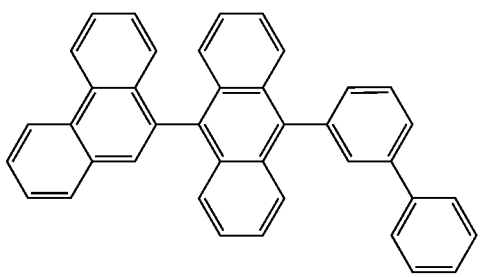
[Chemical Formula115]
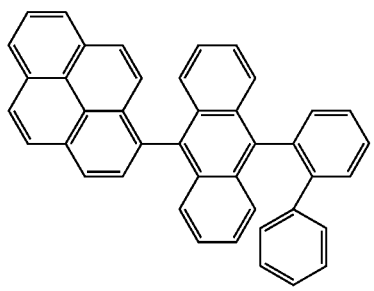
[Chemical Formula116]
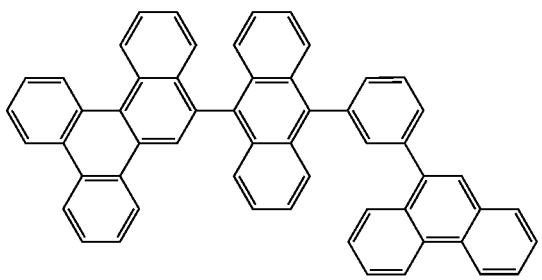
[Chemical Formula117]
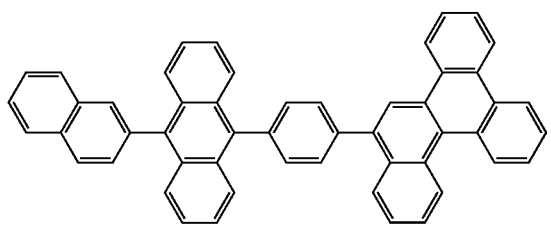
[Chemical Formula118]
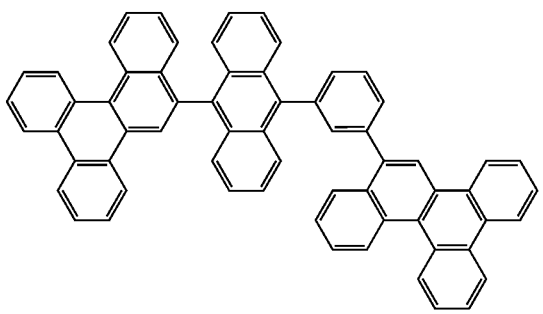
[Chemical Formula119]
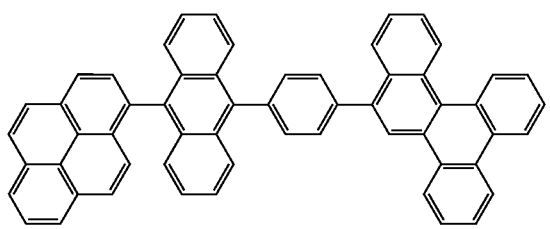
[Chemical Formula120]
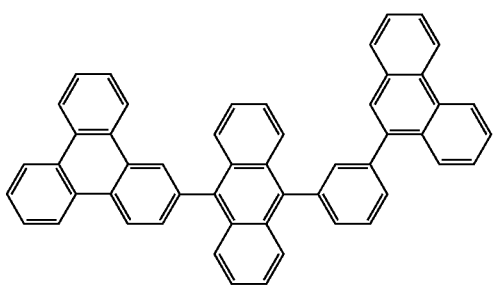

-continued
[Chemical Formula121]
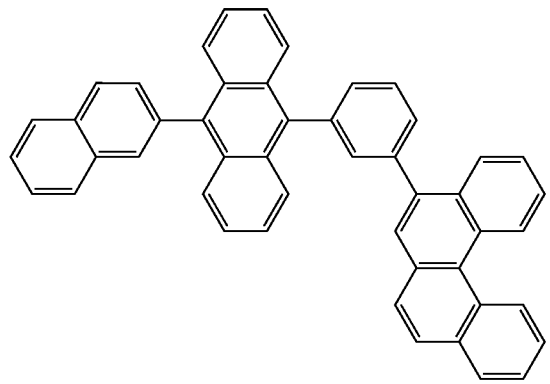
[Chemical Formula122]
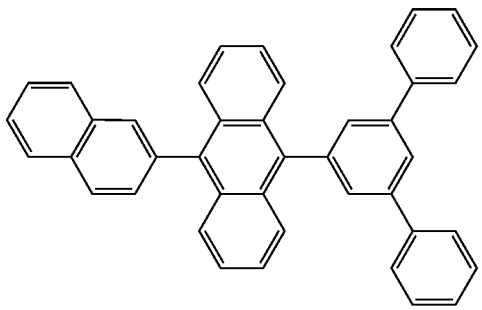
[Chemical Formula123]
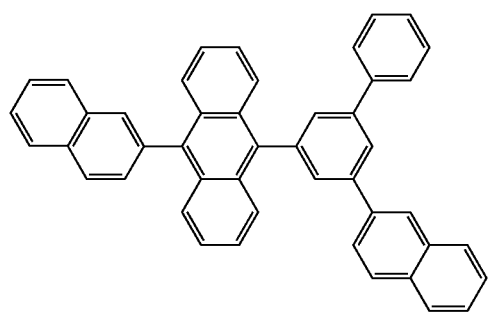
[Chemical Formula124]
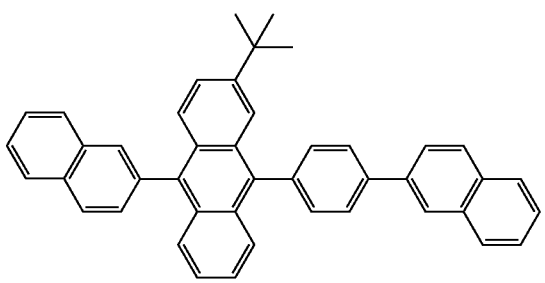
[Chemical Formula125]
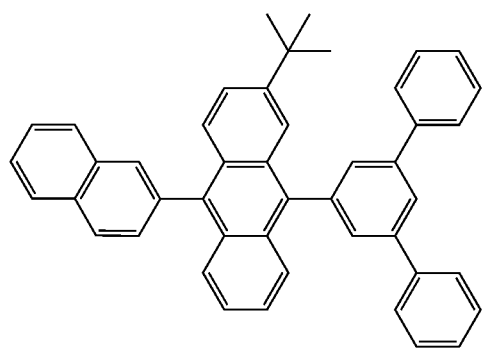
[Chemical Formula126]
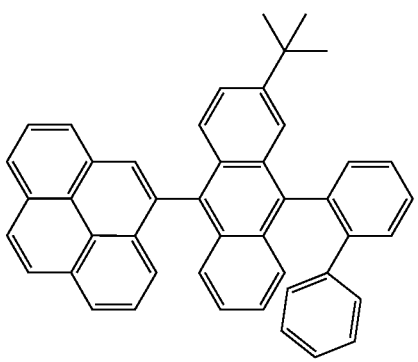
[Chemical Formula127]
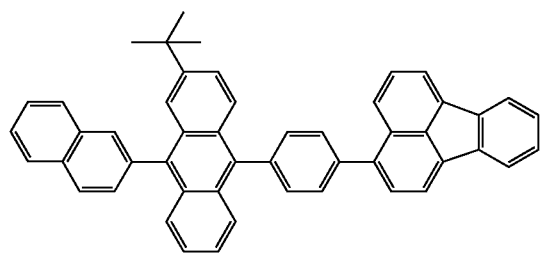
[Chemical Formula128]
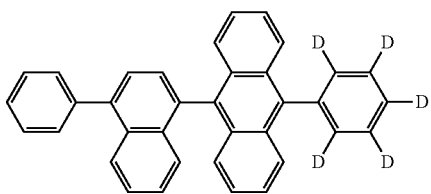

[Chemical Formula129]
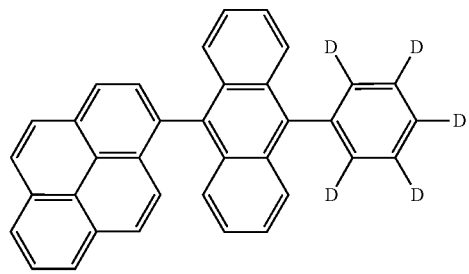
[Chemical Formula130]
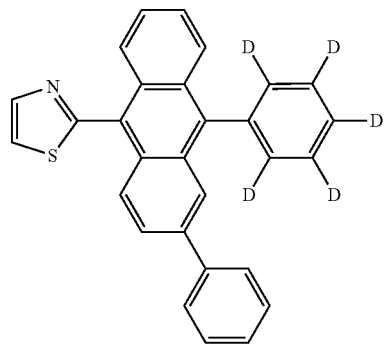
[Chemical Formula131]
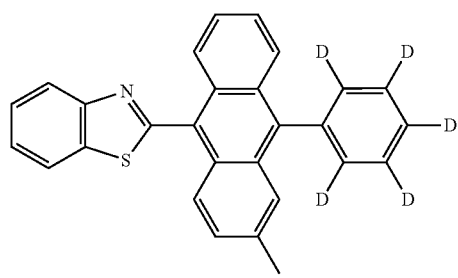
[Chemical Formula132]
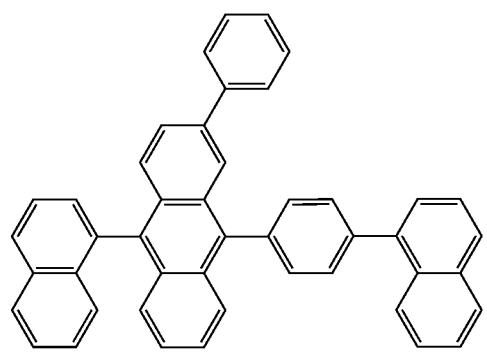
[Chemical Formula133]
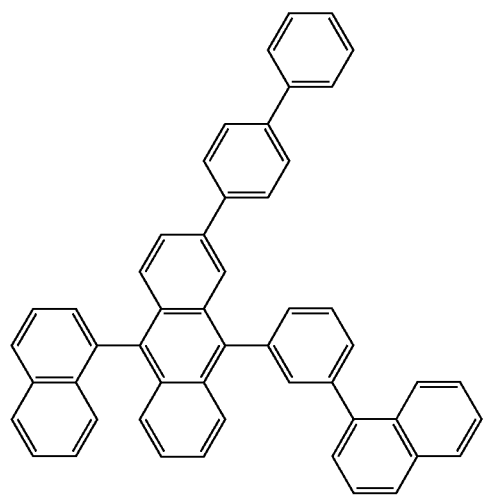
[Chemical Formula134]
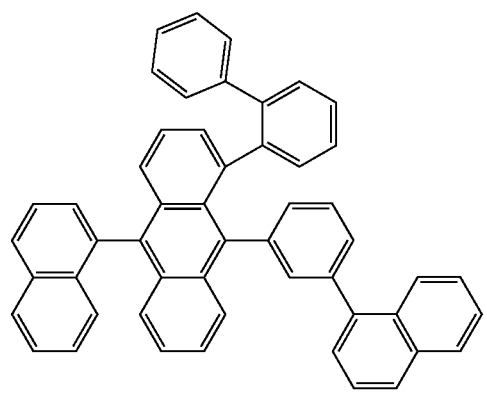

[Chemical Formula135] [Chemical Formula136]

[Chemical Formula137] [Chemical Formula138]

[Chemical Formula139] [Chemical Formula140]

-continued
[Chemical Formula141]
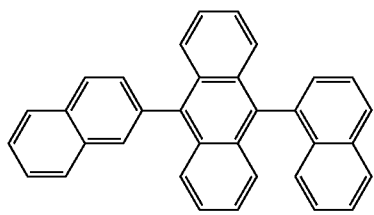
[Chemical Formula142]
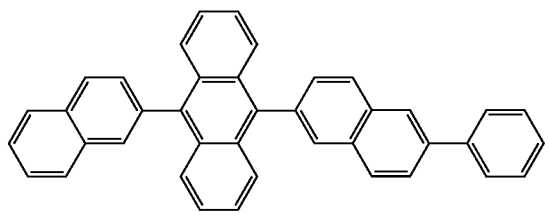
[Chemical Formula143]
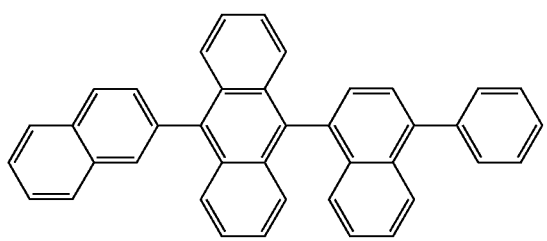
[Chemical Formula144]
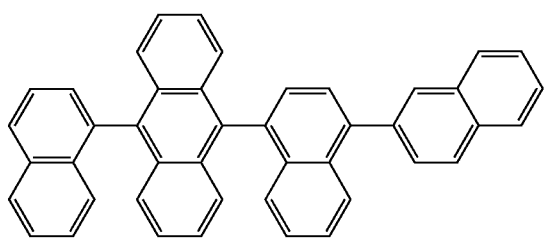
[Chemical Formula145]
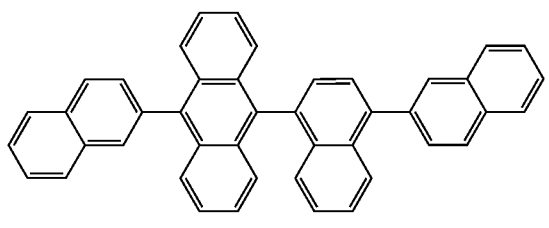
[Chemical Formula146]
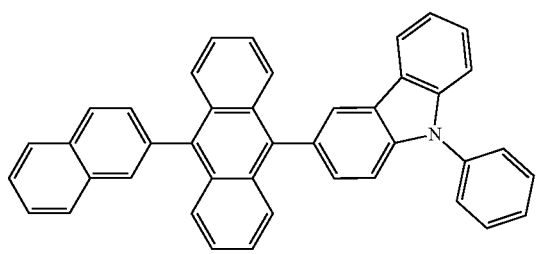
[Chemical Formula147]
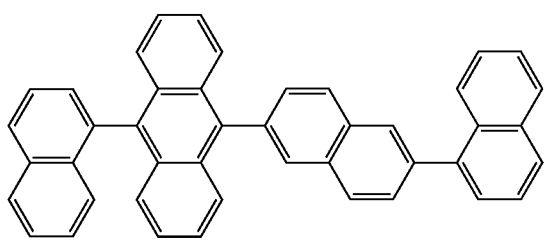
[Chemical Formula148]
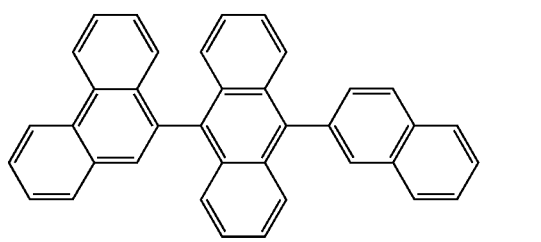
[Chemical Formula149]
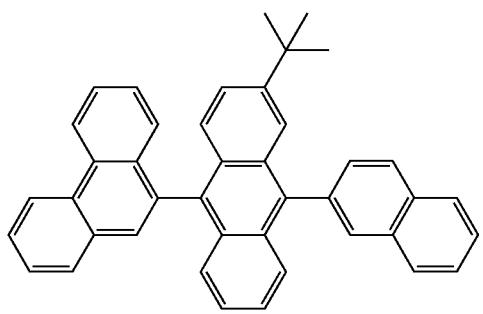
[Chemical Formula150]
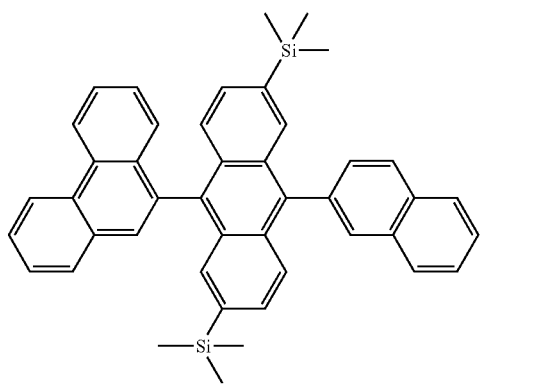

-continued
[Chemical Formula151]
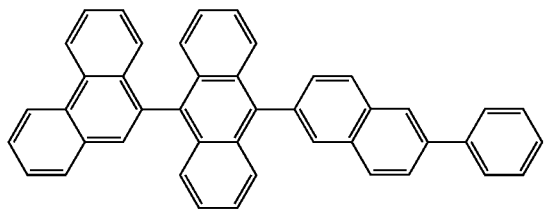
[Chemical Formula152]
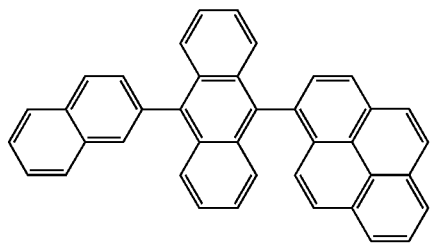
[Chemical Formula153]
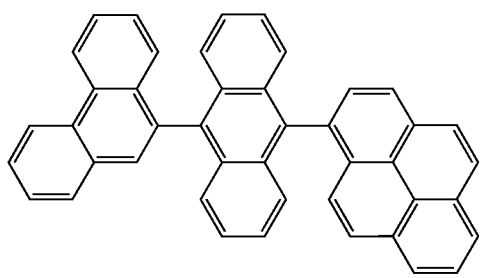
[Chemical Formula154]
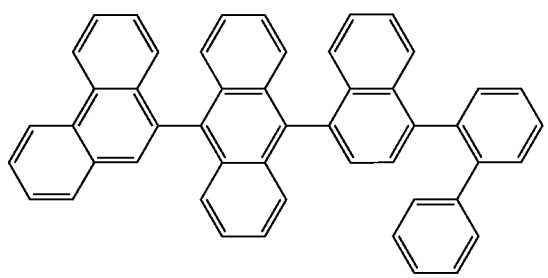
[Chemical Formula155]
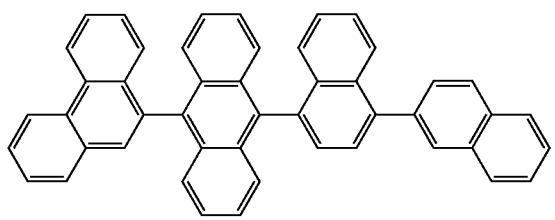
[Chemical Formula156]
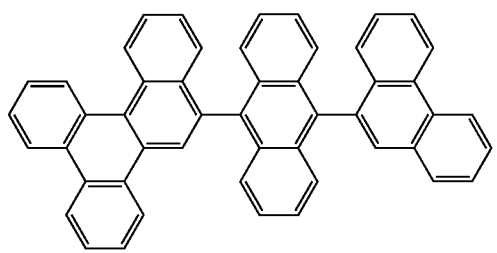
[Chemical Formula157]
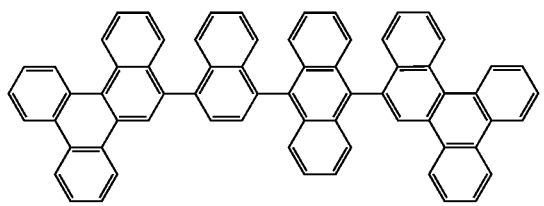
[Chemical Formula158]
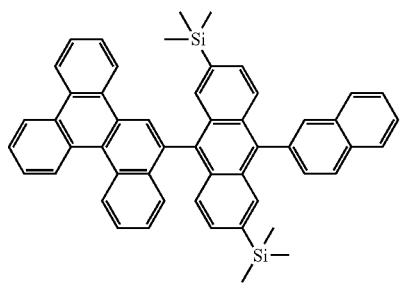
[Chemical Formula159]
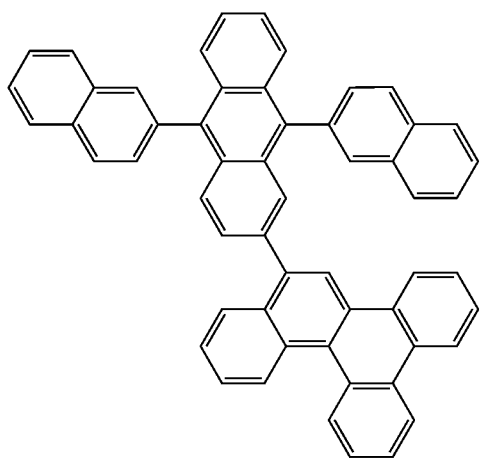
[Chemical Formula160]
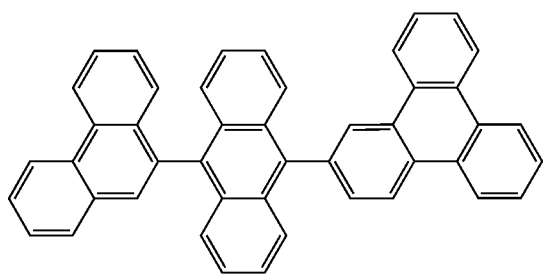

-continued
[Chemical Formula161]
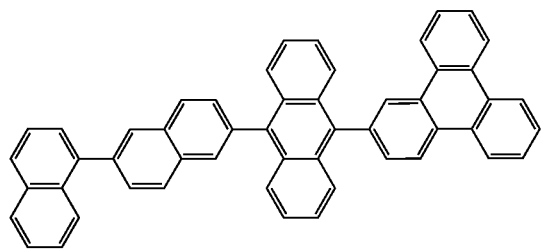
[Chemical Formula162]
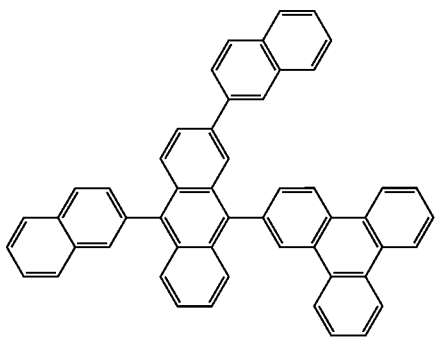
[Chemical Formula163]
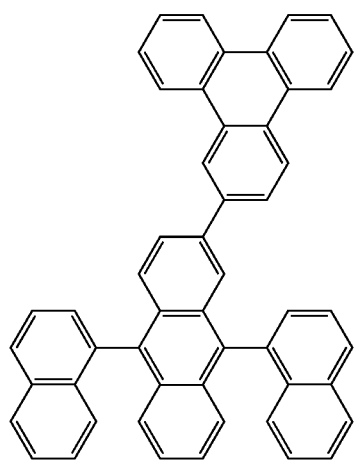
[Chemical Formula164]
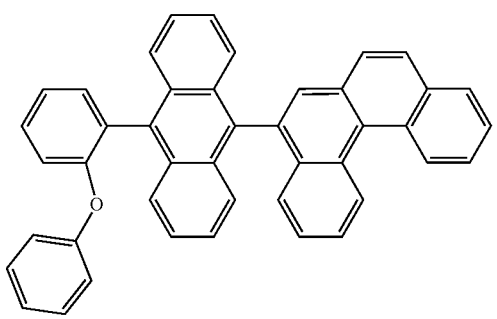
[Chemical Formula165]
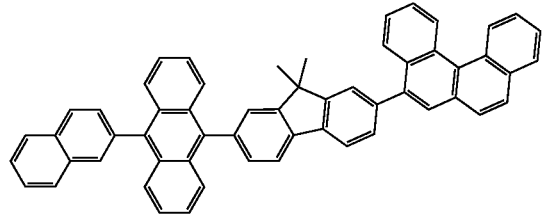
[Chemical Formula166]
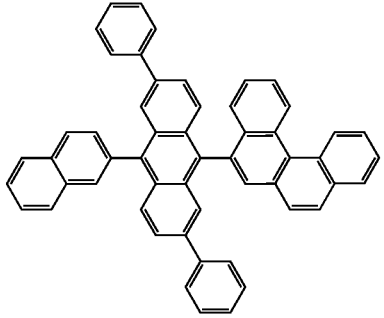
[Chemical Formula167]
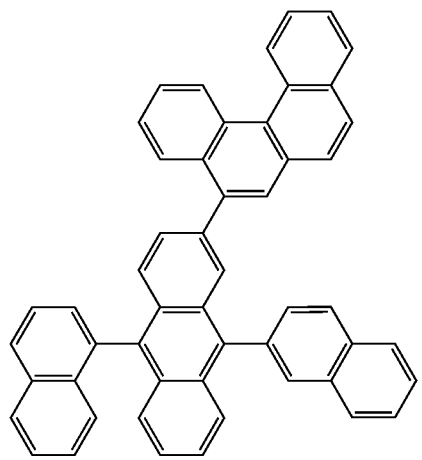
[Chemical Formula168]
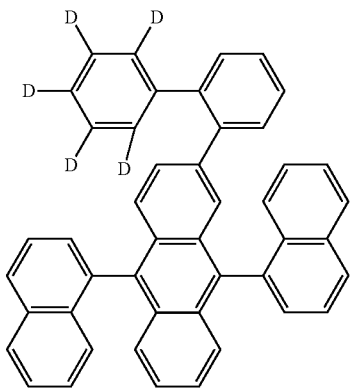

-continued
[Chemical Formula169]
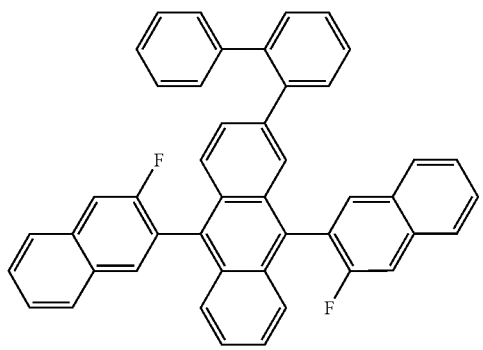
[Chemical Formula170]
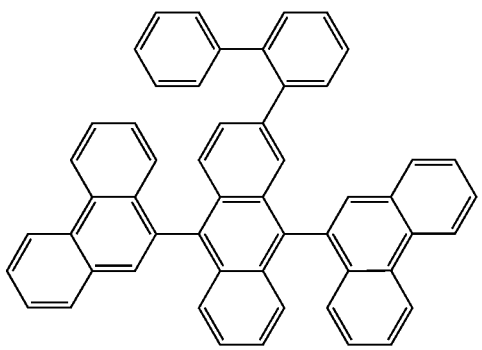
[Chemical Formula171]
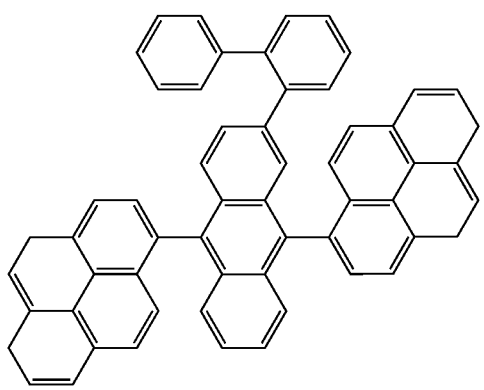
[Chemical Formula172]
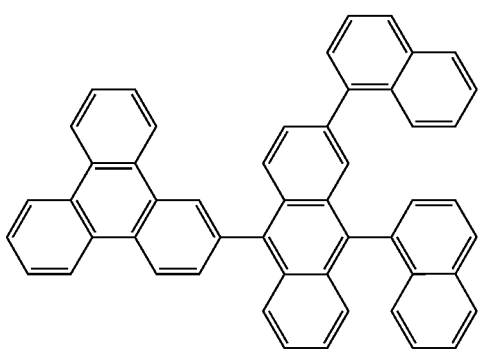
[Chemical Formula173]
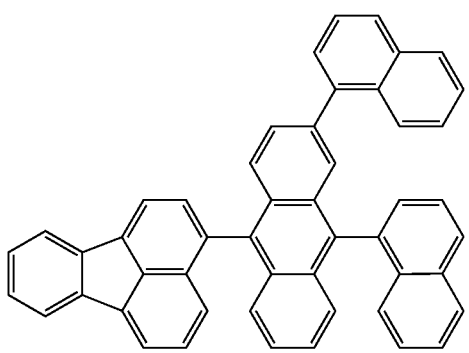
[Chemical Formula174]
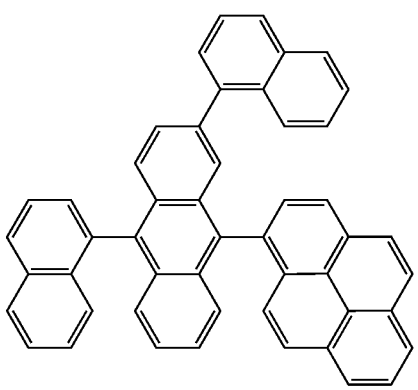
[Chemical Formula175]
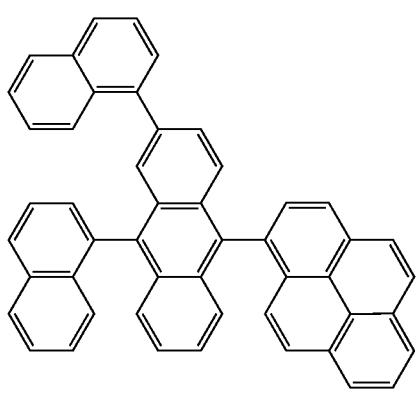
[Chemical Formula176]
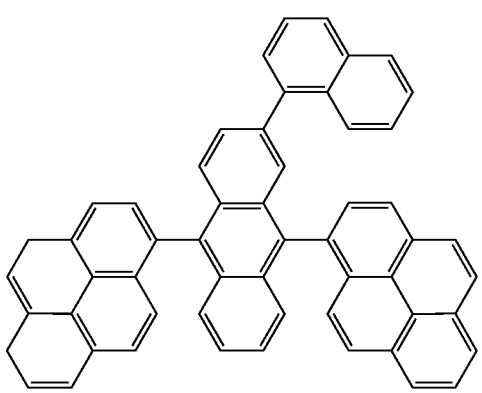

[Chemical Formula177]
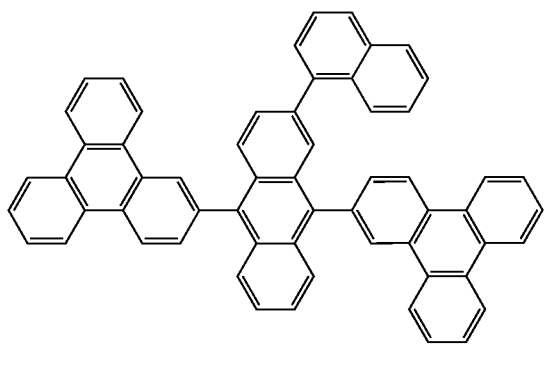
[Chemical Formula178]
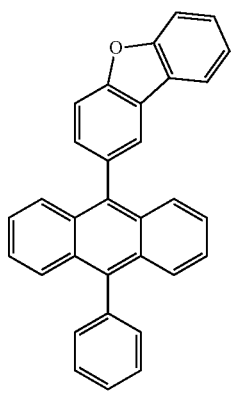
[Chemical Formula179]
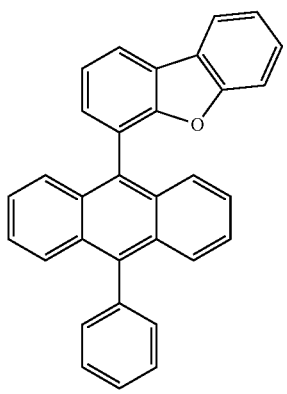
[Chemical Formula180]
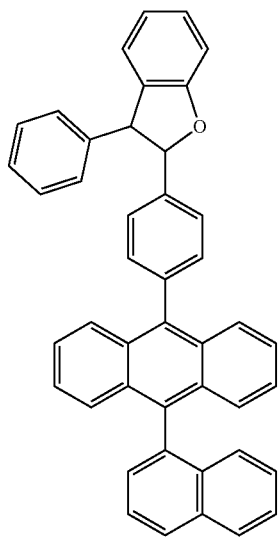
[Chemical Formula181]
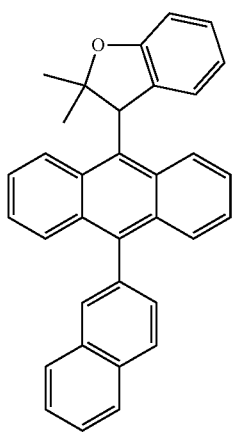
[Chemical Formula182]
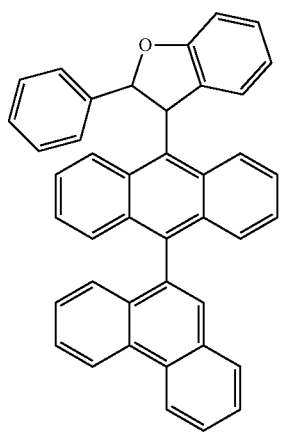

-continued
[Chemical Formula183]
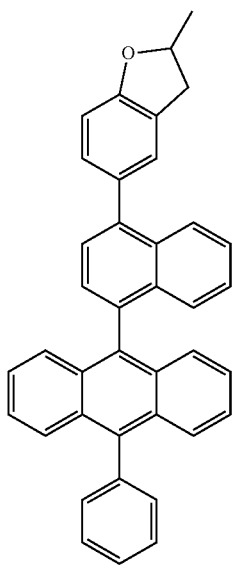
[Chemical Formula184]
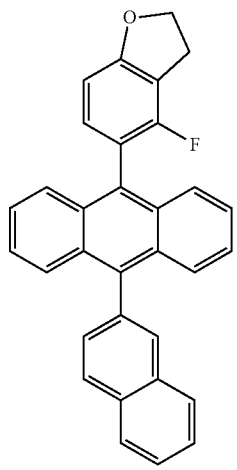
[Chemical Formula185]
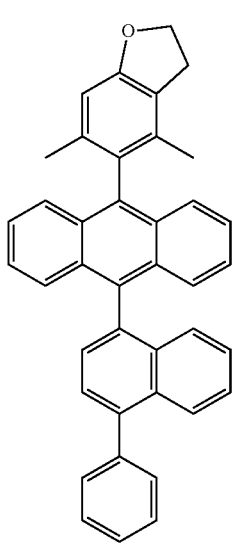
[Chemical Formula186]
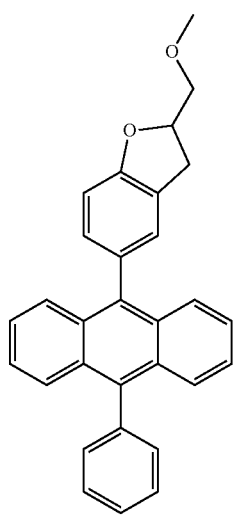
[Chemical Formula187]
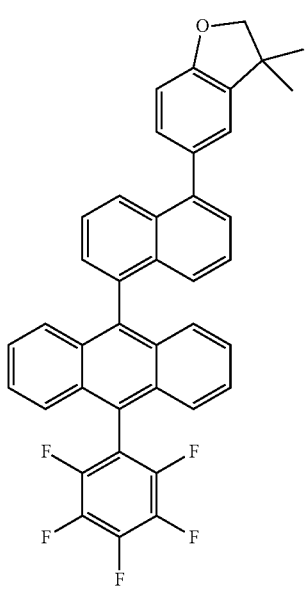
[Chemical Formula188]
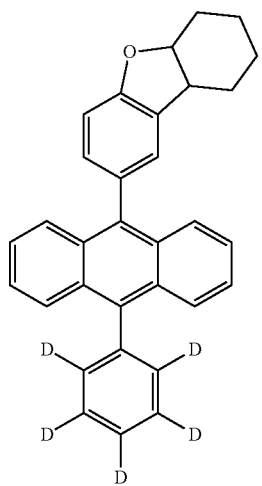

[Chemical Formula189]
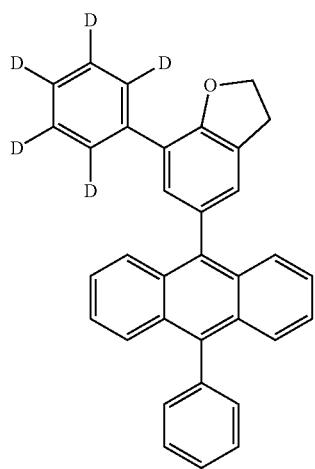
[Chemical Formula190]
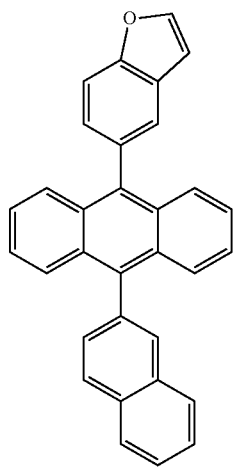
[Chemical Formula191]
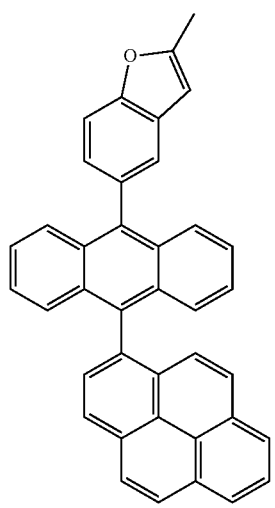
[Chemical Formula192]
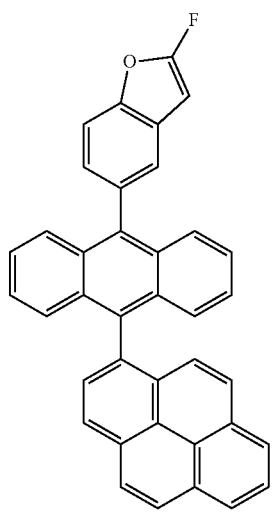
[Chemical Formula193]
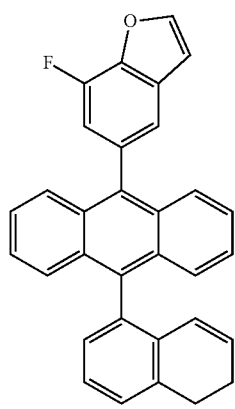
[Chemical Formula194]
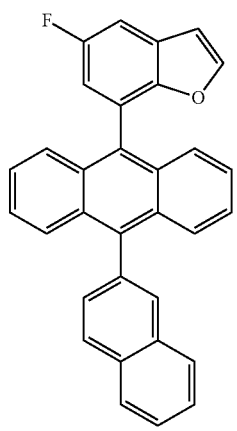

[Chemical Formula195]
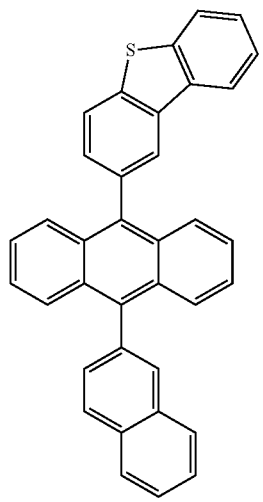
[Chemical Formula196]
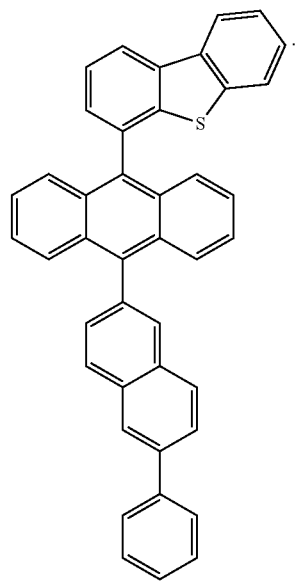
In addition, the light emitting layer of the present disclosure may contain as a dopant compound at least one of the compounds represented by the following Chemical Formula D1 to Chemical Formula D7:
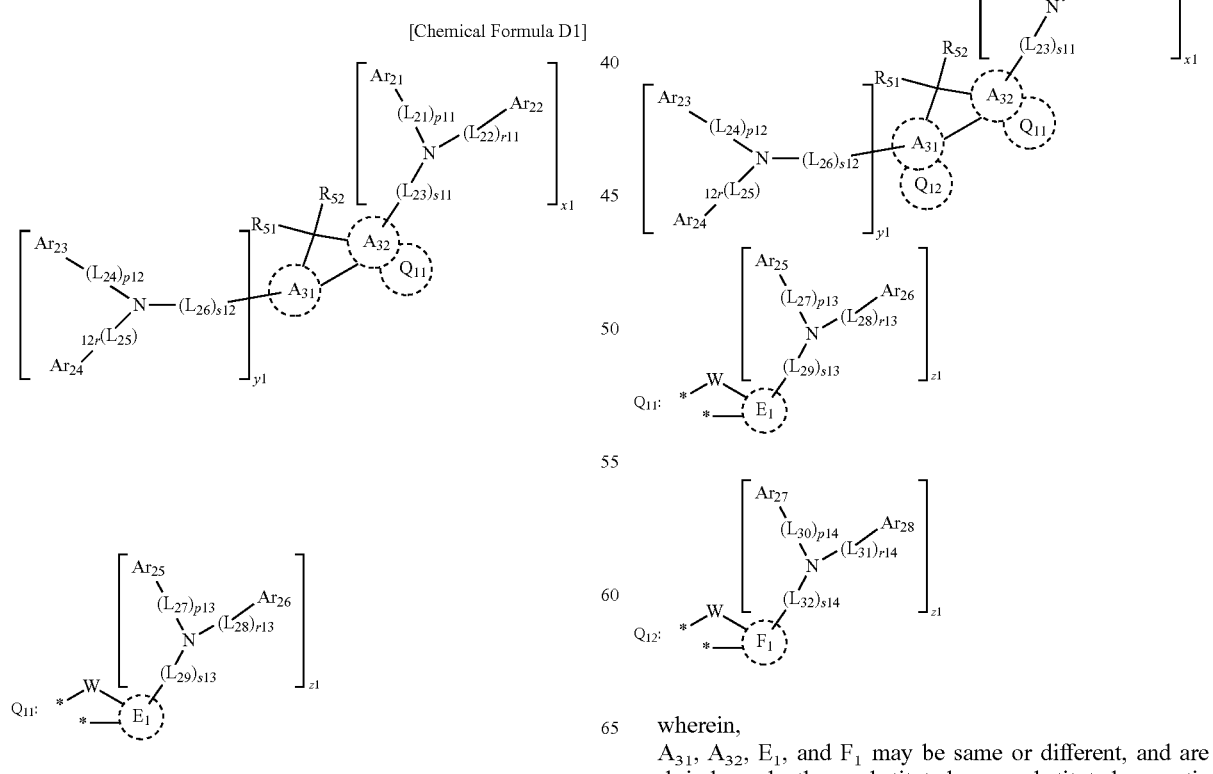
wherein,
$A_{31}$, $A_{32}$, $E_1$, and $F_1$ may be same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_{31}$ and two adjacent carbon atoms of the aromatic ring $A_{32}$ form a 5-membered fused ring together with a carbon atom to which substituents $R_{51}$ and $R_{52}$ are bonded;

linkers $L_{21}$ to $L_{32}$ may be same or different, and are each independently selected from among a singlet bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms W is any one selected from among N—$R_{53}$, $CR_{54}R_{55}$, $SiR_{56}R_{57}$, $GeR_{58}R_{59}$, O, S, and Se;

$R_{51}$ to $R_{59}$, and $Ar_{21}$ to $Ar_{28}$ may be the same or different and are each independently a hydrogen atom, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, wherein that $R_{51}$ and $R_{52}$ together may form a mono- or polycyclic aliphatic or aromatic ring that may be a heterocyclic ring bearing a heteroatom selected from among N, O, P, Si, S, Ge, Se, and Te as a ring member;

p11 to p14, r11 to r14, and s11 to s14 are each independently an integer of 1 to 3, wherein when any of them is 2 or greater, the corresponding $L_{21}$ to $L_{32}$ may be same or different, x1 is an integer of 1 or 2, and y1 and z1 may be same or different and are each independently an integer of 0 to 3; and $Ar_{22}$ may form a ring with $Ar_{22}$, $Ar_{23}$ may form a ring with $Ar_{24}$, $Ar_{25}$ may form a ring with $Ar_{26}$, and $Ar_{27}$ may form a ring with $Ar_{28}$, two adjacent carbon atoms of the $A_{32}$ ring moiety of Chemical Formula D1 may occupy respective positions * of Structural Formula $Q_{11}$ to form a fused ring, two adjacent carbon atoms of the $A_{31}$ ring moiety of Chemical Formula D2 may occupy respective positions * of structural Formula $Q_{12}$ to form a fused ring, and two adjacent carbon atoms of the $A_{32}$ ring moiety may occupy respective positions * of Structural Formula $Q_{11}$ to form a fuse ring;

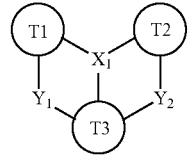

[Chemical Formula D3]

wherein, $X_1$ is any one selected from among B, P, and P=O,

T1 to T3 may be the same or different and are each independently a substituted or unsubstituted aromatic hydrocarbon ring of 6 to 50 carbon atoms, or a substituted or unsubstituted heteroaromatic ring of 2 to 40 carbon atoms;

$Y_1$ is any one selected from among N—R61, CR62R63, O, S, and SiR64R65; and $Y_2$ is any one selected from among N—R66, CR67R68, O, S, and SiR69R70;

wherein R61 to R70 may be the same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen, and R61 to R70 may each be connected to at least one ring of T1 to T3 to further form a mono- or polycyclic aliphatic or aromatic ring;

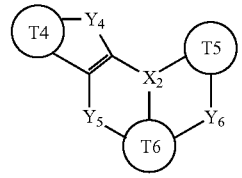

[Chemical Formula D4]

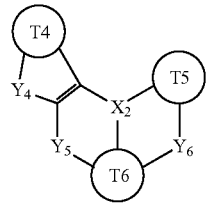

[Chemical Formula D5]

wherein, $X_2$ is any one selected from among B, P, and P=O;

$T_4$ to $T_6$ are as defined for $T_1$ to $T_3$ in [Chemical Formula D3]; and $Y_4$ to $Y_6$ are as defined for $Y_1$ to $Y_2$ in [Chemical Formula D3];

[Chemical Formula D6]

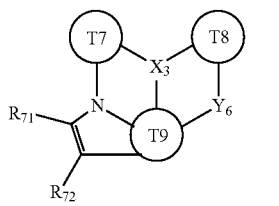

[Chemical Formula D7]

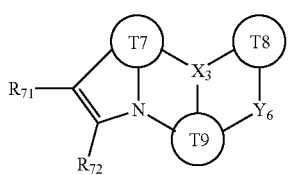

wherein,

X$_3$ is any one selected from among B, P, and P=O,

T$_7$ to T$_9$ are as defined for T$_1$ to T$_3$ in [Chemical Formula D3];

Y$_6$ is as defined for Y$_1$ to Y$_2$ in [Chemical Formula D3]; and

R$_{71}$ to R$_{72}$ may be the same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen, wherein R$_{71}$ and R$_{72}$ may be bonded to each other to further form a mono- or polycyclic aliphatic or aromatic ring or may be connected to the Q1 ring or Q3 ring to further form a mono- or polycyclic aliphatic or aromatic ring, wherein, the term "substituted" in the expression "substituted or unsubstituted" used for [Chemical Formula D1] to [Chemical Formula D7] means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

In the boron compounds represented by [Chemical Formula D3] to [Chemical Formula D7] according to the present disclosure, the aromatic hydrocarbon rings or the heteroaromatic rings of T1 to T9 may have a deuterium atom, an alkyl of 1 to 24 carbon atoms, an aryl of 6 to 24 carbon atoms, an alkylamino of 1 to 24 carbon atoms, or an arylamino of 6 to 24 carbon atoms as a substituent thereon, wherein the aryl group or aryl group in the alkylamino of 1 to 24 carbon atoms and the arylamino of 6 to 24 carbon atoms may be connected to each other, and preferably may have an alkyl of 1 to 12 carbon atoms, an aryl of 6 to 18 carbon atoms, an alkylamino of 1 to 12 carbon atoms, or an arylamino of 6 to 18 carbon atoms as a substituent thereon, wherein the alkyl group or aryl group in the alkylamino of 1 to 12 carbon atoms and the arylamino of 6 to 18 carbon atoms may be connected to each other.

In addition, concrete examples of the dopant compounds represented by [Chemical Formula D1] to [Chemical Formula D2] include compounds represented by Chemical Formula d1 to Chemical Formula d239:

<Chemical Formula d1>

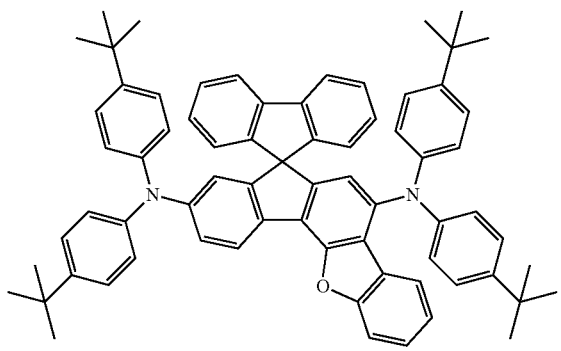

<Chemical Formula d2>

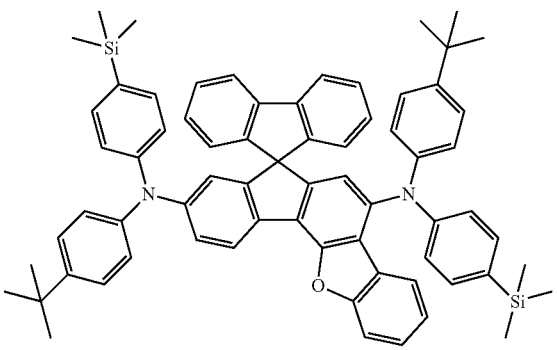

-continued
<Chemical Formula d3>
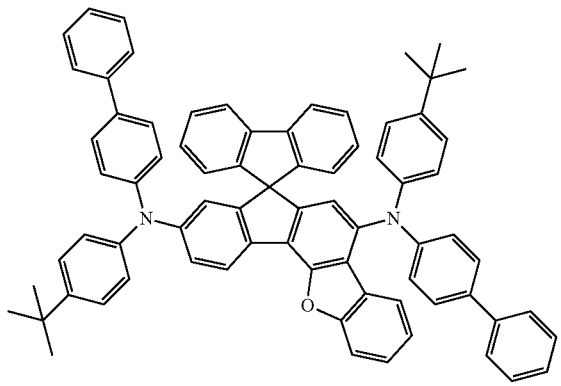
<Chemical Formula d4>
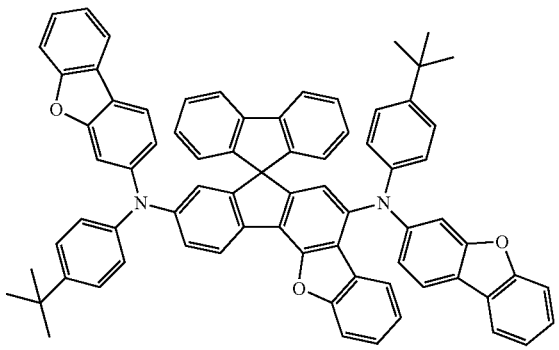
<Chemical Formula d5>
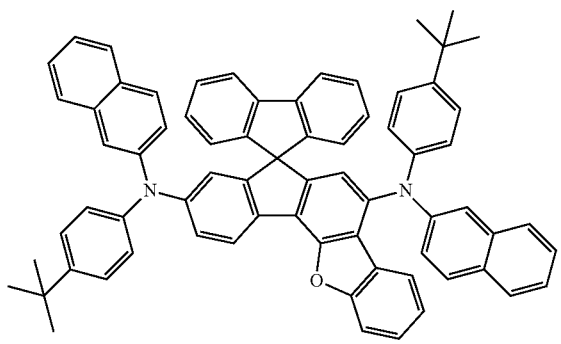
<Chemical Formula d6>
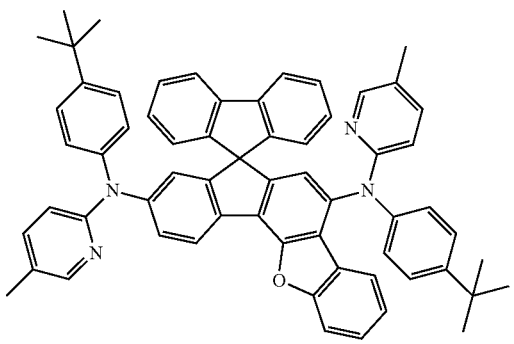
<Chemical Formula d7>
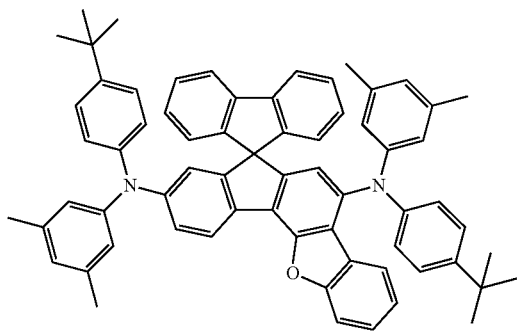
<Chemical Formula d8>
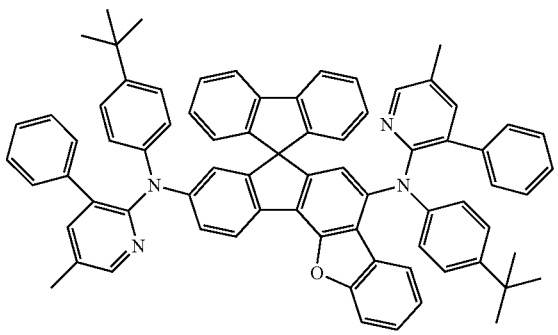
<Chemical Formula d9>
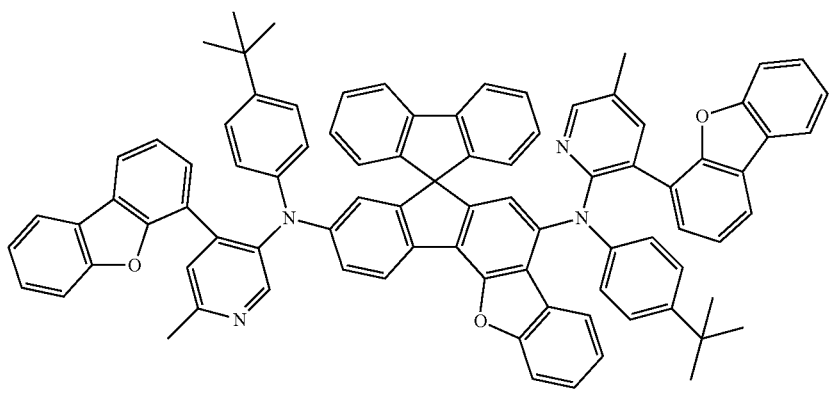

<Chemical Formula d10>
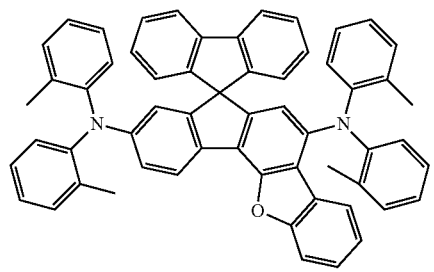
<Chemical Formula d11>
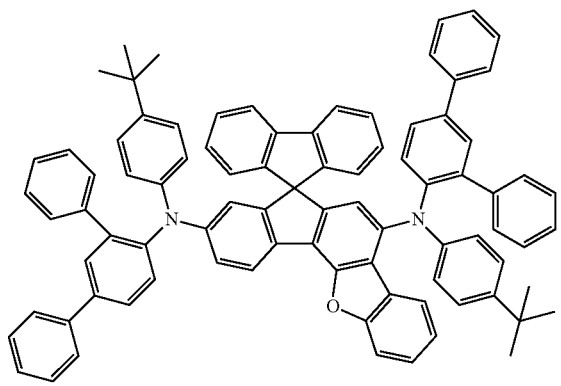
<Chemical Formula d12>
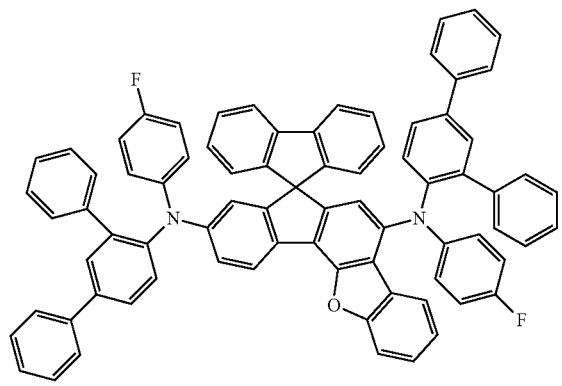
<Chemical Formula d13>
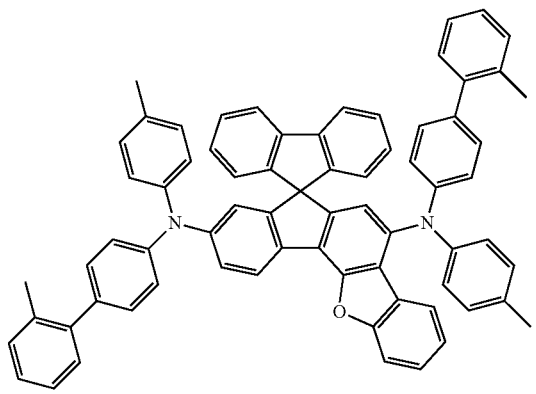
<Chemical Formula d14>
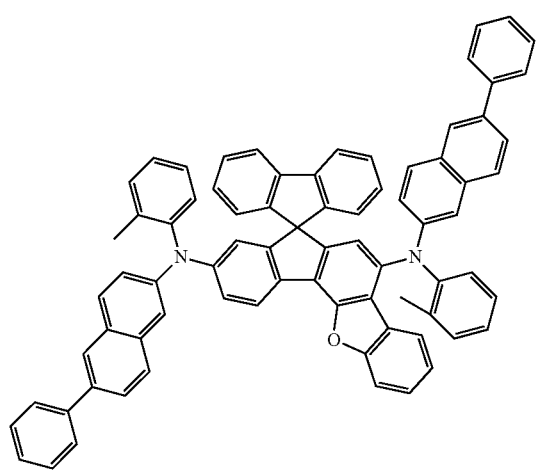
<Chemical Formula d15>
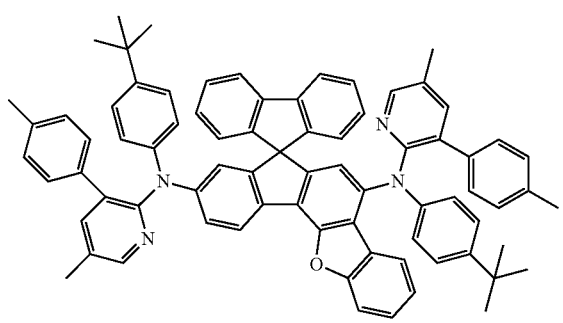

<Chemical Formula d16>
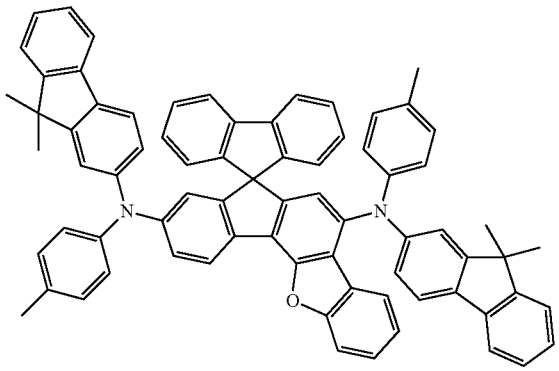
<Chemical Formula d17>
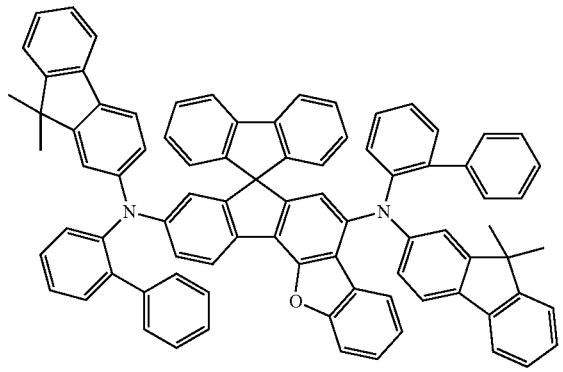
<Chemical Formula d18>
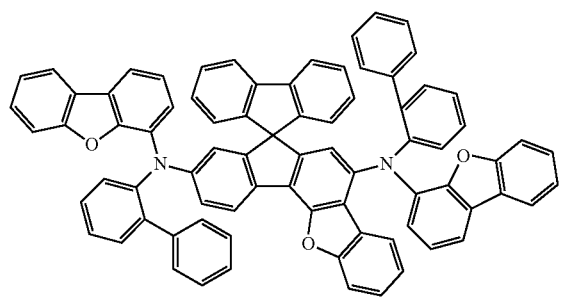
<Chemical Formula d19>
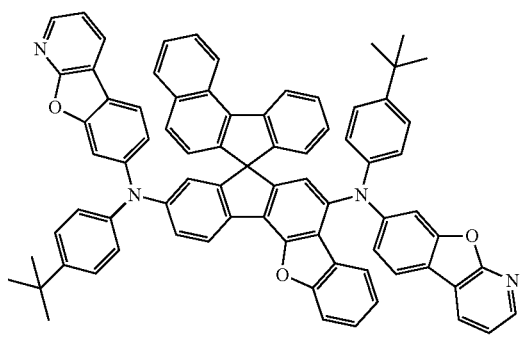
<Chemical Formula d20>
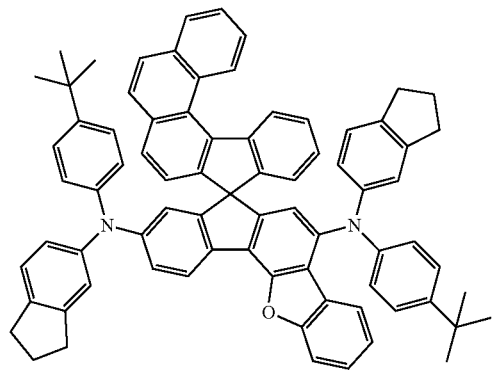
<Chemical Formula d21>
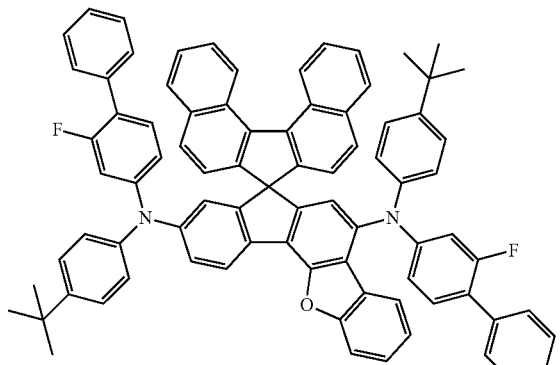
<Chemical Formula d22>
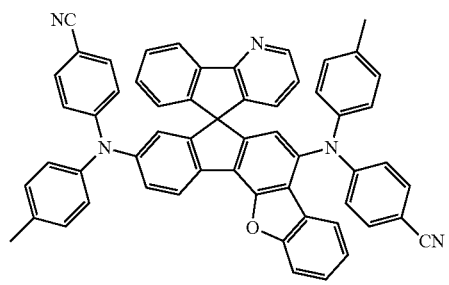
<Chemical Formula d23>
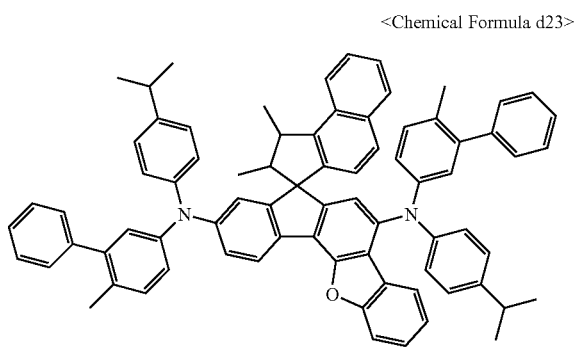

<Chemical Formula d24>
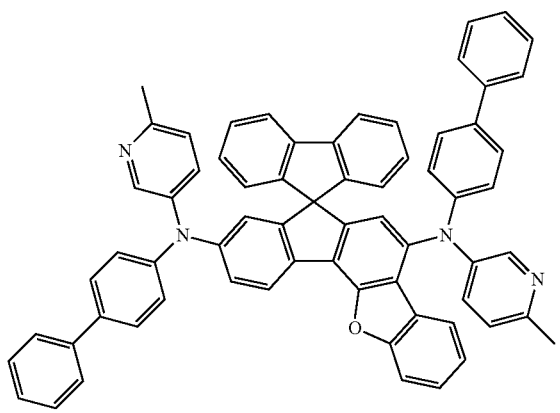
<Chemical Formula d25>
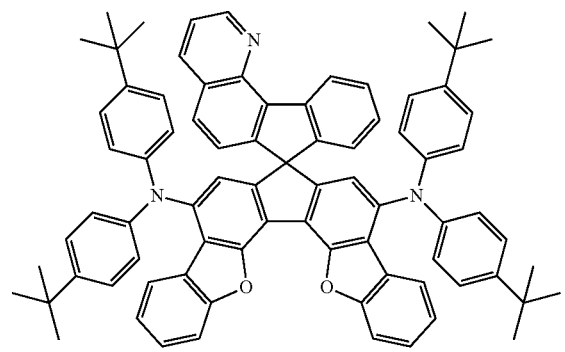
<Chemical Formula d26>
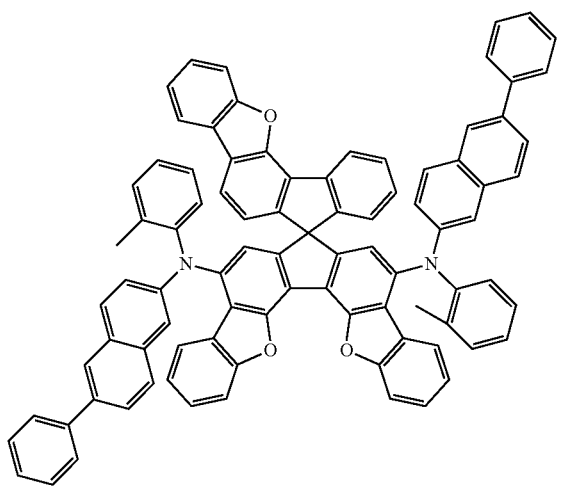
<Chemical Formula d27>
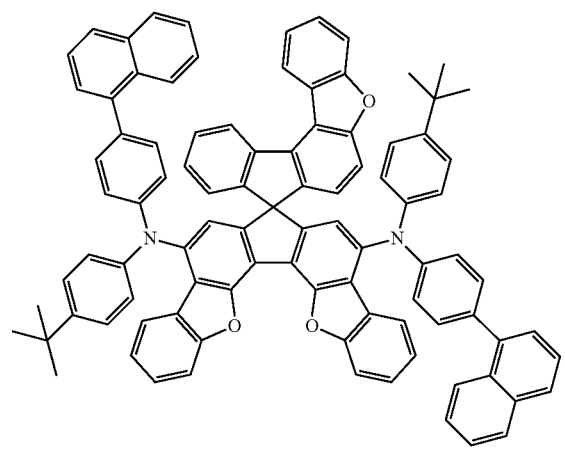
<Chemical Formula d28>
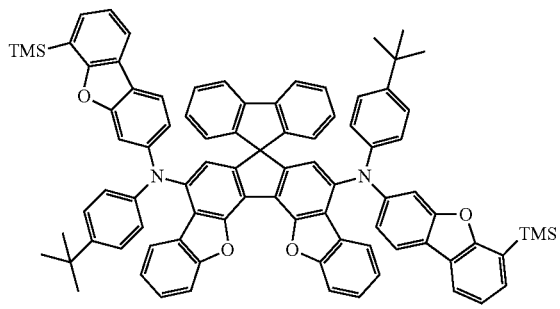
<Chemical Formula d29>
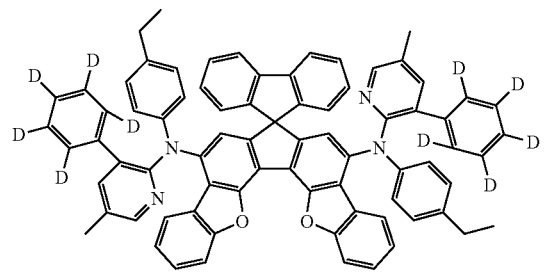

<Chemical Formula d30>
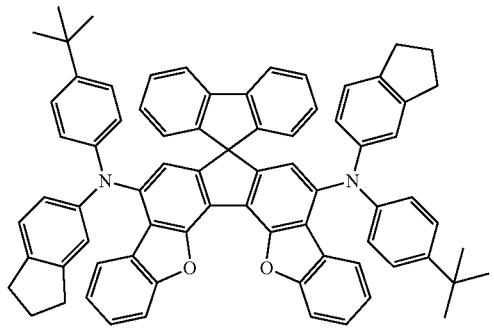
<Chemical Formula d31>
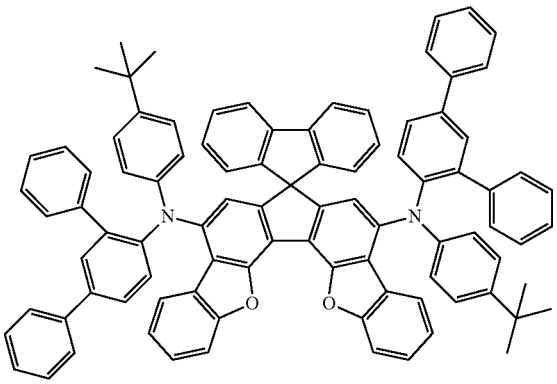
<Chemical Formula d32>
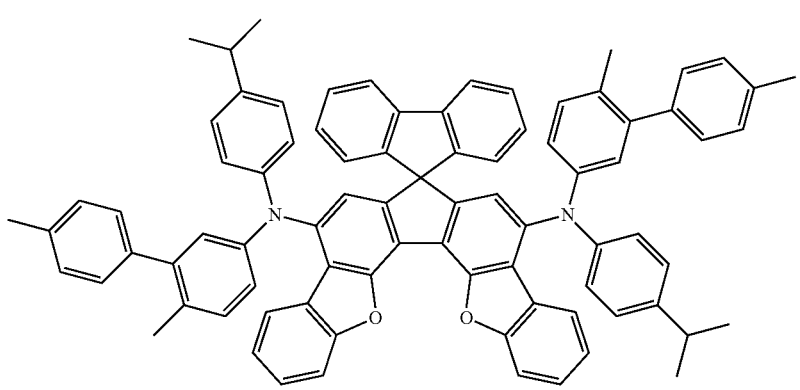
<Chemical Formula d33>
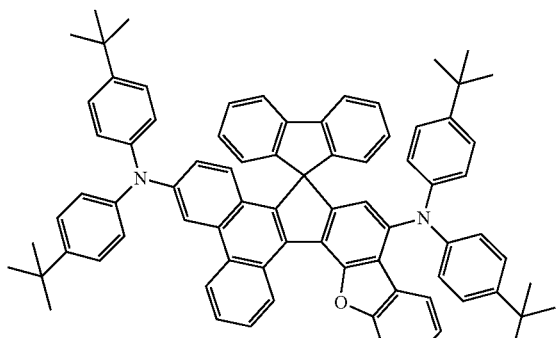
<Chemical Formula d34>
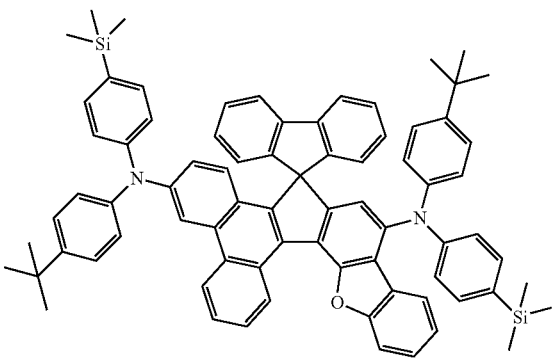
<Chemical Formula d35>
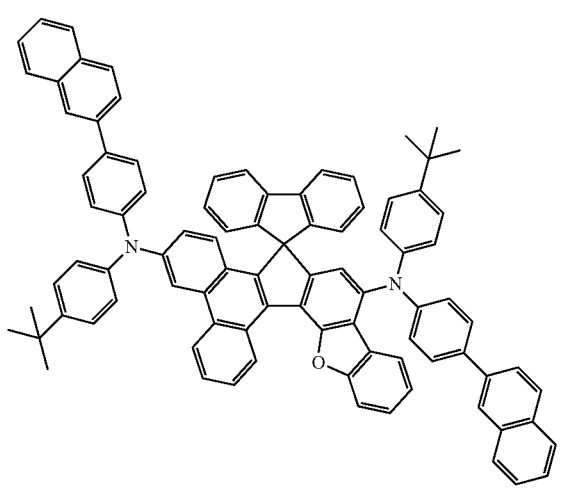
<Chemical Formula d36>
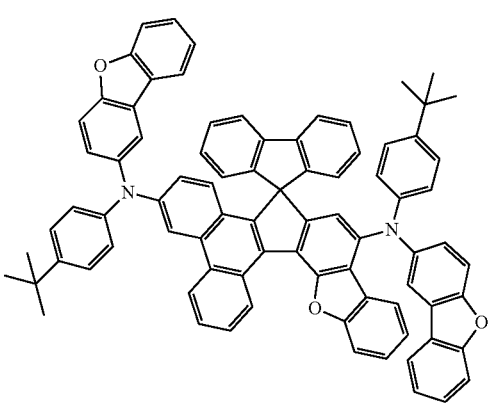

<Chemical Formula d37>
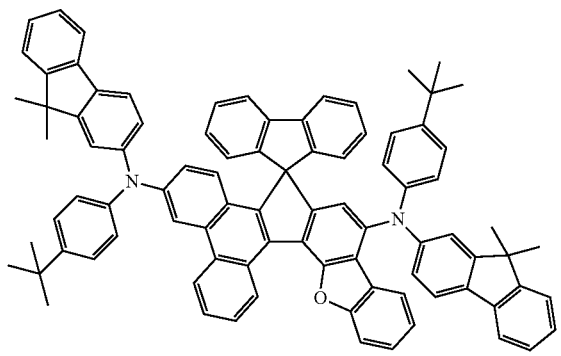
<Chemical Formula d38>
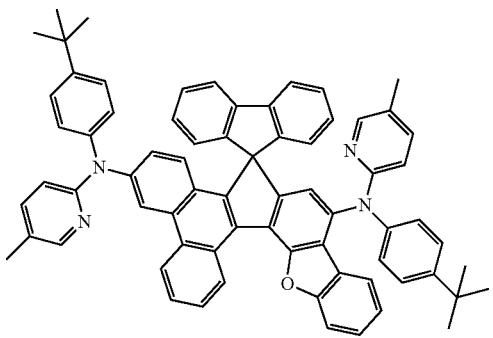
<Chemical Formula d39>
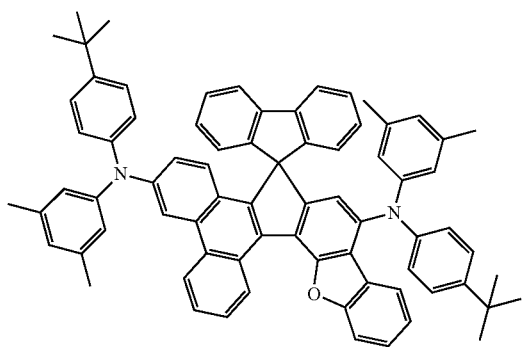
<Chemical Formula d40>
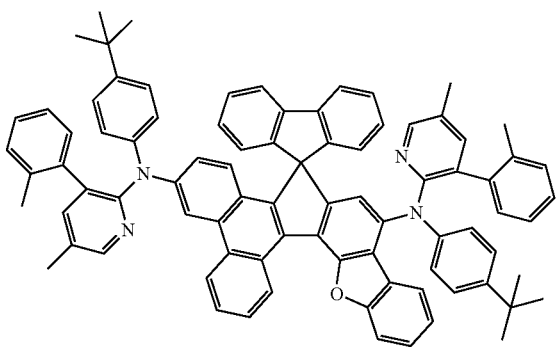
<Chemical Formula d41>
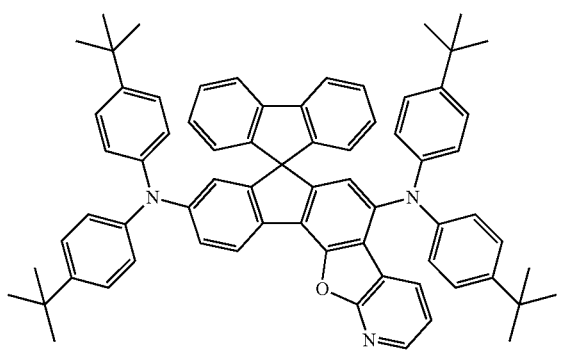
<Chemical Formula d42>
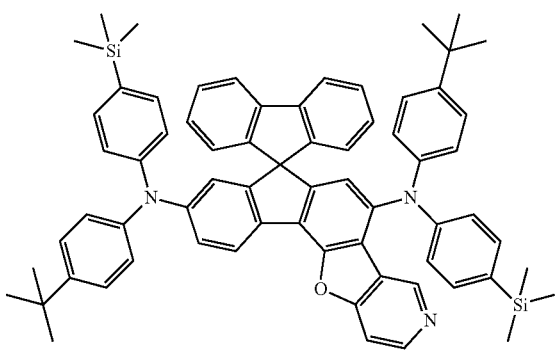
<Chemical Formula d43>
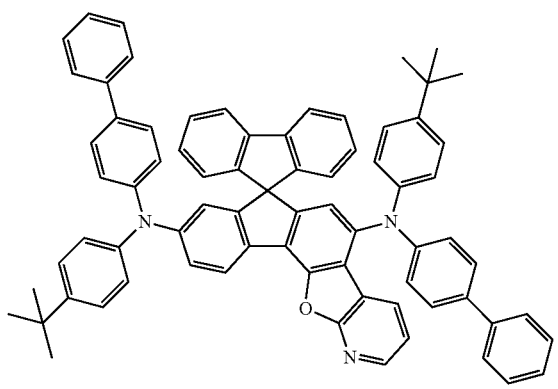
<Chemical Formula d44>
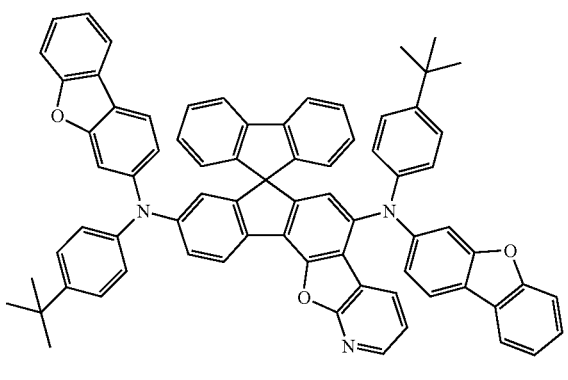

-continued
<Chemical Formula d45>
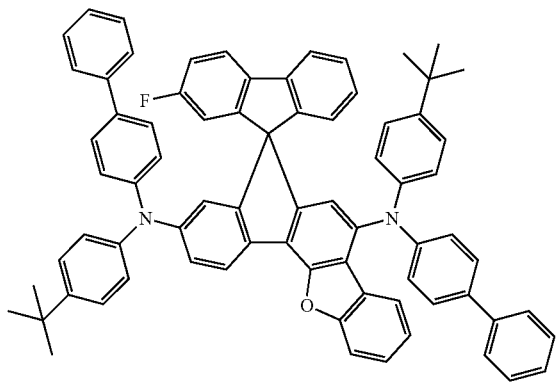
<Chemical Formula d46>
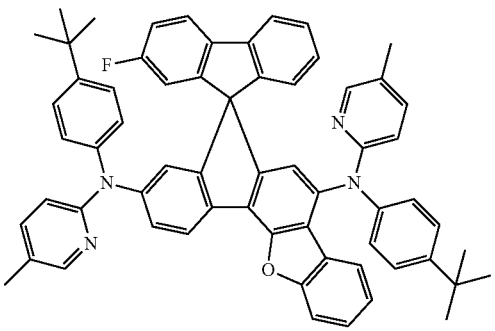
<Chemical Formula d47>
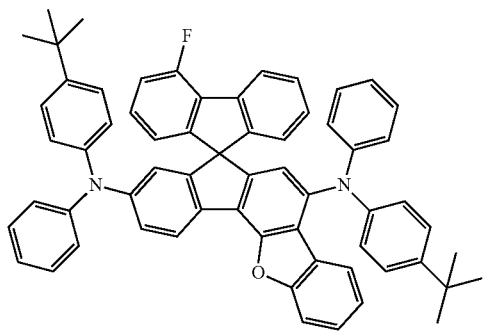
<Chemical Formula d48>
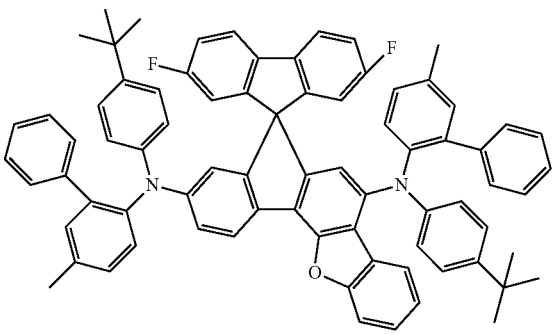
<Chemical Formula d49>
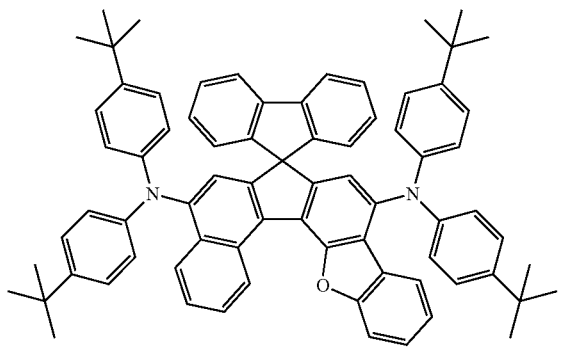
<Chemical Formula d50>
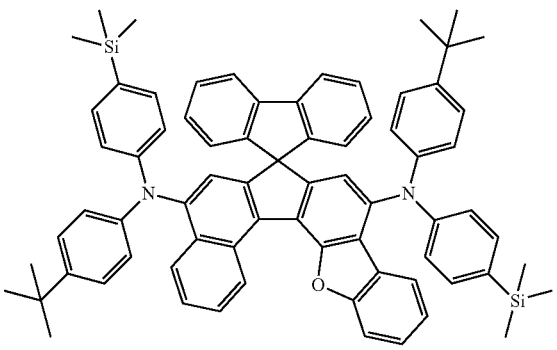
<Chemical Formula d51>
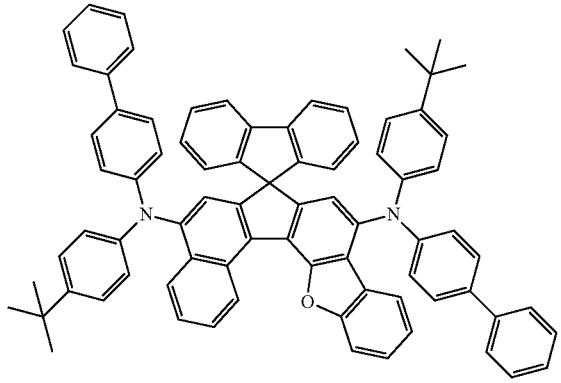
<Chemical Formula d52>
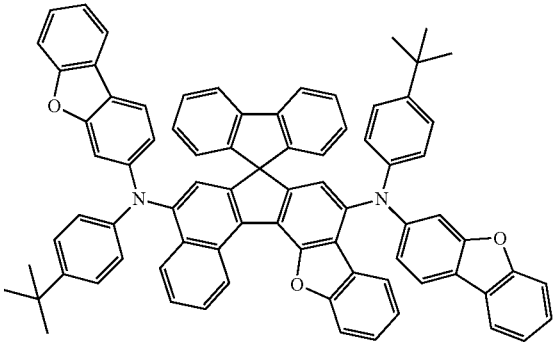

-continued
<Chemical Formula d53>
<Chemical Formula d54>
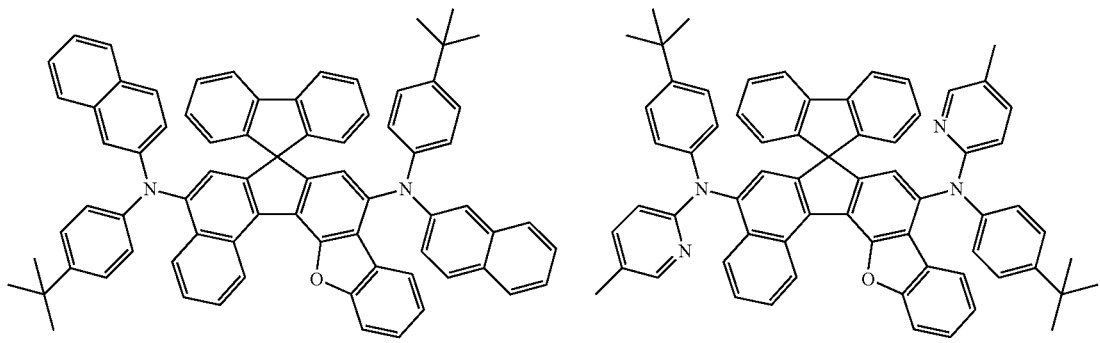
<Chemical Formula d55>
<Chemical Formula d56>
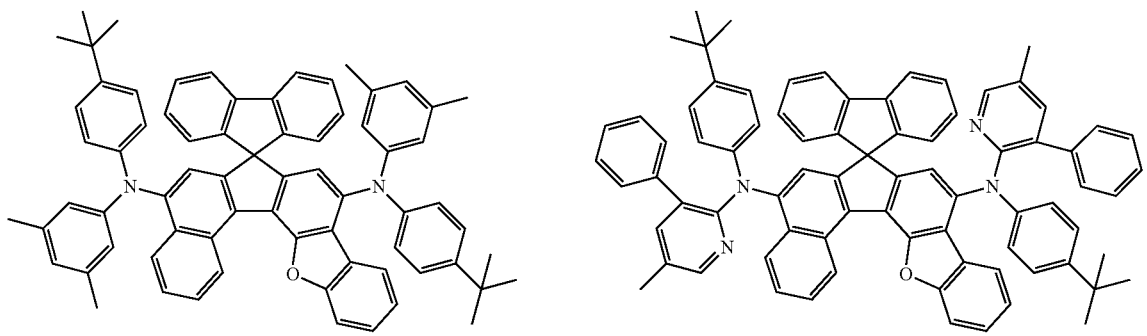
<Chemical Formula d57>
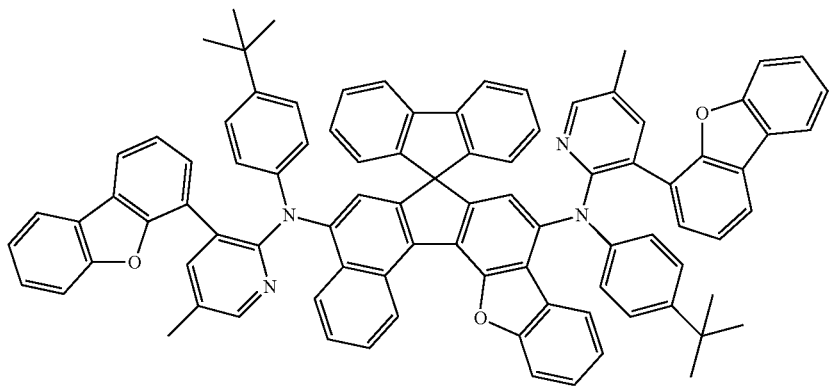
<Chemical Formula d58>
<Chemical Formula d59>
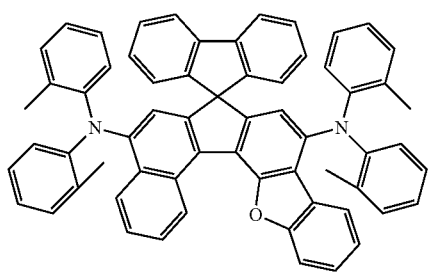
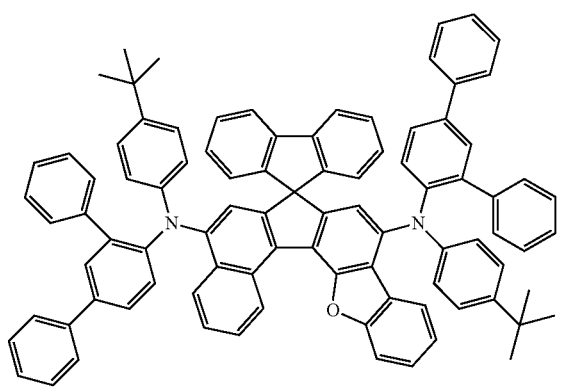

-continued
<Chemical Formula d60>
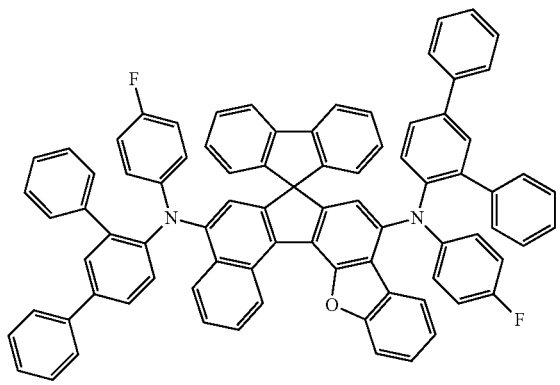
<Chemical Formula d61>
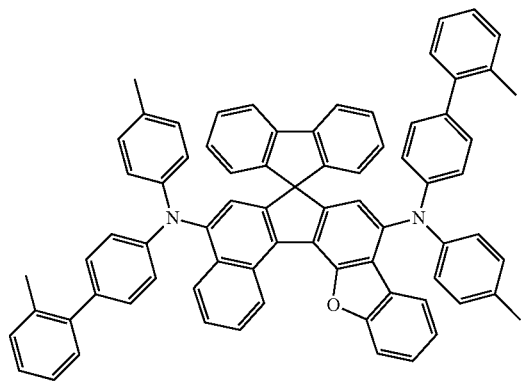
<Chemical Formula d62>
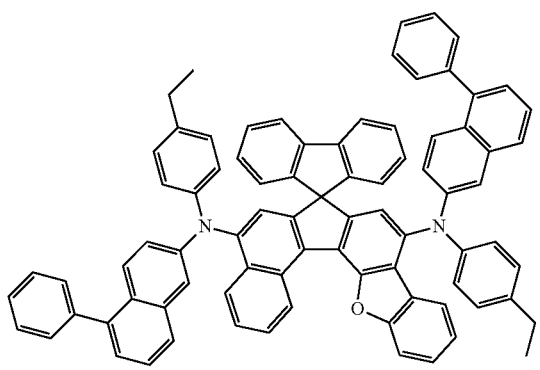
<Chemical Formula d63>
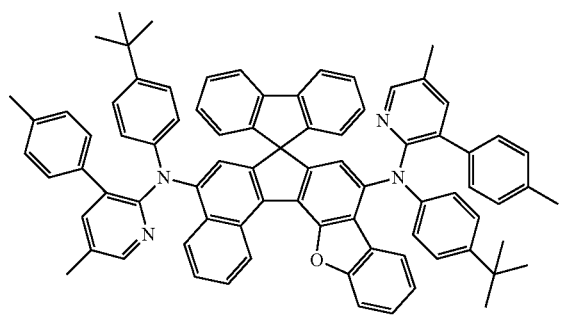
<Chemical Formula d64>
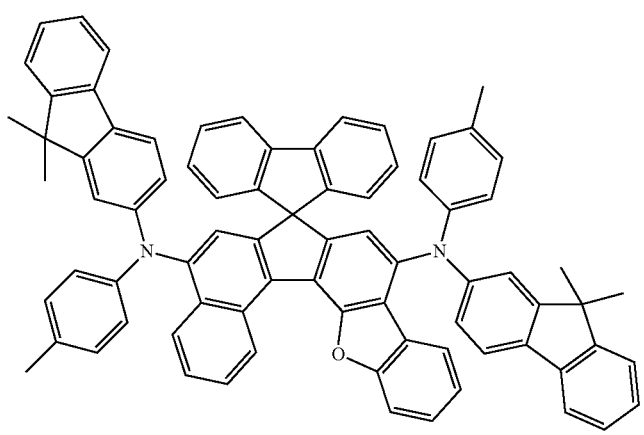

<Chemical Formula d65>
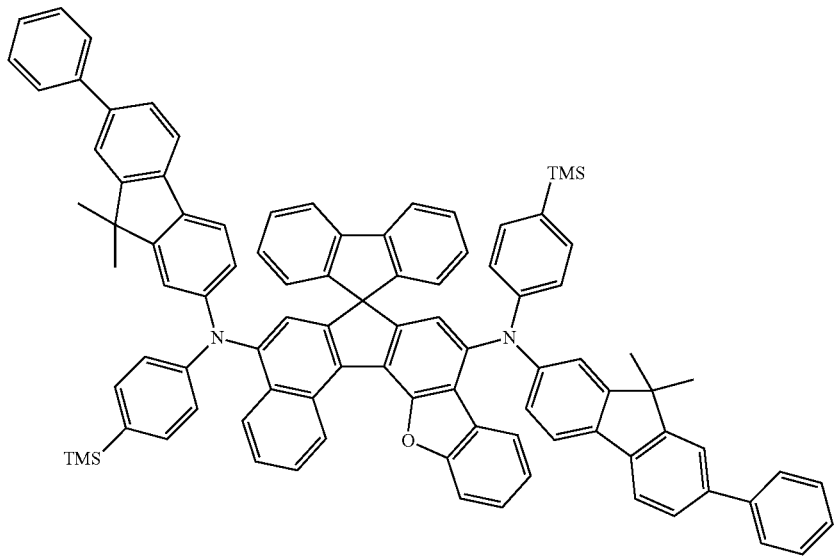
<Chemical Formula d66> <Chemical Formula d67>
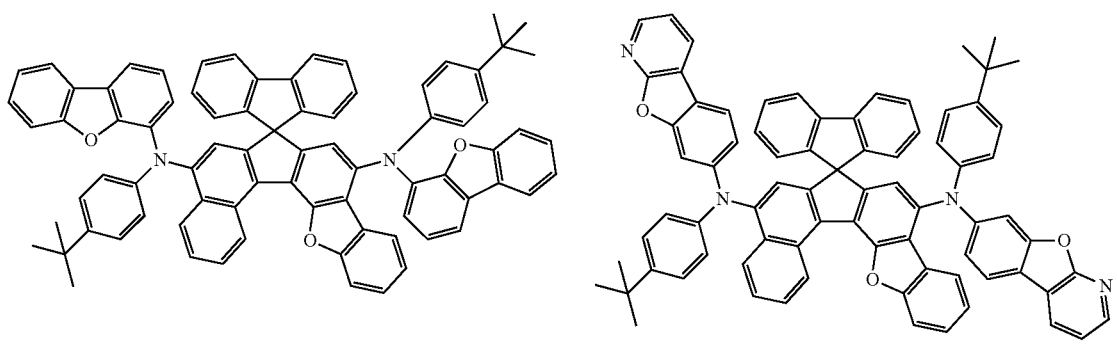
<Chemical Formula d68> <Chemical Formula d69>
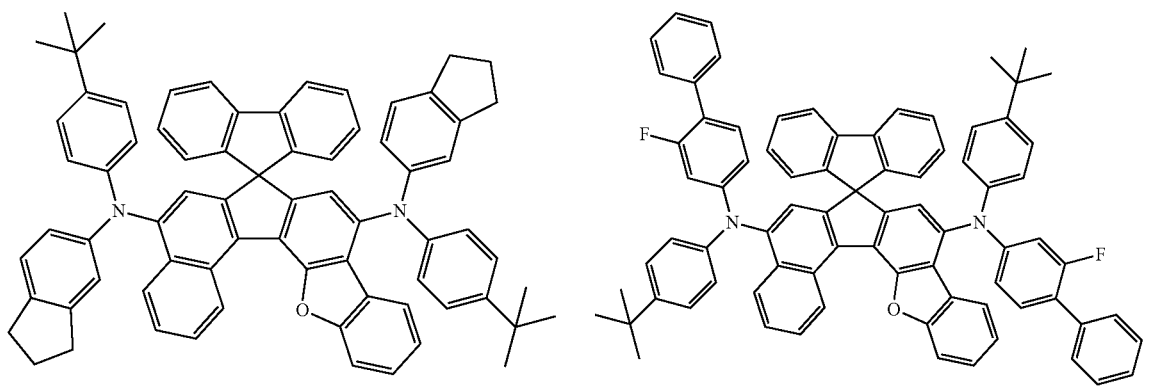
<Chemical Formula d70> <Chemical Formula d71>
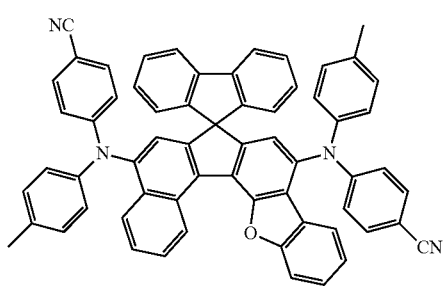 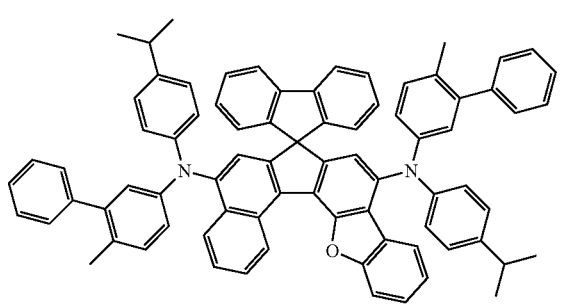

-continued
<Chemical Formula d72>
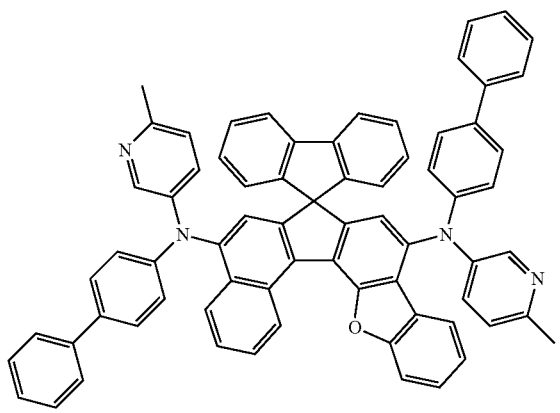
<Chemical Formula d73>
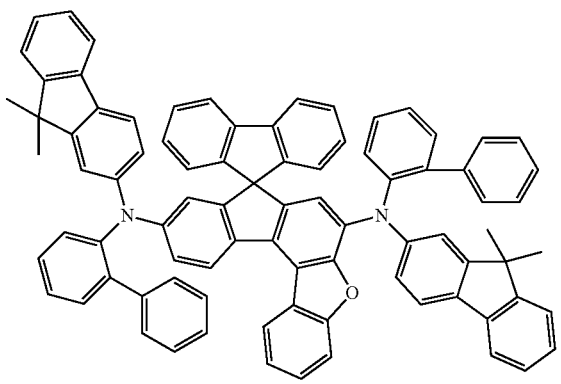
<Chemical Formula d74>
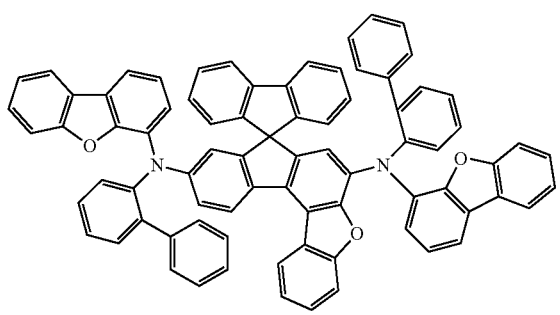
<Chemical Formula d75>
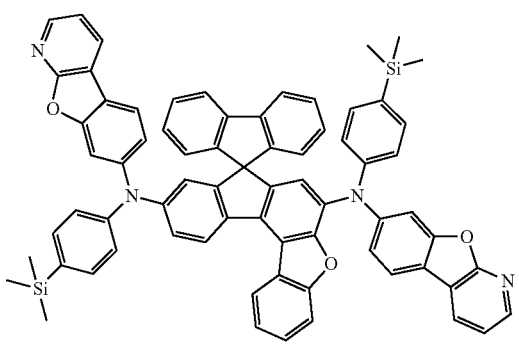
<Chemical Formula d76>
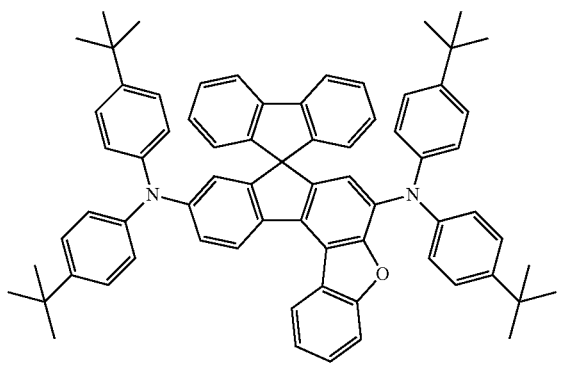
<Chemical Formula d77>
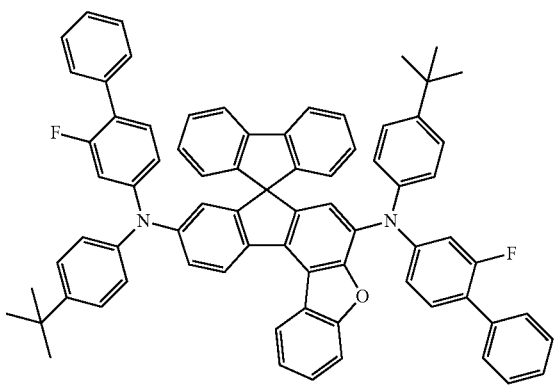
<Chemical Formula d78>
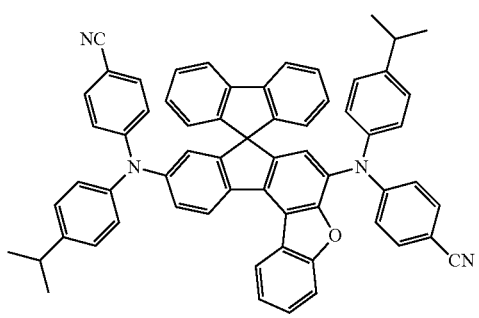
<Chemical Formula d79>
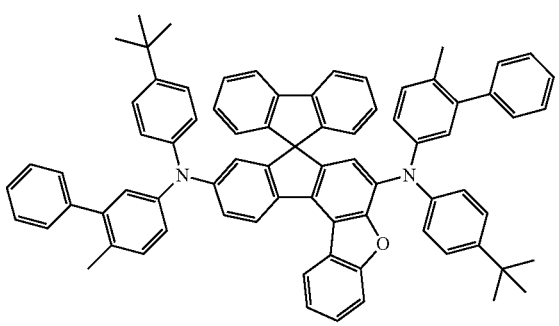

-continued
<Chemical Formula d80>
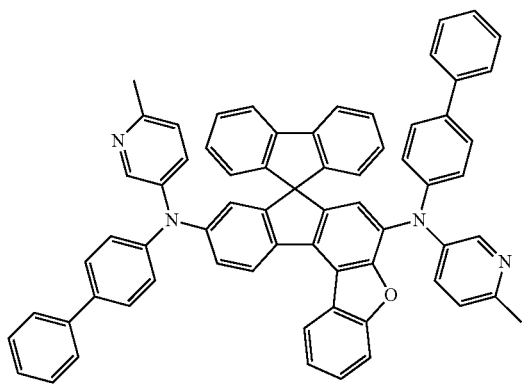
<Chemical Formula d81>
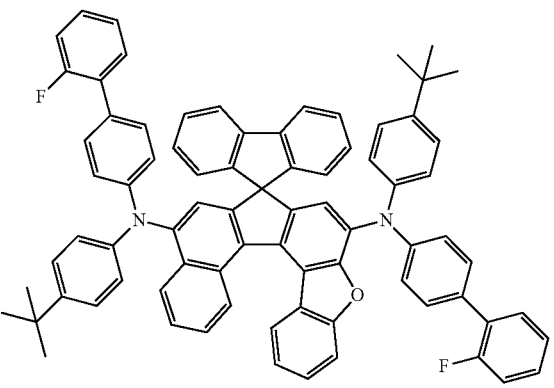
<Chemical Formula d82>
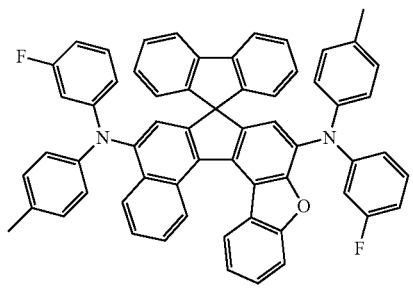
<Chemical Formula d83>
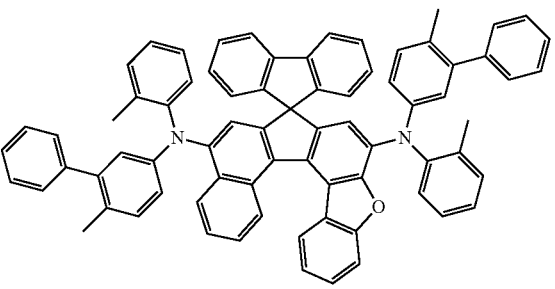
<Chemical Formula d84>
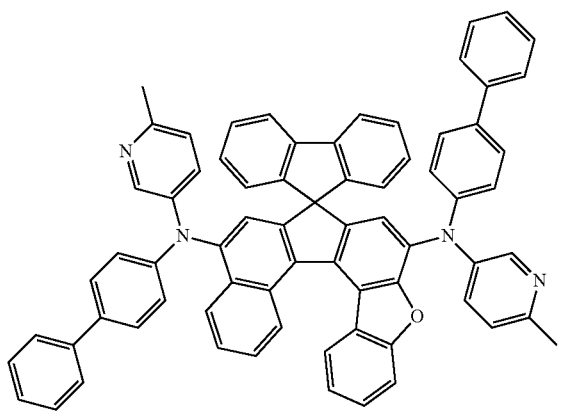
<Chemical Formula d85>
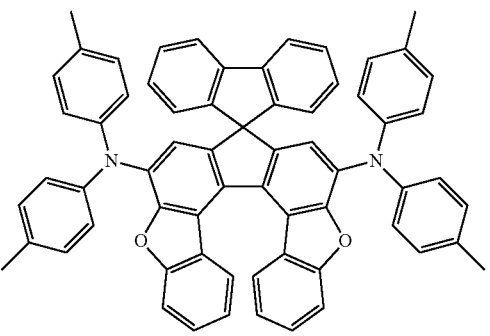
<Chemical Formula d86>
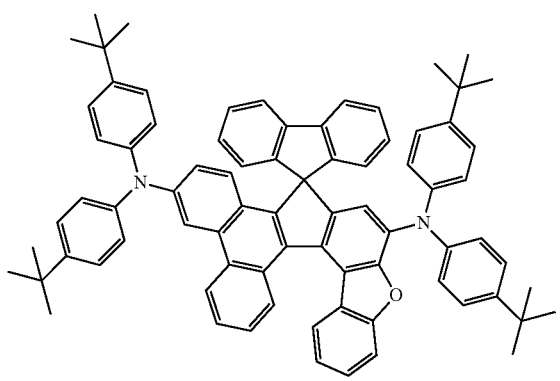
<Chemical Formula d87>
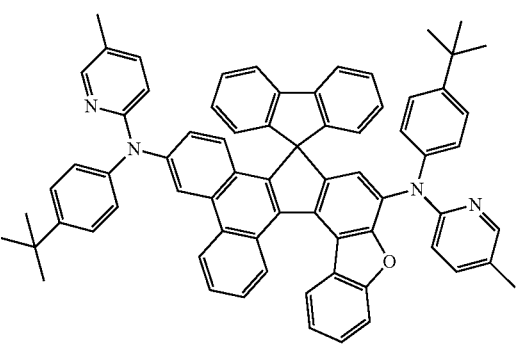

-continued
<Chemical Formula d88>
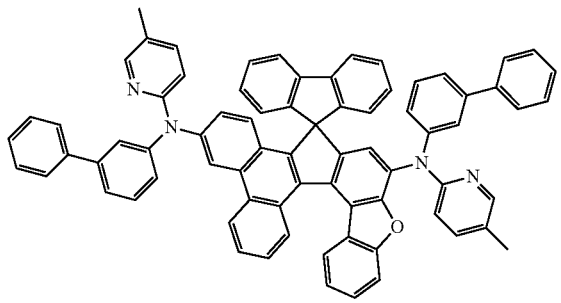
<Chemical Formula d89>
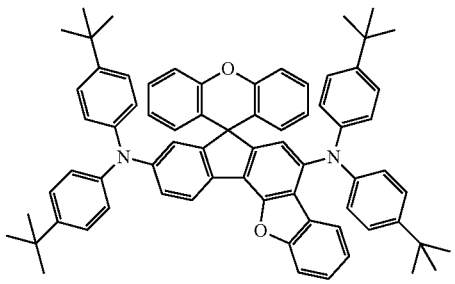
<Chemical Formula d90>
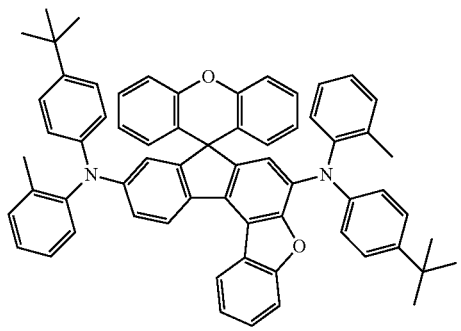
<Chemical Formula d91>
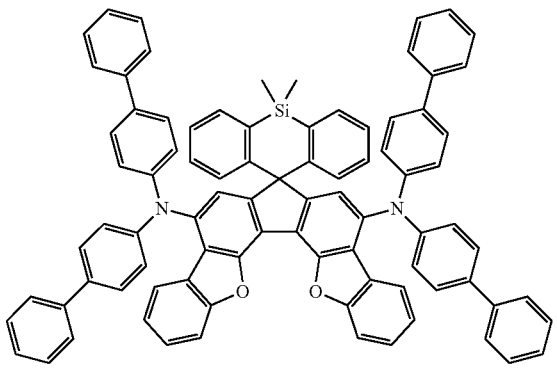
<Chemical Formula d92>
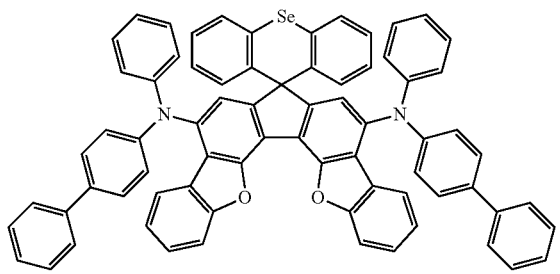
<Chemical Formula d93>
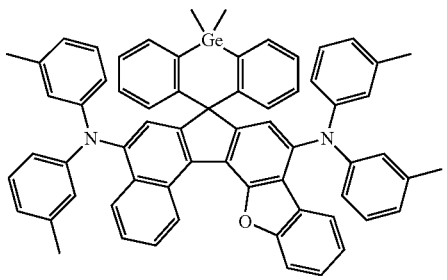
<Chemical Formula d94>
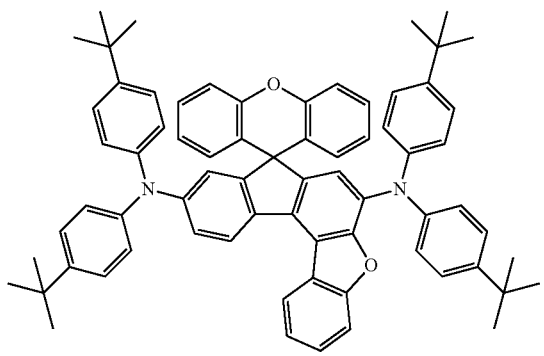
<Chemical Formula d95>
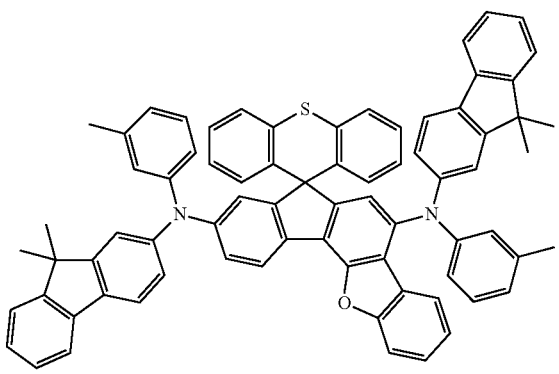

-continued
<Chemical Formula d96>
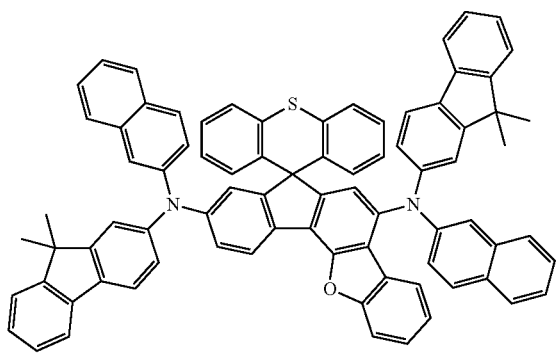
<Chemical Formula d97>
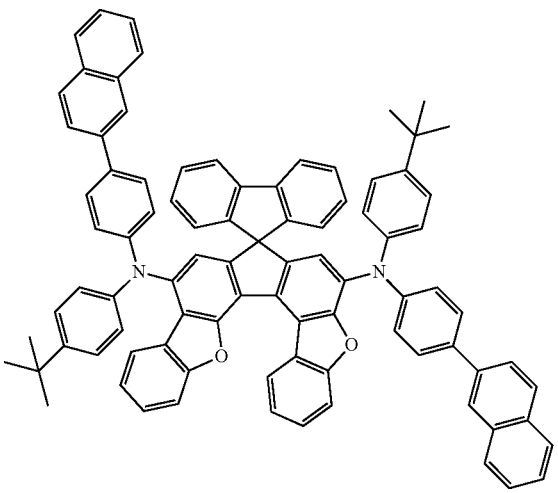
<Chemical Formula d98>
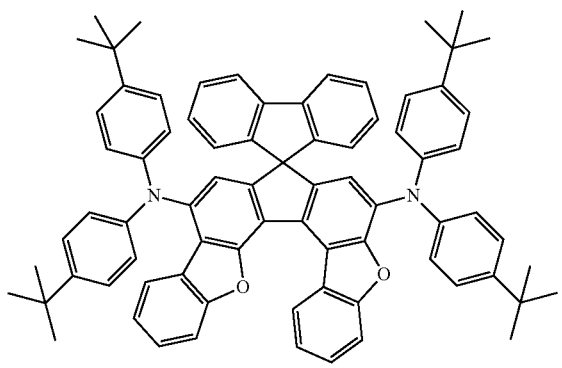
<Chemical Formula d99>
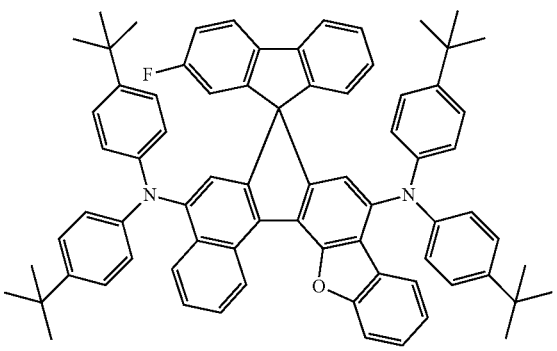
<Chemical Formula d100>
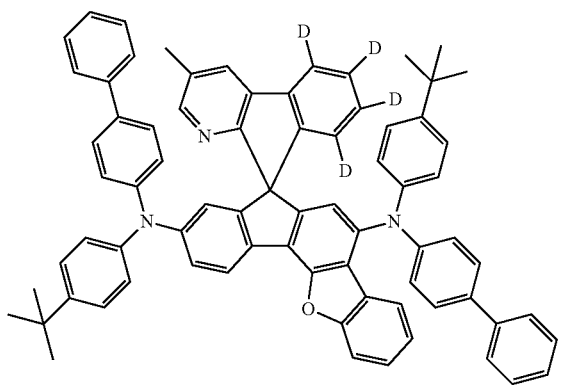
<Chemical Formula d101>
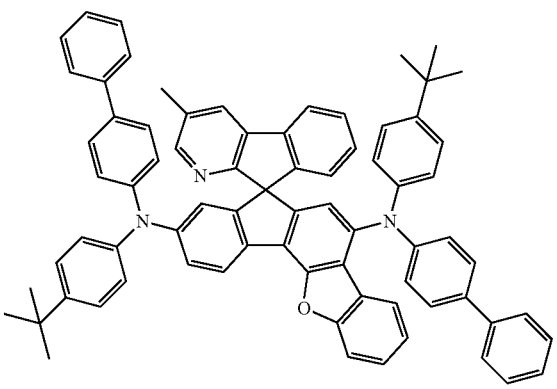

-continued
<Chemical Formula d102>
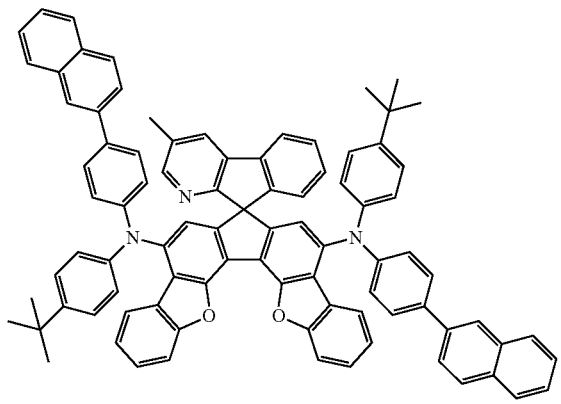
<Chemical Formula d103>
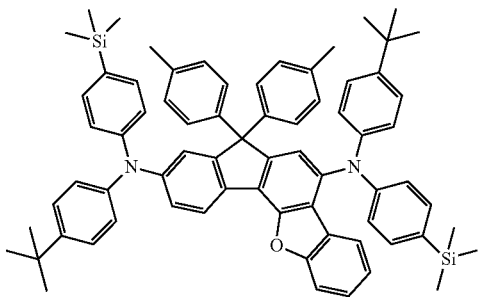
<Chemical Formula d104>
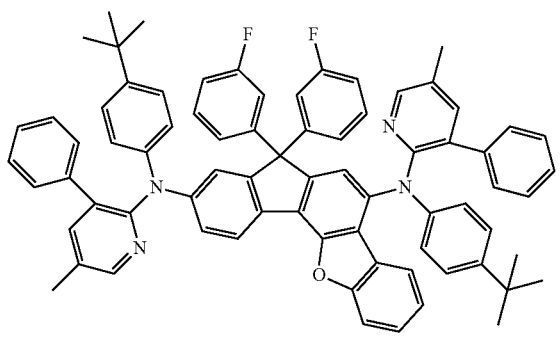
<Chemical Formula d105>
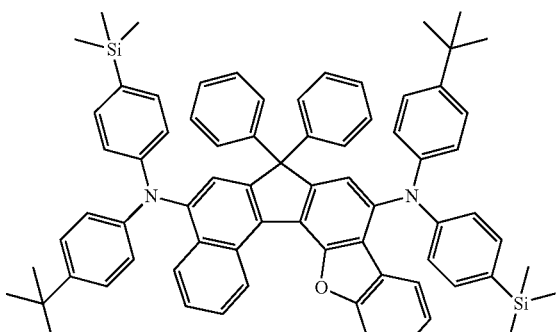
<Chemical Formula d106>
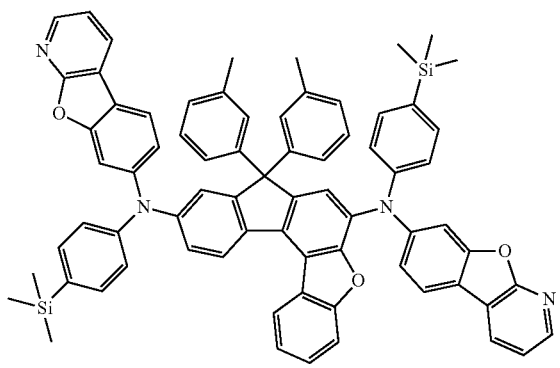
<Chemical Formula d107>
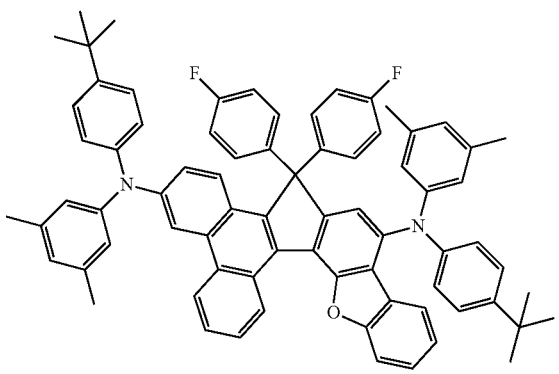
<Chemical Formula d108>
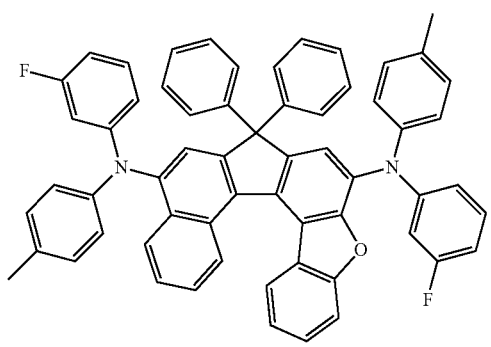
<Chemical Formula d109>
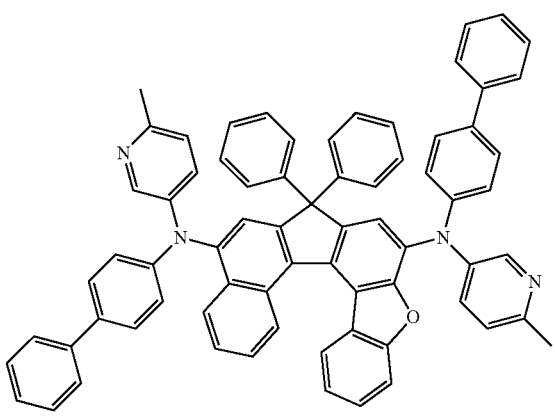

<Chemical Formula d110>
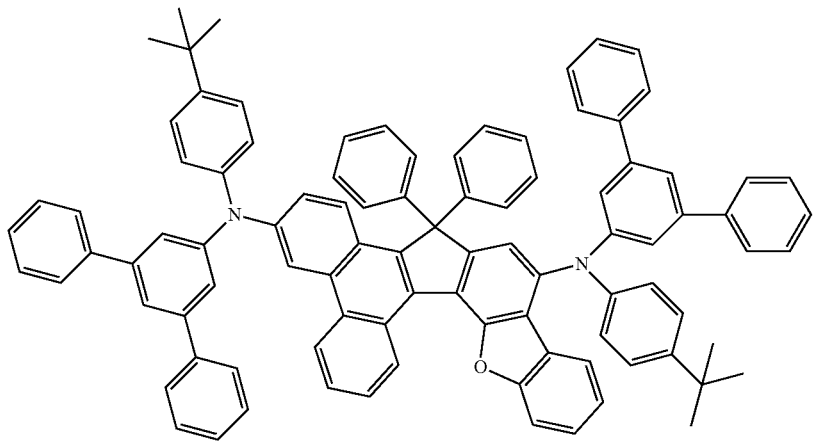
<Chemical Formula d111>  <Chemical Formula d112>
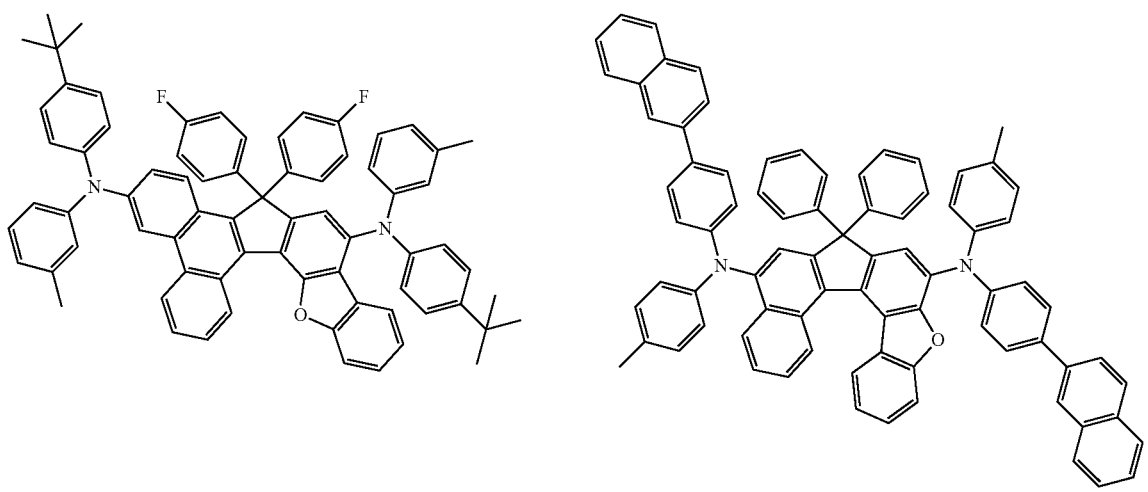
<Chemical Formula d113>  <Chemical Formula d114>
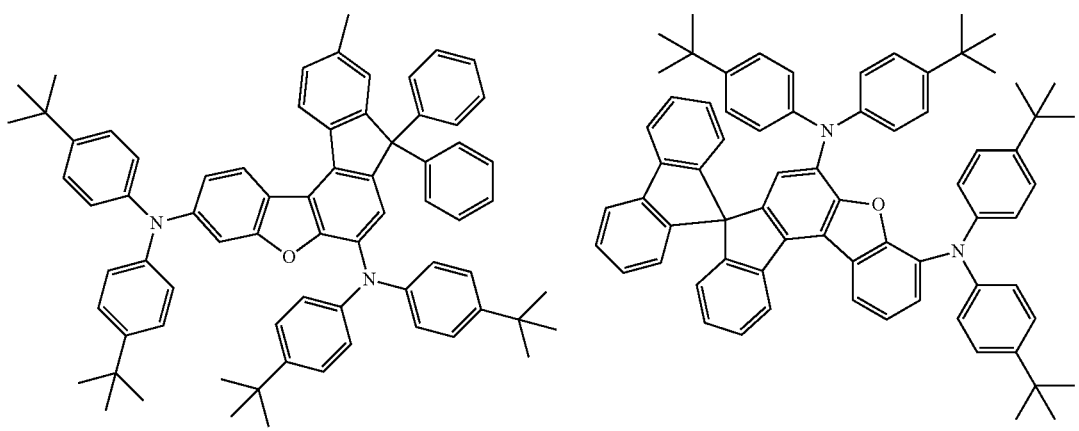

<Chemical Formula d115>
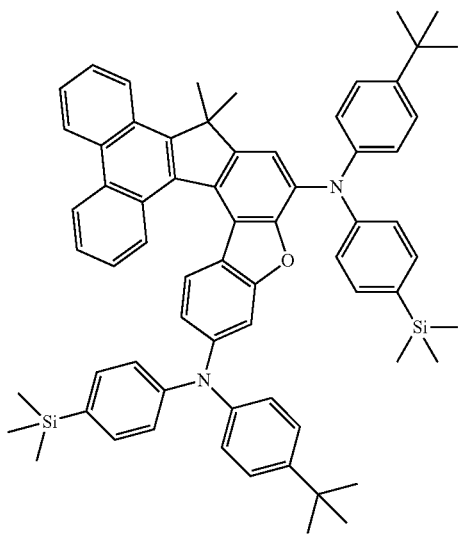
<Chemical Formula d116>
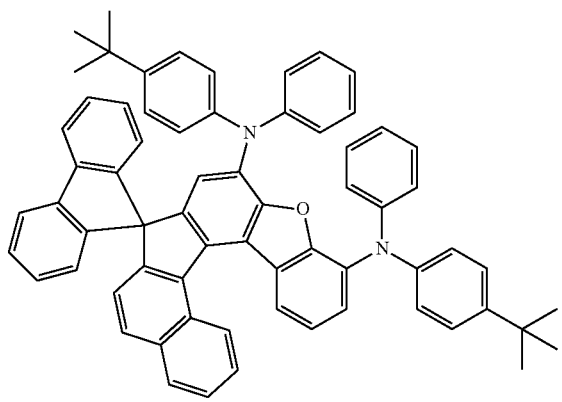
<Chemical Formula d117>
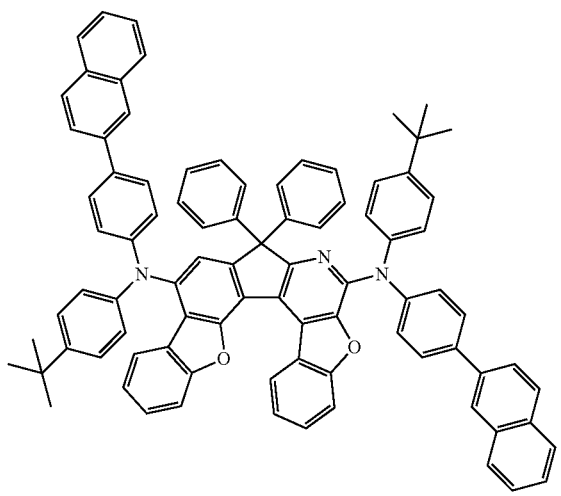
<Chemical Formula d118>
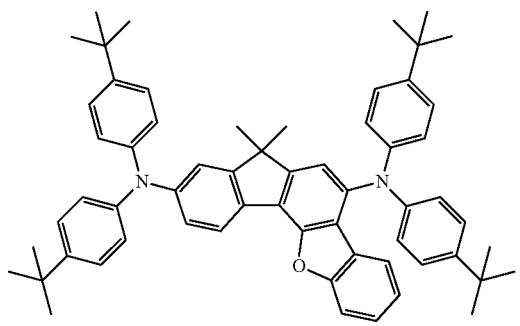
<Chemical Formula d119>
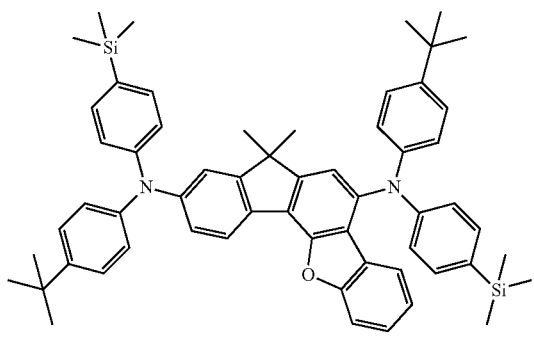
<Chemical Formula d120>
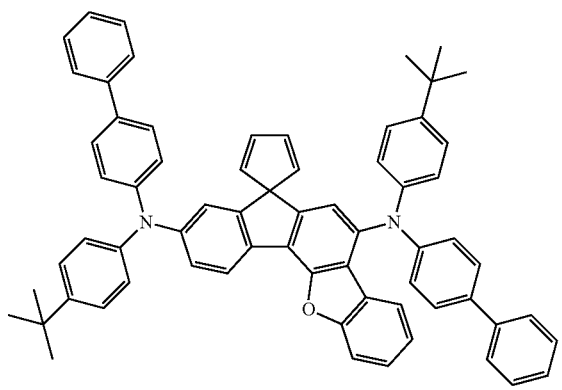

-continued
<Chemical Formula d121>
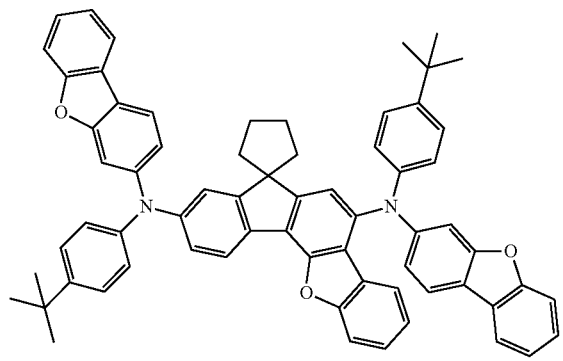
<Chemical Formula d122>
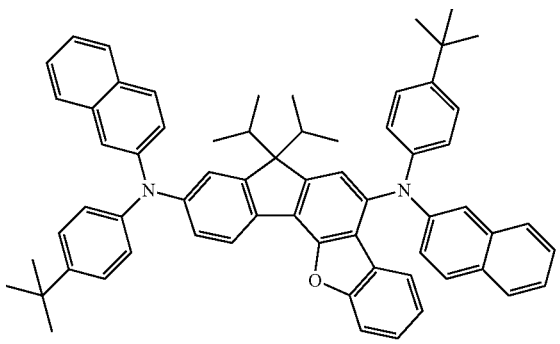
<Chemical Formula d123>
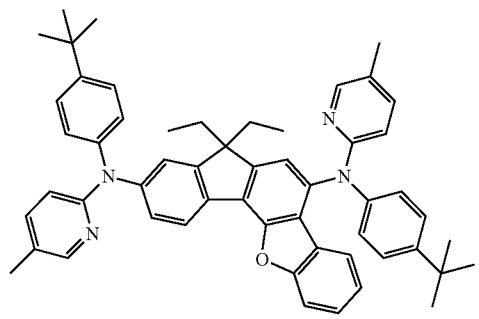
<Chemical Formula d124>
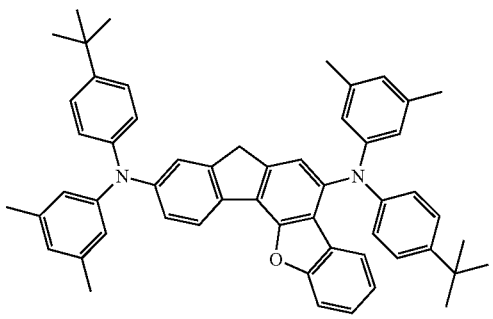
<Chemical Formula d125>
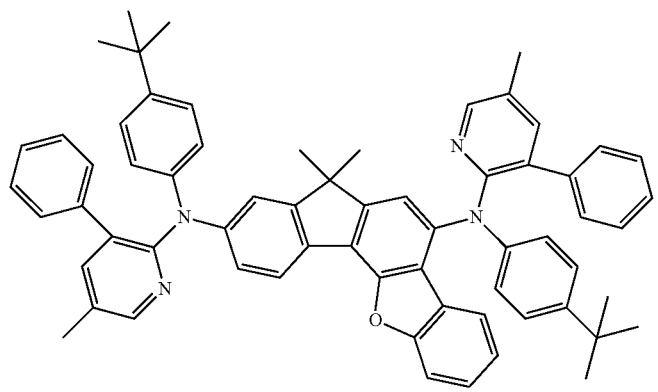
<Chemical Formula d126>
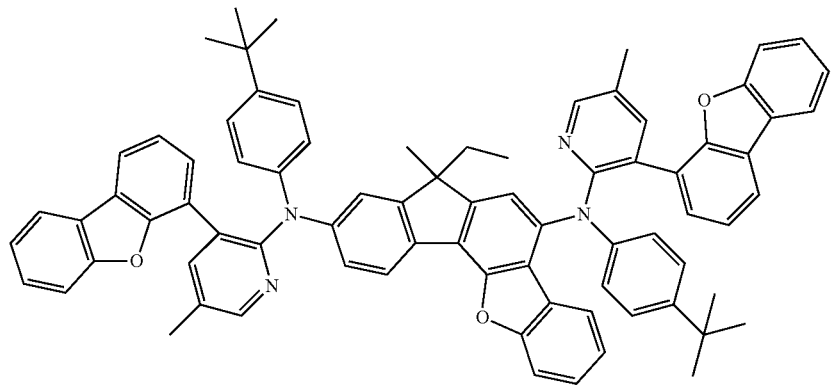

-continued
<Chemical Formula d127>
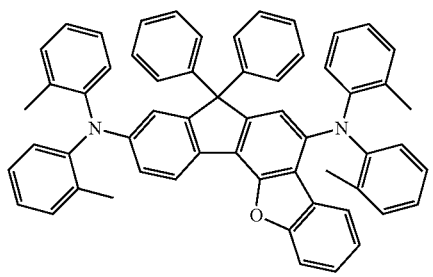
<Chemical Formula d128>
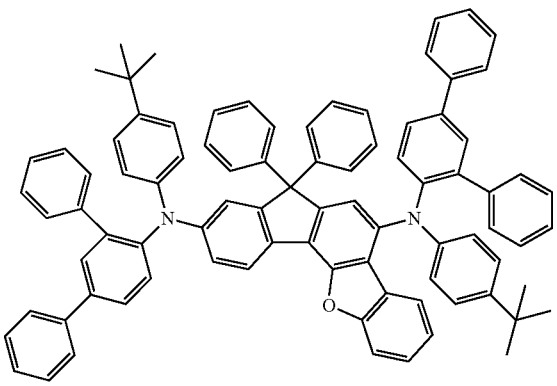
<Chemical Formula d129>
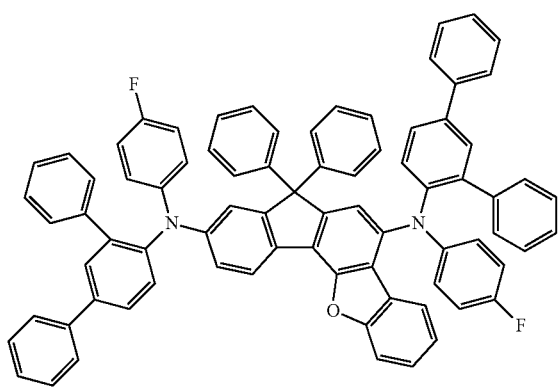
<Chemical Formula d130>
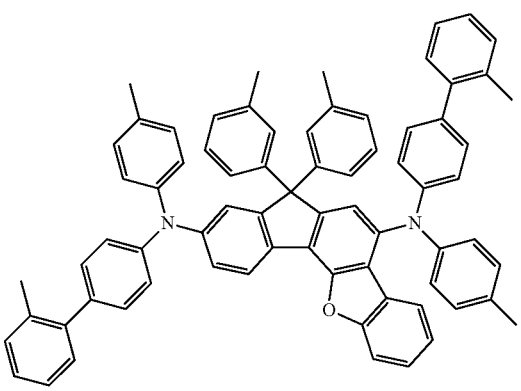
<Chemical Formula d131>
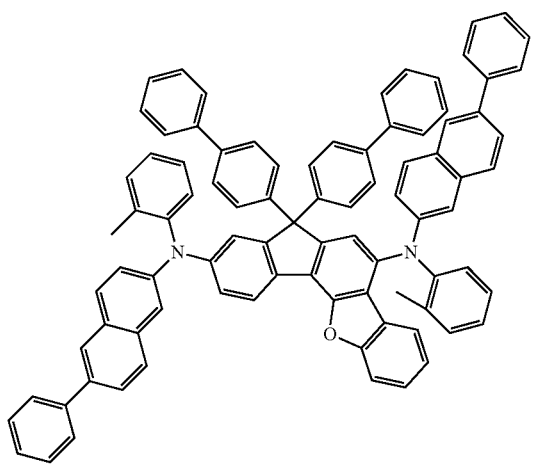
<Chemical Formula d132>
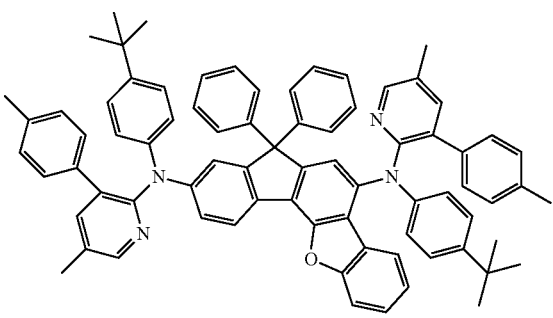

<Chemical Formula d133>
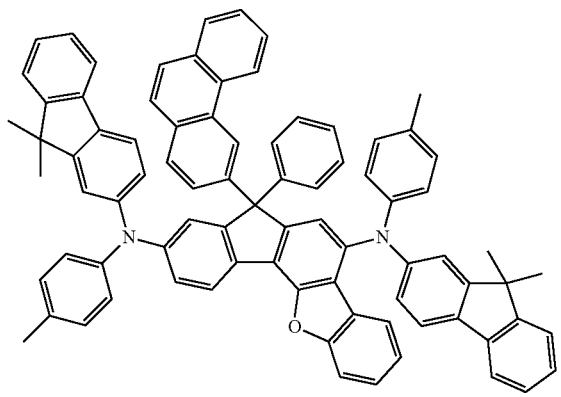
<Chemical Formula d134>
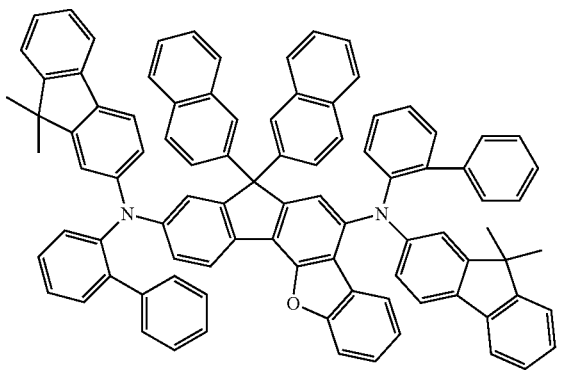
<Chemical Formula d135>
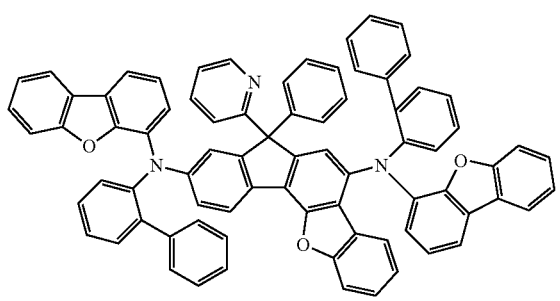
<Chemical Formula d136>
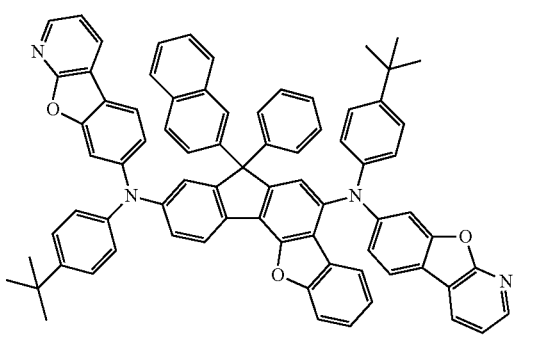
<Chemical Formula d137>
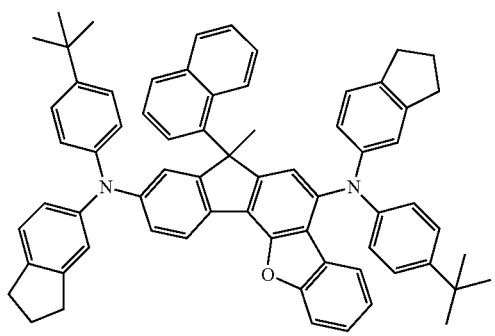
<Chemical Formula d138>
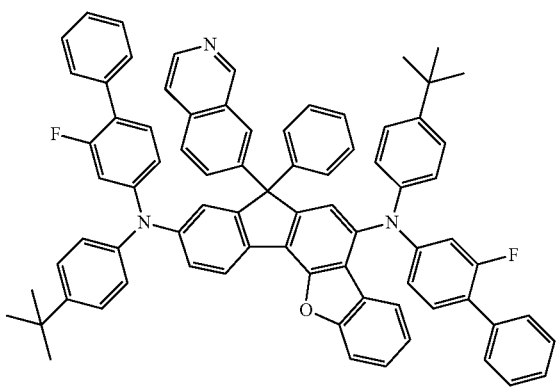
<Chemical Formula d139>
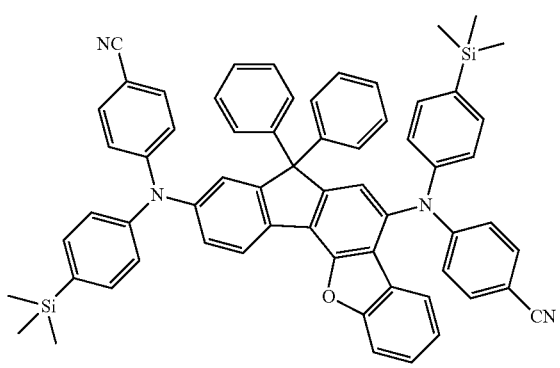
<Chemical Formula d140>
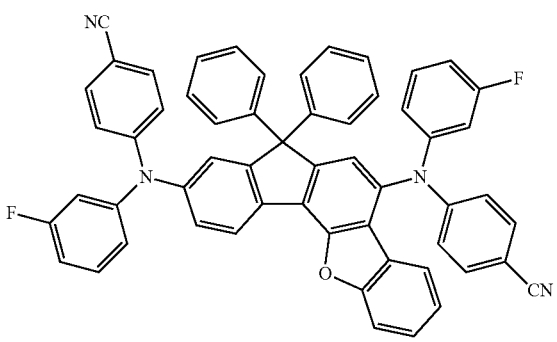

-continued
<Chemical Formula d141>
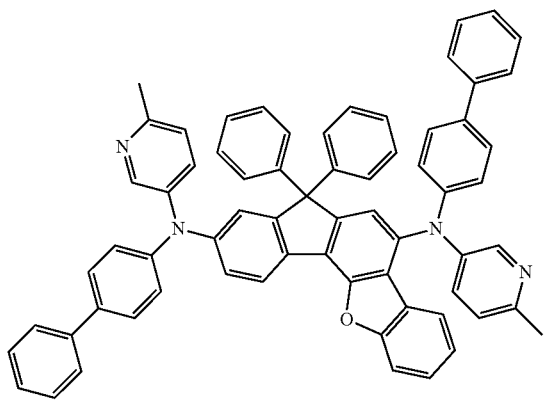
<Chemical Formula d142>
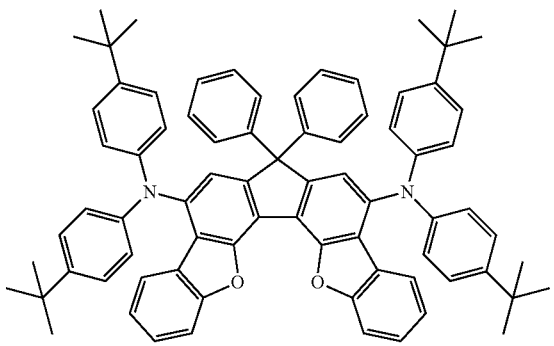
<Chemical Formula d143>
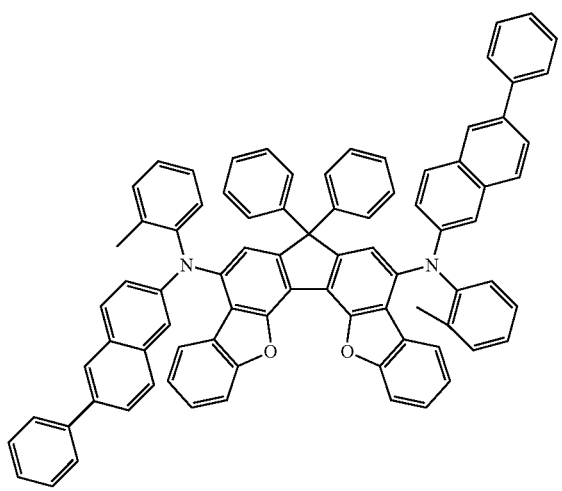
<Chemical Formula d144>
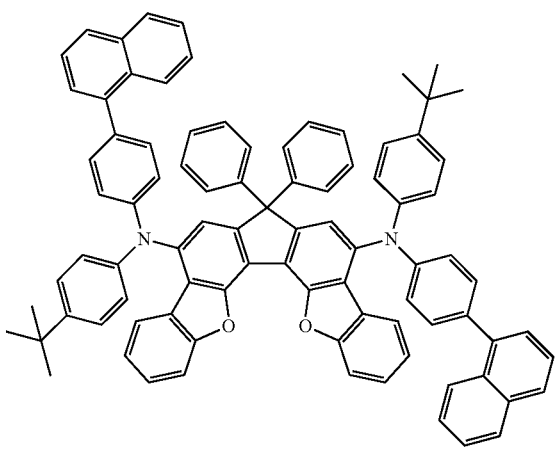
<Chemical Formula d145>
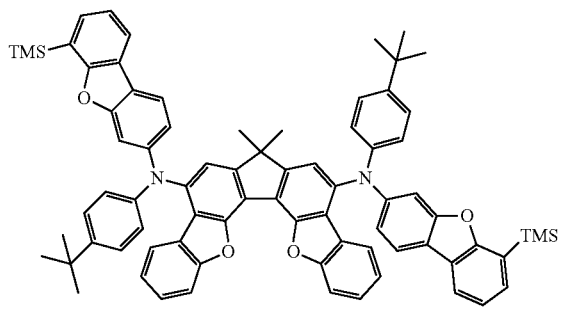
<Chemical Formula d146>
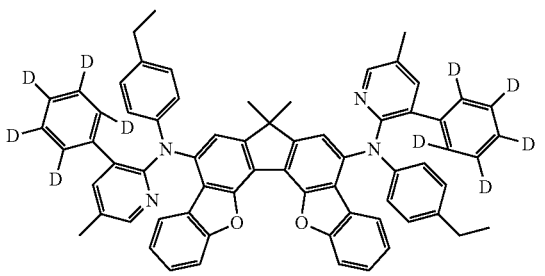
<Chemical Formula d147>
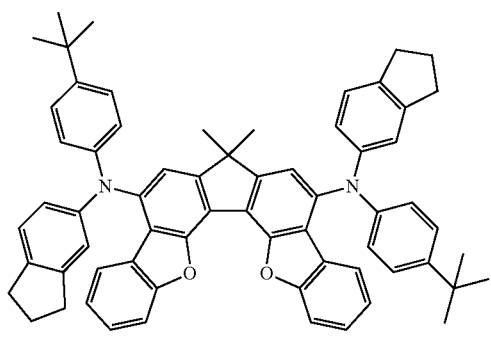
<Chemical Formula d148>
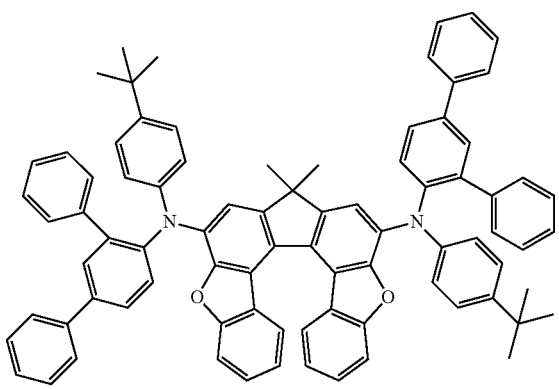

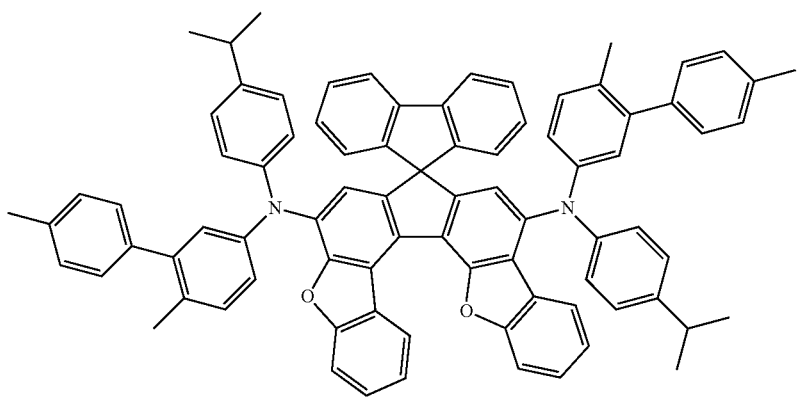
<Chemical Formula d149>
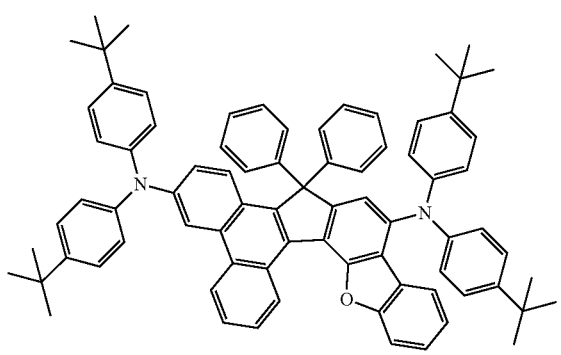
<Chemical Formula d150>
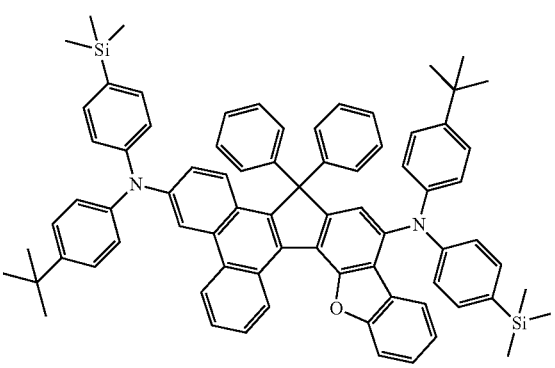
<Chemical Formula d151>
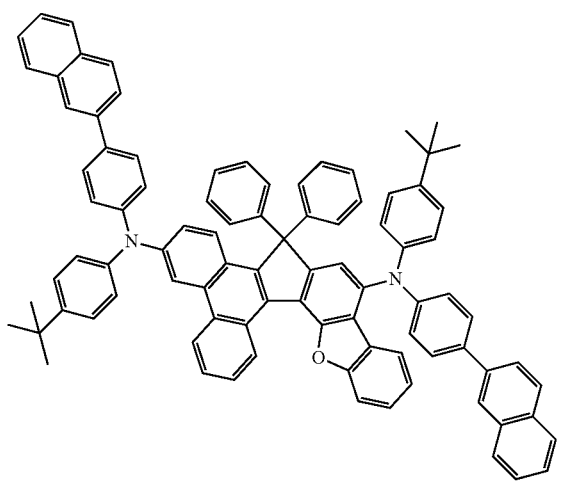
<Chemical Formula d152>
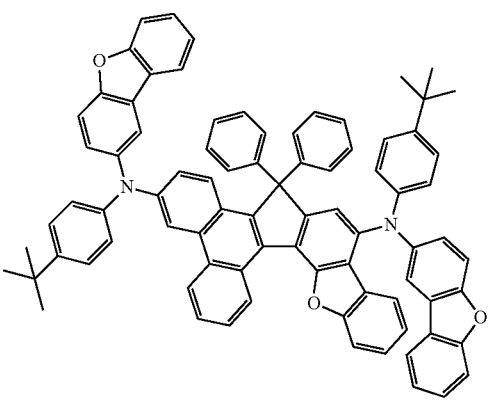
<Chemical Formula d153>
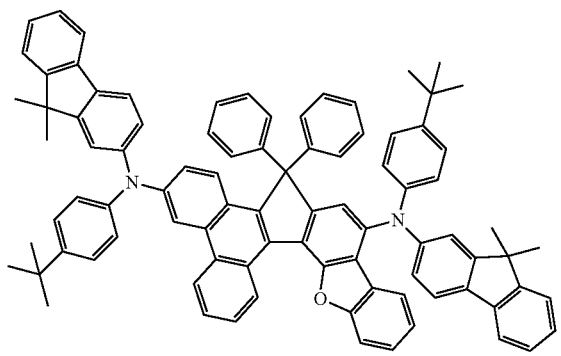
<Chemical Formula d154>
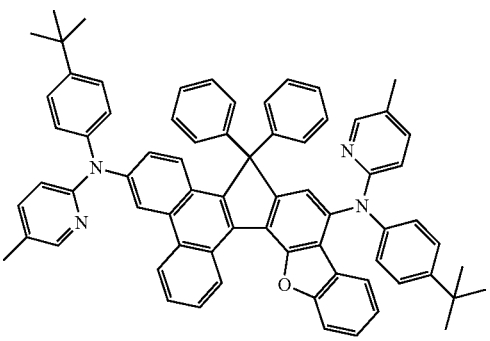
<Chemical Formula d155>

-continued
<Chemical Formula d156>
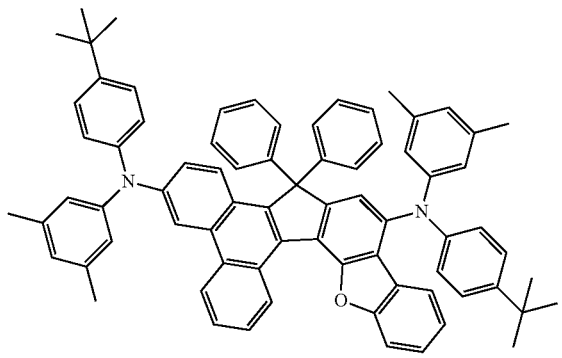
<Chemical Formula d157>
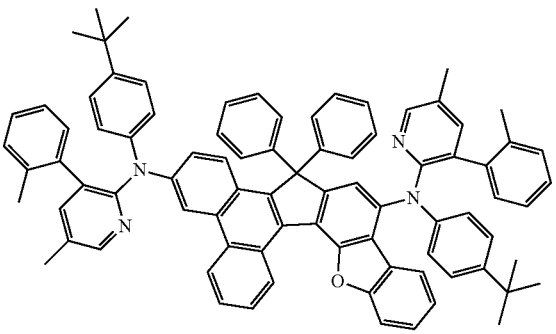
<Chemical Formula d158>
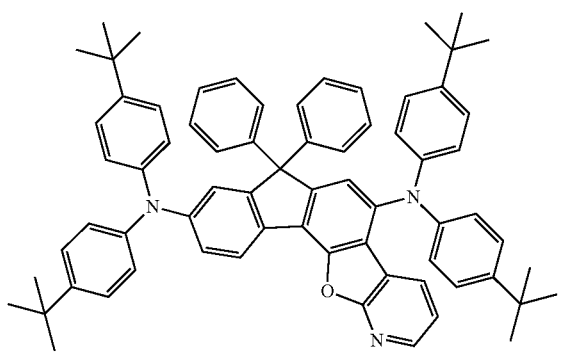
<Chemical Formula d159>
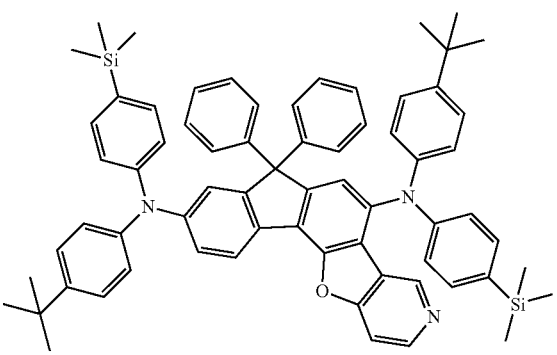
<Chemical Formula d160>
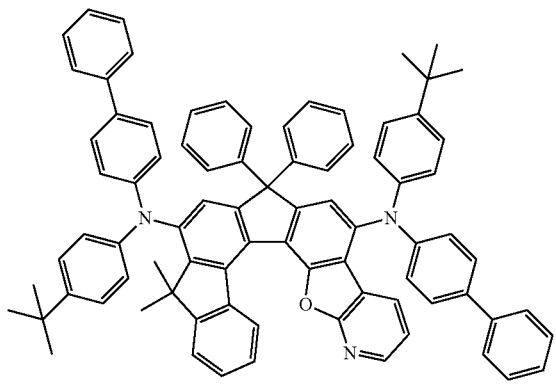
<Chemical Formula d161>
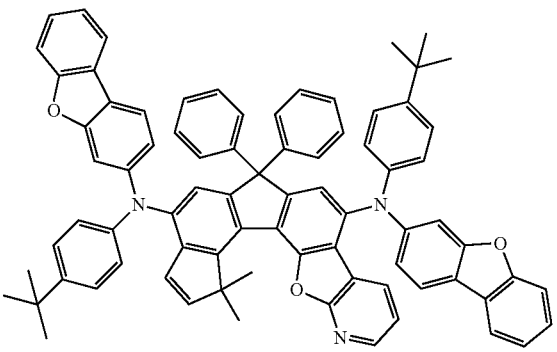
<Chemical Formula d162>
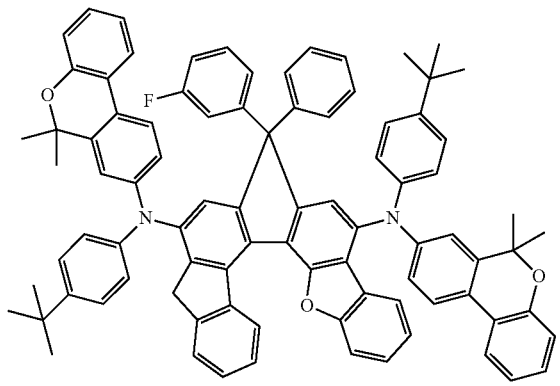
<Chemical Formula d163>
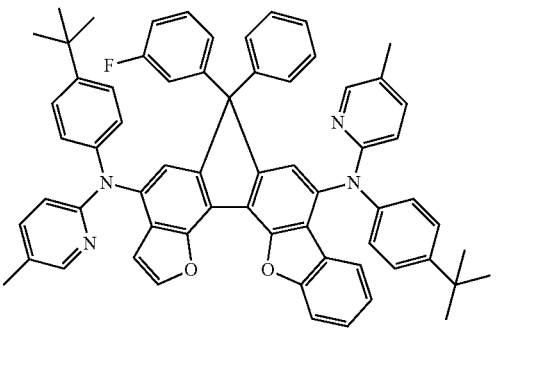

-continued
<Chemical Formula d164>
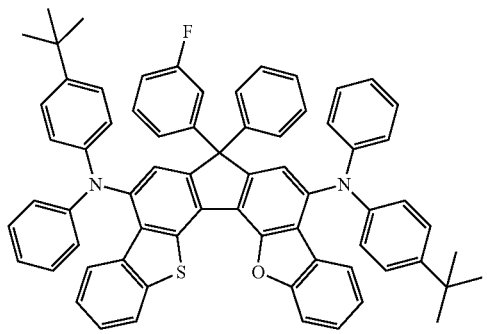
<Chemical Formula d165>
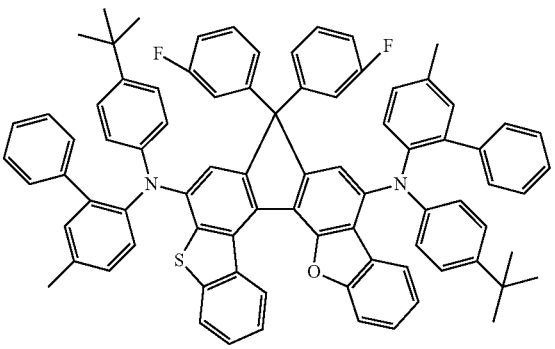
<Chemical Formula d166>
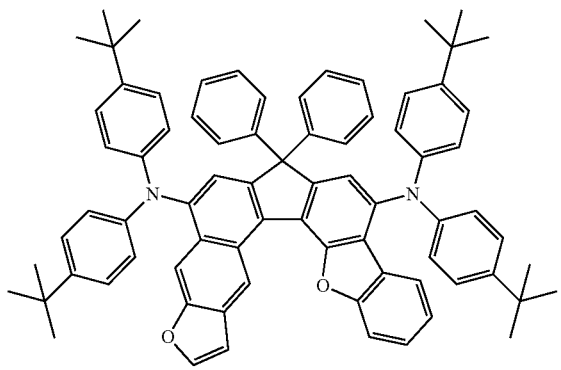
<Chemical Formula d167>
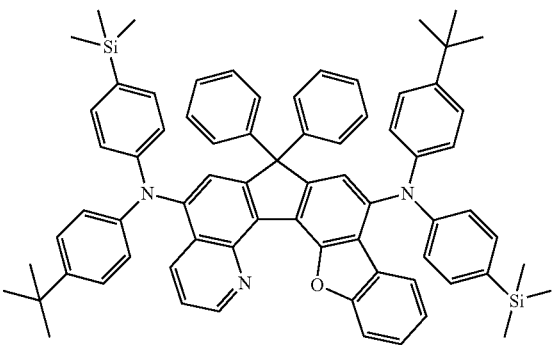
<Chemical Formula d168>
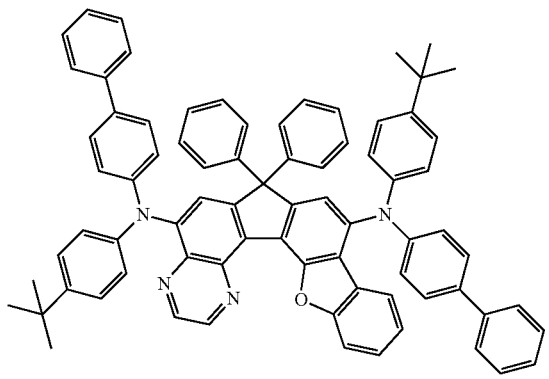
<Chemical Formula d169>
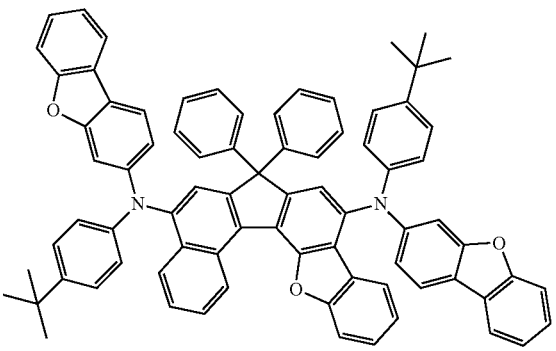
<Chemical Formula d170>
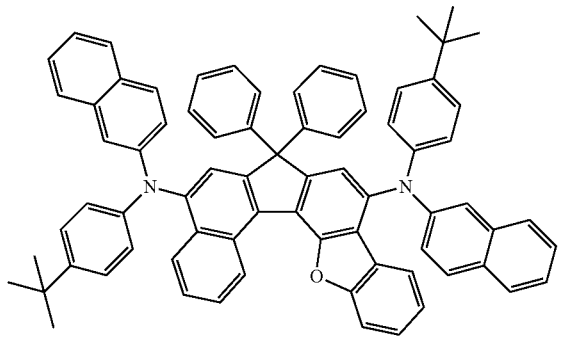
<Chemical Formula d171>
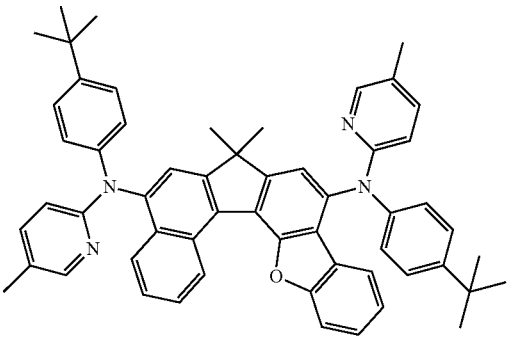

-continued
<Chemical Formula d172>
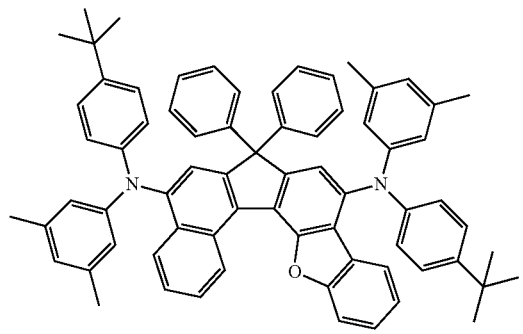
<Chemical Formula d173>
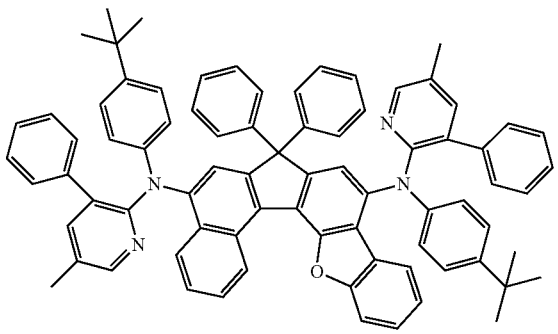
<Chemical Formula d174>
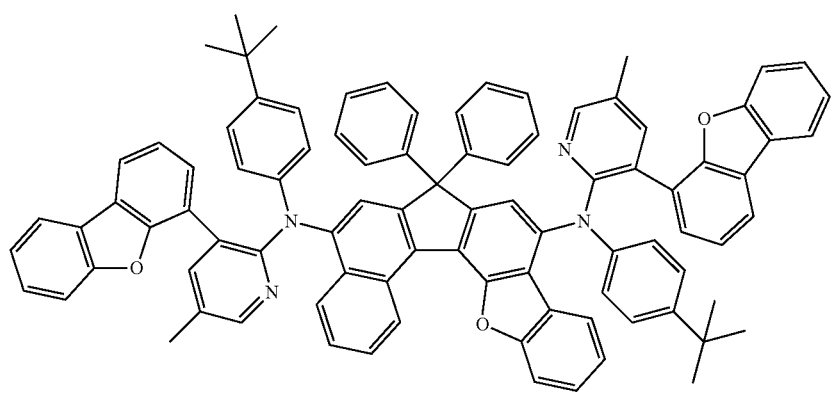
<Chemical Formula d175>
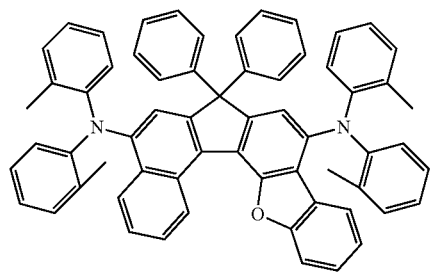
<Chemical Formula d176>
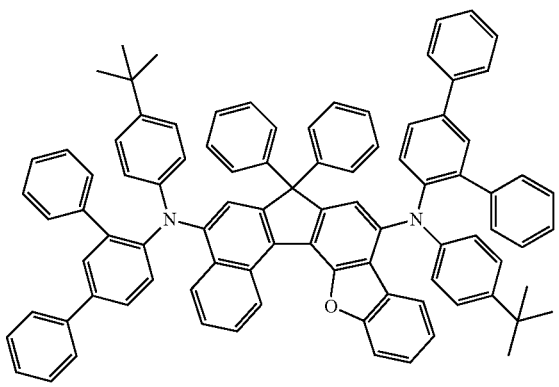
<Chemical Formula d177>
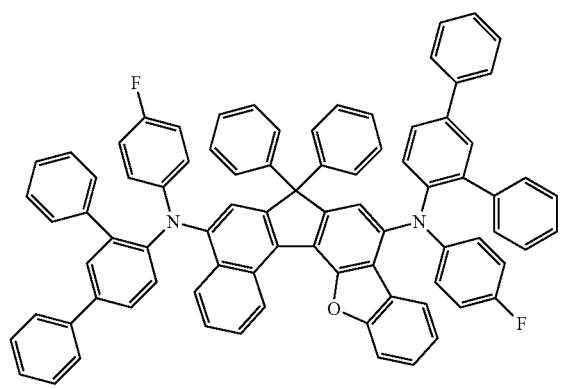
<Chemical Formula d178>
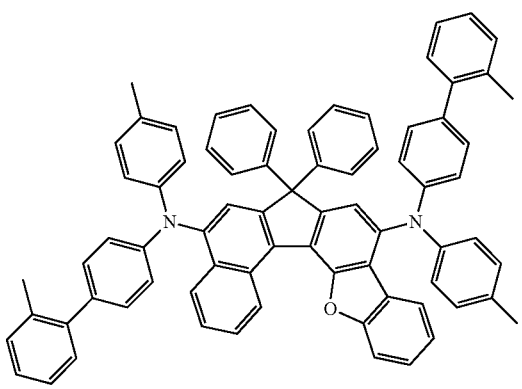

<Chemical Formula d179>
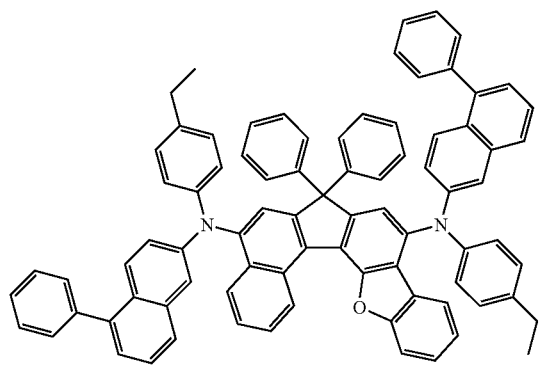
<Chemical Formula d180>
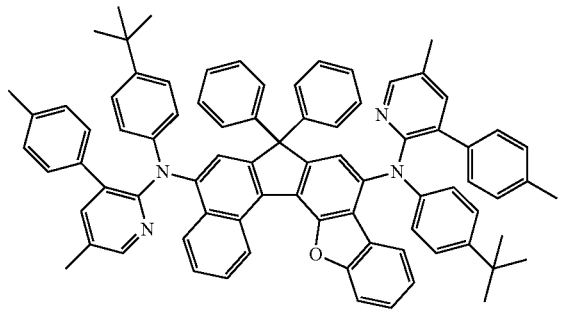
<Chemical Formula d181>
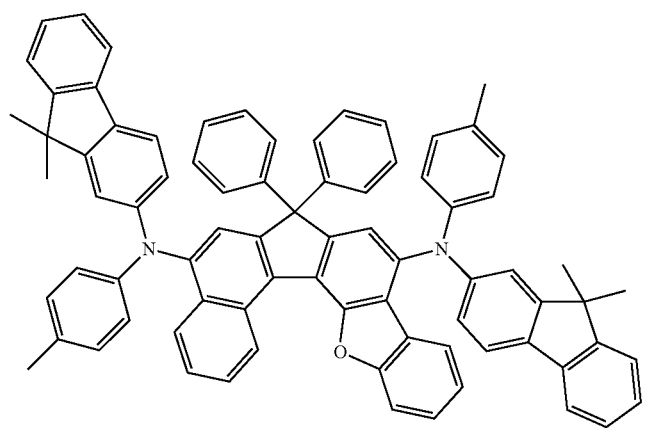
<Chemical Formula d182>
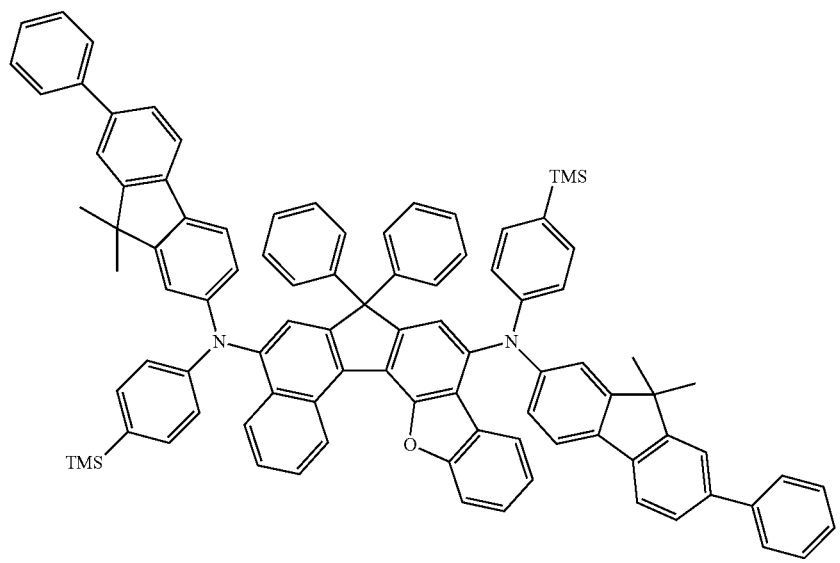

-continued
<Chemical Formula d183>
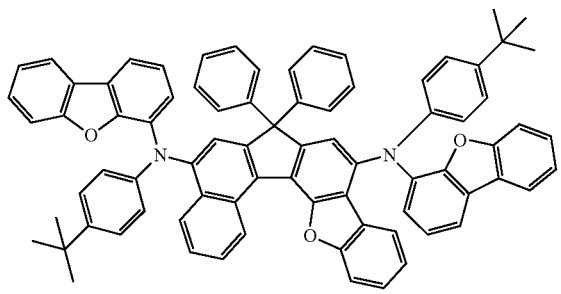
<Chemical Formula d184>
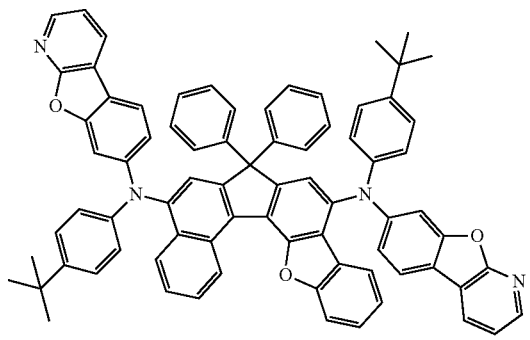
<Chemical Formula d185>
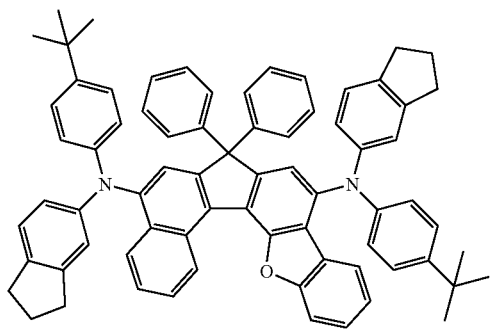
<Chemical Formula d186>
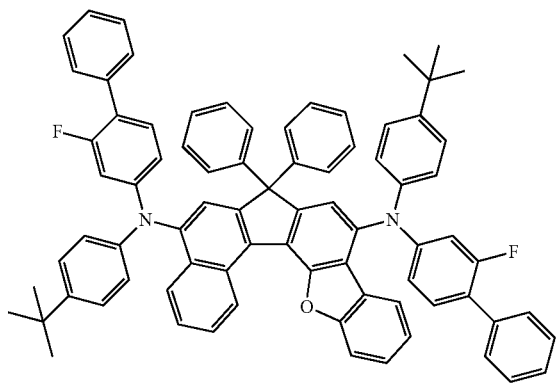
<Chemical Formula d187>
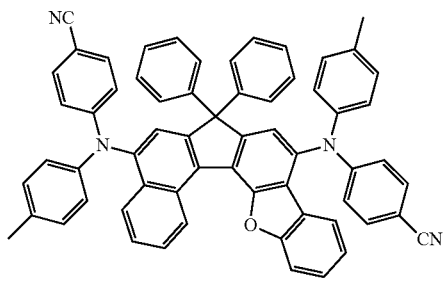
<Chemical Formula d188>
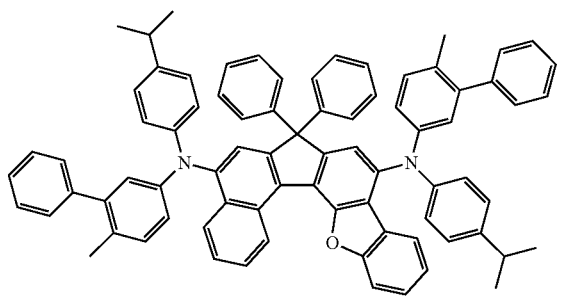
<Chemical Formula d189>
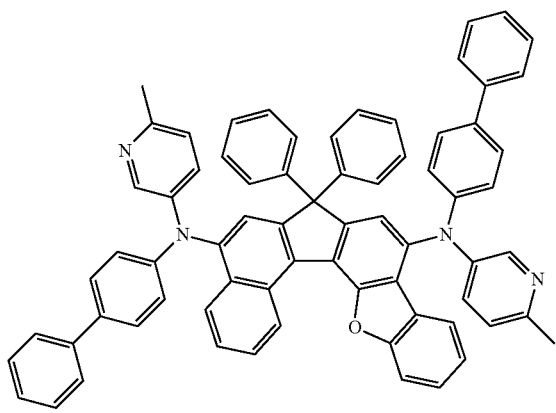
<Chemical Formula d190>
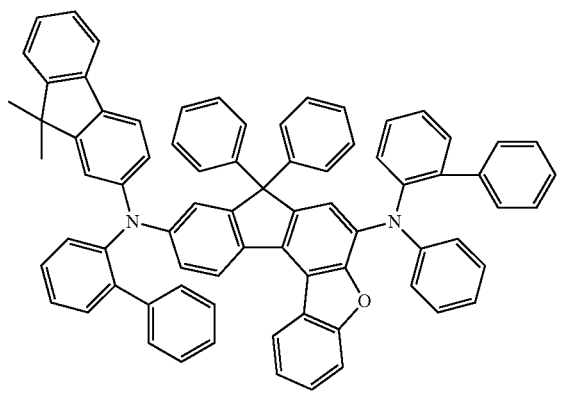

<Chemical Formula d191>
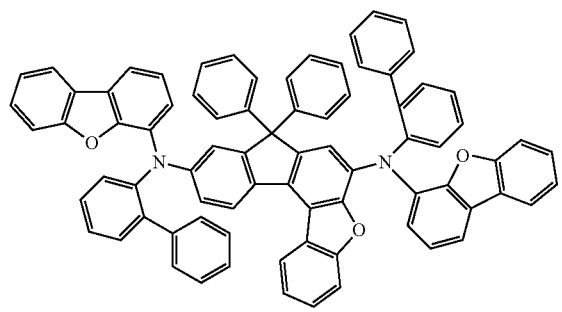
<Chemical Formula d192>
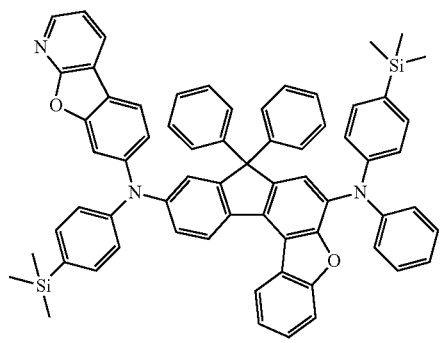
<Chemical Formula d193>
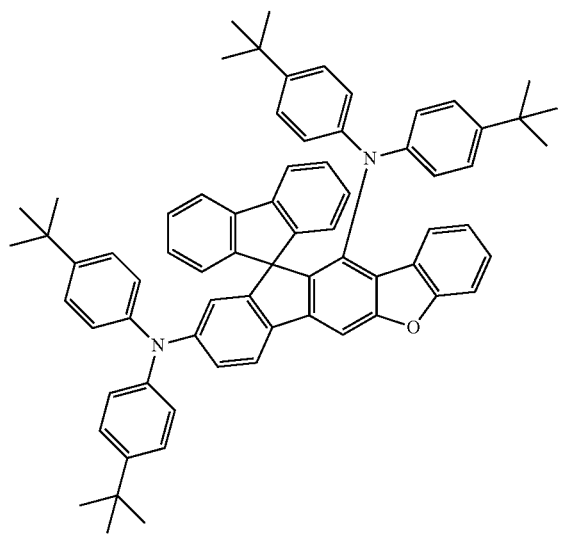
<Chemical Formula d194>
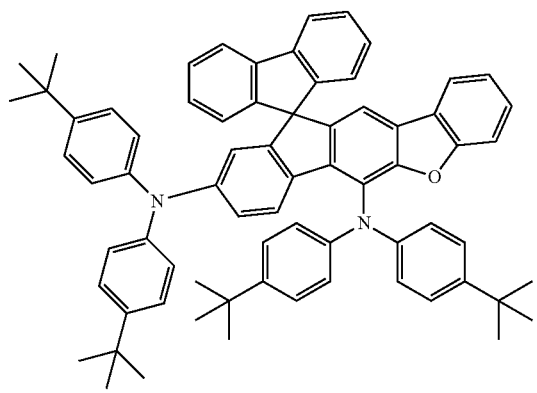
<Chemical Formula d195>
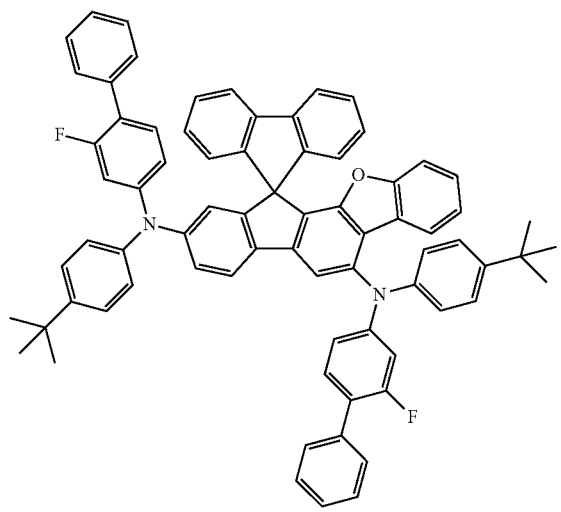
<Chemical Formula d196>
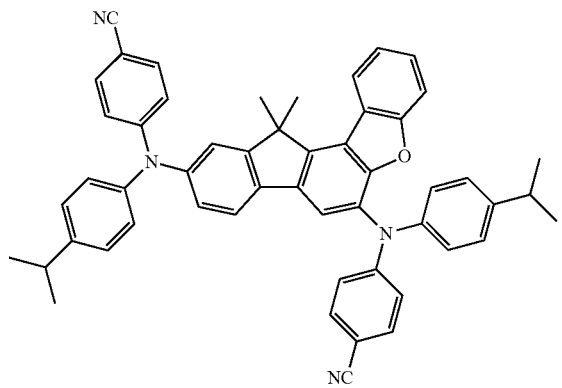

<Chemical Formula d197>
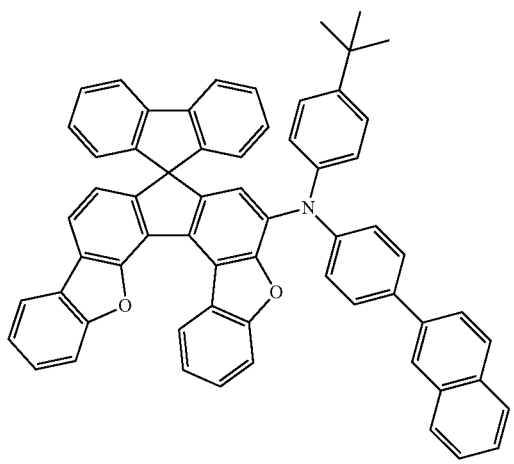
<Chemical Formula d198>
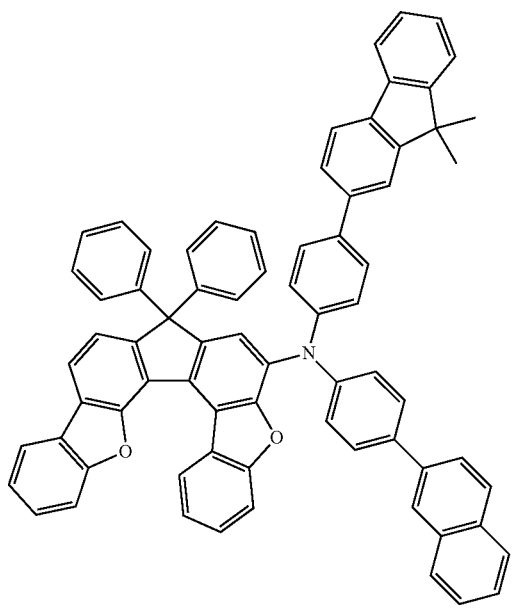
<Chemical Formula d199>
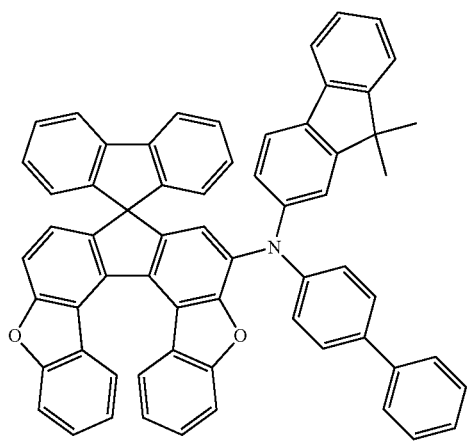
<Chemical Formula d200>
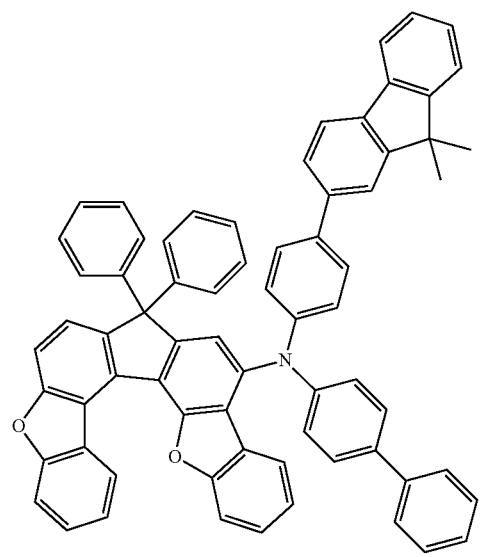

-continued
<Chemical Formula d201>
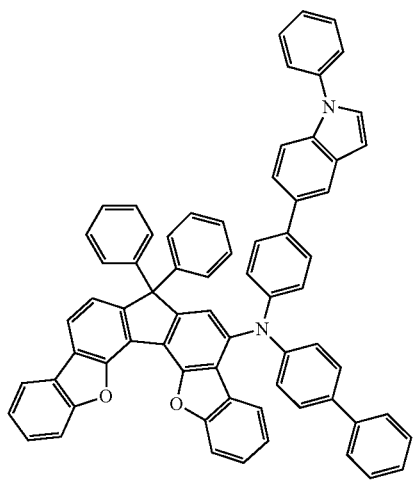
<Chemical Formula d202>
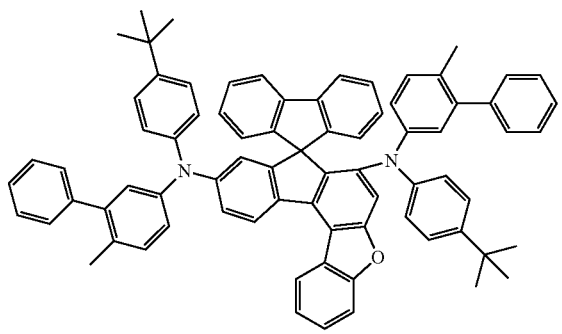
<Chemical Formula d203>
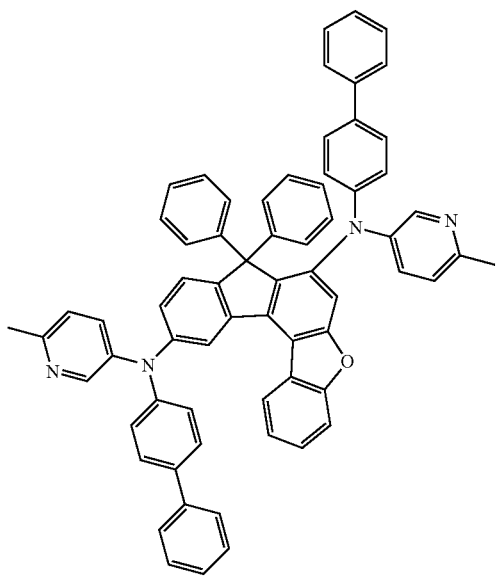
<Chemical Formula d204>
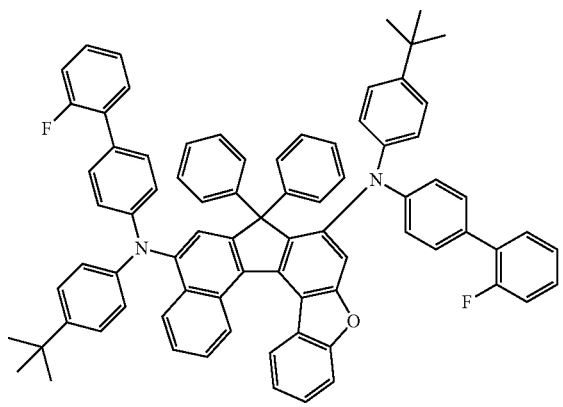
<Chemical Formula d205>
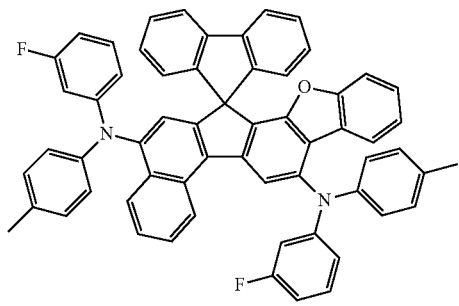
<Chemical Formula d206>
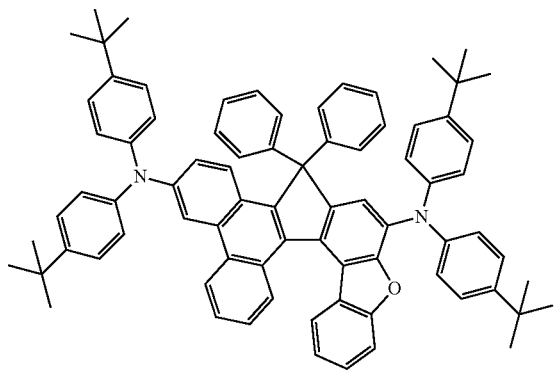

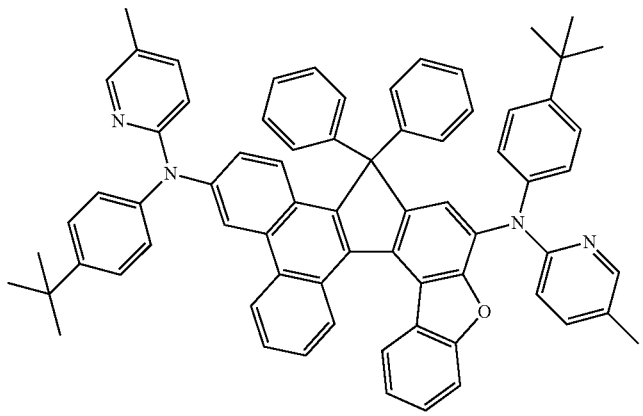
<Chemical Formula d207>
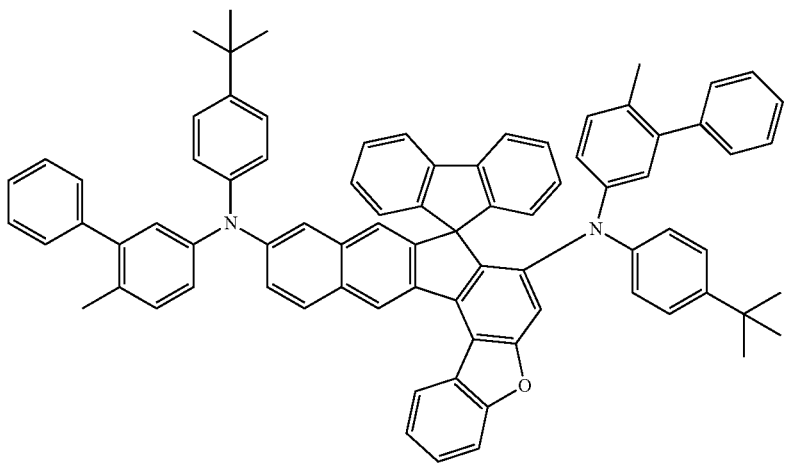
<Chemical Formula d208>
<Chemical Formula d209>
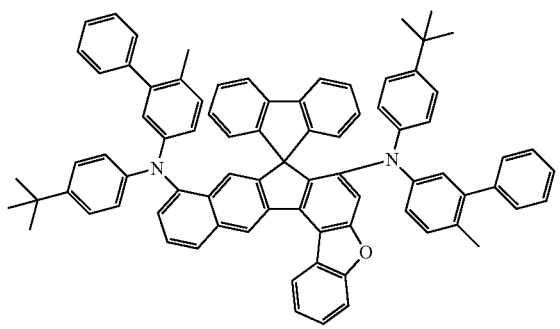
<Chemical Formula d210>
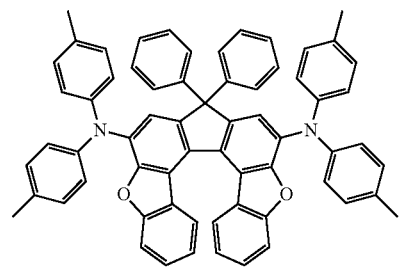

<Chemical Formula d211>
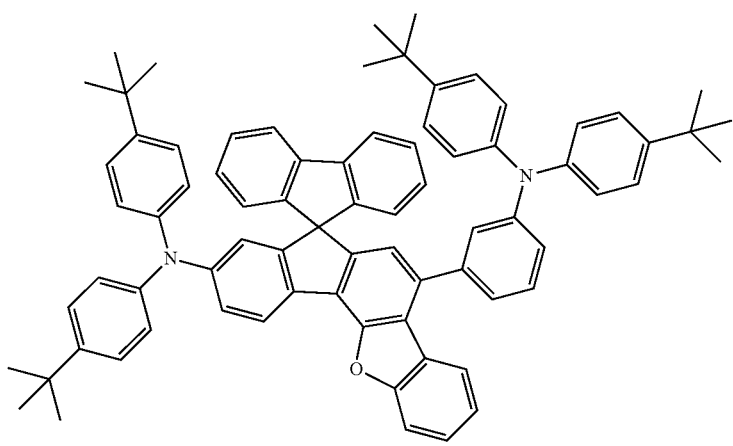
<Chemical Formula d212>
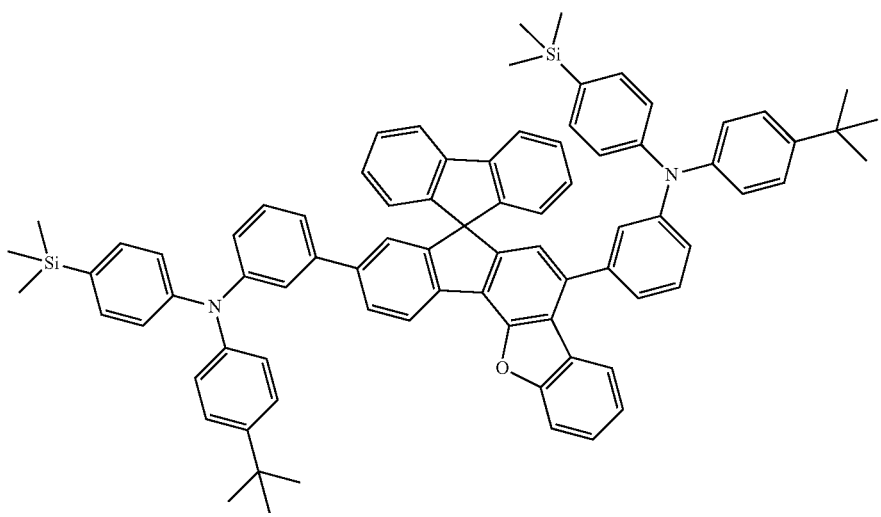
<Chemical Formula d213>
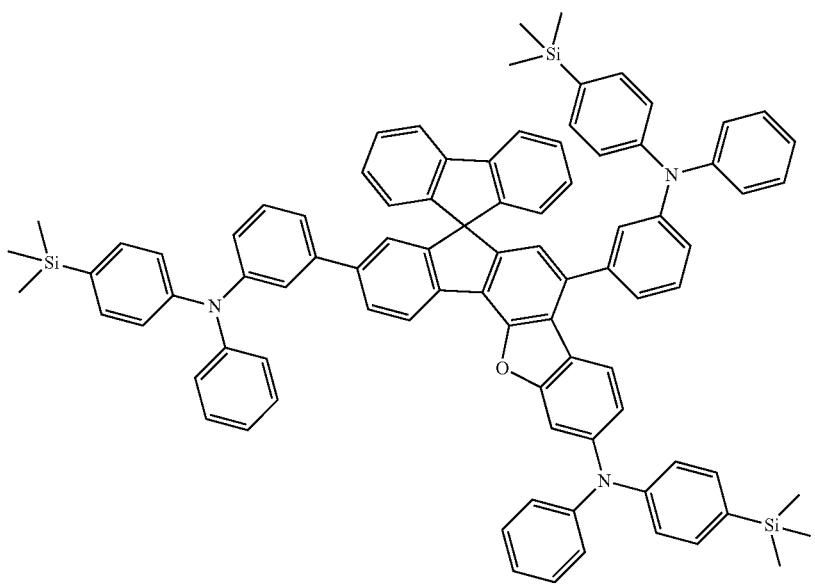

-continued
<Chemical Formula d214>
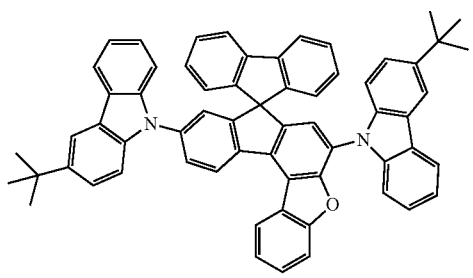
<Chemical Formula d215>
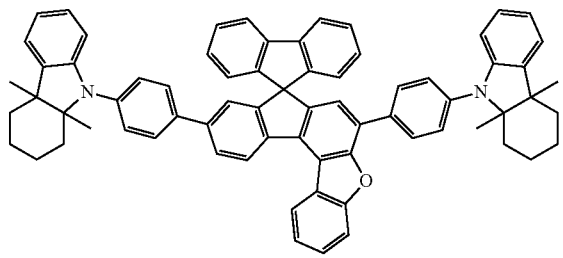
<Chemical Formula d216>
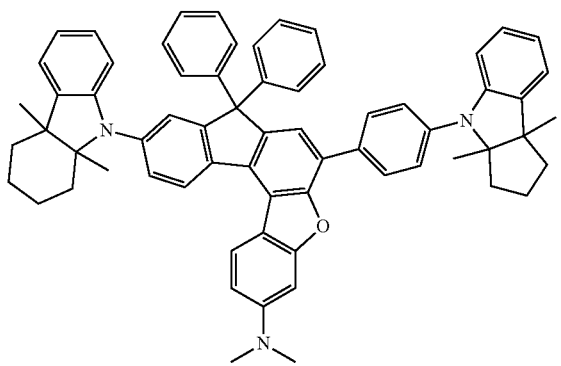
<Chemical Formula d217>
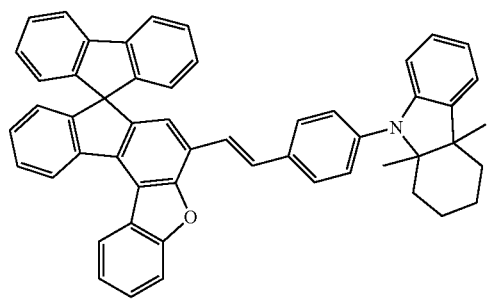
<Chemical Formula d218>
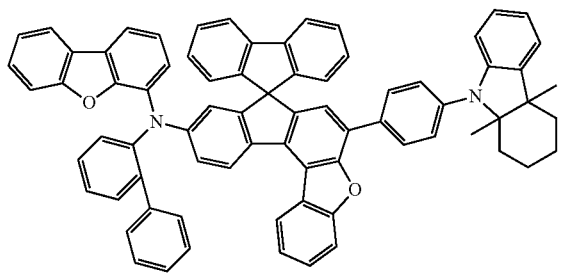
<Chemical Formula d219>
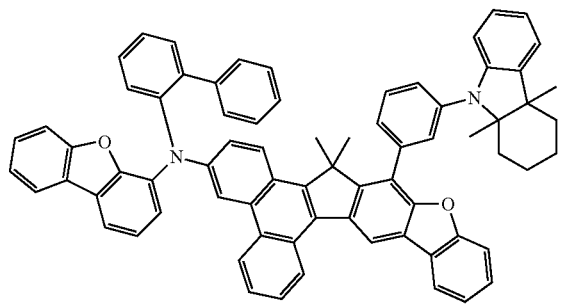
<Chemical Formula d220>
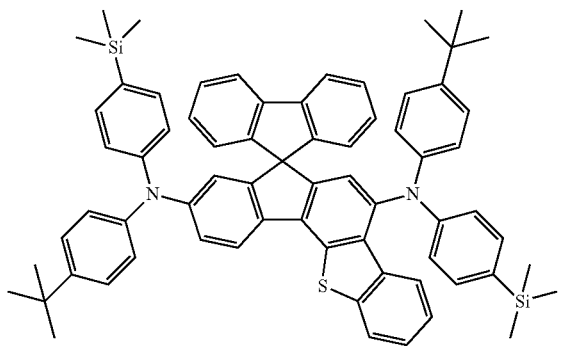
<Chemical Formula d221>
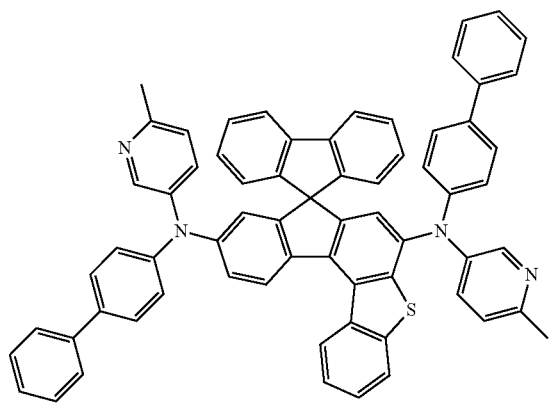

-continued
<Chemical Formula d222>
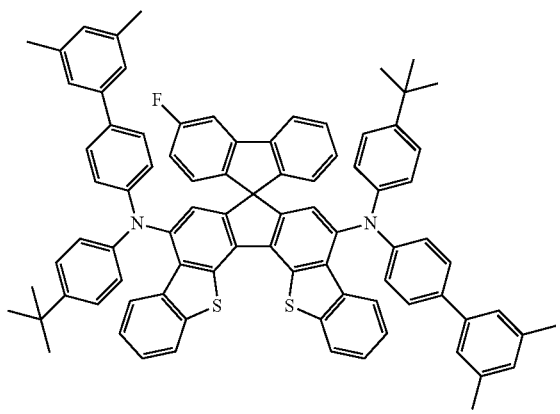
<Chemical Formula d223>
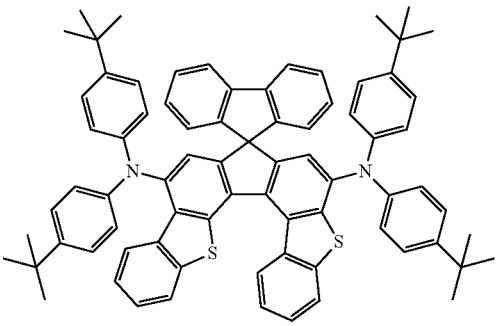
<Chemical Formula d224>
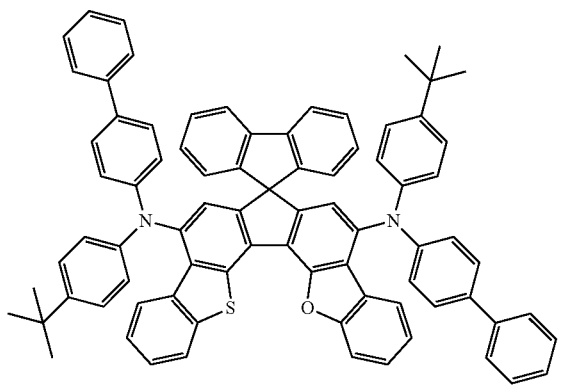
<Chemical Formula d225>
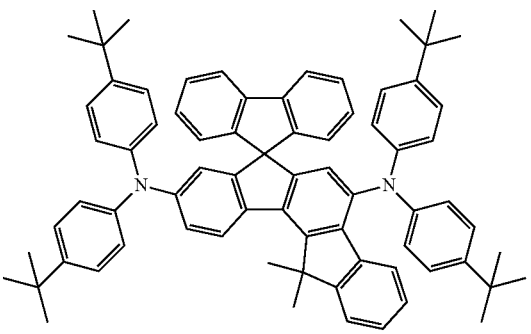
<Chemical Formula d226>
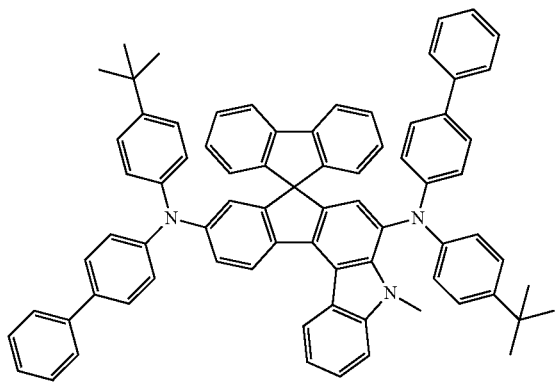
<Chemical Formula d227>
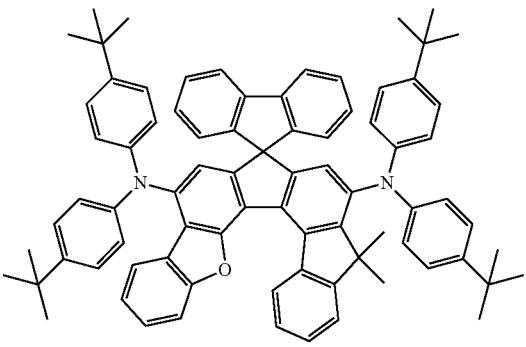
<Chemical Formula d228>
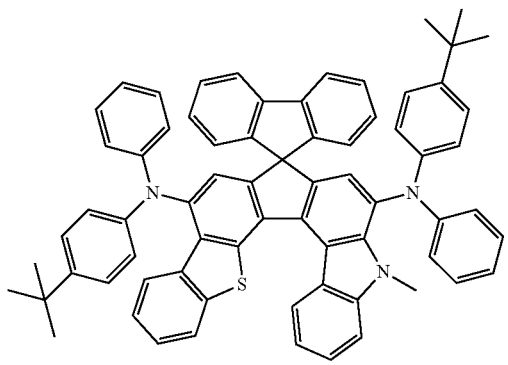
<Chemical Formula d229>
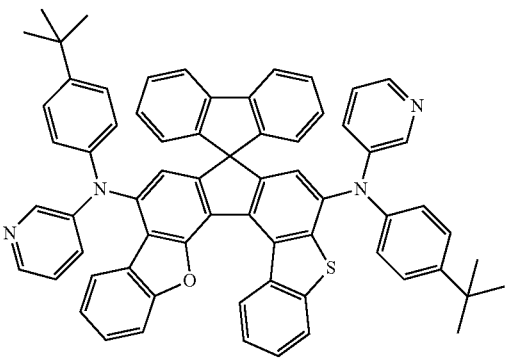

-continued
<Chemical Formula d230>
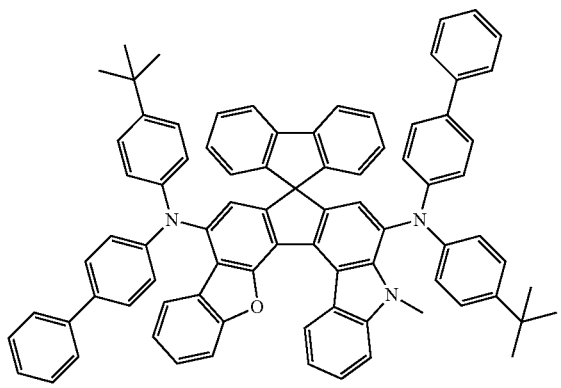
<Chemical Formula d232>
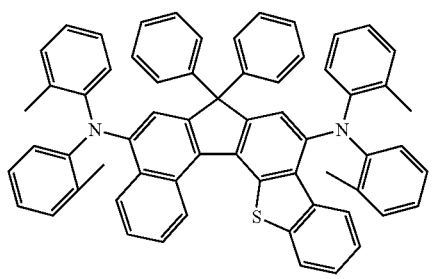
<Chemical Formula d234>
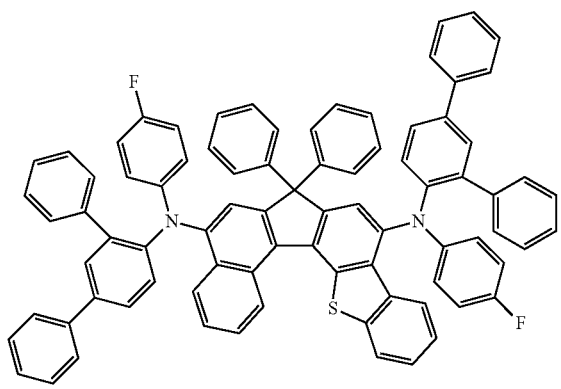
<Chemical Formula d236>
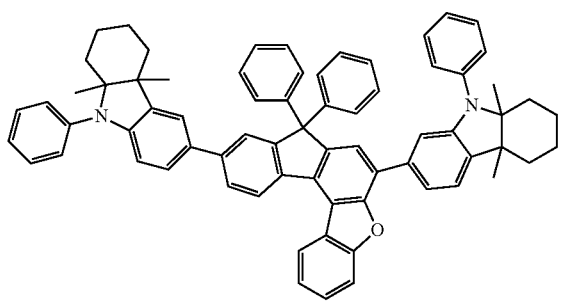
<Chemical Formula d231>
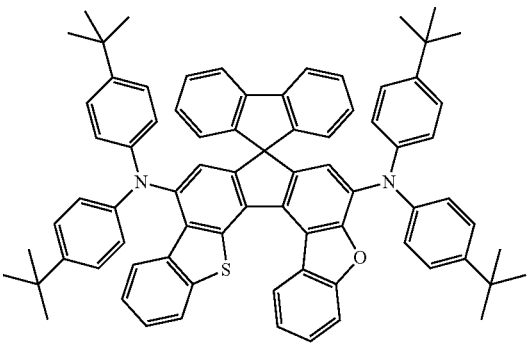
<Chemical Formula d233>
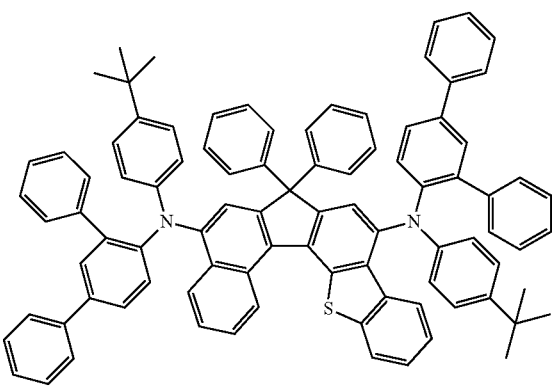
<Chemical Formula d235>
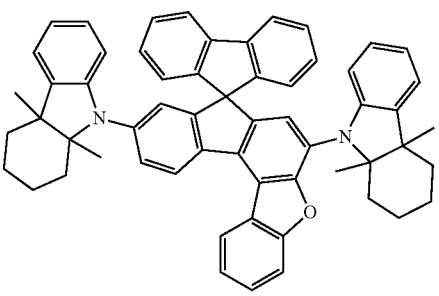
<Chemical Formula d237>
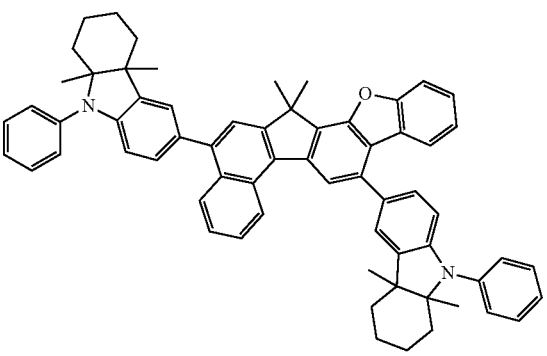

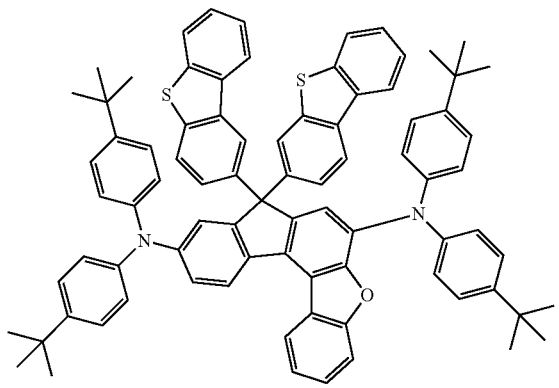
<Chemical Formula d238>
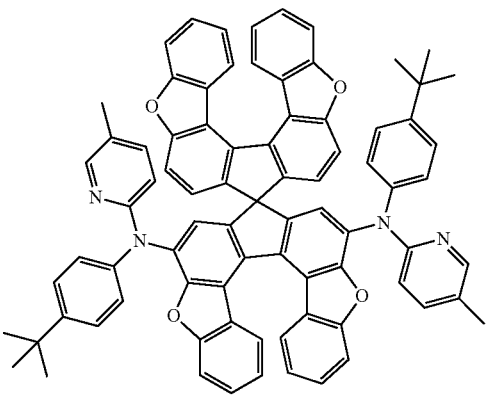
<Chemical Formula d239>
In addition, the compound represented by [Chemical Formula D3] may be any one selected from compounds of <Chemical Formula D 101> to <Chemical Formula D130>:
<Chemical Formula D 101>
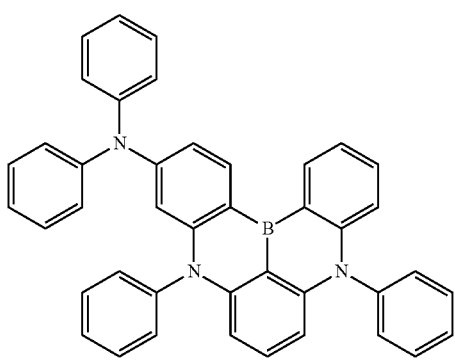
<Chemical Formula D 102>
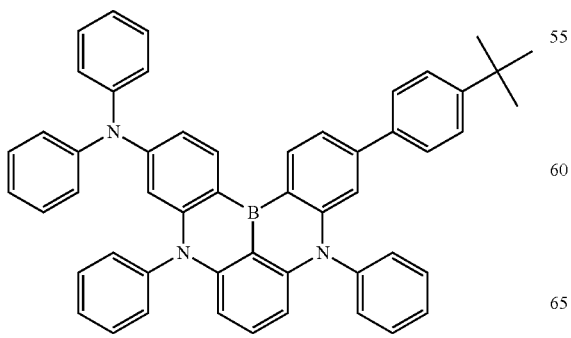
-continued
<Chemical Formula D 103>
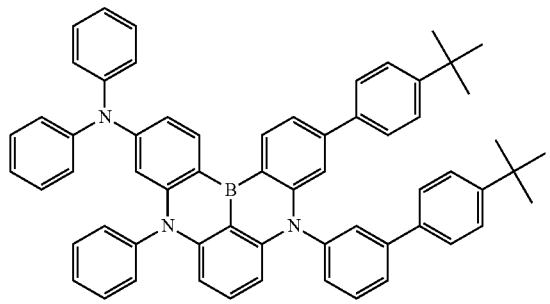
<Chemical Formula D 104>
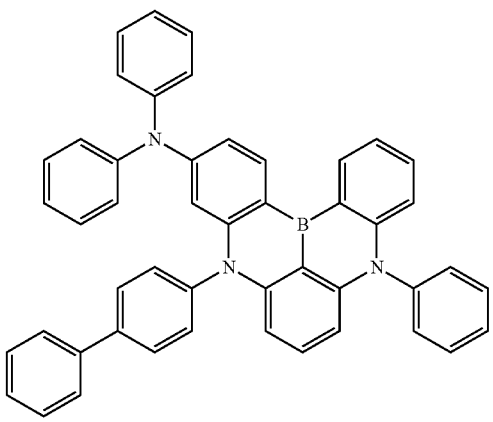

<Chemical Formula D 105>
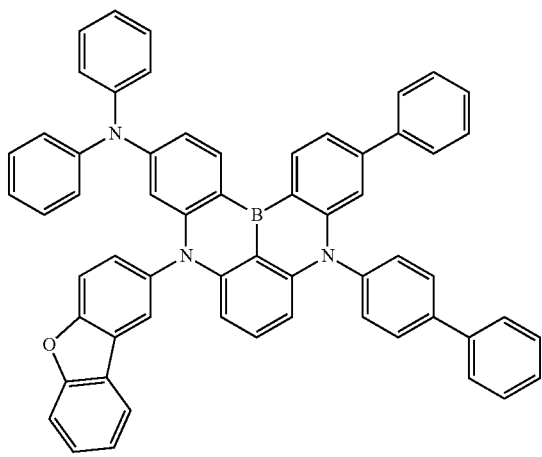
<Chemical Formula D 106>
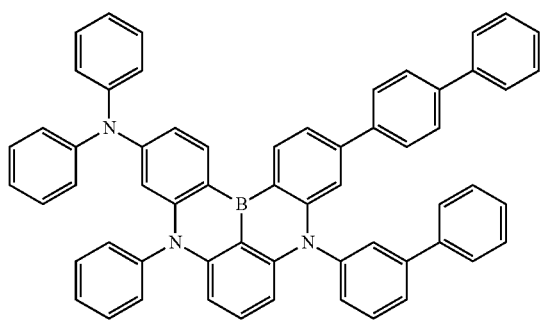
<Chemical Formula D 107>
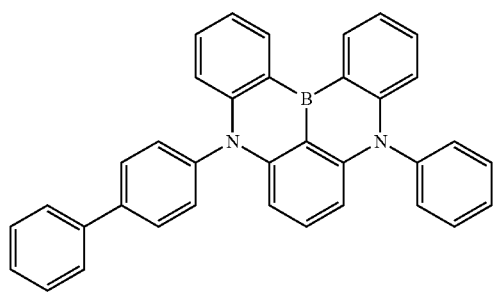
<Chemical Formula D 108>
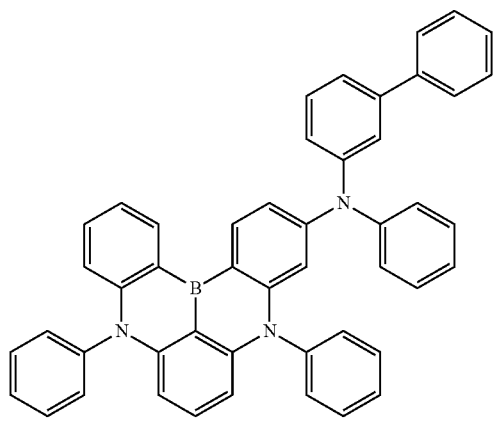
<Chemical Formula D 109>
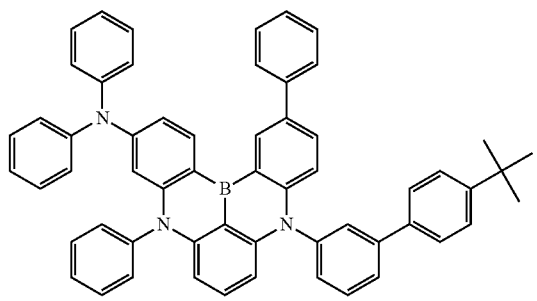
<Chemical Formula D 110>
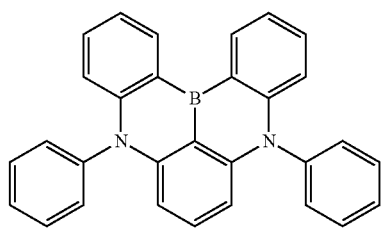
<Chemical Formula D 111>
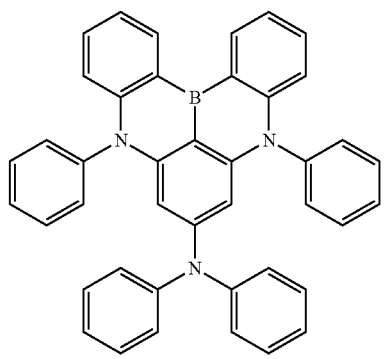
<Chemical Formula D 112>
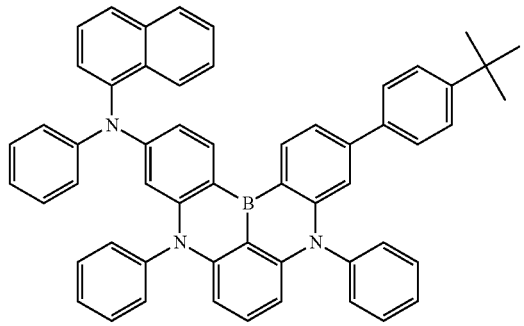

-continued
<Chemical Formula D 113>
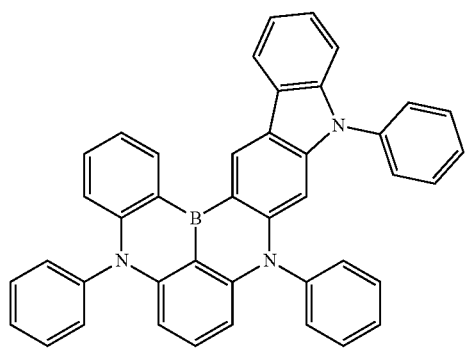
<Chemical Formula D 114>
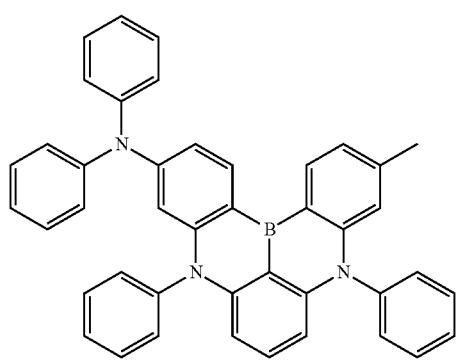
<Chemical Formula D 115>
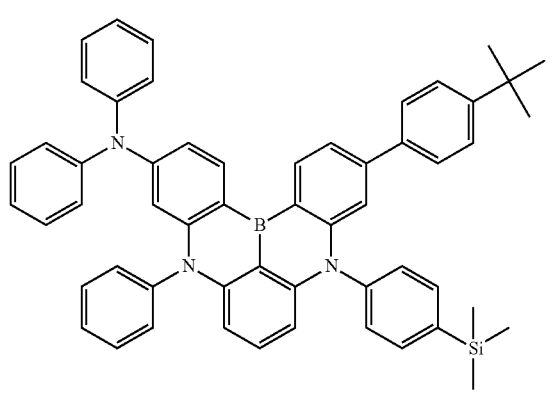
<Chemical Formula D 116>
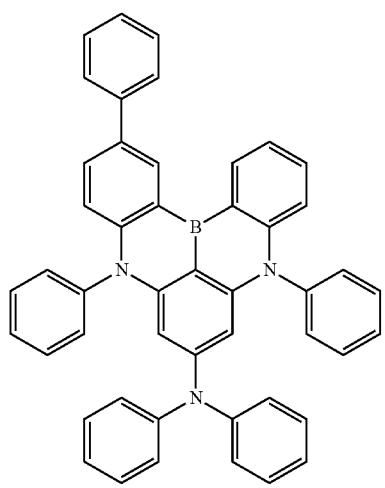
-continued
<Chemical Formula D 117>
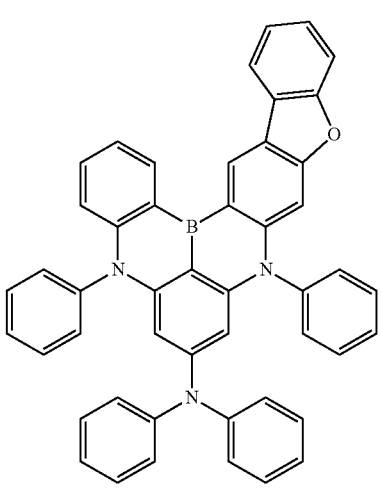
<Chemical Formula D 118>
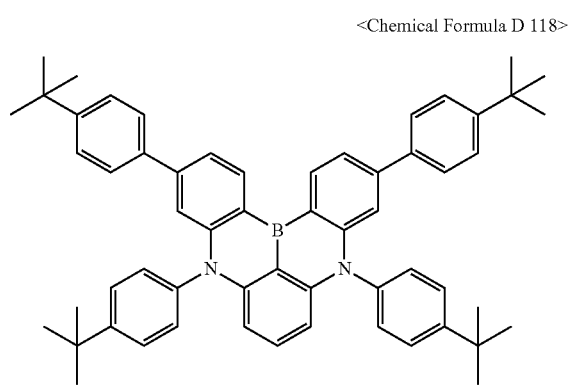
<Chemical Formula D 119>
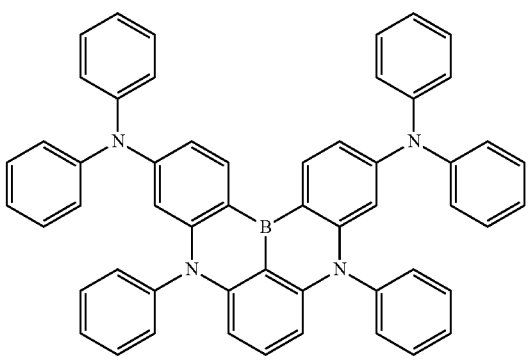

<Chemical Formula D 120>
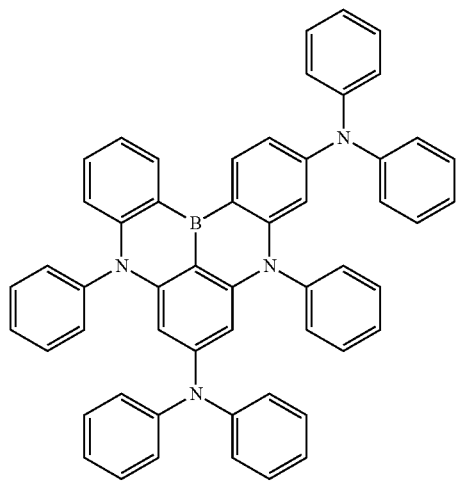
<Chemical Formula D 121>
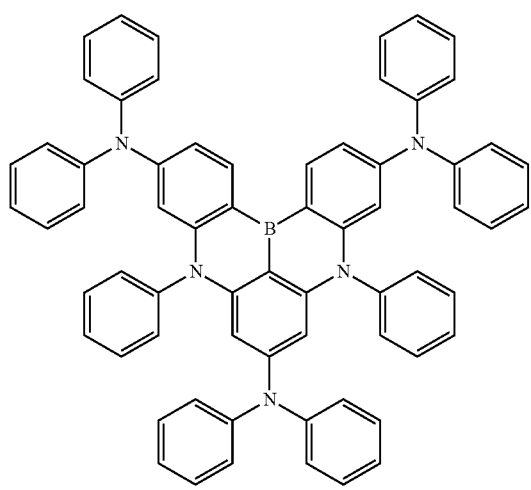
<Chemical Formula D 122>
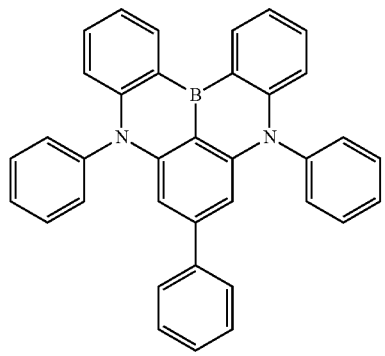
<Chemical Formula D 123>
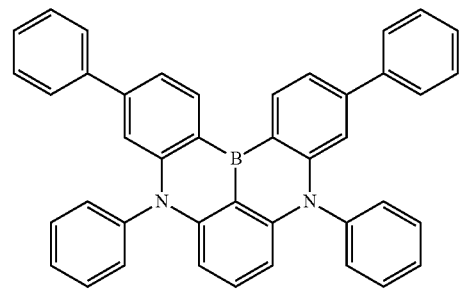
<Chemical Formula D 124>
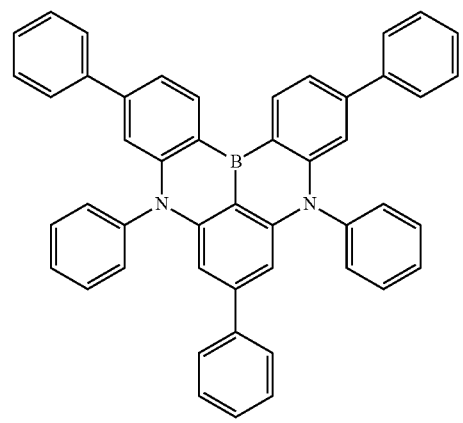
<Chemical Formula D 125>
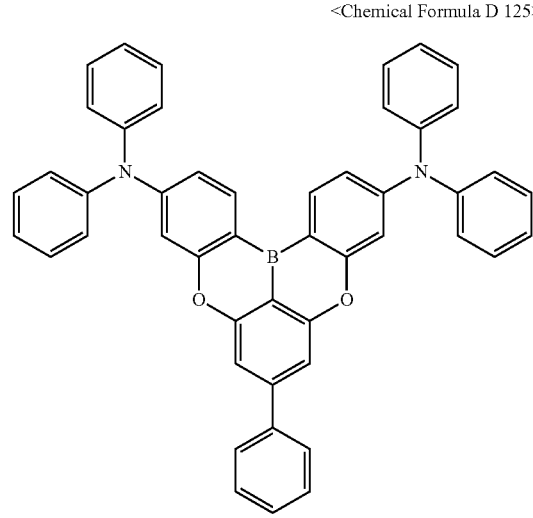

<Chemical Formula D 126>
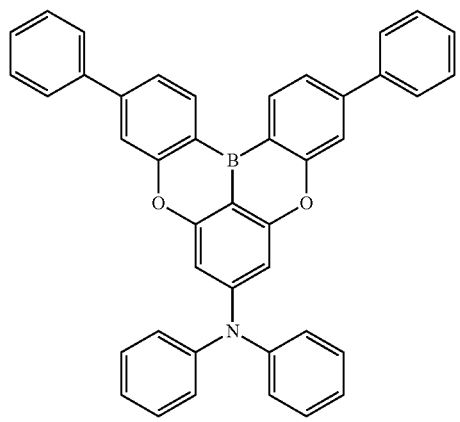
<Chemical Formula D 127>
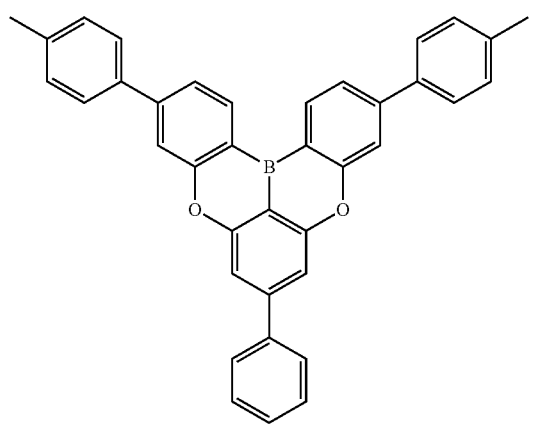
<Chemical Formula D 128>
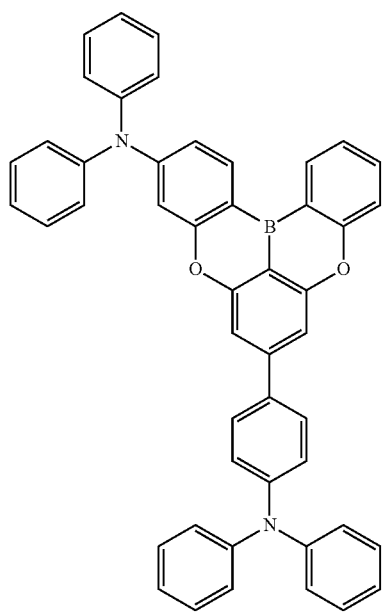
<Chemical Formula D 129>
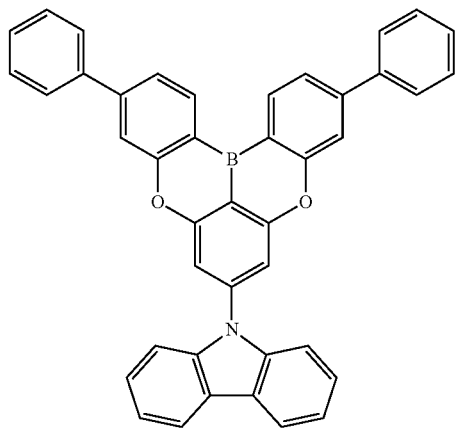
<Chemical Formula D 130>
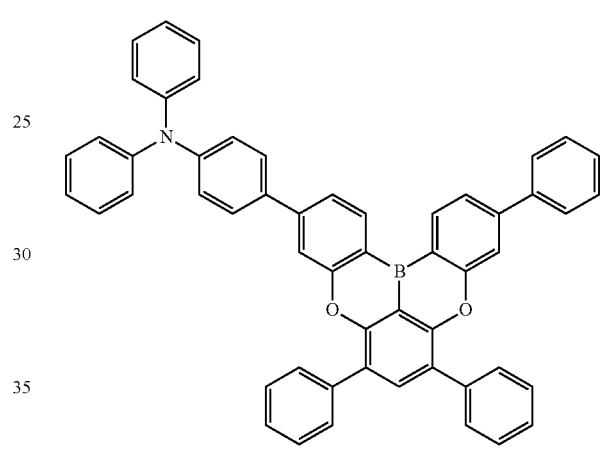
In addition, the compound represented by any one of [Chemical Formula D4] and [Chemical Formula D5] may be any one selected from compounds of <Chemical Formula D201> to <Chemical Formula D280>:
[Chemical Formula D201]
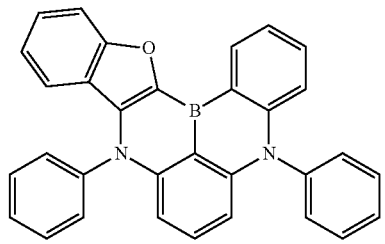
[Chemical Formula D202]
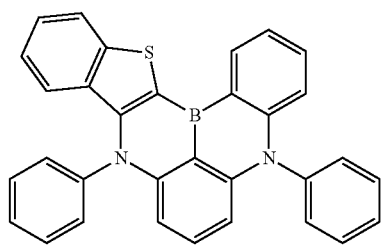

[Chemical Formula D203]
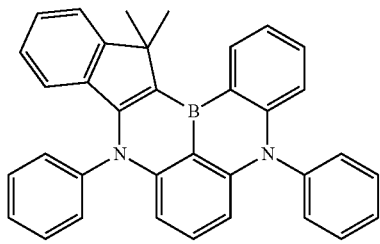
[Chemical Formula D204]
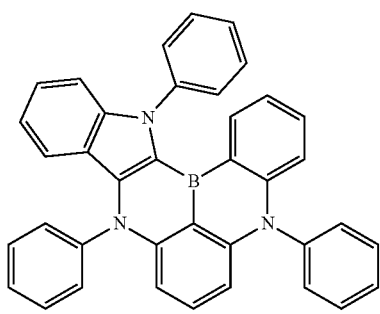
[Chemical Formula D205]
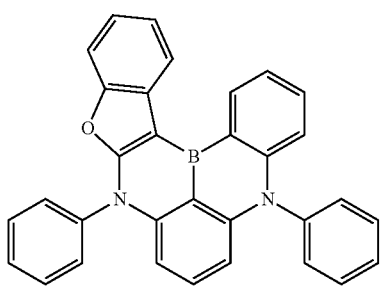
[Chemical Formula D206]
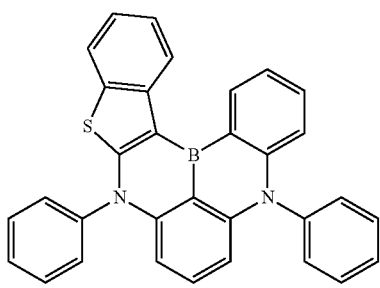
[Chemical Formula D207]
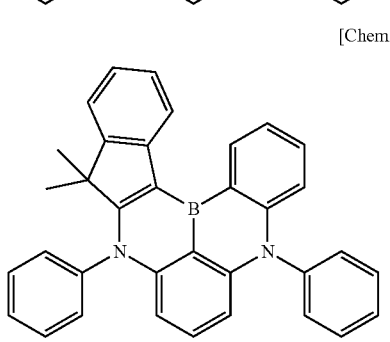
[Chemical Formula D208]
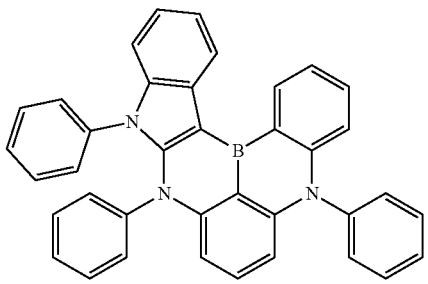
[Chemical Formula D209]
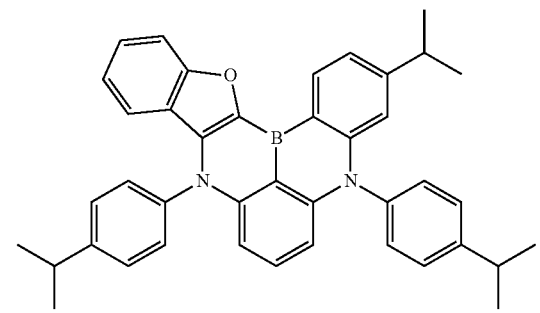
[Chemical Formula D210]
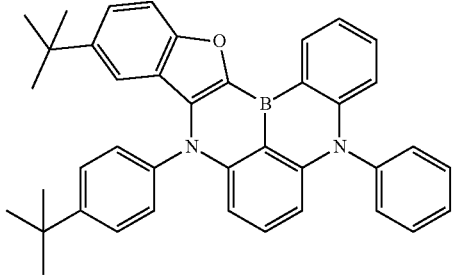
[Chemical Formula D211]

[Chemical Formula D212]
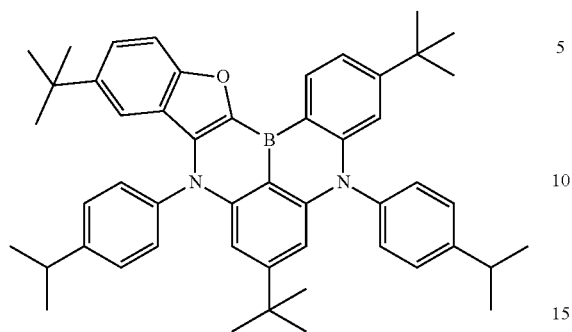
[Chemical Formula D216]
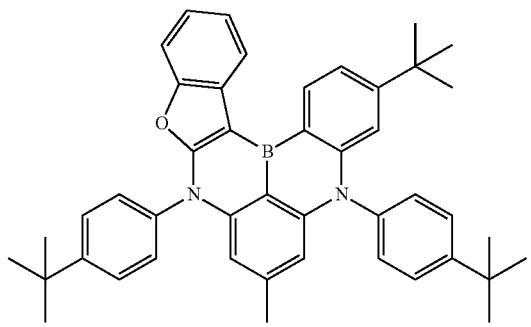
[Chemical Formula D213]
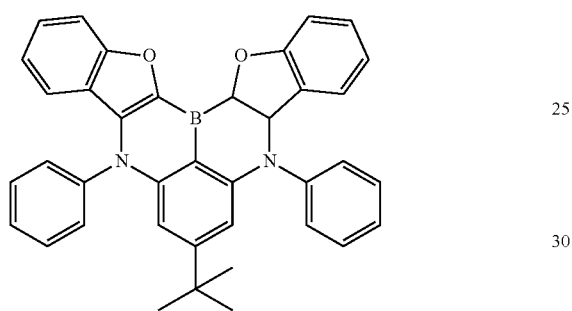
[Chemical Formula D217]
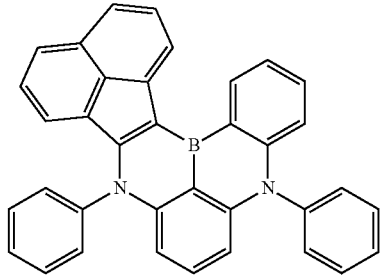
[Chemical Formula D214]
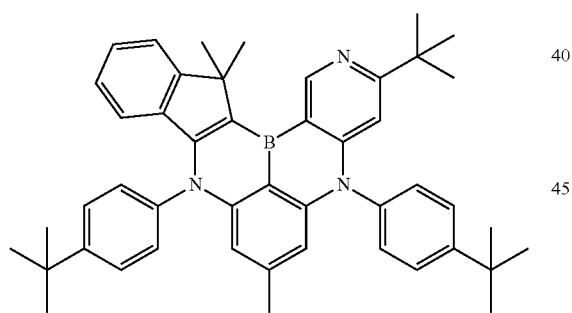
[Chemical Formula D218]
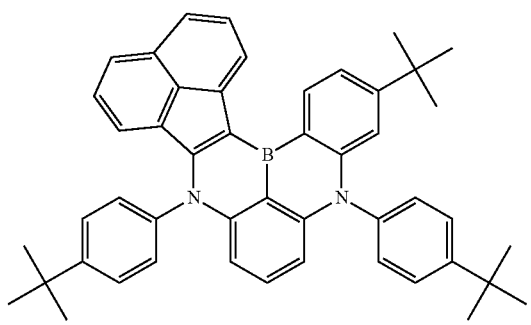
[Chemical Formula D215]
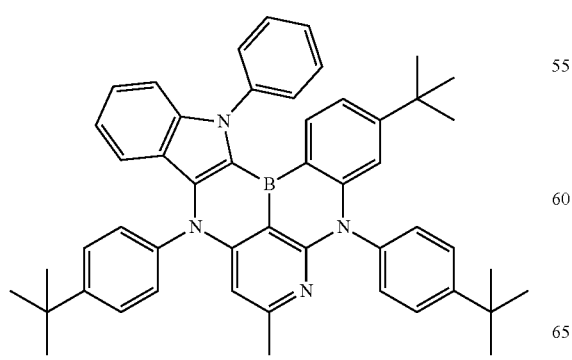
[Chemical Formula D219]
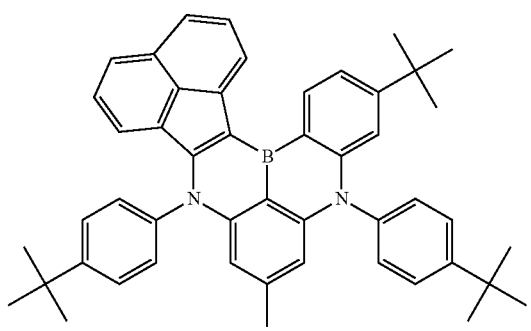

[Chemical Formula D220]
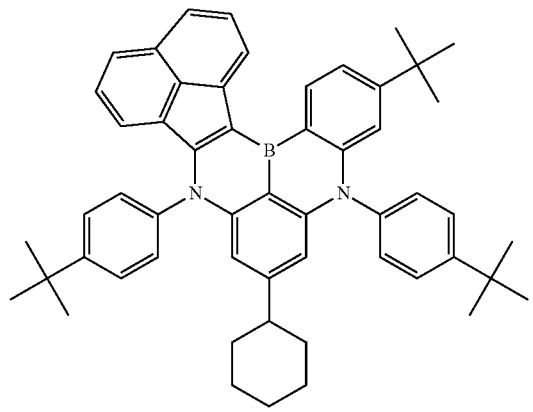
[Chemical Formula D221]
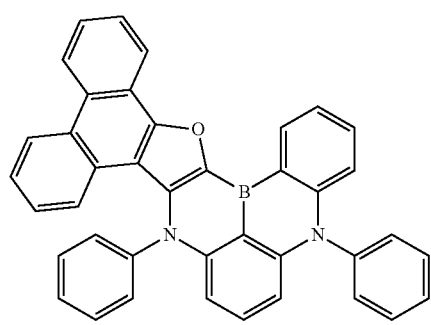
[Chemical Formula D222]
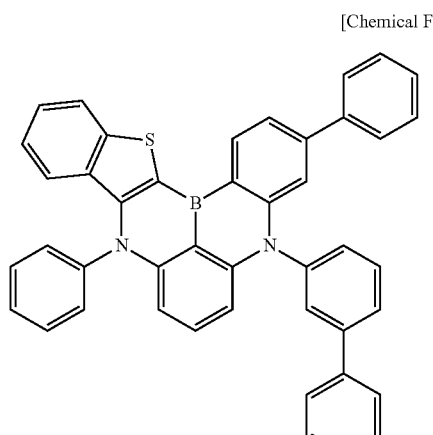
[Chemical Formula D223]
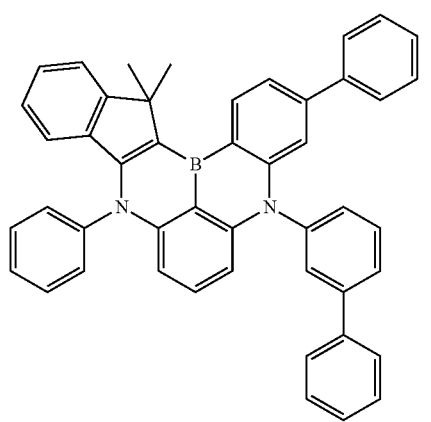
[Chemical Formula D224]
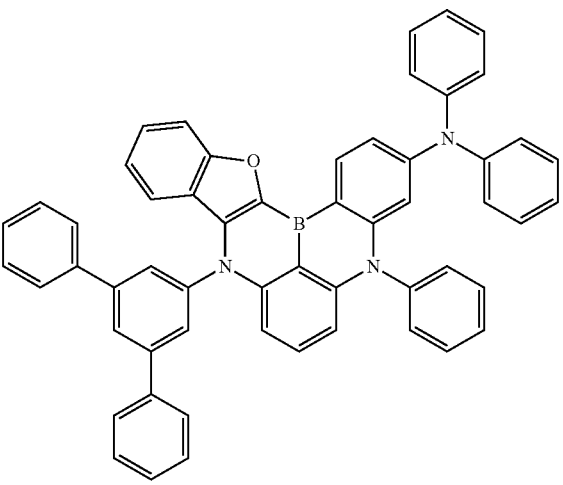
[Chemical Formula D225]
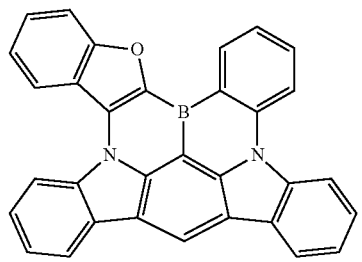
[Chemical Formula D226]
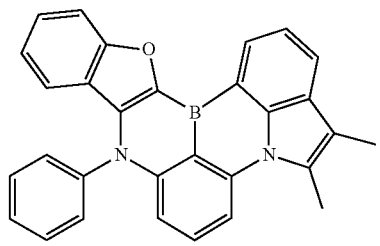
[Chemical Formula D227]
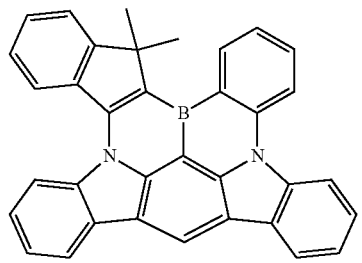

[Chemical Formula D228]
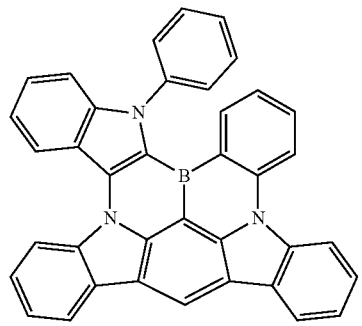
[Chemical Formula D229]
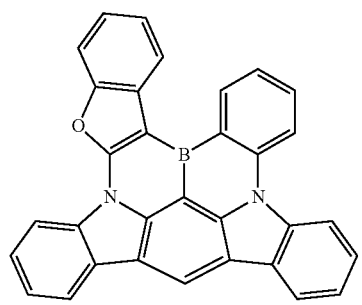
[Chemical Formula D230]
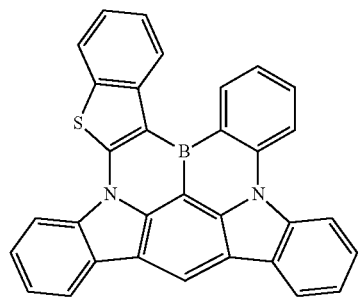
[Chemical Formula D231]
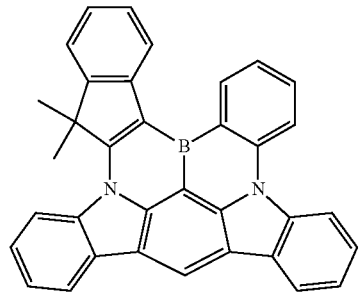
[Chemical Formula D232]
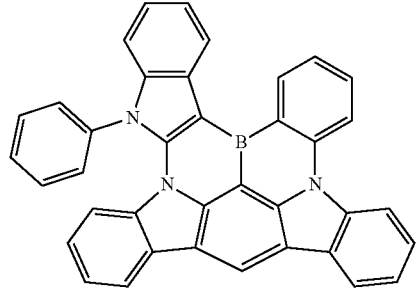
[Chemical Formula D233]
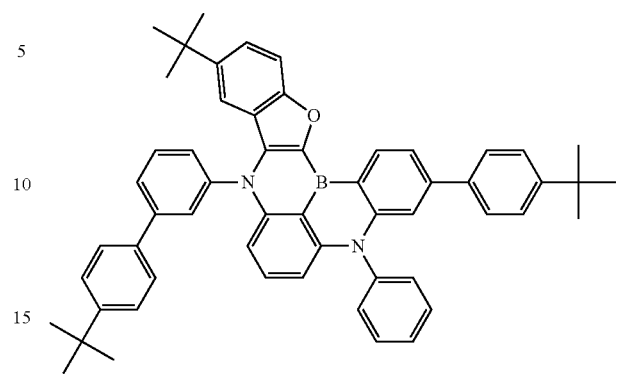
[Chemical Formula D234]
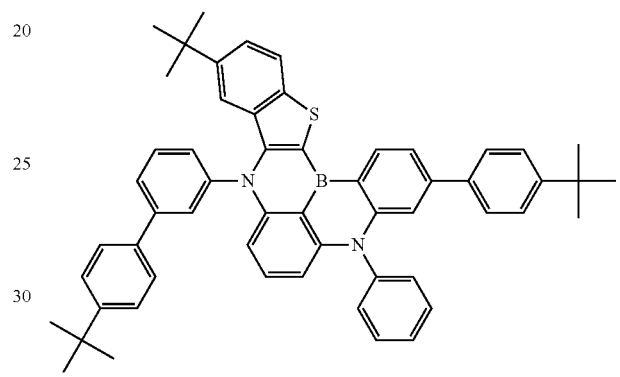
[Chemical Formula D235]
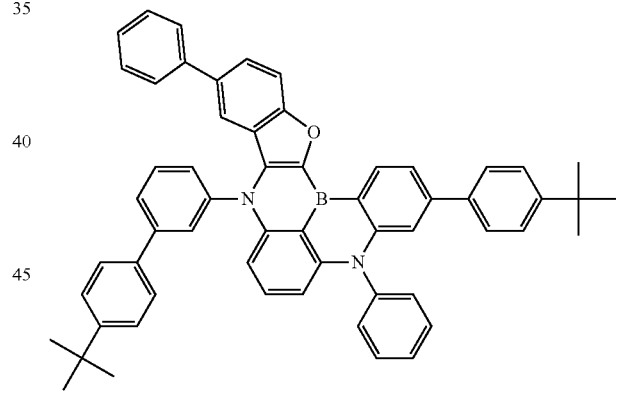
[Chemical Formula D236]
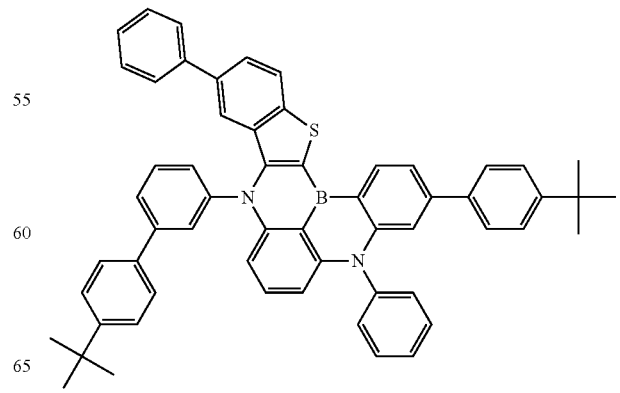

[Chemical Formula D237]
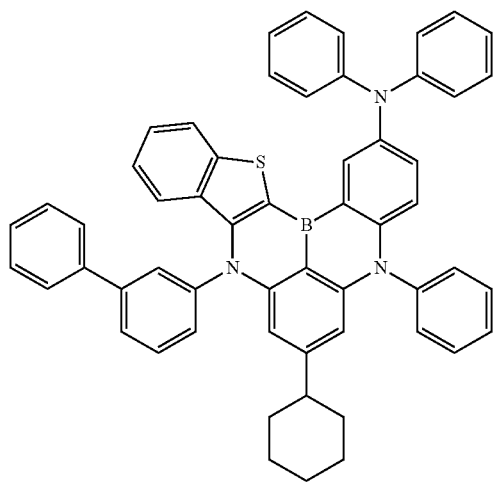
[Chemical Formula D238]
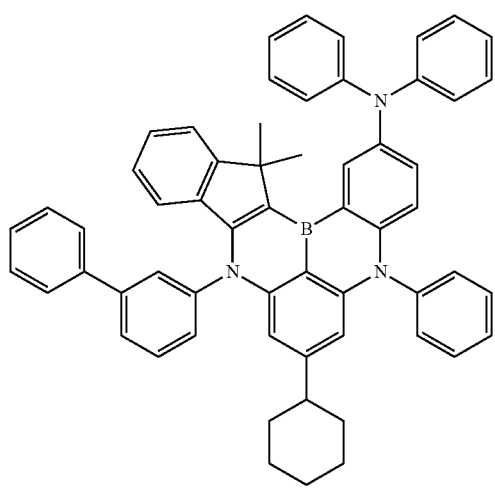
[Chemical Formula D239]
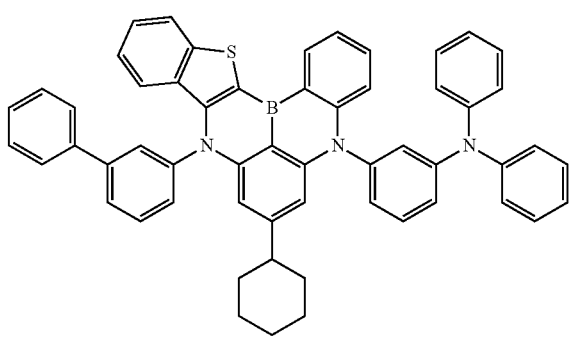
[Chemical Formula D240]
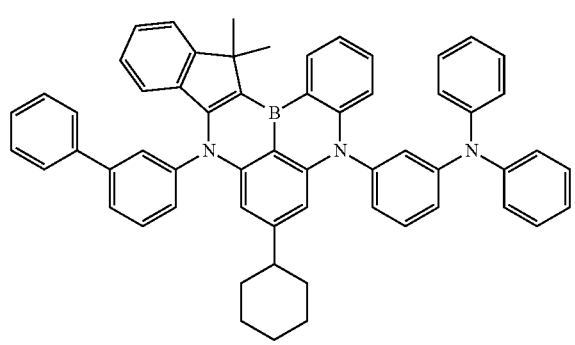
[Chemical Formula D241]
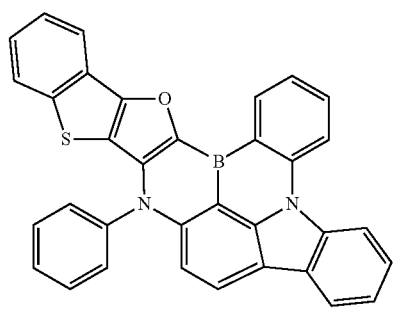
[Chemical Formula D242]
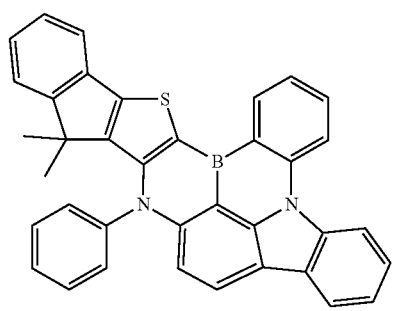
[Chemical Formula D243]
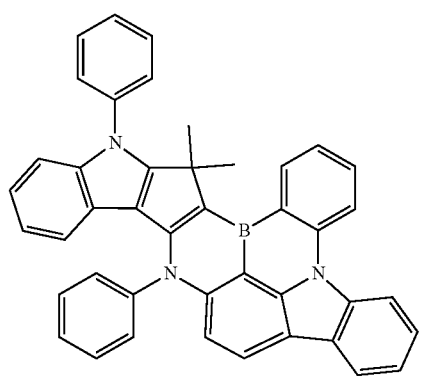

[Chemical Formula D244]
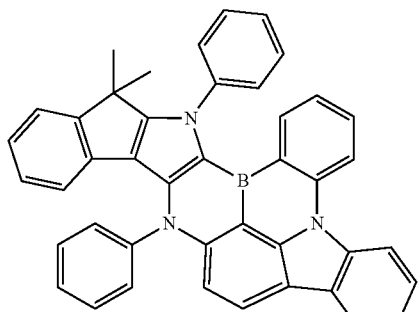
[Chemical Formula D245]
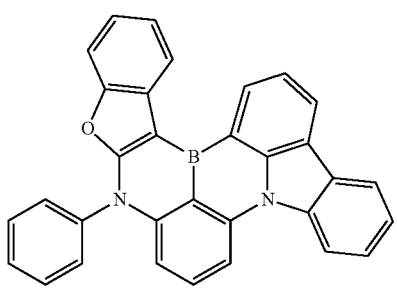
[Chemical Formula D246]
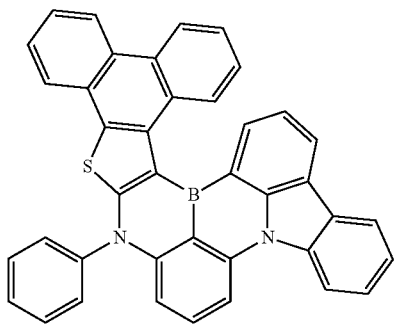
[Chemical Formula D247]
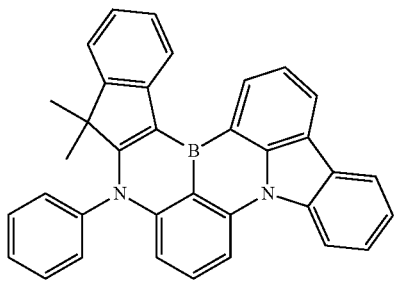
[Chemical Formula D248]
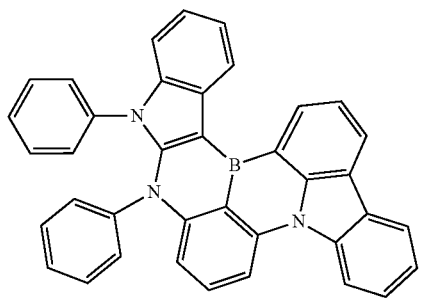
[Chemical Formula D249]
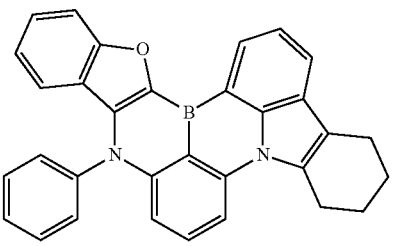
[Chemical Formula D250]
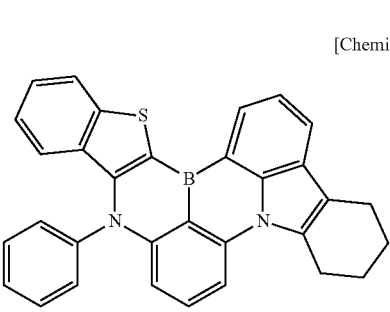
[Chemical Formula D251]
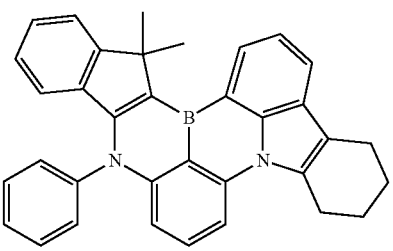
[Chemical Formula D252]
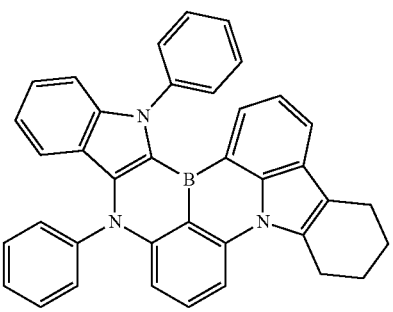
[Chemical Formula D253]
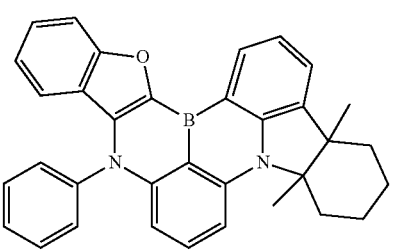

[Chemical Formula D254]
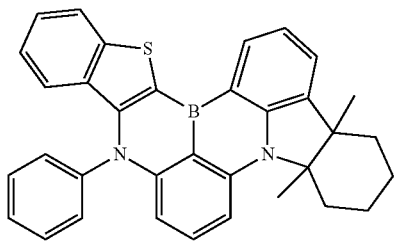
[Chemical Formula D255]
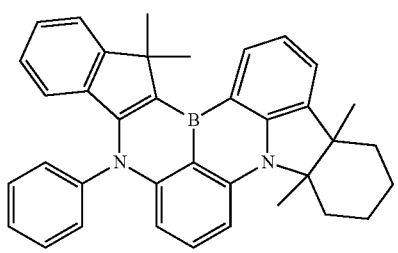
[Chemical Formula D256]
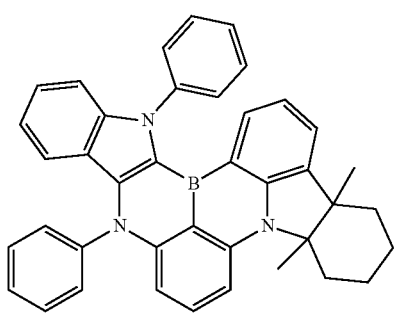
[Chemical Formula D257]
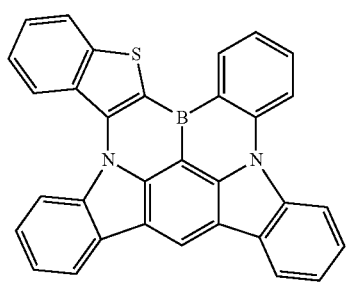
[Chemical Formula D258]
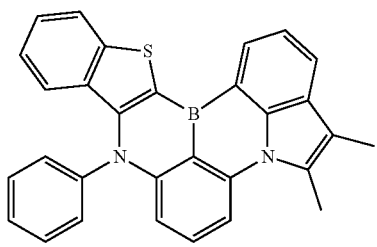
[Chemical Formula D259]
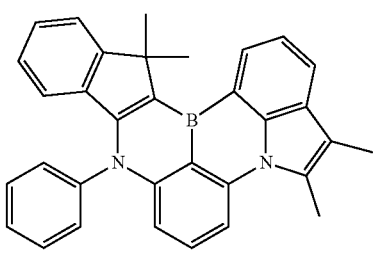
[Chemical Formula D260]
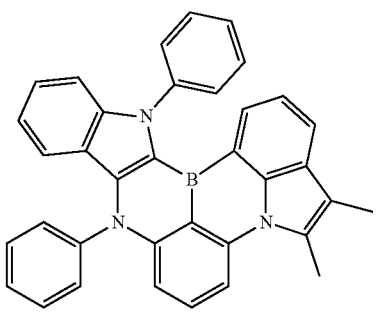
[Chemical Formula D261]
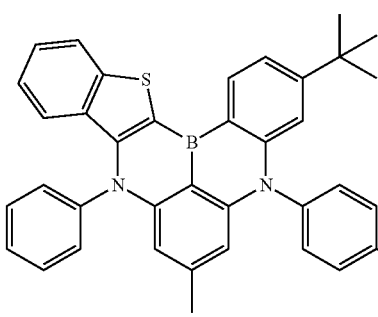
[Chemical Formula D262]
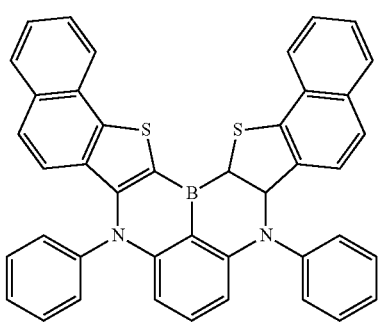
[Chemical Formula D263]
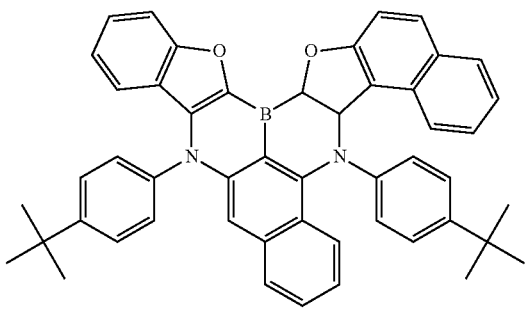

[Chemical Formula D264]
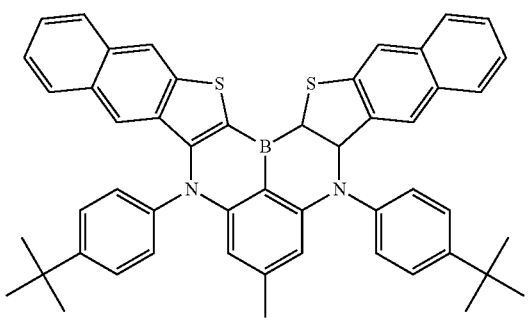
[Chemical Formula D265]
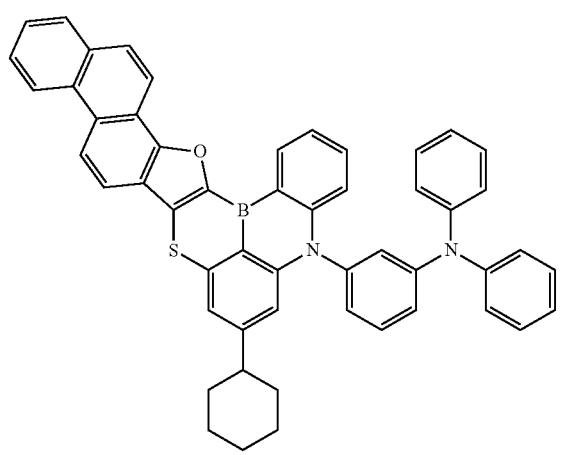
[Chemical Formula D266]
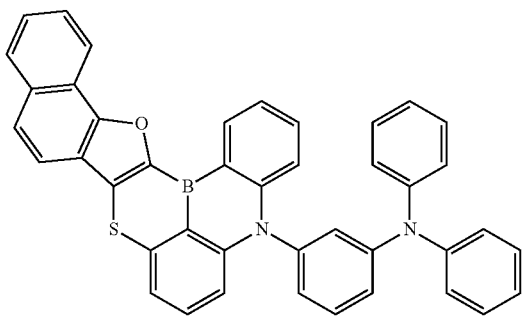
[Chemical Formula D267]
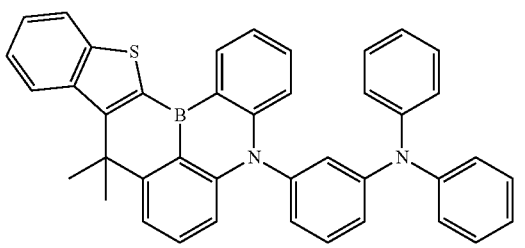
[Chemical Formula D268]
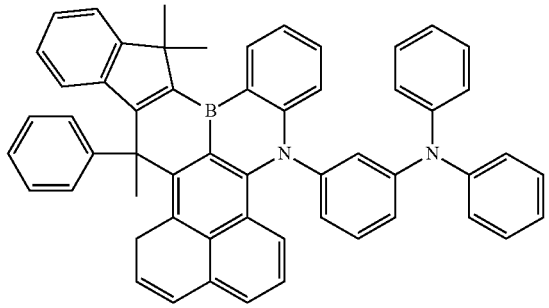
[Chemical Formula D269]
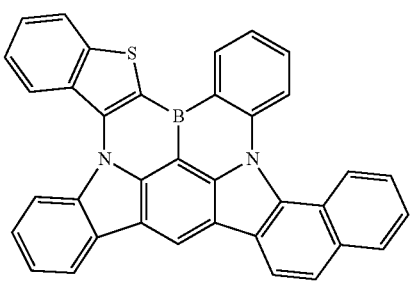
[Chemical Formula D270]
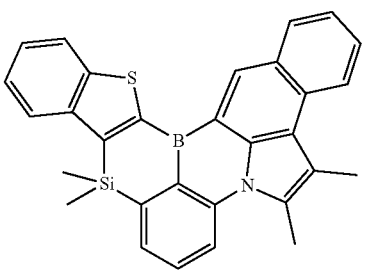
[Chemical Formula D271]
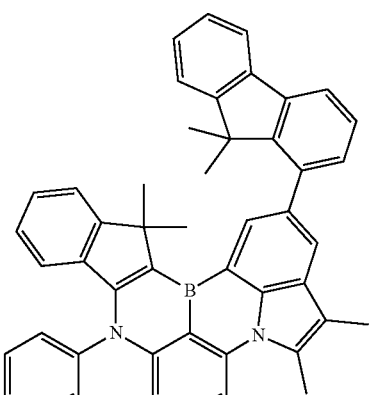
[Chemical Formula D272]
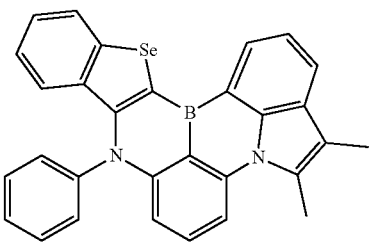

[Chemical Formula D273]
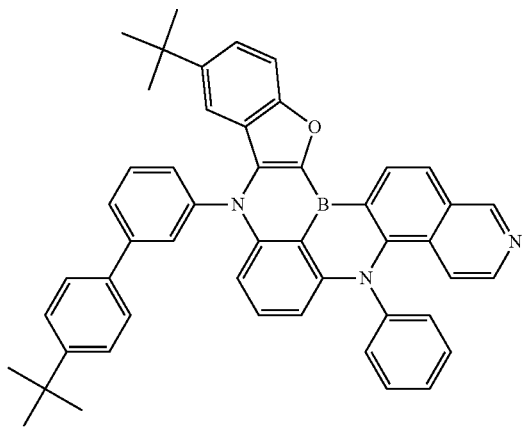
[Chemical Formula D274]
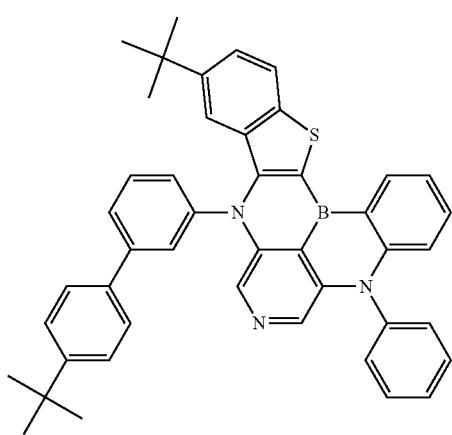
[Chemical Formula D275]
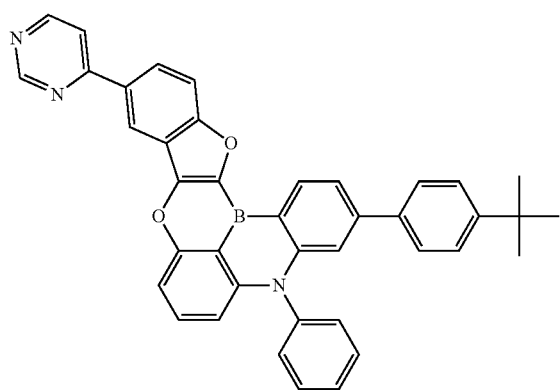
[Chemical Formula D276]
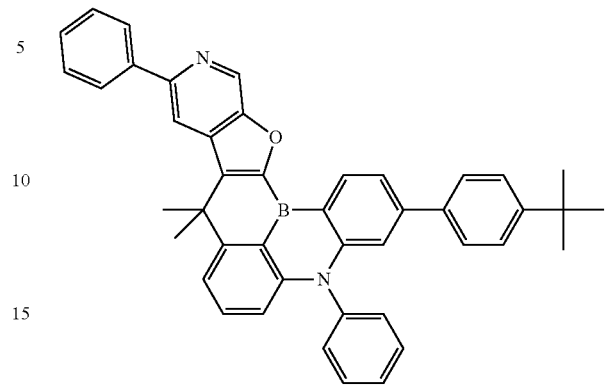
[Chemical Formula D277]
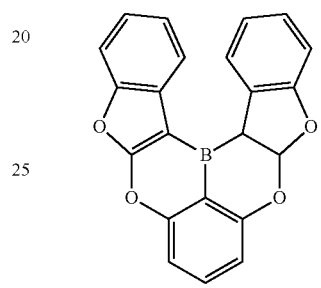
[Chemical Formula D278]
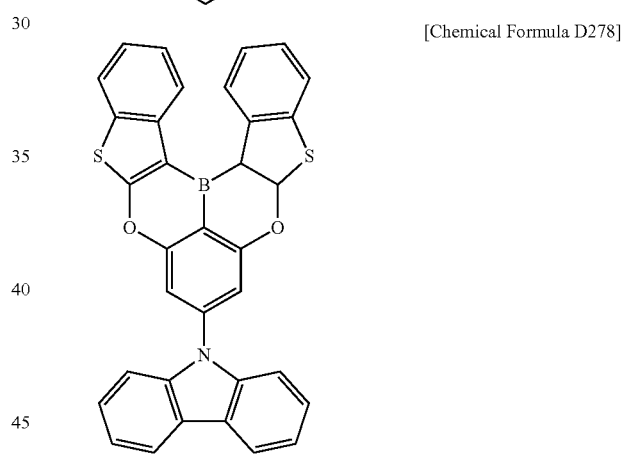
[Chemical Formula D279]
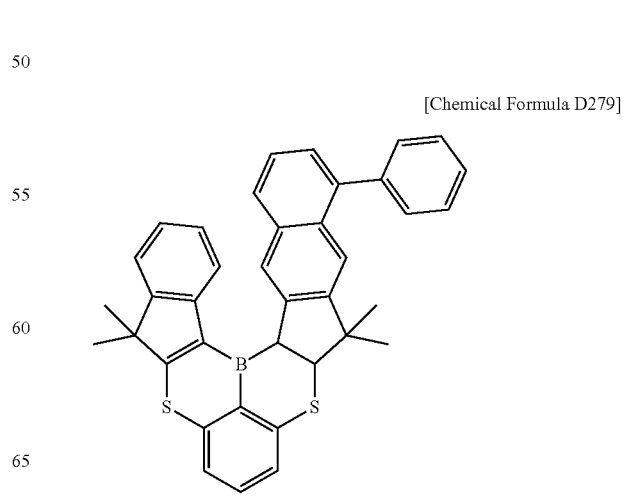

[Chemical Formula D280]

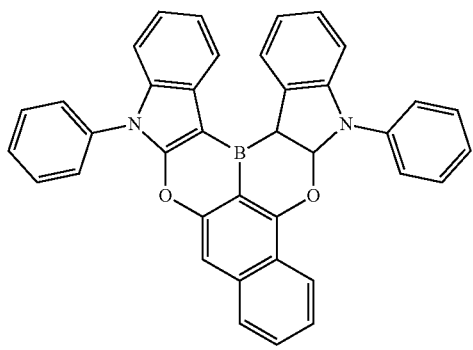

<Chemical Formula D304>

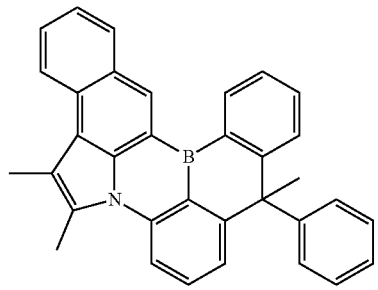

In addition, the compound represented by any one of [Chemical Formula D6] and [Chemical Formula D7] may be selected from the compounds of the following <Chemical Formula D301> to <Chemical Formula D387>:

<Chemical Formula D305>

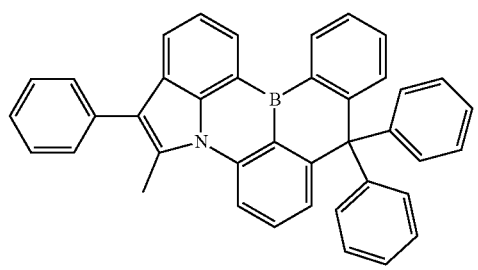

<Chemical Formula D301>

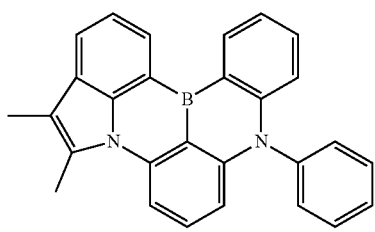

<Chemical Formula D306>

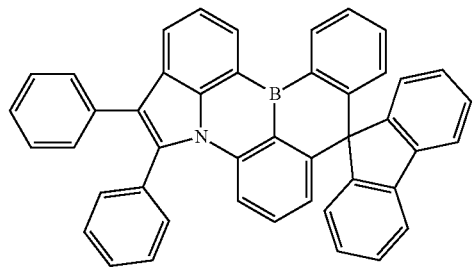

<Chemical Formula D302>

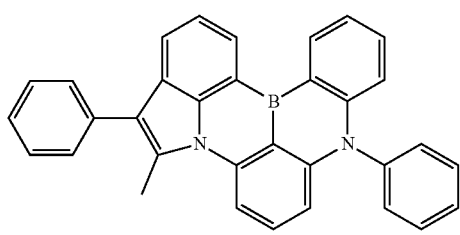

<Chemical Formula D307>

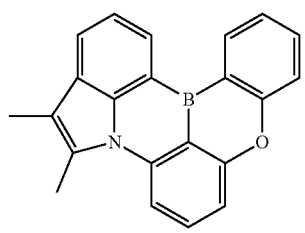

<Chemical Formula D303>

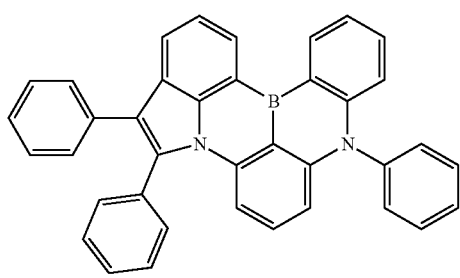

<Chemical Formula D308>

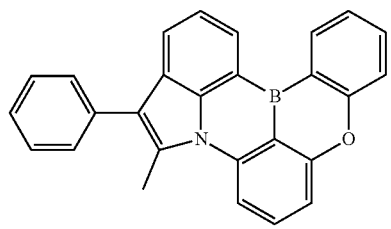

183
-continued
<Chemical Formula D309>
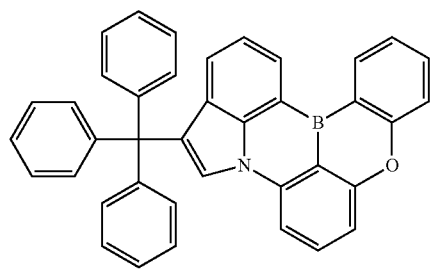
<Chemical Formula D310>
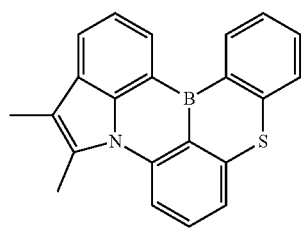
<Chemical Formula D311>
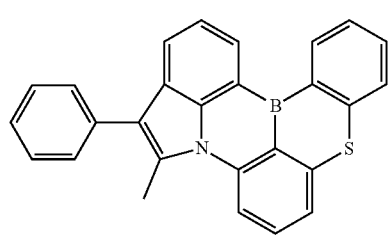
<Chemical Formula D312>
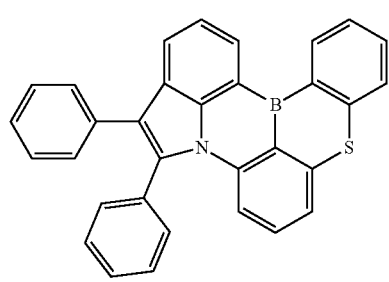
<Chemical Formula D313>
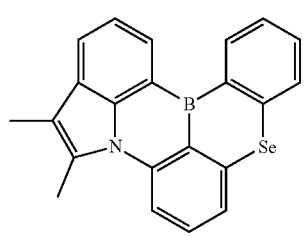
<Chemical Formula D314>
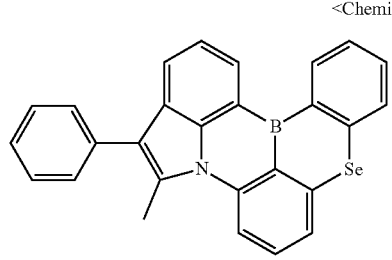
184
-continued
<Chemical Formula D315>
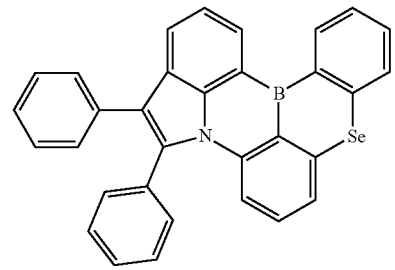
<Chemical Formula D316>
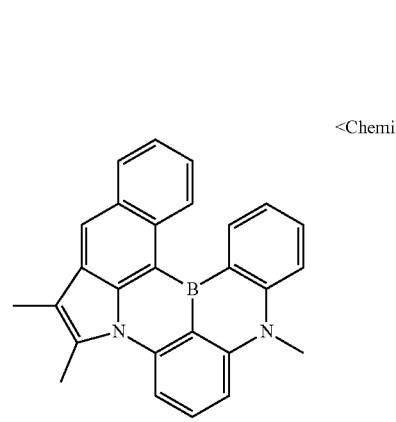
<Chemical Formula D317>
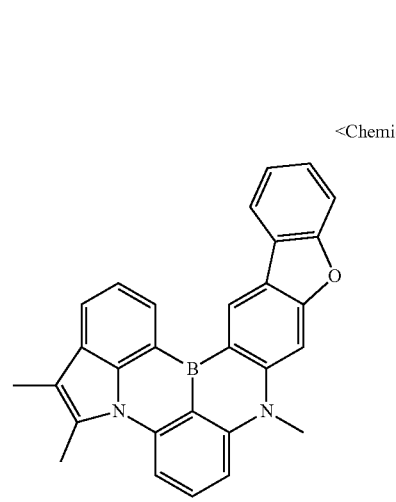
<Chemical Formula D318>
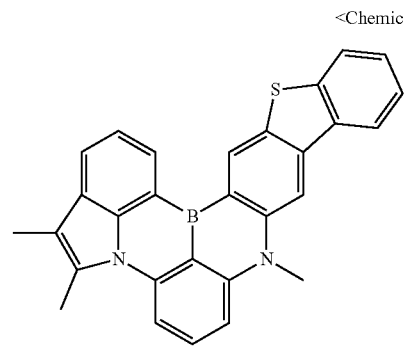

<Chemical Formula D319>
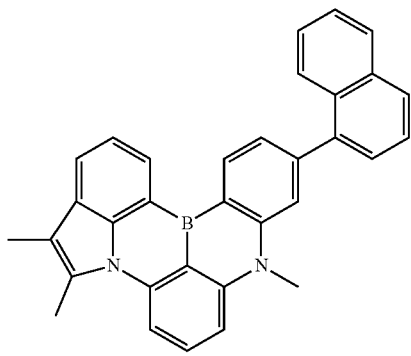
<Chemical Formula D320>
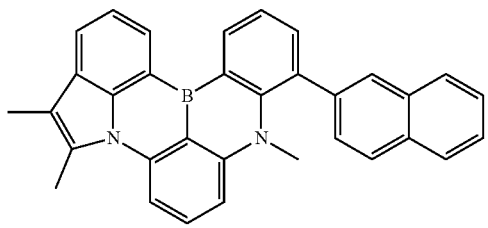
<Chemical Formula D321>
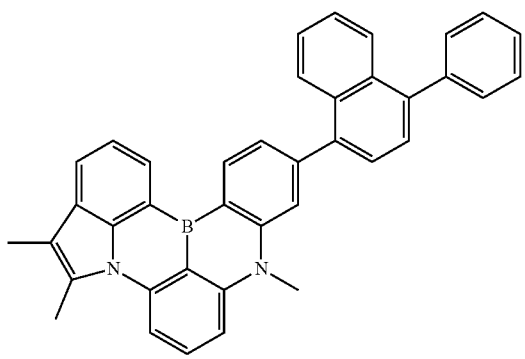
<Chemical Formula D322>
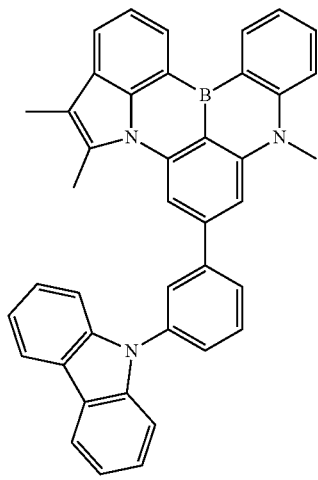
<Chemical Formula D323>
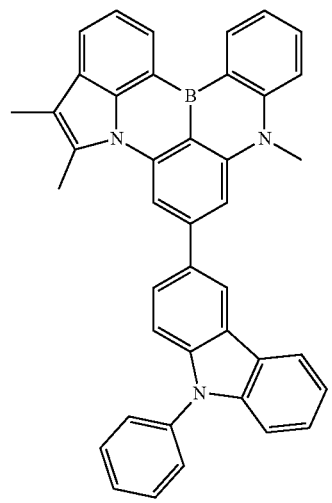
<Chemical Formula D324>
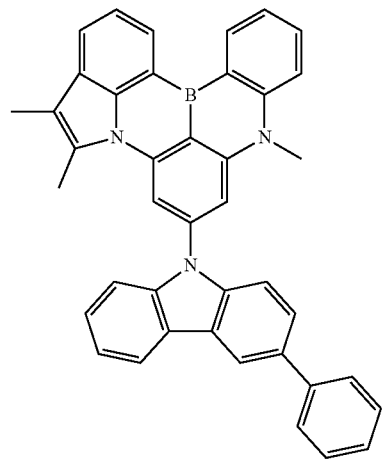
<Chemical Formula D325>
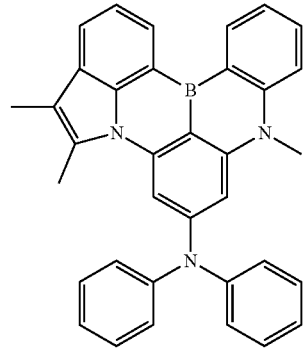

<Chemical Formula D326>
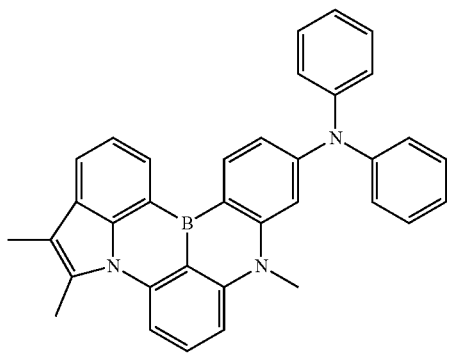
<Chemical Formula D327>
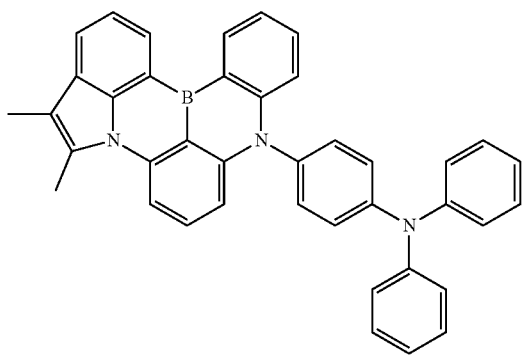
<Chemical Formula D328>
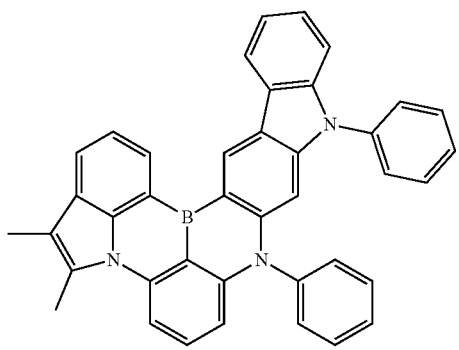
<Chemical Formula D329>
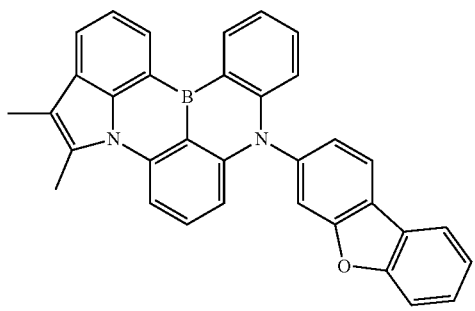
<Chemical Formula D330>
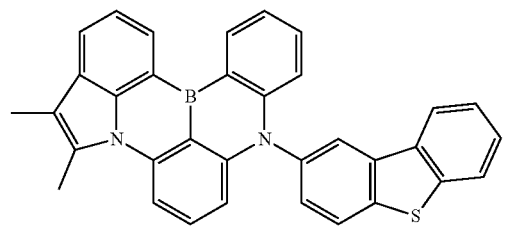
<Chemical Formula D331>
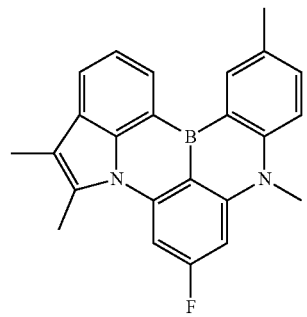
<Chemical Formula D332>
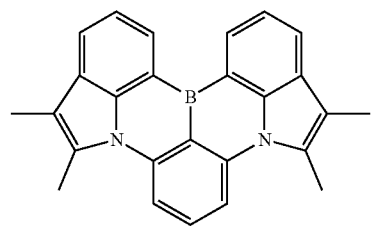
<Chemical Formula D333>
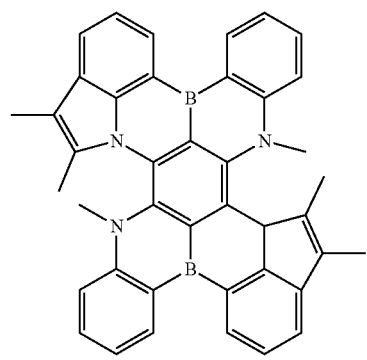
<Chemical Formula D334>
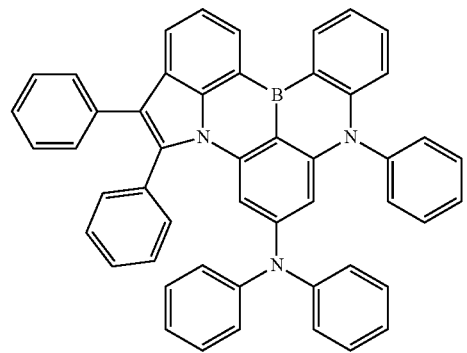

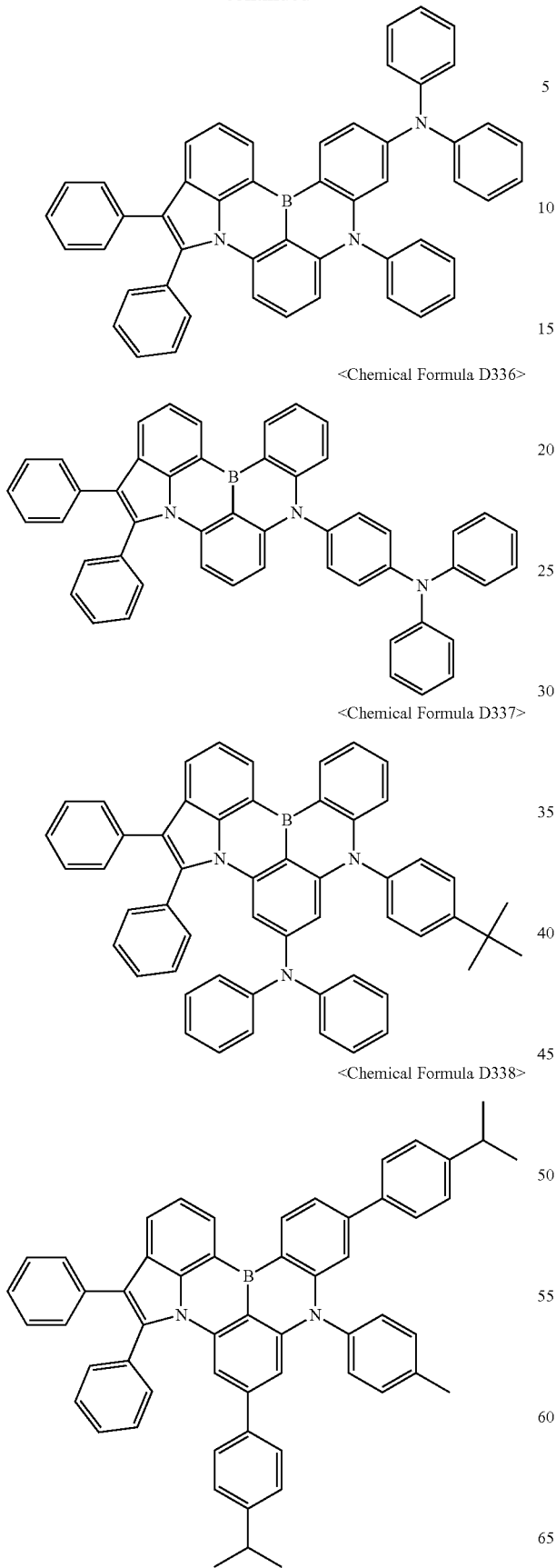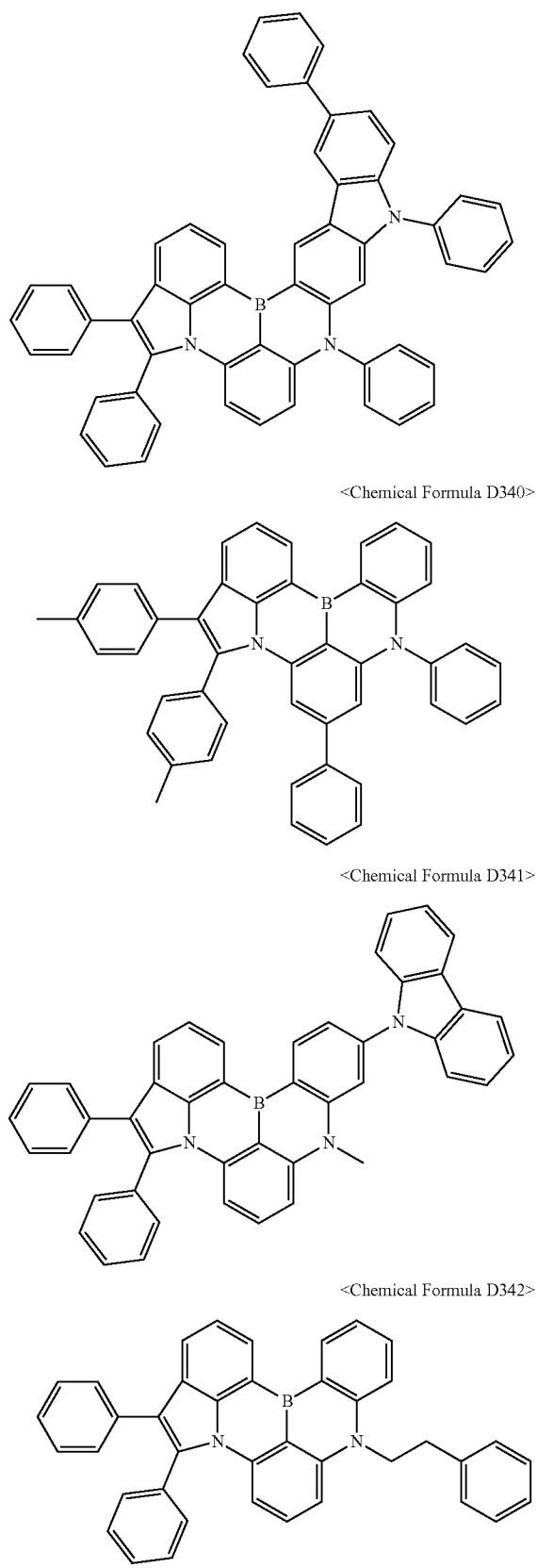

<Chemical Formula D343>
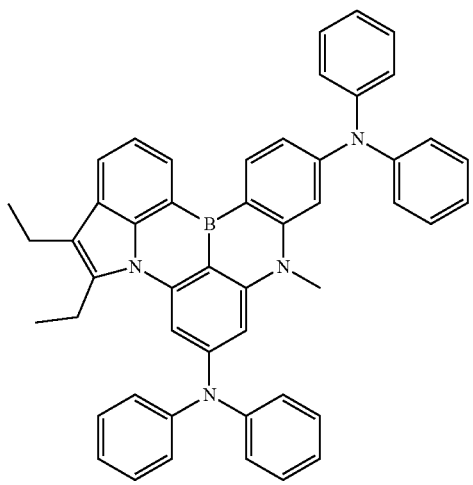
<Chemical Formula D344>
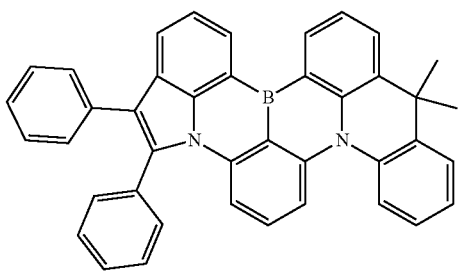
<Chemical Formula D345>
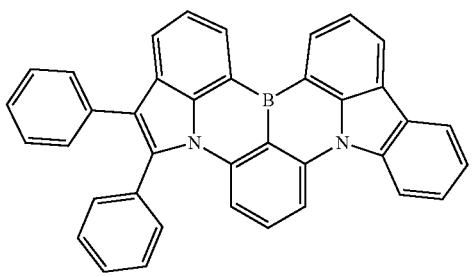
<Chemical Formula D346>
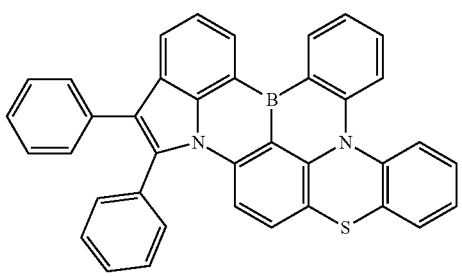
<Chemical Formula D347>
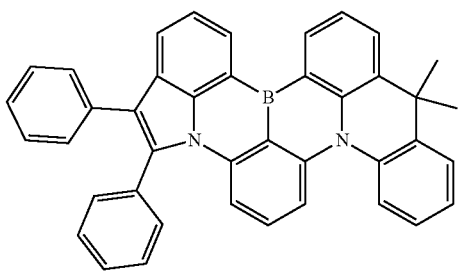
<Chemical Formula D348>
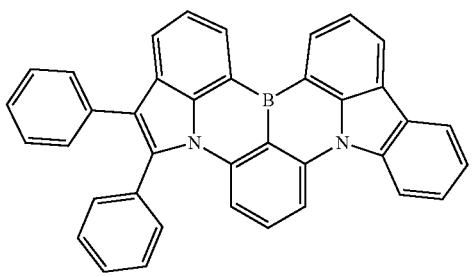
<Chemical Formula D349>
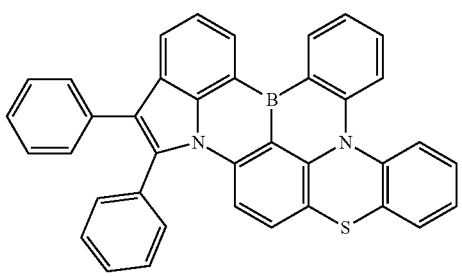
<Chemical Formula D350>
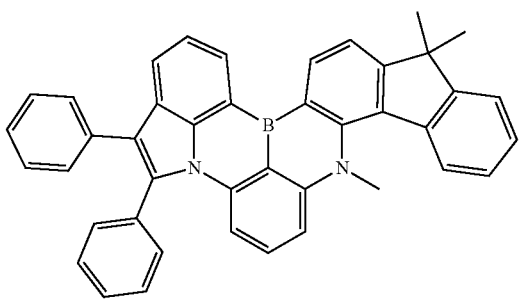
<Chemical Formula D351>
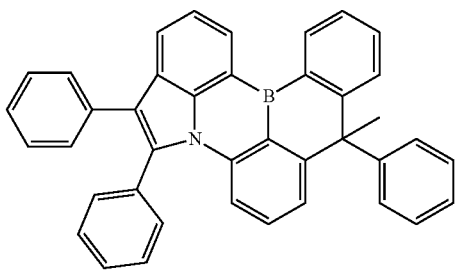

<Chemical Formula D352>
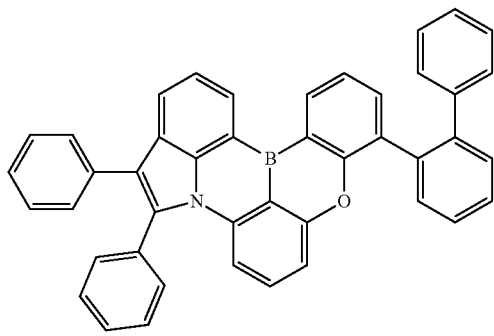
<Chemical Formula D353>
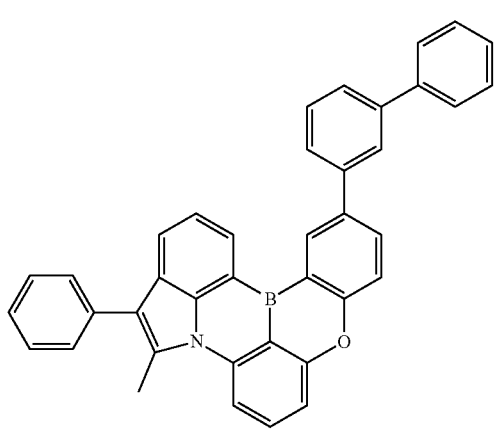
<Chemical Formula D354>
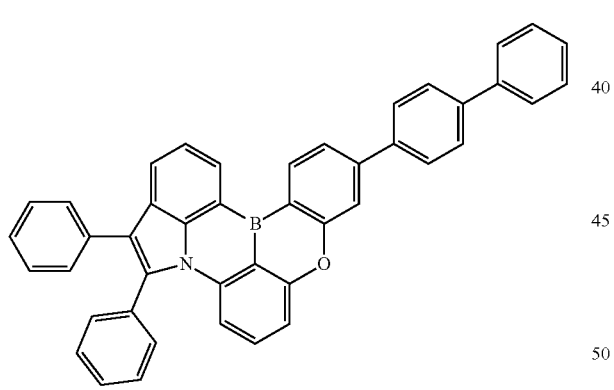
<Chemical Formula D355>
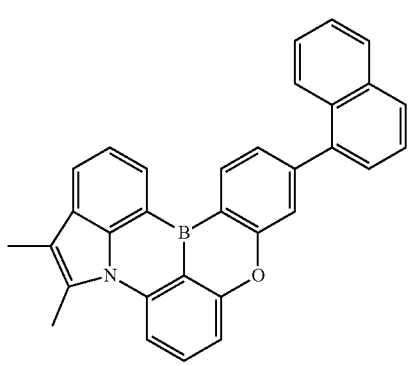
<Chemical Formula D356>
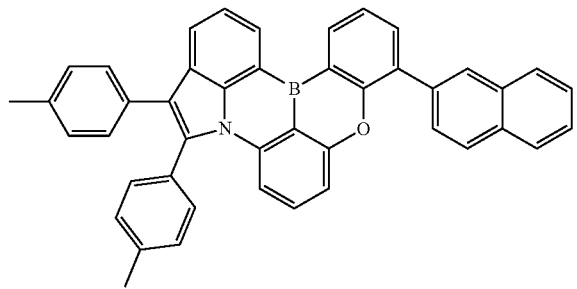
<Chemical Formula D357>
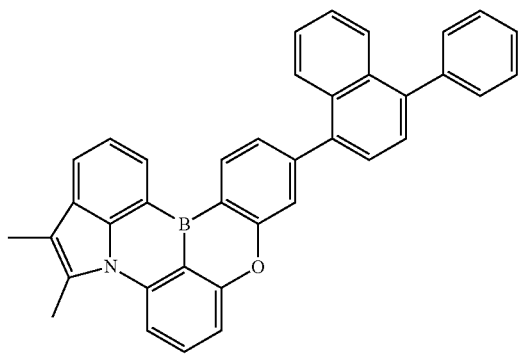
<Chemical Formula D358>
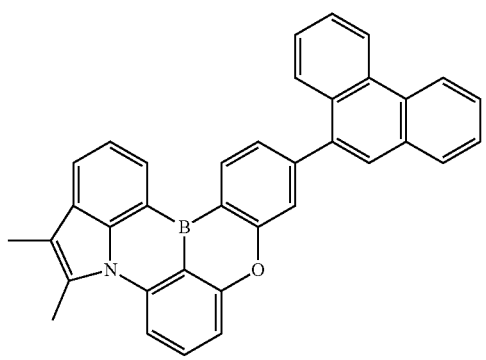
<Chemical Formula D359>
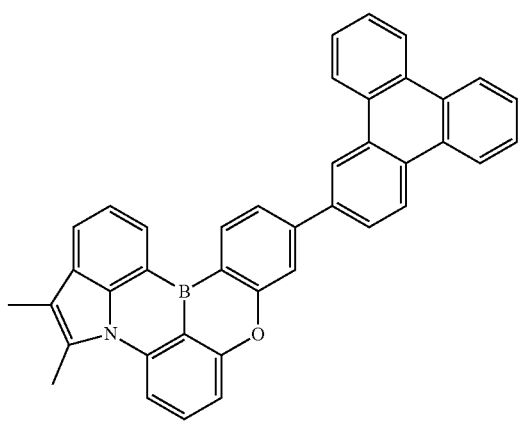

<Chemical Formula D360>
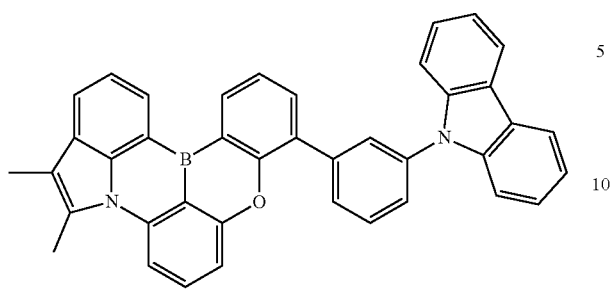
<Chemical Formula D361>
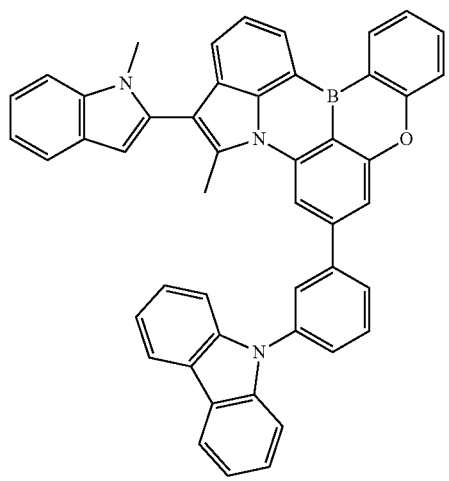
<Chemical Formula D362>
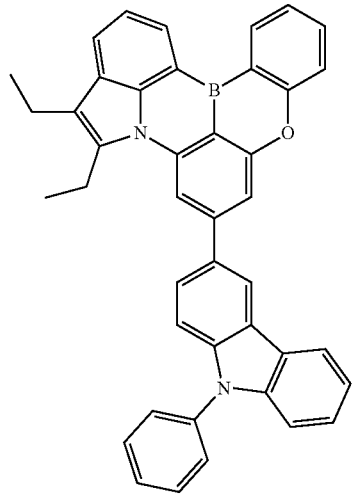
<Chemical Formula D363>
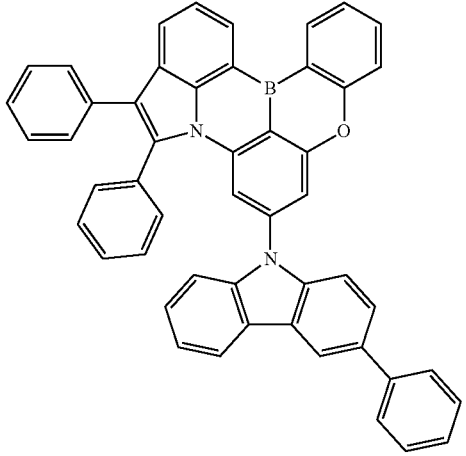
<Chemical Formula D364>
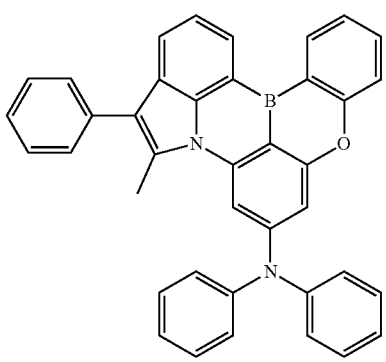
<Chemical Formula D365>
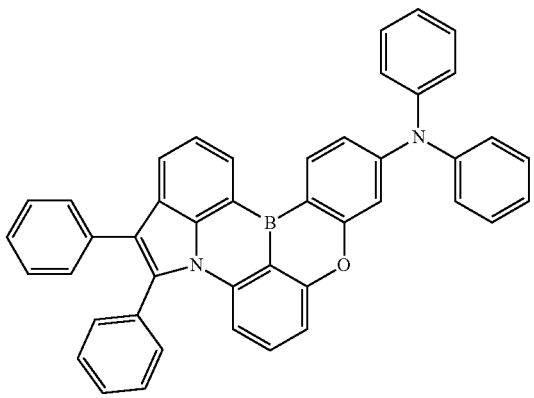
<Chemical Formula D366>
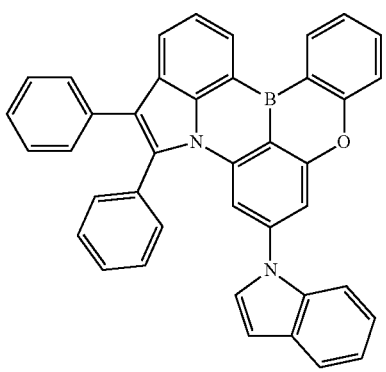

<Chemical Formula D367>
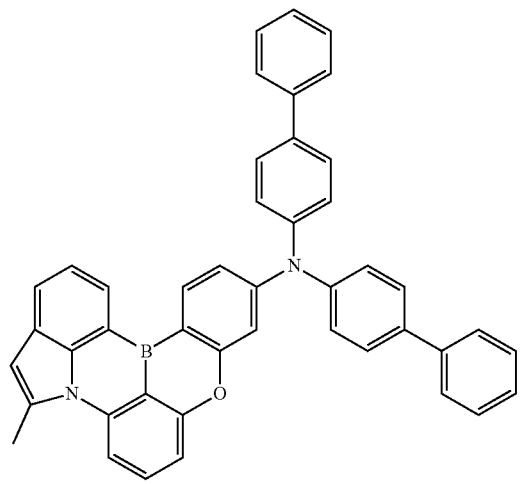
<Chemical Formula D368>
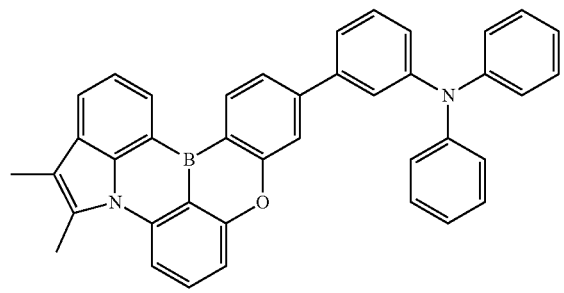
<Chemical Formula D369>
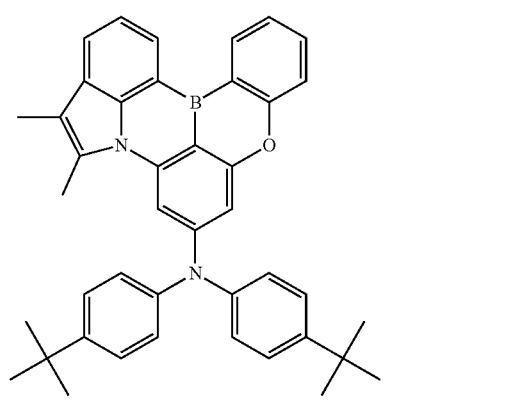
<Chemical Formula D370>
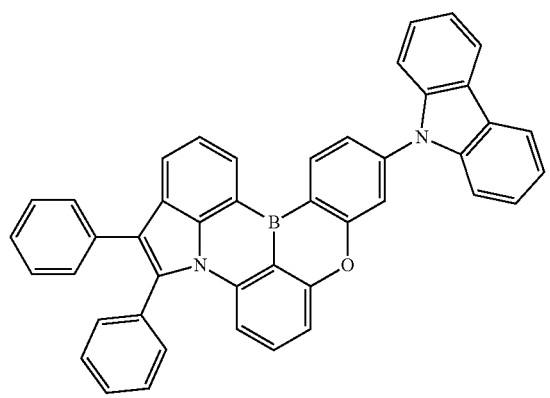
<Chemical Formula D371>
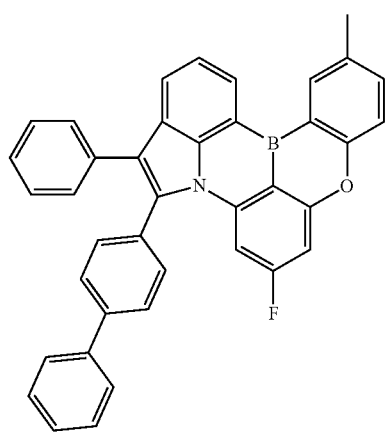
<Chemical Formula D372>
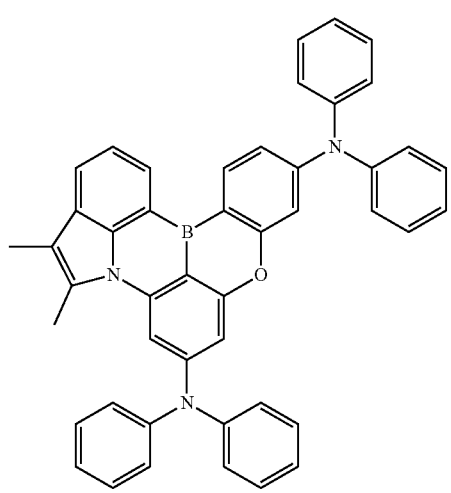
<Chemical Formula D373>
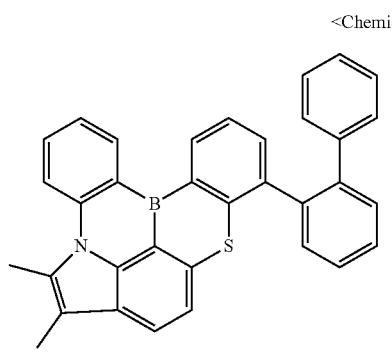

<Chemical Formula D374>
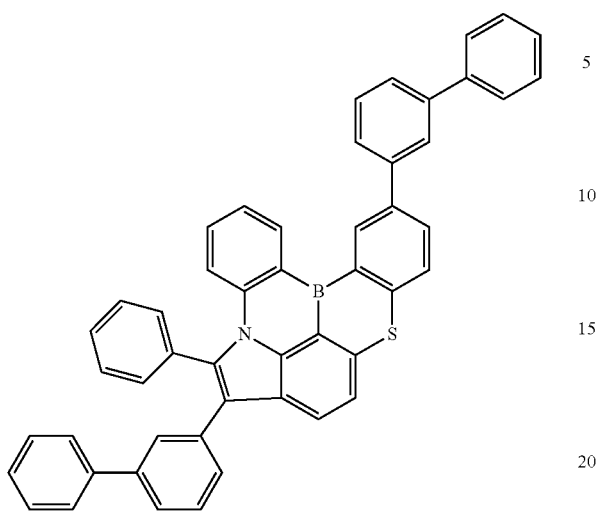
<Chemical Formula D375>
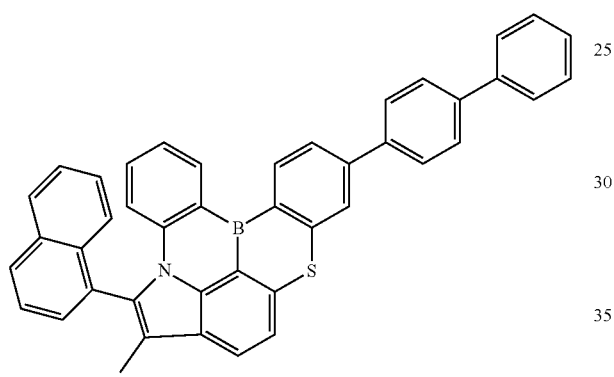
<Chemical Formula D376>
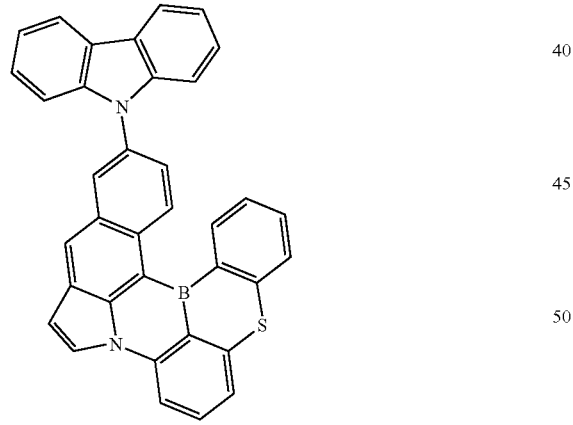
<Chemical Formula D377>
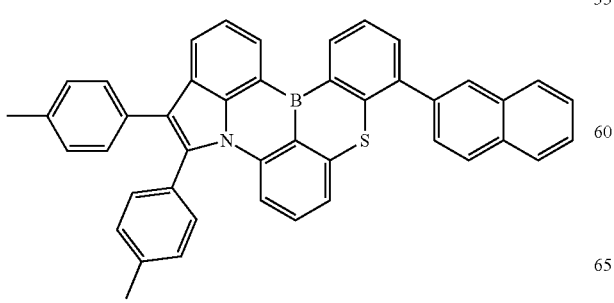
<Chemical Formula D378>
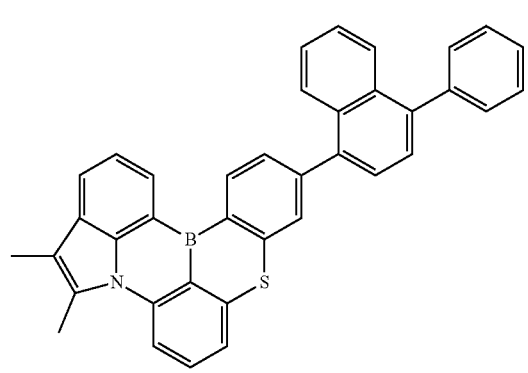
<Chemical Formula D379>
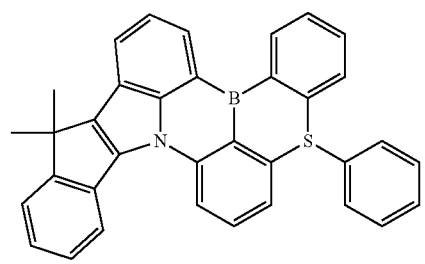
<Chemical Formula D380>
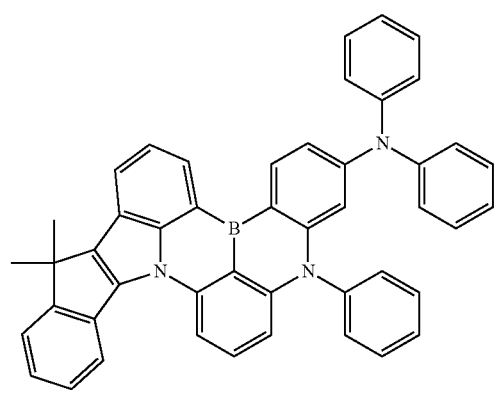
<Chemical Formula D381>
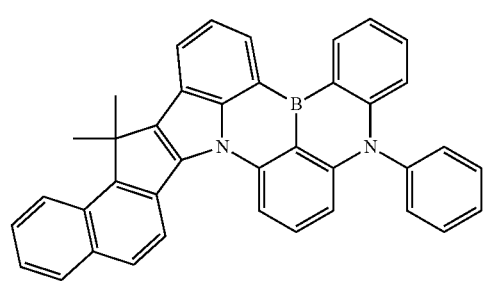

<Chemical Formula D382>

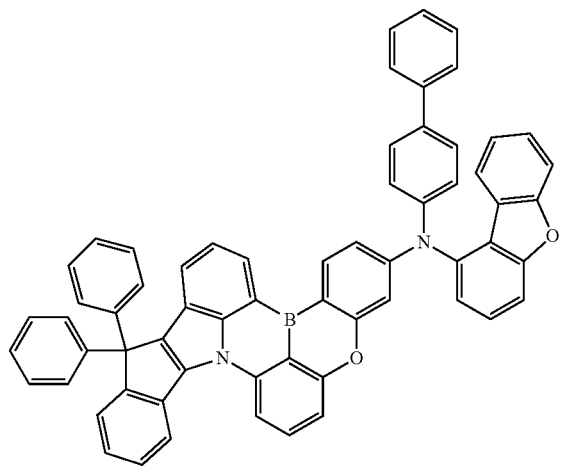

<Chemical Formula D383>

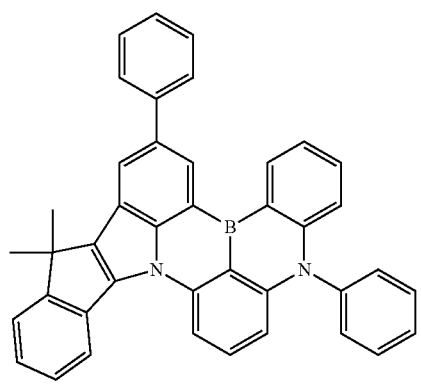

<Chemical Formula D384>

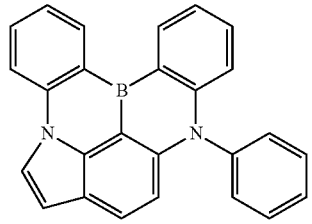

<Chemical Formula D385>

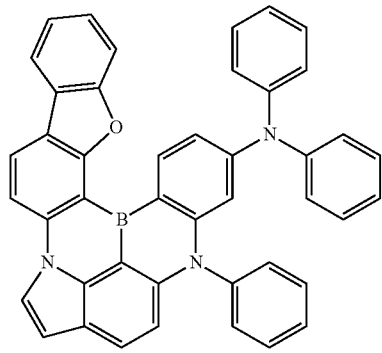

<Chemical Formula D386>

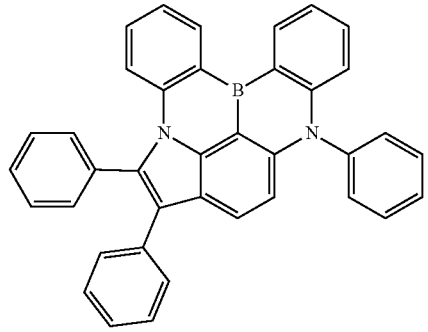

<Chemical Formula D387>

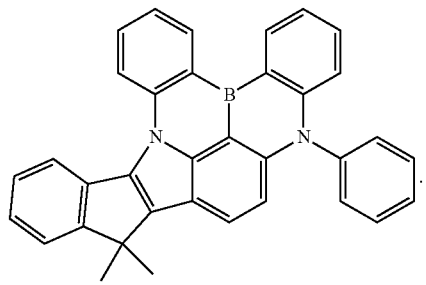

After being deposited on the light emitting layer by a vacuum deposition method or a spin-coating method, an electron transport layer 60 is overlaid with an electron injection layer 70. A cathode metal is deposited on the electron injection layer 70 by thermal deposition in a vacuum to form a cathode 80, thus fabricating an organic light emitting diode.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate) aluminum (Alq3), Liq, TAZ, Balq, beryllium bis(benzoquinolin-10-olate) (Bebq2), ADN, Compound 201, Compound 202, BCP, and oxadiazole derivatives such as PBD, BMD, and BND, but are not limited thereto:

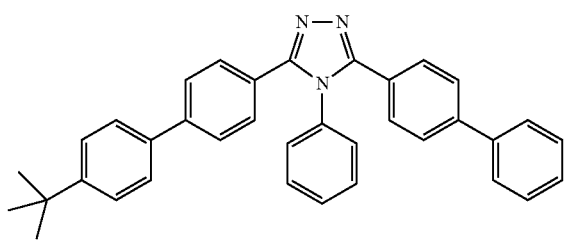

TAZ

-continued

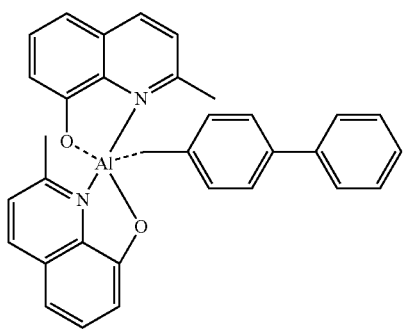

BAlq

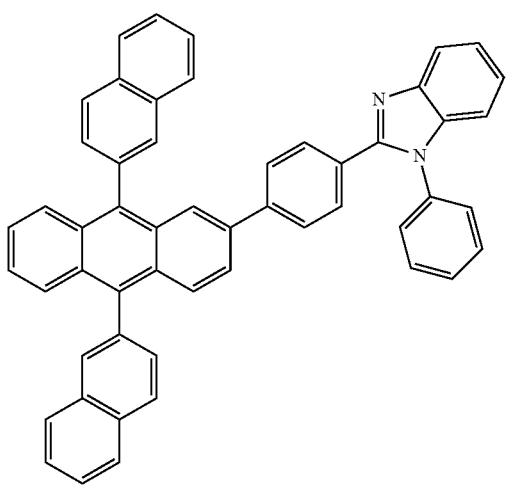

<Compound 201>

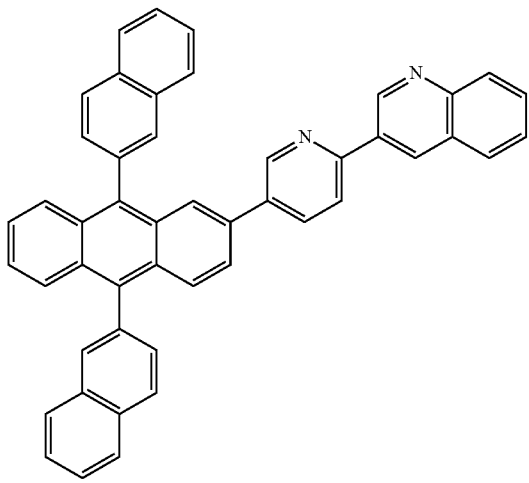

<Compound 202>

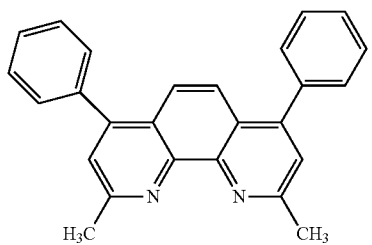

-continued

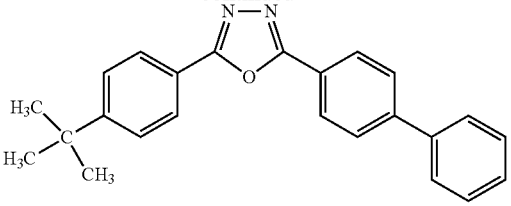

PBD

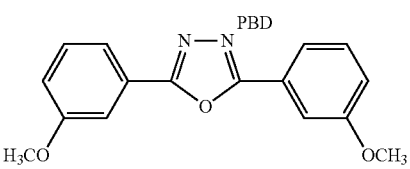

BMD

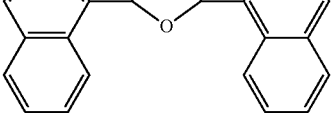

BND

In addition, the organic metal compound represented by Chemical Formula F may be used, either alone or in combination with the aforementioned electron transport layer material in the present disclosure:

$$Y_{m11}\text{-M-}(OA)_{n11} \qquad [\text{Chemical Formula F}]$$

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond;

M is an alkali metal, an alkaline earth metal, an aluminum (Al) atom, or a boron (B) atom, with the proviso that:

when M is an alkali metal, m11=1 and n11=0;

when M is an alkaline earth metal, m11=1 and n11=1, or m11=2 and n11=0; or when M is aluminum or a boron, m11 is an integer of 1 to 3 and n11 is an integer of 0 to 2, satisfying the relationship m11+n11=3; and OA is a monodentate ligand capable of forming a single bond or a coordinate bond with M, O is oxygen, and A is any one selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing at least one of O, N, S, and Si as a heteroatom, wherein the term 'substituted' in the expression "a substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

In the present disclosure, Y's, which may be the same or different, are each one selected from among, but not limited to, the following [Structural Formula C1] to [Structural Formula C39]:
[Structural FormulaC1]
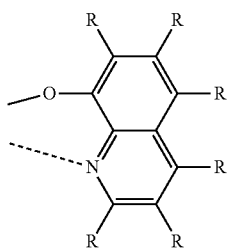
[Structural FormulaC2]
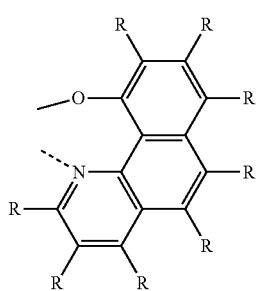
[Structural FormulaC3]
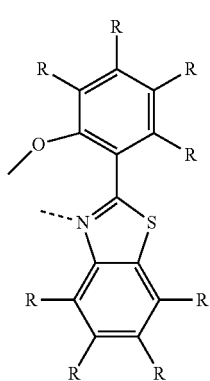
[Structural FormulaC4]
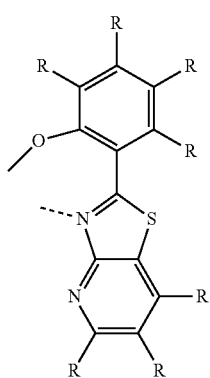
-continued
[Structural FormulaC5]
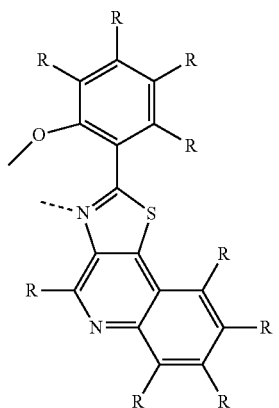
[Structural FormulaC6]
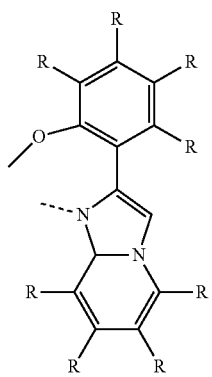
[Structural FormulaC7]
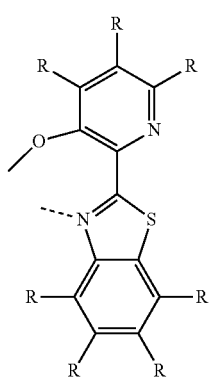
[Structural FormulaC8]
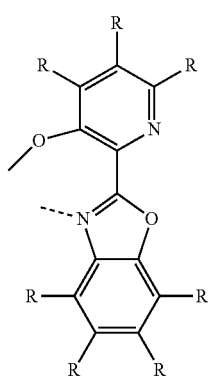

[Structural FormulaC9]
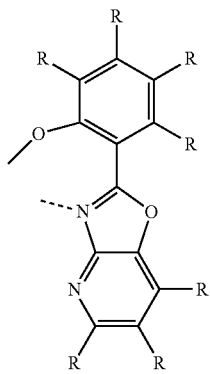
[Structural FormulaC10]
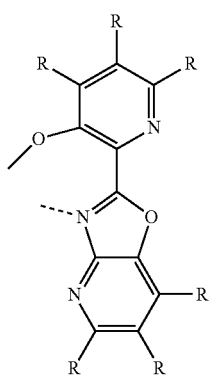
[Structural FormulaC11]
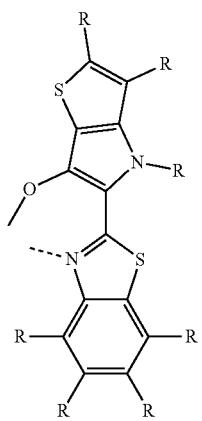
[Structural FormulaC12]
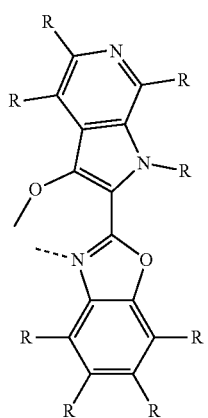
[Structural FormulaC13]
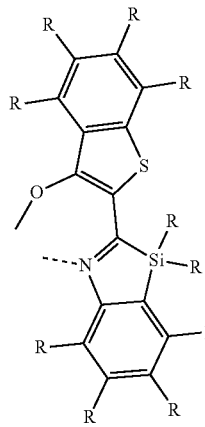
[Structural FormulaC14]
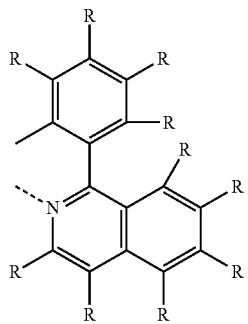
[Structural FormulaC15]
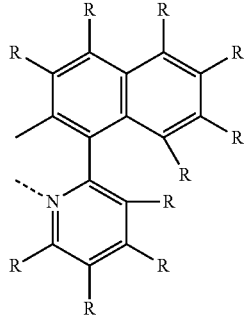
[Structural FormulaC16]
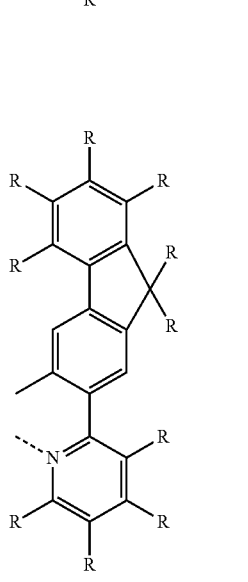

[Structural FormulaC17]
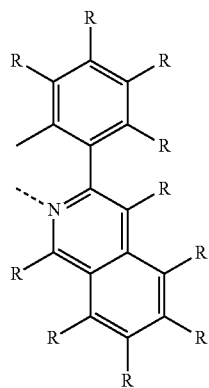
[Structural FormulaC18]
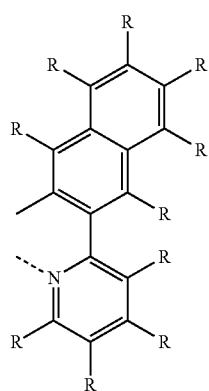
[Structural FormulaC19]
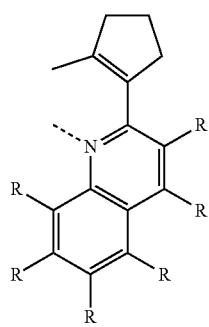
[Structural FormulaC20]
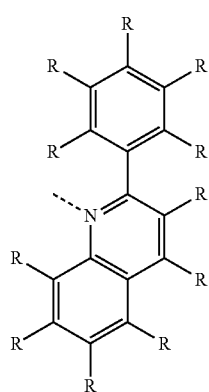
[Structural FormulaC21]
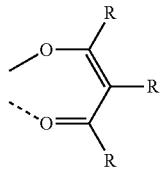
[Structural FormulaC22]
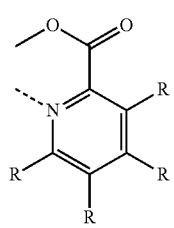
[Structural FormulaC23]
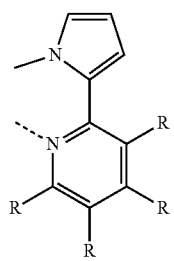
[Structural FormulaC24]
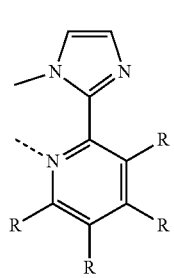
[Structural FormulaC25]
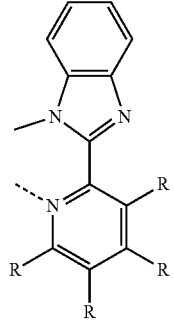
[Structural FormulaC26]
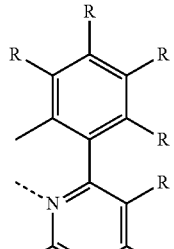
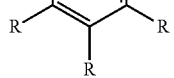

-continued
[Structural FormulaC27]
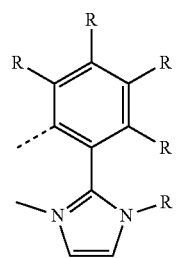
[Structural FormulaC28]
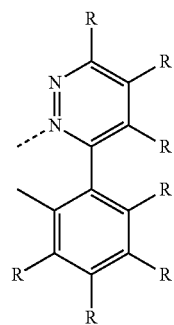
[Structural FormulaC29]
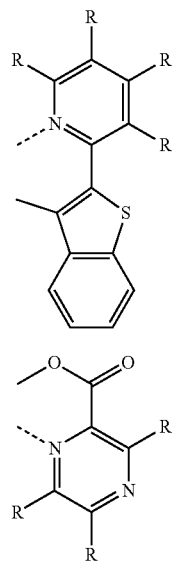
[Structural FormulaC30]
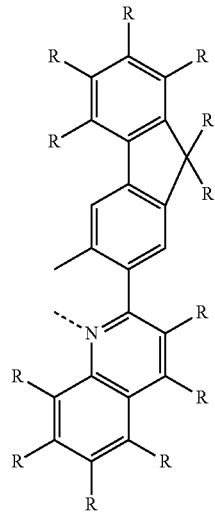
[Structural FormulaC31]
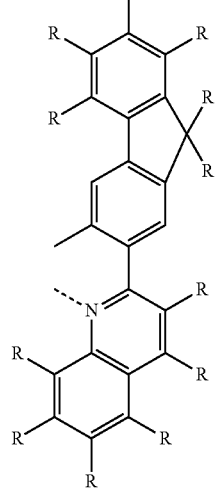
-continued
[Structural FormulaC32]
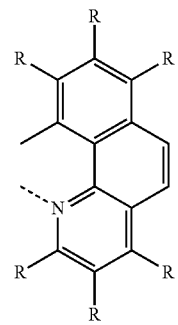
[Structural FormulaC33]
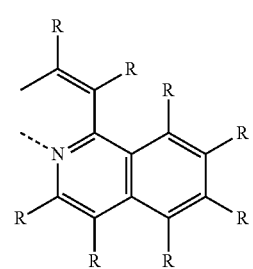
[Structural FormulaC34]
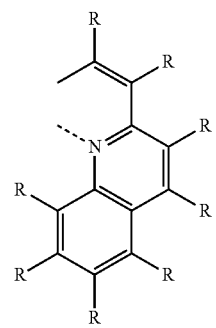
[Structural FormulaC35]
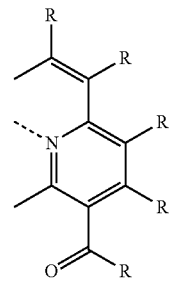
[Structural FormulaC36]
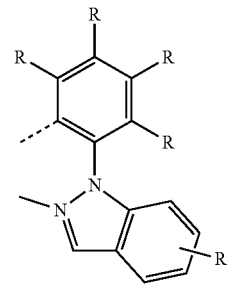

-continued

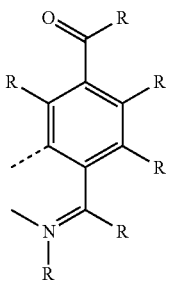

[Structural FormulaC37]

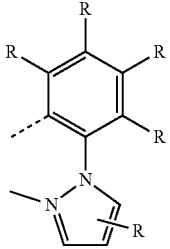

[Structural FormulaC38]

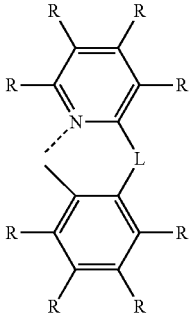

[Structural FormulaC39]

wherein,

R's, which may be the same or different, are each independently selected from among a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker.

In the organic light emitting diode of the present disclosure, an electron injection layer (EIL) that functions to facilitate electron injection from the cathode may be deposited on the electron transport layer. The material for the EIL is not particularly limited.

So long as it is conventionally used in the art, any material can be available for the electron injection layer without particular limitations. Examples include LiF, NaCl, CsF, $Li_2O$, and BaO. Deposition conditions for the electron injection layer may vary, depending on compounds used, but may be generally selected from condition scopes that are almost the same as for the formation of hole injection layers.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting device of the present disclosure may have a multilayer structure in which the additional blue, green, and/or red light-emitting layer may be made of a fluorescent or phosphorescent material.

Further, one or more layers selected from among a hole injection layer, a hole transport layer, a light emitting layer, an electron transport layer, and an electron injection layer may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present invention.

Preparation of Host

Synthesis Example 1: Synthesis of Compound 1

Synthesis Example 1-(1): Synthesis of Intermediate 1-a

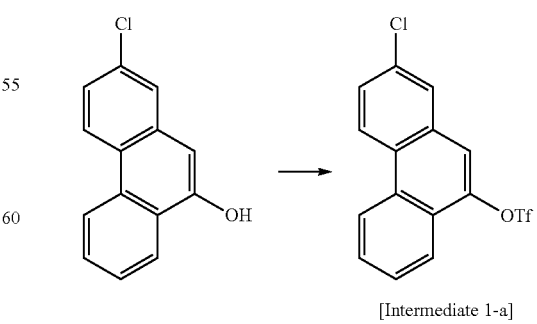

[Intermediate 1-a]

A dried reactor was filled with nitrogen, and then 2-chloro-9-hydroxyphenanthrene (30 g, 131 mmol), pyridine (31.1 g, 393 mmol), and methyl chloride (300 ml) were added thereto and cooled to zero degree of celcius. Subsequently, drops of trifluoromethanesulfonic anhydride (44.42 g, 157 mmol) was slowly added to the mixture which was then stirred for 1 hour.

After completion of the reaction, drops of 5° C. distilled water (200 ml) were slowly added. The reaction mixture was extracted with methylene chloride and distilled water, followed by recrystallization in methylene chloride and hexane to afford [Intermediate 1-a] (33.0 g, 70%).

Synthesis Example 1-(2): Synthesis of Intermediate 1-b

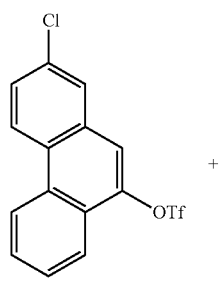

[Intermediate 1-a]

+

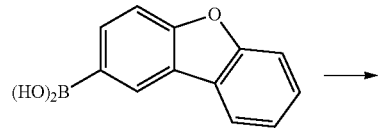

→

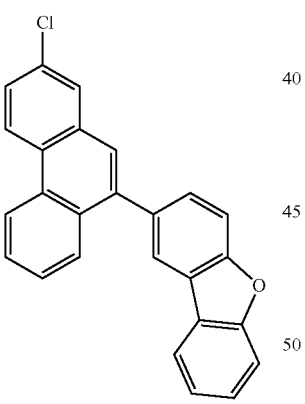

[Intermediate 1-b]

To a 250-ml round-bottom flask were added [Intermediate 1-a] (33 g, 91 mmol), 2-dibenzofuran boronic acid (21.3 g, 101 mmol), tetrakis(triphenylphosphine)palladium (2.11 g, 2 mmol), and potassium carbonate (25.29 g, 183 mmol). Toluene (270 ml), ethanol (90 ml), and water (60 ml) were then added and the temperature of the reactor was elevated to 80° C. before the mixture was stirred for 12 hours. After completion of the reaction, the reaction mixture was cooled to room temperature, added with methanol, and stirred. The organic layer thus formed was separated and concentrated in a vacuum. Separation by column chromatography afforded [Intermediate 1-b] (24 g, 69%).

Synthesis Example 1-(3): Synthesis of Intermediate 1-c

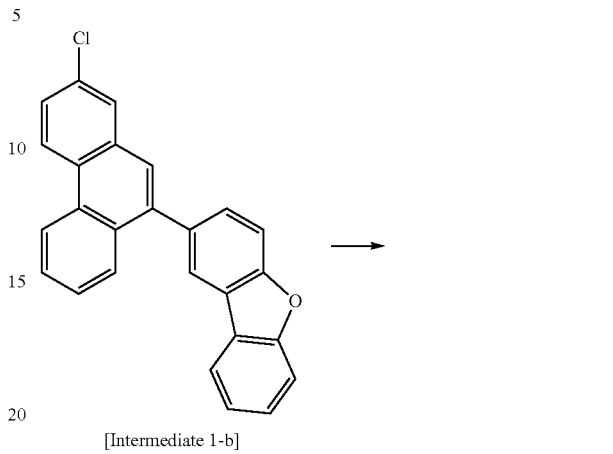

[Intermediate 1-b]

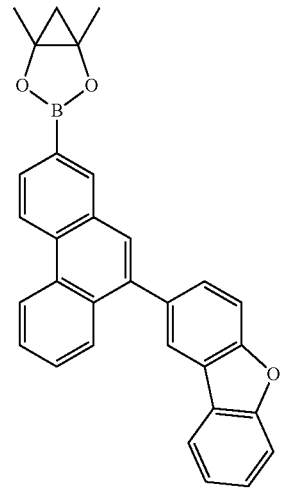

[Intermediate 1-c]

[Intermediate 1-b] (24 g, 63 mmol), bis(pinacolato)diboron (19 g, 75 mmol), palladium (II) chloride-1,1'-bis(diphenylphosphino)ferrocene (5.2 g, 6 mmol), potassium acetate (18.7 g, 170 mmol), and toluene (240 ml) were added and stirred under reflux for 10 hours. After completion of the reaction, the solid was filter off and the filtrate was concentrated in a vacuum. Purification by column chromatography using methylene chloride and heptane afforded [Intermediate 1-c] (19 g, 66%).

Synthesis Example 1-(4): Synthesis of Intermediate 1-d

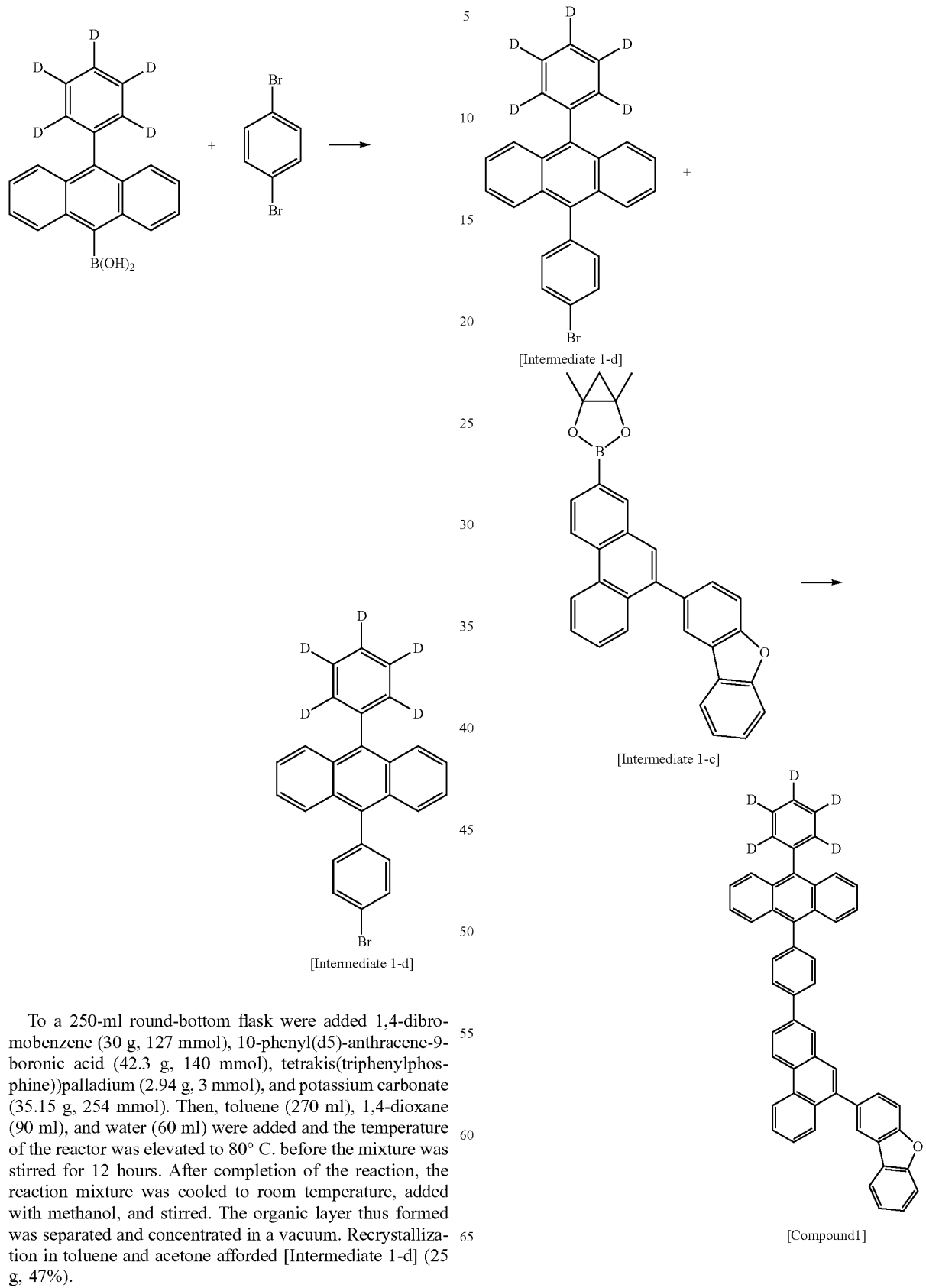

[Intermediate 1-d]

To a 250-ml round-bottom flask were added 1,4-dibromobenzene (30 g, 127 mmol), 10-phenyl(d5)-anthracene-9-boronic acid (42.3 g, 140 mmol), tetrakis(triphenylphosphine))palladium (2.94 g, 3 mmol), and potassium carbonate (35.15 g, 254 mmol). Then, toluene (270 ml), 1,4-dioxane (90 ml), and water (60 ml) were added and the temperature of the reactor was elevated to 80° C. before the mixture was stirred for 12 hours. After completion of the reaction, the reaction mixture was cooled to room temperature, added with methanol, and stirred. The organic layer thus formed was separated and concentrated in a vacuum. Recrystallization in toluene and acetone afforded [Intermediate 1-d] (25 g, 47%).

Synthesis Example 1-(5): Synthesis of Compound 1

To a 250-ml round-bottom flask were added [Intermediate 1-d] (10 g, 24 mmol), [Intermediate 1-c] (12.06 g, 27 mmol), tetrakis(triphenylphosphine))palladium(0.56 g, 0.4 mmol), and potassium carbonate (6.67 g, 48 mmol). Then, toluene (70 ml), ethanol (30 ml), and water (20 ml) were added and the temperature of the reactor was elevated to 80° C. before the mixture was stirred for 12 hours. After completion of the reaction, the reaction mixture was cooled to room temperature, added with methanol, and stirred. The organic layer thus formed was separated and concentrated in a vacuum. Recrystallization in toluene and acetone afforded [Compound 1] (7.5 g, 46%).

MS (MALDI-TOF): m/z 677.28 [M$^+$]

Synthesis Example 2: Synthesis of Compound 2

Synthesis Example 2-(1): Synthesis of Intermediate 2-a

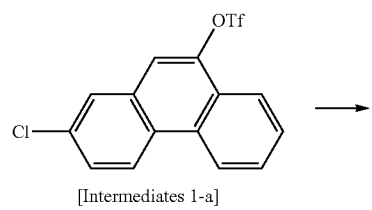

[Intermediates 1-a]

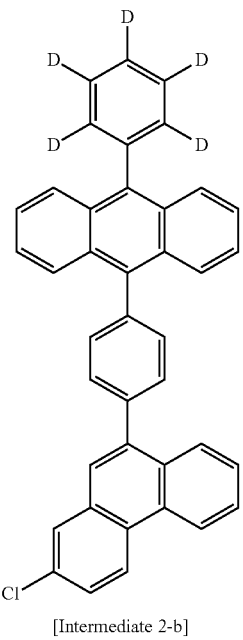

[Intermediate 1-d]

The same procedure as in Synthesis Example 1-(3) was carried out, with the exception of using [Intermediate 1-a] instead of [Intermediate 1-b], to afford [Intermediate 2-a].

Synthesis Example 2-(2): Synthesis of Intermediate 2-b

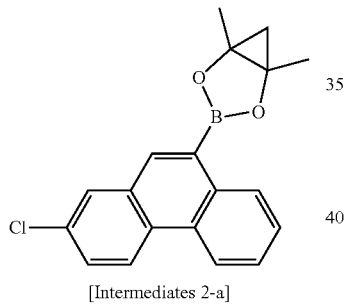

+

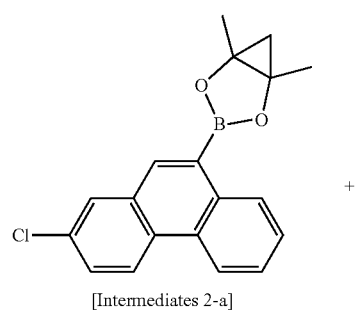

[Intermediates 2-a]

The same procedure as in Synthesis Example 1-(5) was carried out, with the exception of using [Intermediate 2-a] instead of [Intermediate 1-c], to afford [Intermediate 2-b].

Synthesis Example 2-(3): Synthesis of Intermediate 2-c

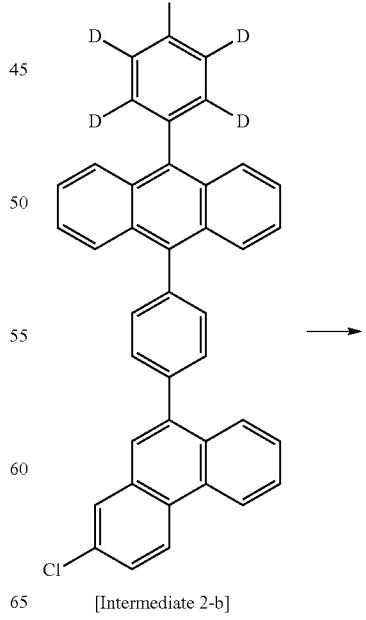

[Intermediate 2-b]

221
-continued

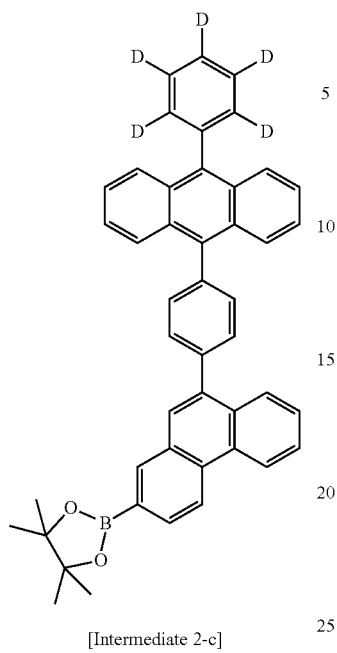

[Intermediate 2-c]

The same procedure as in Synthesis Example 1-(3) was carried out, with the exception of using [Intermediate 2-b] instead of [Intermediate 1-b], to afford [Intermediate 2-c].

Synthesis Example 2-(4): Synthesis of Compound 2

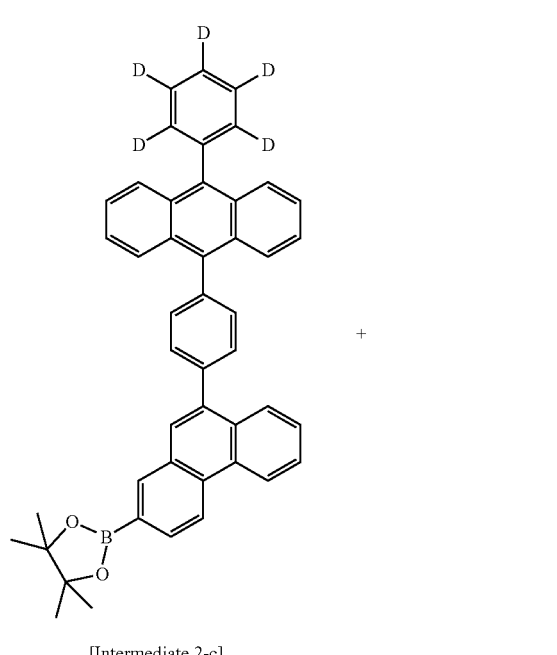

[Intermediate 2-c]

+

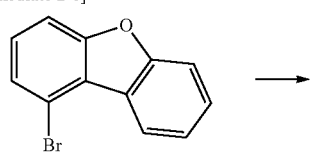

222
-continued

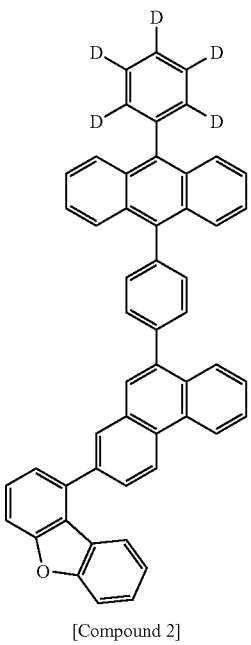

[Compound 2]

The same procedure as in Synthesis Example 1-(5) was carried out, with the exception of using 1-bromodibenzofuran and [Intermediate 2-c] instead of [Intermediate 1-d] and [Intermediate 1-c], respectively, to afford [Compound 2].

MS (MALDI-TOF): m/z 677.28 [M⁺]

Synthesis Example 3: Synthesis of Compound 15

Synthesis Example 3-(1): Synthesis of Intermediate 3-a

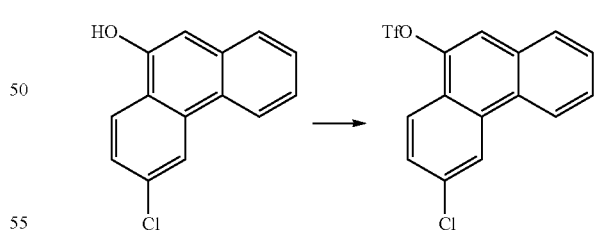

[Intermediate 3-a]

The same procedure as in Synthesis Example 1-(1) was carried out, with the exception of using 3-chloro-10-hydroxyphenanthrene instead of 2-chloro-9-hydroxyphenanthrene, to afford [Intermediate 3-a]. (yield 82%)

Synthesis Example 3-(2): Synthesis of Intermediate 3-b

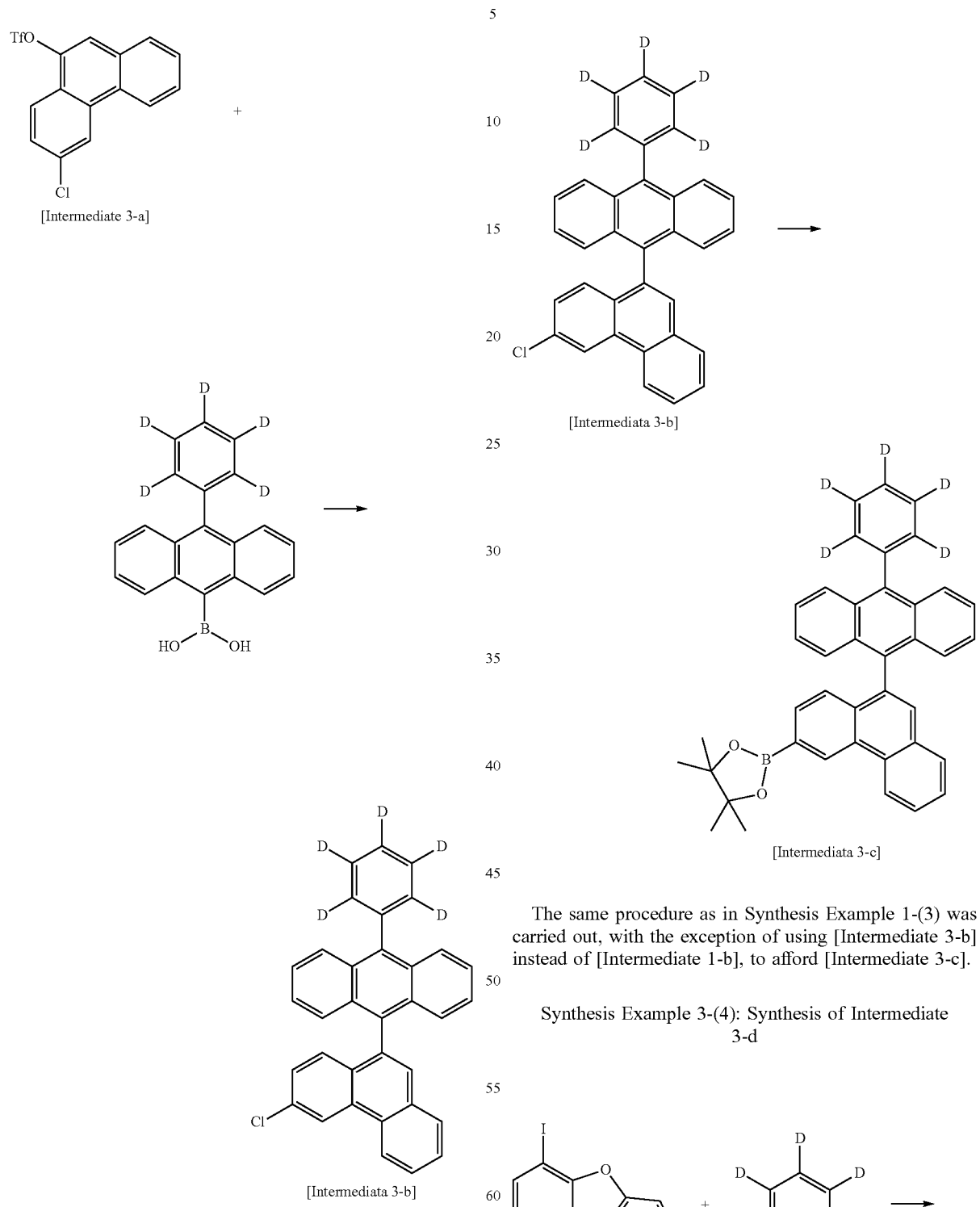

[Intermediata 3-b]

The same procedure as in Synthesis Example 1-(5) was carried out, with the exception of using [Intermediate 3-a] and 10-phenyl(d5)-anthracene-9-boronic acid instead of [Intermediate 1-d] and [Intermediate 1-c], respectively, to afford [Intermediate 3-b].

Synthesis Example 3-(3): Synthesis of Intermediate 3-c

[Intermediata 3-b]

[Intermediata 3-c]

The same procedure as in Synthesis Example 1-(3) was carried out, with the exception of using [Intermediate 3-b] instead of [Intermediate 1-b], to afford [Intermediate 3-c].

Synthesis Example 3-(4): Synthesis of Intermediate 3-d

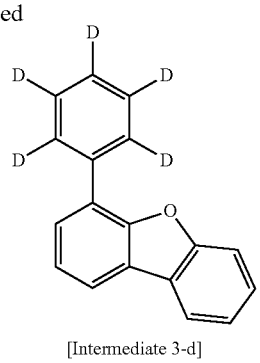

[Intermediate 3-d]

The same procedure as in Synthesis Example 1-(2) was carried out, with the exception of using 4-iododibenzofuran and phenyl-d5-boronic acid instead of [Intermediate 1-a] and 2-dibenzofuran boronic acid, respectively, to afford [Intermediate 3-d].

Synthesis Example 3-(5): Synthesis of Intermediate 3-e

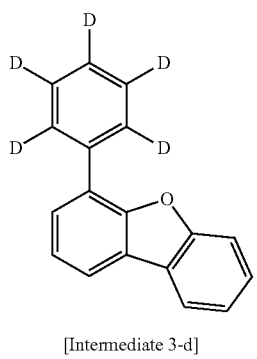

[Intermediate 3-d]

→

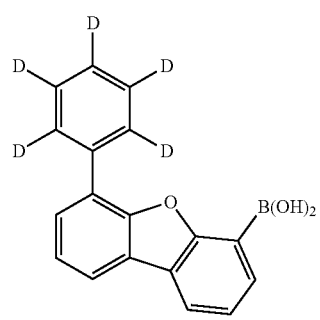

[Intermediate 3-e]

In a 1-L round-bottom flask, [Intermediate 3-d] (40 g, 160 mmol) was dissolved in tetrahydrofuran (400 ml) under nitrogen. After the temperature was lowered to −78° C., n-butyl lithium (105 ml, 176 mmol) was dropwise added. The mixture was stirred at room temperature for 6 hours. After the temperature was reduced to −78° C., trimethylborate (20 g, 193 mmol) was added and stirred overnight.

After completion of the reaction, the reaction mixture was acidified with the slow addition of drops of 2N HCl. Extraction with water and ethyl acetate gave an organic layer which was then dried over magnesium sulfate. The residue thus obtained was concentrated in a vacuum and then recrystallized in heptane and toluene to afford [Intermediate 3-e] (36 g, 77%).

Synthesis Example 3-(6): Synthesis of Intermediate 3-f

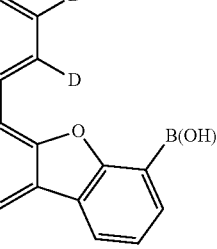 + 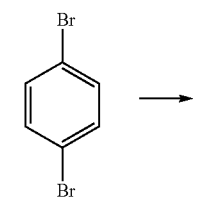 →

[Intermediate 3-e]

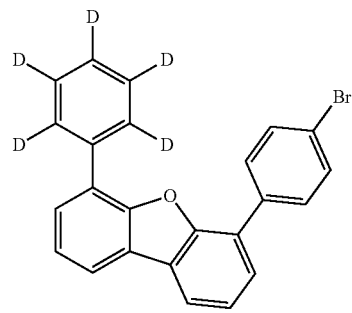

[Intermediate 3-f]

The same procedure as in Synthesis Example 1-(4) was carried out, with the exception of using [Intermediate 3-e] instead of 10-phenyl(d5)-anthracene-9-boronic acid, to afford [Intermediate 3-f]. (yield 43%)

Synthesis Example 3-(7): Synthesis of Intermediate 3-g

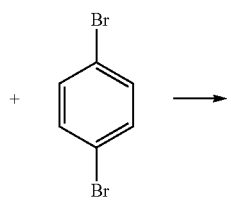 +

[Intermediate 3-f]

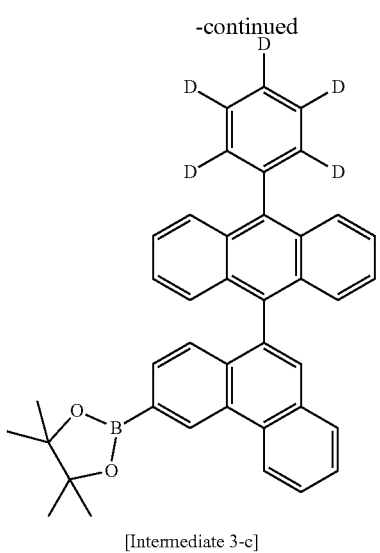

[Intermediate 3-c]

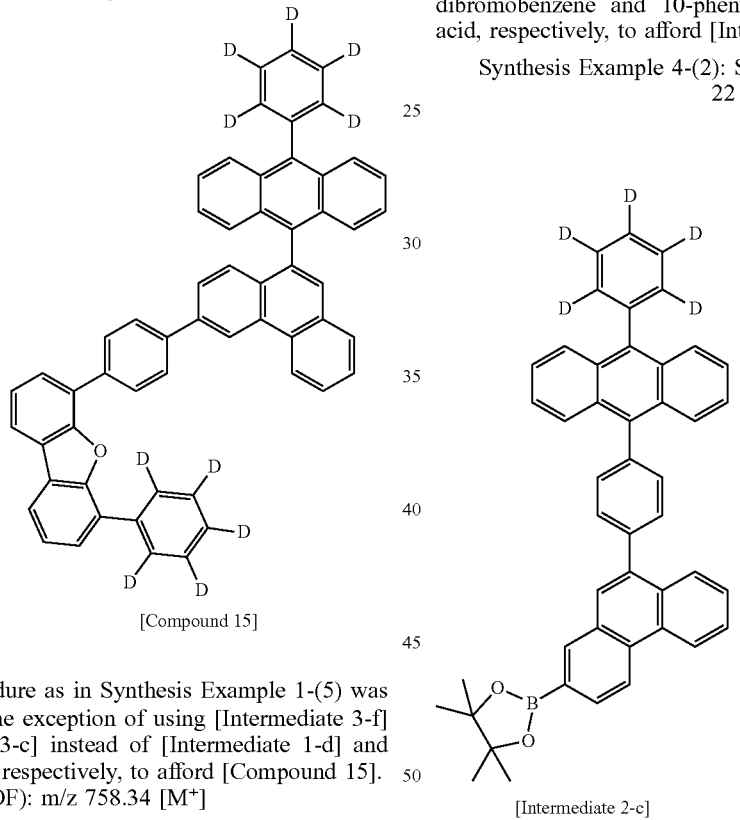

[Compound 15]

The same procedure as in Synthesis Example 1-(5) was carried out, with the exception of using [Intermediate 3-f] and [Intermediate 3-c] instead of [Intermediate 1-d] and [Intermediate 1-c], respectively, to afford [Compound 15].
MS (MALDI-TOF): m/z 758.34 [M⁺]

Synthesis Example 4: Synthesis of Compound 22

Synthesis Example 4-(1): Synthesis of Intermediate 4-a

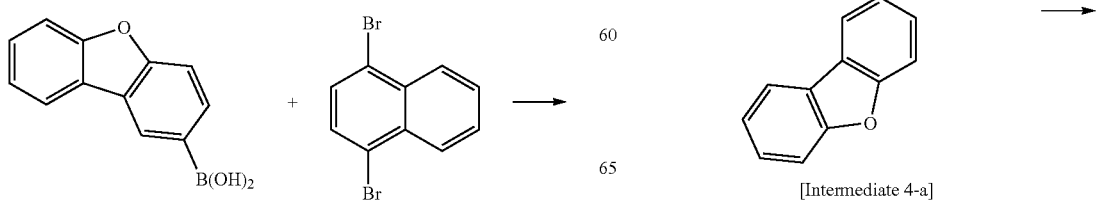

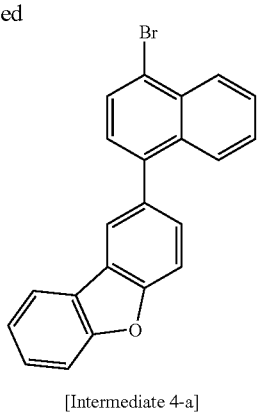

[Intermediate 4-a]

The same procedure as in Synthesis Example 1-(4) was carried out, with the exception of using 1,4-dibromonaphthalene and 2-dibenzofuran boronic acid instead of 1,4-dibromobenzene and 10-phenyl(d5)-anthracene-9-boronic acid, respectively, to afford [Intermediate 4-a].

Synthesis Example 4-(2): Synthesis of Compound 22

-continued

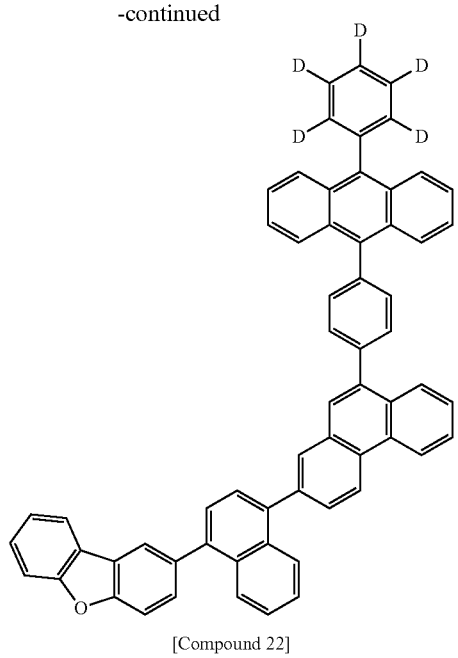

[Compound 22]

The same procedure as in Synthesis Example 1-(5) was carried out, with the exception of using [Intermediate 4-a] and [Intermediate 2-c] instead of [Intermediate 1-d] and [Intermediate 1-c], respectively, to afford [Compound 22].
MS (MALDI-TOF): m/z 803.32 [M$^+$]

Preparation of Dopant

Compound represented by any one of [Chemical Formula D1] and [Chemical Formula D2]: The dopant materials were synthesized with reference to the Examples described in PCT/KR2015/004552.

The compound represented by any one of [Chemical Formula D3] to [Chemical Formula D5] was prepared according to the following Synthesis Examples 5 to 7.

Synthesis Example 5: Synthesis of BD 2

Synthesis Example 5-(1): Synthesis of Intermediate 5-a

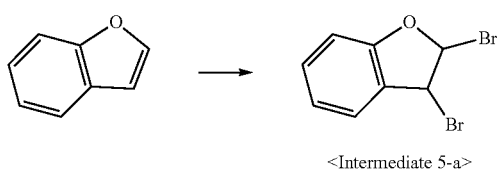 [SMILES: c1ccc2occc2c1 ; BrC1Oc2ccccc2C1Br]

<Intermediate 5-a>

In a 1-L reactor, benzofuran (50 g, 423 mmol) and dichloromethane (500 mL) were stirred together. The mixture was cooled to −10° C. and a dilution of bromine (67.7 g, 423 mmol) in dichloromethane (100 mL) was dropwise added thereto before stirring at 0° C. for 2 hours. After completion of the reaction, a sodium thiosulfate solution was added and stirred. Extraction with ethyl acetate and H$_2$O separated layers. The organic layer thus formed was concentrated in a vacuum and recrystallized in ethanol to afford <Intermediate 5-a> (100 g). (yield 93%)

Synthesis Example 5-(2): Synthesis of Intermediate 5-b

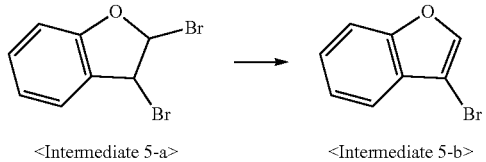 [SMILES: BrC1Oc2ccccc2C1Br ; Brc1coc2ccccc12]

<Intermediate 5-a>  <Intermediate 5-b>

In a 1-L reactor, potassium hydroxide (48.6 g, 866 mmol) was dissolved in ethanol (400 mL). A solution of <Intermediate 5-a> (120 g, 433 mmol) in ethanol was dropwise added at 0° C. and then stirred under reflux for 2 hours. After completion of the reaction, the reaction mixture was concentrated by evaporating the ethanol and the concentrate was extracted with ethyl acetate and water. The organic layer thus formed was concentrated, followed by separation through column chromatography to afford <Intermediate 5-b> (42 g). (yield 50%)

Synthesis Example 5-(3): Synthesis of Intermediate 5-c

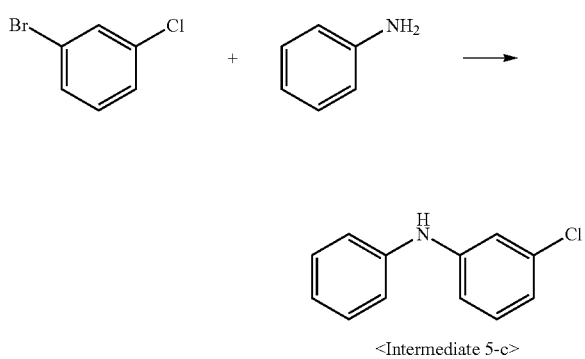

<Intermediate 5-c>

In a 100-mL reactor, 1-bromo-3-iodobenzene (4.5 g, 16 mmol), aniline (5.8 g, 16 mmol), palladium acetate (0.1 g, 1 mmol), sodium tert-butoxide (3 g, 32 mmol), bis(diphenylphosphino)-1,1'-binaphthyl (0.2 g, 1 mmol), and toluene (45 mL) were stirred together for 24 hours under reflux. After completion of the reaction, filtration was carried out. The resulting filtrate was concentrated and separated by column chromatography to afford <Intermediate 5-c> (5.2 g). (yield 82%) Synthesis Example 5-(4): Synthesis of Intermediate 5-d

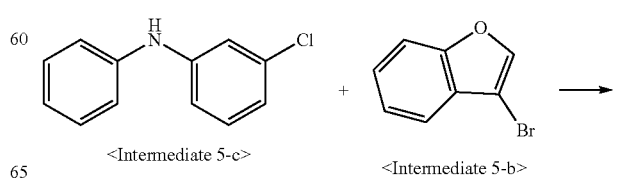

<Intermediate 5-c>  <Intermediate 5-b>

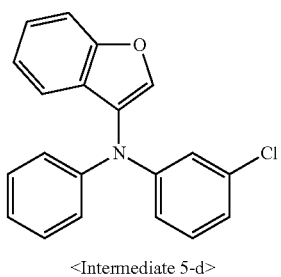

<Intermediate 5-d>

In a 250-mL reactor, <Intermediate 5-c> (20 g, 98 mmol), <Intermediate 5-b> (18.4 g, 98 mmol), palladium acetate (0.5 g, 2 mmol), sodium tert-butoxide (18.9 g, 196 mmol), tri-tert-butylphosphine (0.8 g, 4 mmol), and toluene (200 mL) were stirred together for 5 hours under reflux. After completion of the reaction, filtration was carried out. The filtrate was concentrated and separated by column chromatography to afford <Intermediate 5-d> (22 g). (yield 75%)

Synthesis Example 5-(5): Synthesis of Intermediate 5-e

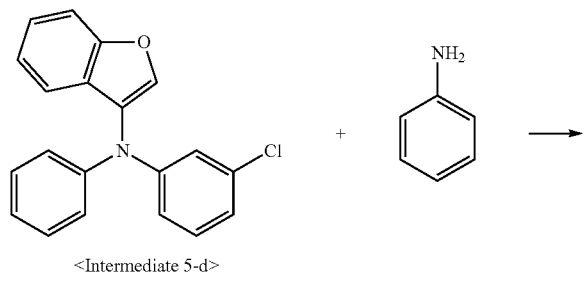

<Intermediate 5-d>

The same procedure as in Synthesis Example 1-3 was carried out, with the exception of using <Intermediate 5-d> instead of 1-bromo-4-iodobenzeneiodobenzene, to afford <Intermediate 5-e>18.5 g. (yield 74.1%)

Synthesis Example 5-(6): Synthesis of Intermediate 5-f

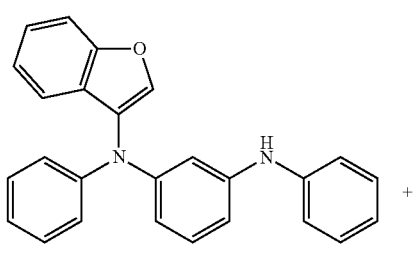

<Intermediate 5-e>

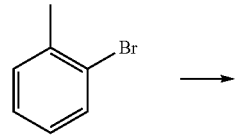

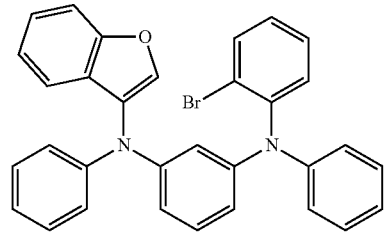

<Intermediate 5-f>

The same procedure as in Synthesis Example 5-4 was carried out, with the exception of using <Intermediate 5-e> and 1-bromo-2-iodobenzene instead of <Intermediate 5-c> and <Intermediate 5-b>, respectively, to afford <Intermediate 5-f>12 g. (yield 84.1%)

Synthesis Example 5-(7): Synthesis of BD 2

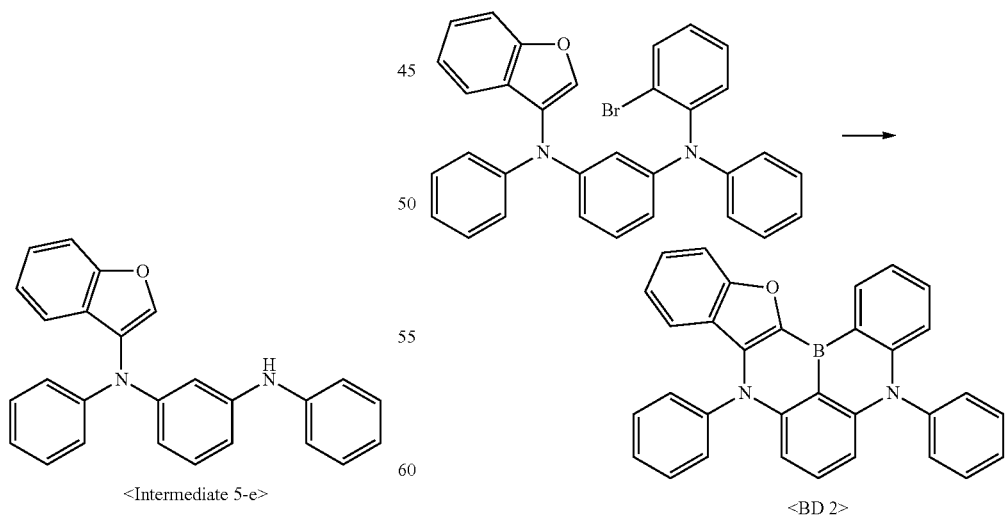

<BD 2>

In a 300-mL reactor were added <Intermediate 5-f> (12 g, 23 mmol) and tert-butyl benzene (120 mL). At −78° C., n-butyl lithium (42.5 mL, 68 mmol) was dropwise added. Then, the mixture was stirred at 60° C. for 3 hours. Subsequently, nitrogen was introduced at 60° C. into the reactor to remove heptane. Boron tribromide (11.3 g, 45 mmol) was dropwise added at −78° C. and then stirred at room temperature. N, N-Diisopropylethylamine (5.9 g, 45 mmol) was added at 0° C. and then stirred at 120° C. for 2 hours. After completion of the reaction, an aqueous sodium acetate solution was added at room temperature and stirred. Extraction was carried out with ethyl acetate. The organic layer was concentrated and separated by column chromatography to afford <BD 2> (0.8 g). (yield 13%)

MS (MALDI-TOF): m/z 460.17 [M$^+$]

Synthesis Example 6: Synthesis of BD 3

Synthesis Example 6-(1): Synthesis of Intermediate 6-a

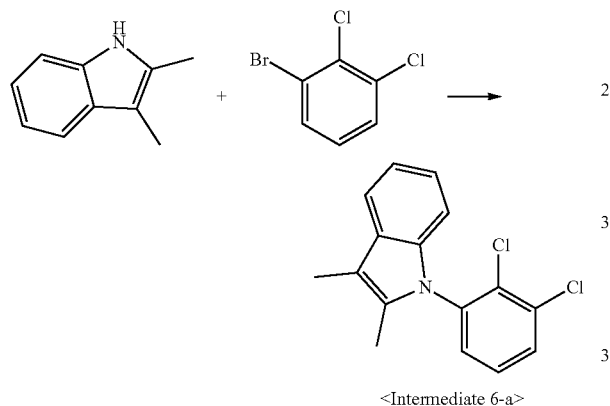

<Intermediate 6-a>

The same procedure as in Synthesis Example 5-(4) was carried out, with the exception of using 2,3-dimethylindone and 1-bromo-2,3-dichlorobenzene instead of <Intermediate 5-c> and 3-bromobenzothiophene, respectively, to afford <Intermediate 6-a>. (yield 47%)

Synthesis Example 6-(2): Synthesis of Intermediate 6-b

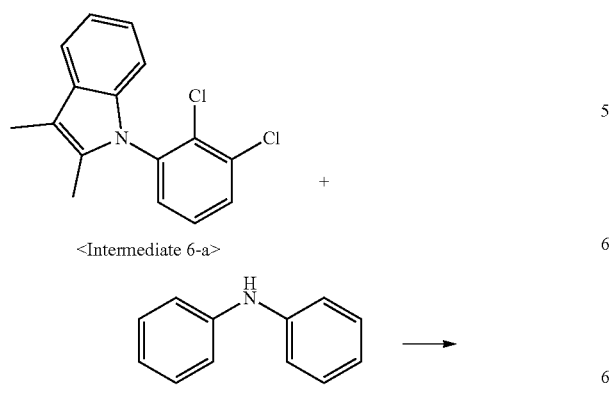

<Intermediate 6-a>

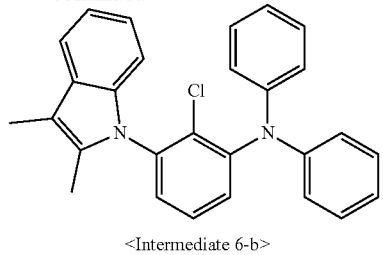

<Intermediate 6-b>

The same procedure as in Synthesis Example 5-(4) was carried out, with the exception of using diphenylamine and <Intermediate 6-a> instead of <Intermediate 5-c> and 3-bromobenzothiophene, respectively, to afford <Intermediate 6-b>. (yield 72%)

Synthesis Example 6-(3): Synthesis of BD 3

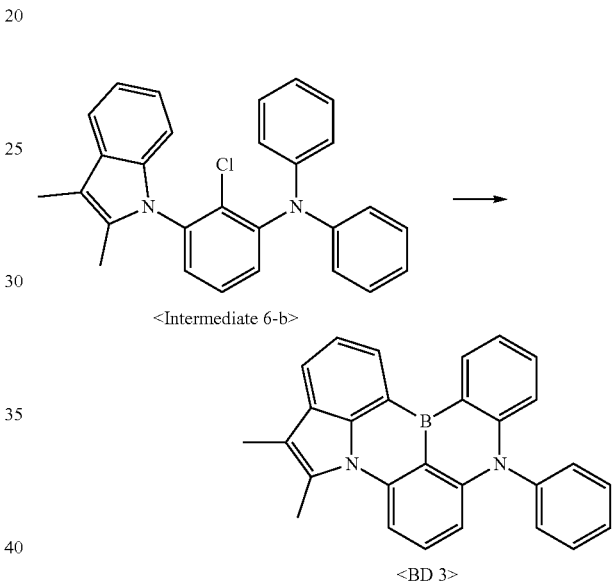

<BD 3>

The same procedure as in Synthesis Example 5-(6) was carried out, with the exception of using <Intermediate 6-b> instead of <Intermediate 5-e>, to afford <BD 3>. (yield 72%)

MS (MALDI-TOF): m/z 369.18 [M$^+$]

Synthesis Example 7: Synthesis of BD 4

Synthesis Example 7-(1): Synthesis of Intermediate 7-a

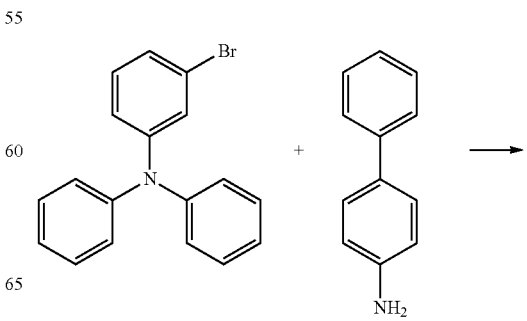

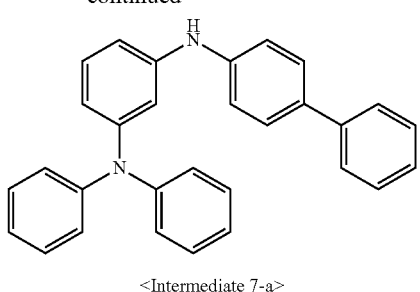

<Intermediate 7-a>

The same procedure as in Synthesis Example 5-(3) was carried out, with the exception of using N-3-bromophenyl-N,N-diphenylamine and 4-aminobiphenyl instead of 1-bromo-5-iodobenzene and 4-tert-butylaniline, respectively, to afford <Intermediate 7-a>. (yield 55%)

Synthesis Example 7-(2): Synthesis of Intermediate 7-b

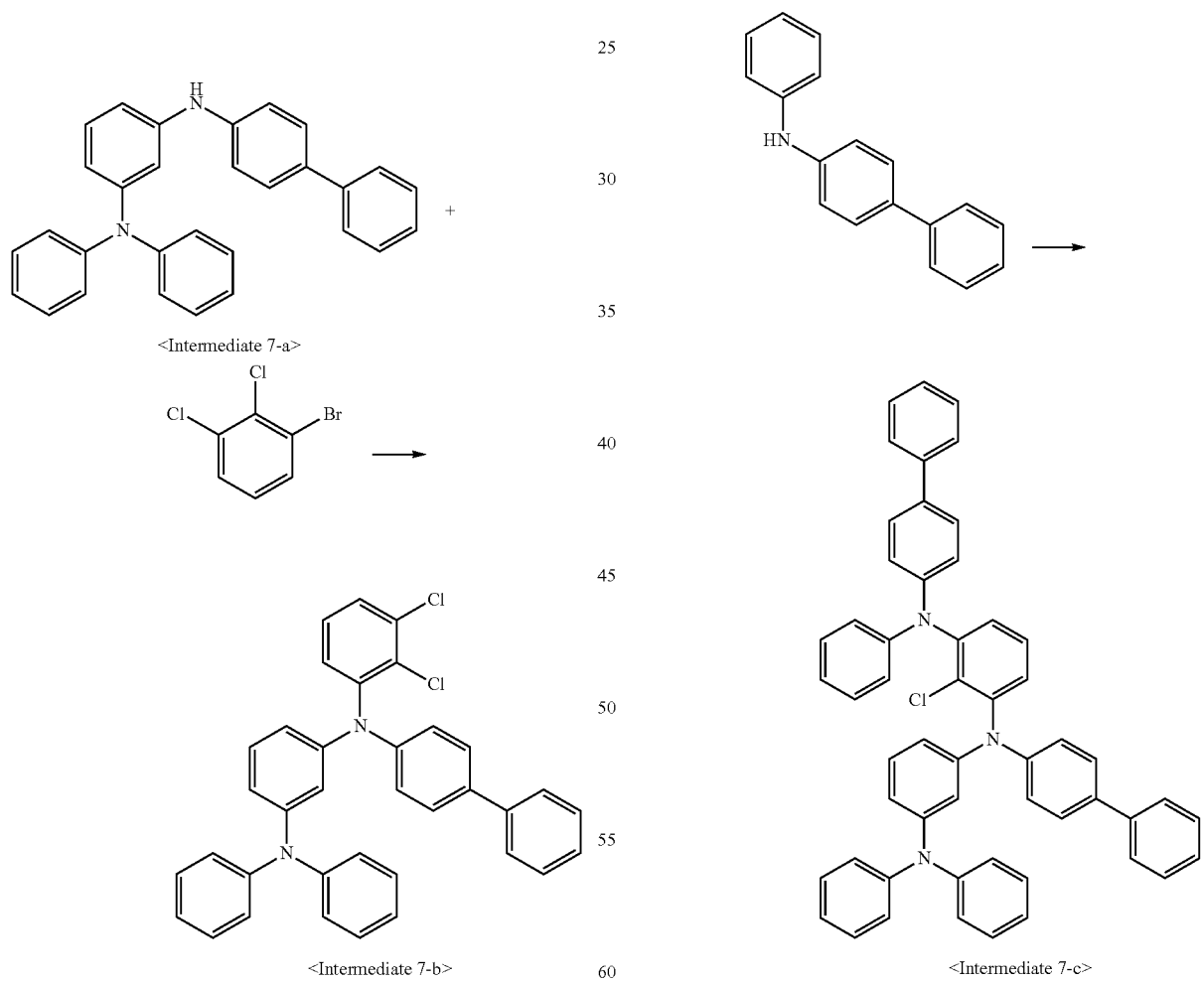

<Intermediate 7-b>

Synthesis Example 7-(3): Synthesis of Intermediate 7-c

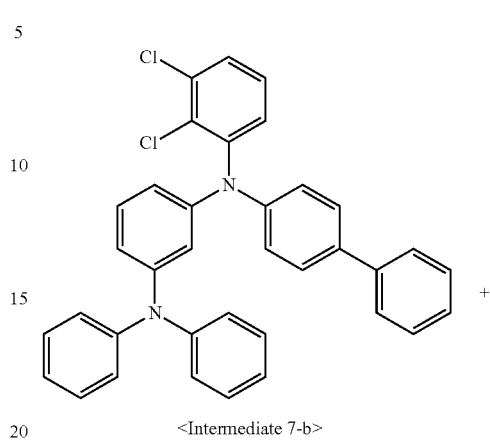

<Intermediate 7-c>

The same procedure as in Synthesis Example 5-(4) was carried out, with the exception of using <Intermediate 7-a> and 1-bromo-2,3-dichlorobenzene instead of <Intermediate 5-c> and 3-bromobenzothiophene, respectively, to afford <Intermediate 7-b>. (yield 53%)

The same procedure as in Synthesis Example 5-(4) was carried out, with the exception of using 4-phenyldiphenylamine and <Intermediate 7-b> instead of <Intermediate 5-c> and 3-bromobenzothiophene, respectively, to afford <Intermediate 7-c>. (yield 57%)

Synthesis Example 7-(4): Synthesis of BD 4

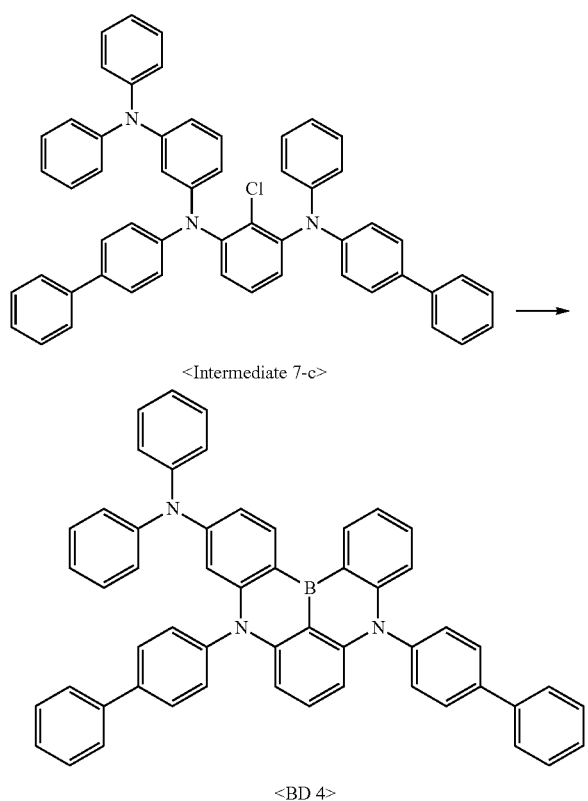

<BD 4>

The same procedure as in Synthesis Example 5-(6) was carried out, with the exception of using <Intermediate 7-c> instead of <Intermediate 5-e>, to afford <BD 4>.
(yield 61%)
MS (MALDI-TOF): m/z 739.32 [M$^+$]

Synthesis Example 8: Synthesis of BD 5

Synthesis Example 8-(1): Synthesis of Intermediate 8-a

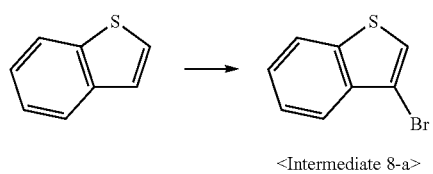 [SMILES: c1ccc2sccc2c1 ; Brc1csc2ccccc12]

<Intermediate 8-a>

In a 1-L reactor, benzothiophene (50 g, 373 mmol) and chloroform (500 mL) were stirred together and cooled to −0° C. A dilution of bromine (59.5 g, 373 mmol) in chloroform (100 mL) was dropwise added. The mixture was stirred at room temperature for 4 hours. After completion of the reaction, an aqueous sodium thiosulfate solution was added and stirred. Extraction was carried out with ethyl acetate and H$_2$O. The organic layer thus obtained was concentrated in a vacuum and then separated by column chromatography to afford <Intermediate 8-a> (70 g). (yield 91%)

Synthesis Example 8-(2): Synthesis of Intermediate 8-b

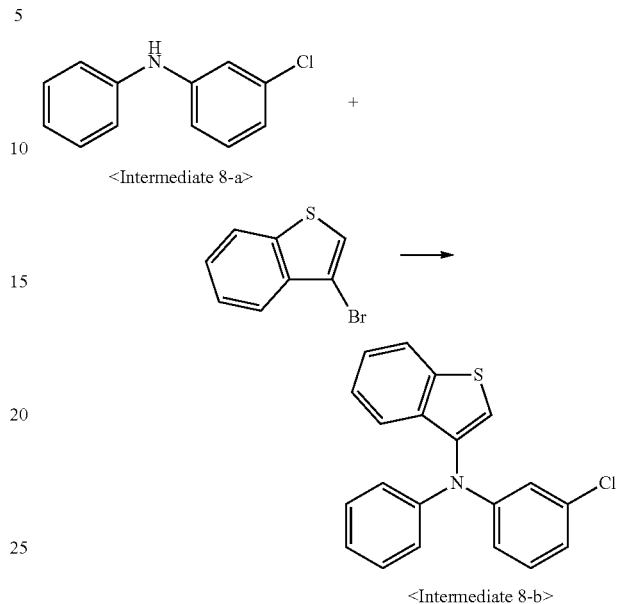

<Intermediate 8-b>

The same procedure as in Synthesis Example 5-4 was carried out, with the exception of using <Intermediate 8-a> instead of <Intermediate 5-b>, to afford <Intermediate 8-b> (32 g). (yield 75.4%)

Synthesis Example 8-(3): Synthesis of Intermediate 8-c

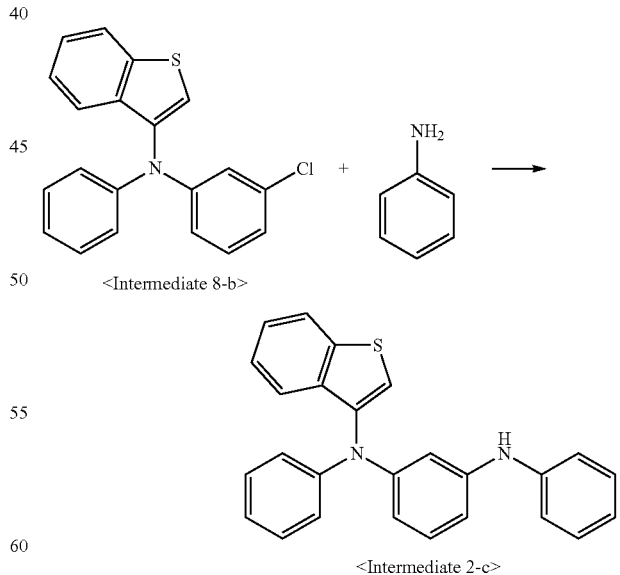

<Intermediate 2-c>

The same procedure as in Synthesis Example 5-3 was carried out, with the exception of using <Intermediate 8-b> instead of 1-bromo-4-iodobenzene, to afford <Intermediate 8-c> (24.5 g). (yield 73.1%)

Synthesis Example 8-(4): Synthesis of Intermediate 8-d

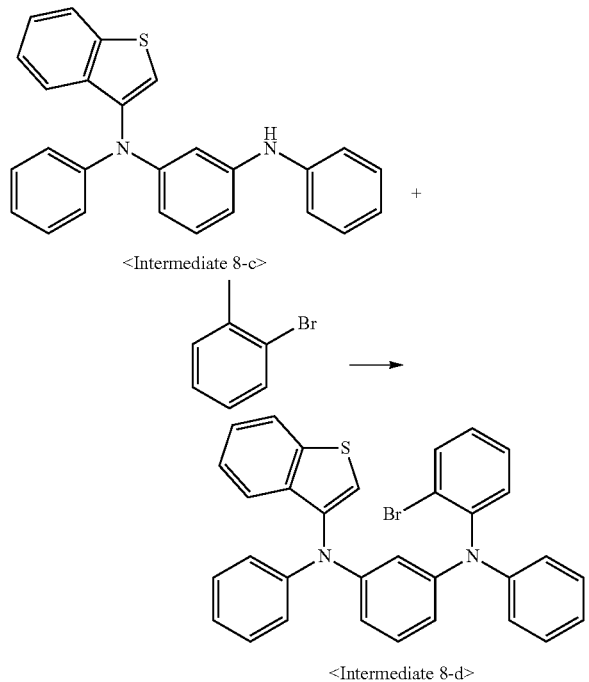

<Intermediate 8-d>

The same procedure as in Synthesis Example 5-4 was carried out, with the exception of using <Intermediate 8-c> and 1-bromo-2-iodobenzene instead of <Intermediate 5-c> and <Intermediate 5-b>, to afford <Intermediate 8-d> (21 g). (yield 77.5%)

Synthesis Example 8-(5): Synthesis of BD 5

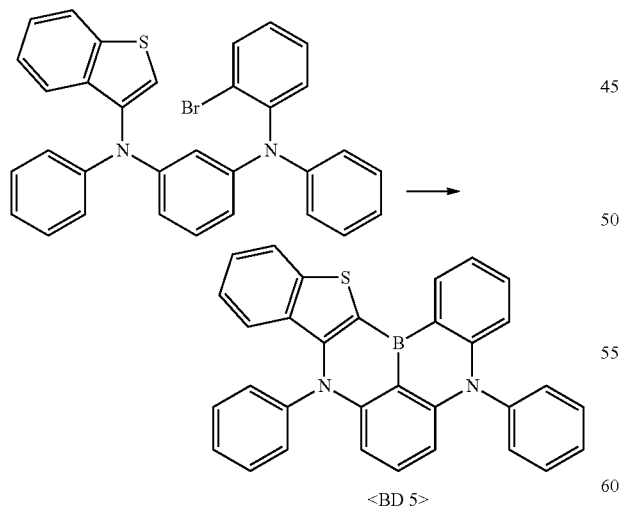

<BD 5>

The same procedure as in Synthesis Example 5-7 was carried out, with the exception of using <Intermediate 8-d> instead of <Intermediate 5-f>, to afford <BD 5>(1.5 g). (yield 10.1%)

MS (MALDI-TOF): m/z 467.15 [M+]

Examples 1-12: Fabrication of Organic Light Emitting Diodes

An ITO glass substrate was patterned to have a translucent area of 2 mm×2 mm and cleansed. The ITO glass was mounted in a vacuum chamber that was then set to have a base pressure of $1 \times 10^{-7}$ torr. On the ITO glass substrate, films were sequentially formed of 2-TNATA (400 Å) and HT(200 Å). Subsequently, a light-emitting layer (250 Å) was formed of a combination of a host compound and 3 wt % of a dopant compounds listed in Table 1. Then, [Chemical Formula E-1] was deposited to form an electron transport layer (300 Å), on which an electron injecting layer of Liq (10 Å) was formed and then covered with an Al layer (1000 Å) to fabricate an organic light-emitting diode. The organic light-emitting diodes thus obtained were measured at 10 mA/cm² for luminescence properties:

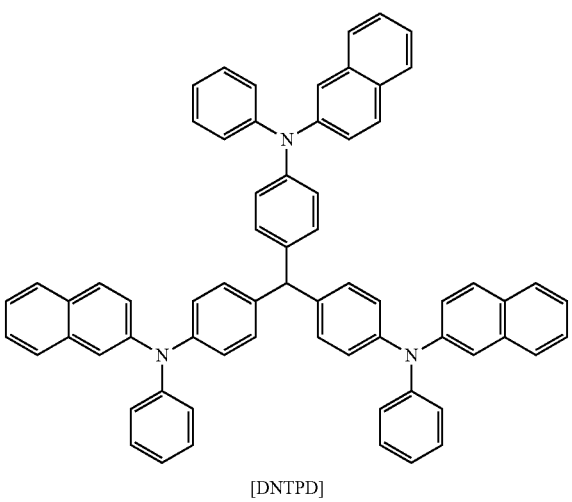

[DNTPD]

[HT]

[Chemical Formula E-1]

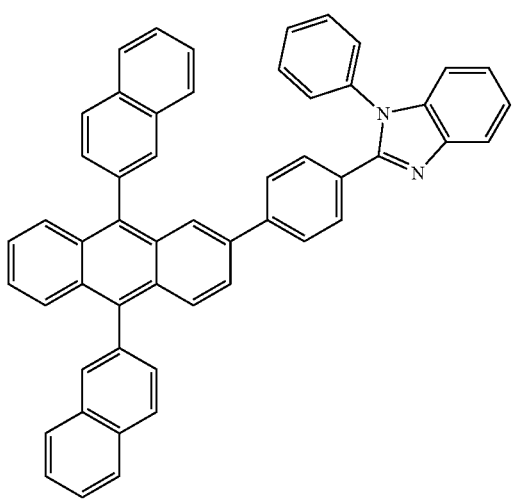

[BD 1]

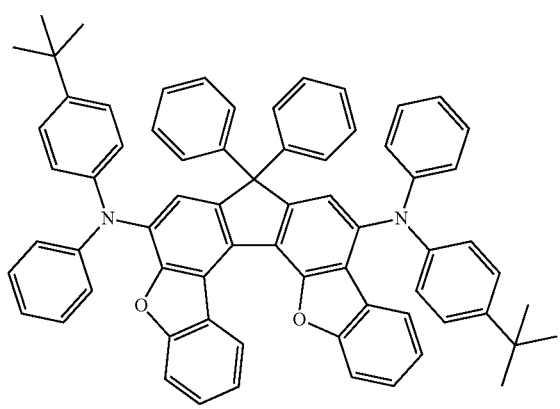

[BD 2]

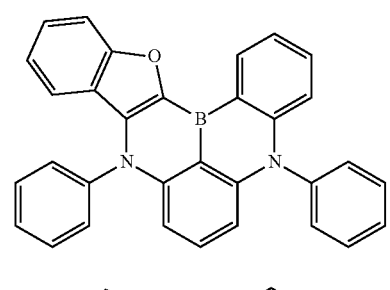

[BD 3]

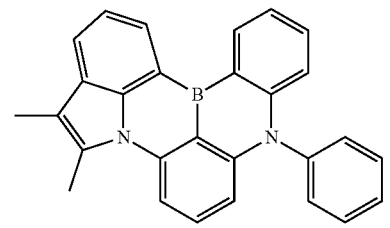

[BD 4]

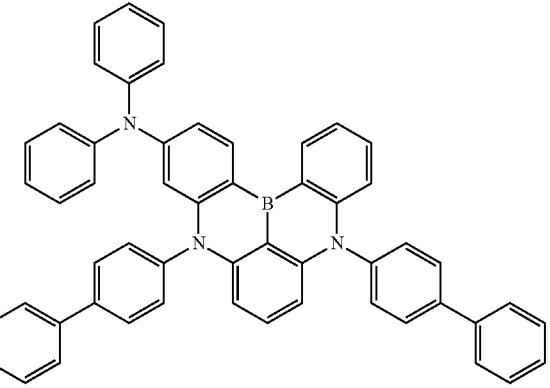

[BD 5]

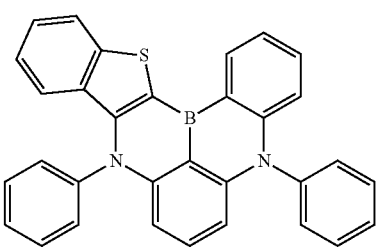

[BD 6]

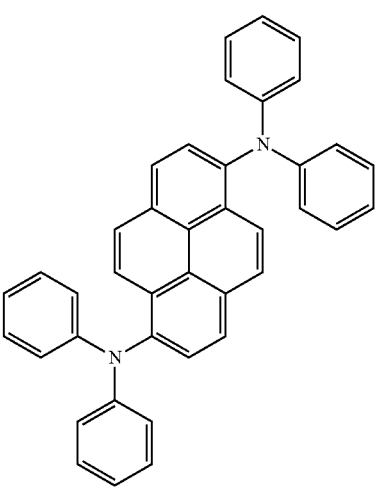

Comparative Examples 1 to 11

Organic light emitting diodes were fabricated in the same manner as in Examples 1 to 12, with the exception that [BH 1] to [BH 7] compounds were used instead of the host compounds. The luminescence of the organic light-emitting diodes thus obtained was measured at 10 mA/cm² and the measurements are summarized in Table 1.

TABLE 1
[BH 1]
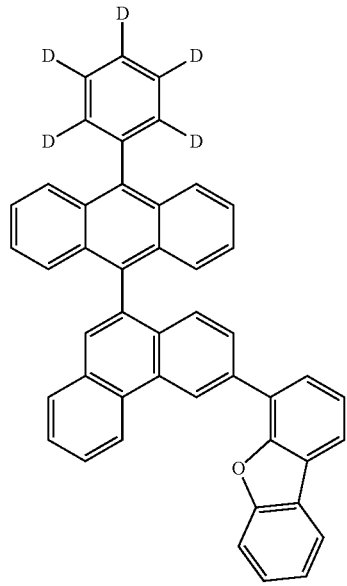 [SMILES: [2H]c1c([2H])c([2H])c(-c2c3ccccc3c(-c3cc4ccccc4c4cc(-c5cccc6c5oc5ccccc56)ccc34)c3ccccc23)c([2H])c1[2H]]
[BH 2]
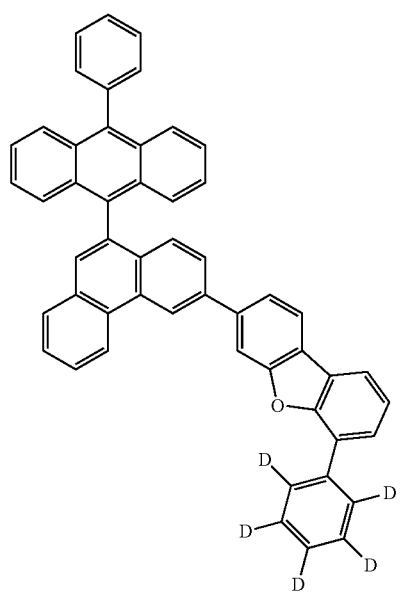 [SMILES: [2H]c1c([2H])c([2H])c(-c2cccc3c2oc2cc(-c4ccc5c(-c6c7ccccc7c(-c7ccccc7)c7ccccc67)cc6ccccc6c5c4)ccc23)c([2H])c1[2H]]

TABLE 1-continued
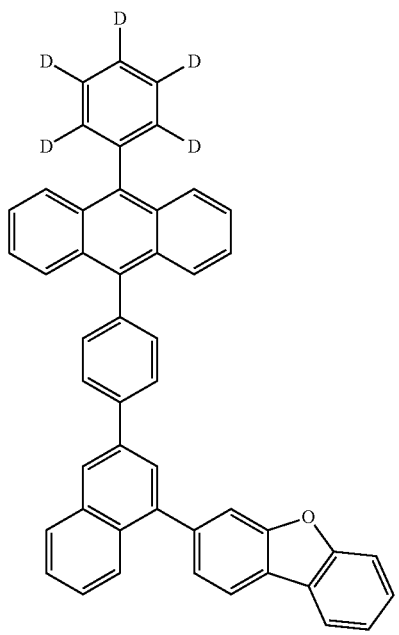 [SMILES: [2H]c1c([2H])c([2H])c(-c2c3ccccc3c(-c3ccc(-c4cc(-c5ccc6c(c5)oc5ccccc56)c5ccccc5c4)cc3)c3ccccc23)c([2H])c1[2H]]
[BH 3]
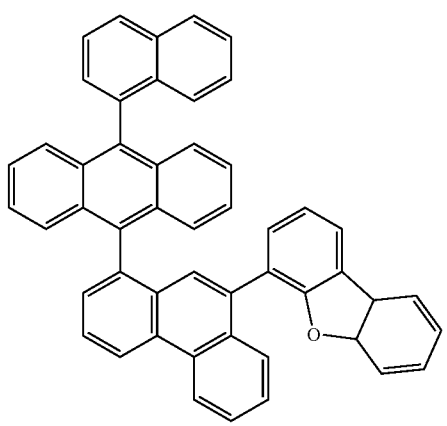 [SMILES: C1=CC2Oc3c(-c4cc5c(-c6c7ccccc7c(-c7cccc8ccccc78)c7ccccc67)cccc5c5ccccc45)cccc3C2C=C1]
[BH 4]
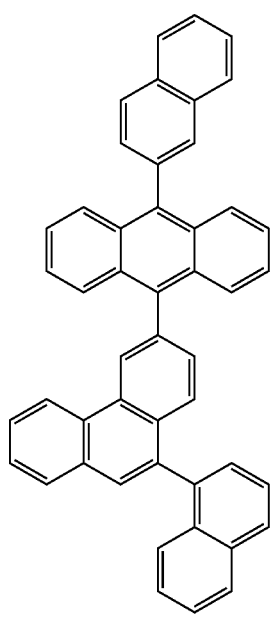 [SMILES: c1ccc2cc(-c3c4ccccc4c(-c4ccc5c(-c6cccc7ccccc67)cc6ccccc6c5c4)c4ccccc34)ccc2c1]
[BH 5]

TABLE 1-continued

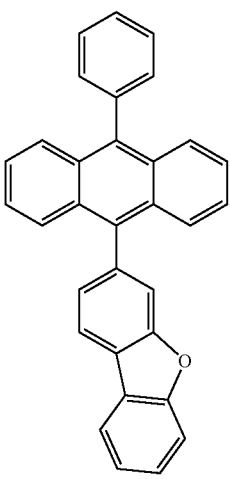 [SMILES: c1ccc(-c2c3ccccc3c(-c3ccc4c(c3)oc3ccccc34)c3ccccc23)cc1]

[BH 6]

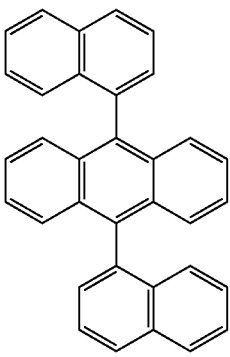 [SMILES: c1ccc2c(-c3c4ccccc4c(-c4cccc5ccccc45)c4ccccc34)cccc2c1]

[BH 7]

|  | Host | Dopant | Volt. (V) | EQE | T97 |
| --- | --- | --- | --- | --- | --- |
| Example 1 | Compound 1 | BD 1 | 3.7 | 9.9 | 122 |
| Example 2 | Compound 2 | BD 2 | 3.6 | 10.1 | 116 |
| Example 3 | Compound 11 | BD 1 | 4.0 | 9.5 | 118 |
| Example 4 | Compound 15 | BD 2 | 4.2 | 10.3 | 125 |
| Example 5 | Compound 16 | BD 1 | 3.5 | 9.8 | 127 |
| Example 6 | Compound 22 | BD 3 | 3.8 | 9.7 | 122 |
| Example 7 | Compound 11 | BD 3 | 4.0 | 9.5 | 110 |
| Example 8 | Compound 15 | BD 4 | 4.3 | 9.6 | 105 |
| Example 9 | Compound 16 | BD 3 | 3.5 | 9.8 | 125 |
| Example 10 | Compound 22 | BD 4 | 3.9 | 9.7 | 108 |
| Example 11 | Compound 1 | BD 5 | 3.7 | 10.0 | 138 |
| Example 12 | Compound 4 | BD 5 | 3.5 | 10.1 | 131 |
| C. Example 1 | BH 1 | BD 1 | 4.3 | 8.4 | 88 |
| C. Example 2 | BH 2 | BD 2 | 4.1 | 8.9 | 88 |
| C. Example 3 | BH 3 | BD 1 | 4.1 | 8.3 | 83 |
| C. Example 4 | BH 4 | BD 2 | 4.4 | 8.2 | 75 |
| C. Example 5 | BH 1 | BD 3 | 4.3 | 8.5 | 93 |
| C. Example 6 | BH 2 | BD 4 | 4.0 | 7.8 | 79 |
| C. Example 7 | BH 3 | BD 3 | 4.1 | 8.8 | 92 |
| C. Example 8 | BH 4 | BD 4 | 4.4 | 7.9 | 75 |
| C. Example 9 | BH 5 | BD 1 | 4.1 | 8.5 | 85 |
| C. Example 10 | BH 6 | BD 2 | 4.0 | 8.6 | 90 |
| C. Example 11 | BH 7 | BD 6 | 4.1 | 8.5 | 62 |

As understood from the data of Table 1, organic light emitting diodes employing the organic light emitting compound of the present disclosure as host materials exhibit longer life span and higher efficiency characteristics, compared to those employing the comparative compounds of Comparative Examples 1 to 11 as host materials and as such, can be highly available as organic light emitting diodes.

As described hitherto, when used as a host in a light emitting layer, the organic light emitting compound represented by Chemical Formula 1 according to the present disclosure exhibits a longer life span and higher efficiency, compared to conventional materials, thereby imparting improved characteristics to an organic light emitting diode.

What is claimed is:
1. An organic light-emitting compound represented by the following [Chemical Formula 1]:

[Chemical Formula 1]

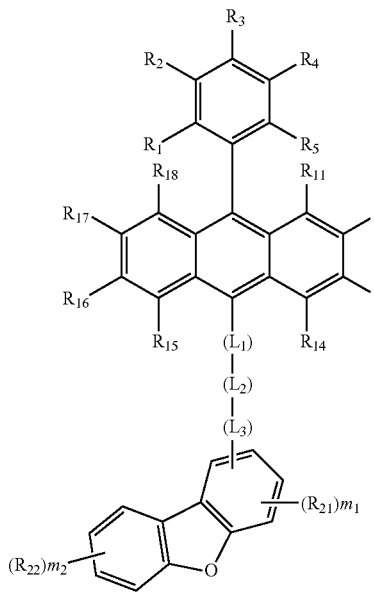

wherein,
$R_1$ to $R_5$ and $R_{11}$ to $R_{18}$ are same or different and are each independently a hydrogen atom or a deuterium atom;
$R_{21}$ and $R_{22}$ are same or different and are each independently any one selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heteroring member, a cyano, a nitro, a halogen, a substituted or unsubstituted alkylsilyl of 1 to 30 carbon atoms, and a substituted or unsubstituted arylsilyl of 6 to 30 carbon atoms;
$m_1$ is an integer of 0-3 wherein when $m_1$ is 2 or greater, the corresponding $R_{21}$'s are same or different;
$m_2$ is an integer of 0-4 wherein when $m_2$ is 2 or greater, the corresponding $R_{22}$'s are same or different;
the carbon atoms of the aromatic rings in the dibenzofuran moiety are each bonded with a hydrogen atom or a deuterium atom when $R_{21}$ or $R_{22}$ is not bonded thereto;
$L_1$ to $L_3$ are same or different and are each independently a linker selected from a single bond, a substituted or unsubstituted arylene of 6 to 50 carbon atoms, and a substituted or unsubstituted heteroarylene of 2 to 50 carbon atoms,
any two of the linkers $L_1$ to $L_3$ being same or different and being each independently selected from the linker represented by the following Structural Formula 1 and a substituted or unsubstituted arylene of 6 to 50 carbon atoms:

[Structural Formula 1]

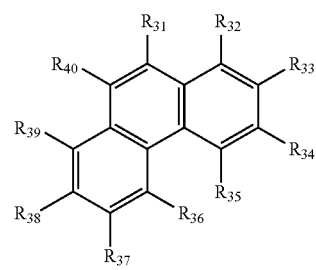

wherein,
any two of the substituents $R_{31}$ to $R_{40}$ are each a single bond connected to the anthracenyl moiety, the linkers $L_1$ to $L_3$, or the dibenzofuran moiety in the compound represented by Chemical Formula 1, and
the eight remaining substituents among $R_{31}$ to $R_{40}$, none of which is a single bonds, are same or different and are each independently any one selected from a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms bearing O, N, or S as an heteroring member, a cyano, a nitro, a halogen, a substituted or unsubstituted alkylsilyl of 1 to 30 carbon atoms, and a substituted or unsubstituted arylsilyl of 6 to 30 carbon atoms,
wherein the term "substituted" in the expression "substituted or unsubstituted" means having at least one substituent selected from the group consisting of a deuterium atom, a cyano, a halogen, a nitro, an alkyl of 1 to 24 carbon atoms, a cycloalkyl of 3 to 24 carbon atoms, a halogenated alkyl of 1 to 24 carbon atoms, an arylalkyl of 7 to 24 carbon atoms, an aryl of 6 to 24 carbon atoms, a heteroaryl of 2 to 24 carbon atoms, an alkoxy of 1 to 24 carbon atoms, an alkylsilyl of 1 to 24 carbon atoms, and an arylsilyl of 6 to 24 carbon atoms, an aryloxy of 6 to 24 carbon atoms.

2. The organic light emitting compound of claim 1, wherein the substituents $R_1$ to $R_5$ are each a deuterium atom.

3. The organic light emitting compound of claim 1, wherein the one of the linkers $L_1$ to $L_3$, which is neither the linker represented by Structural Formula 1, nor a substituted or unsubstituted arylene of 6 to 50 carbon atoms, is a single bond.

4. The organic light emitting compound of claim 1, wherein two among the linkers $L_1$ to $L_3$ are same or different and are each independently a substituted or unsubstituted arylene of 6 to 50 carbon atoms, and the other one linker which is not a substituted or unsubstituted arylene of 6 to 50 carbon atoms is a linker represented by Structural Formula 1.

5. The organic light emitting compound of claim 3, wherein the linker which corresponds to a substituted or unsubstituted arylene of 6 to 50 carbon atoms are selected from a phenyl group, a naphthylene group and a phenanthrylene group.

6. The organic light emitting compound of claim 4, wherein the two among the linkers $L_1$ to $L_3$, which correspond to a substituted or unsubstituted arylene of 6 to 50 carbon atoms are same or different and are each independently selected from a phenylene group, a naphthylene group and a phenanthrylene group.

7. The organic light emitting compound of claim 1, wherein the eight remaining substituents among $R_{31}$ to $R_{40}$ in Structural Formula 1, none of which is a single bond, are same or different and are each independently a hydrogen atom or a deuterium atom.

8. The organic light emitting compound of claim 1, wherein the substituent $R_{21}$ and $R_{22}$ are same or different and are each independently a hydrogen atom, a deuterium atom, an unsubstituted or at least partially deuterium-substituted aryl of 6 to 50 carbon atoms.

9. The organic light emitting compound of claim 8, wherein the substituents $R_{21}$ and $R_{22}$ are same or different and are each independently a deuterium-substituted or unsubstituted aryl of 6 to 50 carbon atoms.

10. The organic light emitting compound of claim 1, wherein $m_2$ is 0 and $m_2$ is 1 or 2; or $m_2$ is 1 or 2 and $m_2$ is 0.

11. The organic light emitting compound of claim 1, wherein the two single bonds in Structural Formula 1 is selected from $R_{31}$, $R_{34}$, $R_{36}$, and $R_{38}$, through which the linker of Structural Formula 1 is connected to the anthracenyl moiety, or the dibenzofuran moiety, or any one among L1 to L3, which is not Structural Formula 1.

12. The organic light emitting compound of claim 11, wherein the two single bonds in Structural Formula 1 is selected from $R_{31}$, $R_{34}$, and $R_{38}$, through which the linker of Structural Formula 1 is connected to the anthracenyl moiety, or the dibenzofuran moiety, or any one among L1 to L3, which is not Structural Formula 1.

13. The organic light emitting compound of claim 11, wherein the two single bonds in Structural Formula 1 are selected from $R_{31}$, and $R_{36}$.

14. The organic light emitting compound of claim 11, wherein the substituent $R_{31}$ in Structural Formula 1 is a single bond connected to the anthracenyl moiety or to any one of L1 to L3 which is not Structural Formula 1; and $R_{34}$ or $R_{38}$ is a single bond connected to any one of L1 to L3, which is not Structural Formula 1 or to the dibenzofuran moiety.

15. The organic light emitting compound of claim 11, wherein the substituent $R_{31}$ is selected from among the single bond connected to the anthracenyl moiety and a single bond connected to any one of L1 to L3 which is not Structural Formula 1; and $R_{36}$ is selected from among the single bond connected to the dibenzofuran moiety and the single bond connected to any one of L1 to L3 which is not Structural Formula 1; or the substituent $R_{38}$ is selected from among the single bond connected to the anthracenyl moiety and the single bond connected to any one of L1 to L3 which is not Structural Formula 1; and the substituent $R_{31}$ is selected from the single bond connected to the dibenzofuran moiety and the single bond connected to any one of L1 to L3 which is not Structural Formula 1.

16. The organic light emitting compound of claim 1, being a compound represented by the following Chemical Formula 1-1 or Chemical Formula 1-2]:

[Chemical Formula 1-1]

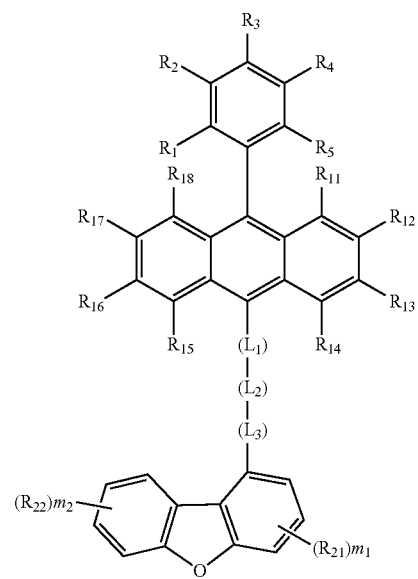

[Chemical Formula 1-2]
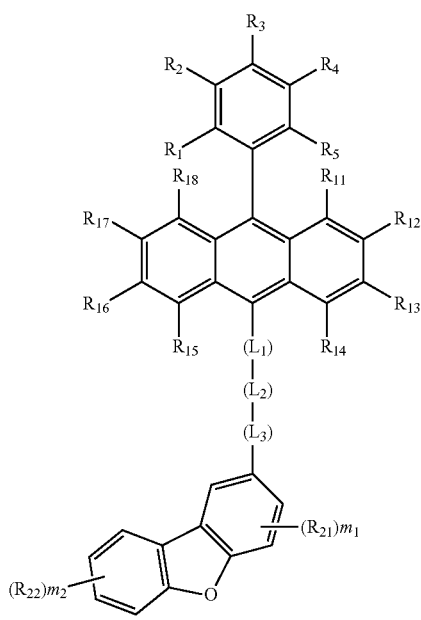
wherein $R_1$ to $R_5$, $R_{11}$ to $R_{18}$, $L_1$ to $L_3$, $R_{21}$, $R_{22}$, $m_1$, and $m_2$ are as defined in claim 1.
17. The organic light emitting compound of claim 1, being any one selected from among the following <Compound 1> to <Compound 24>:
<Compound 1>
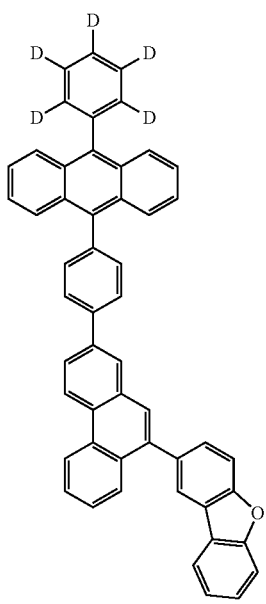
<Compound 2>
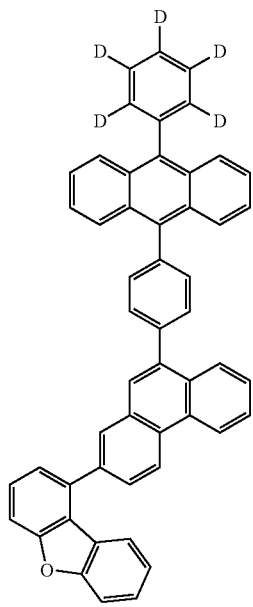
<Compound 3>
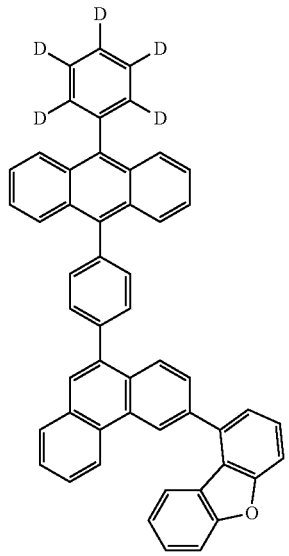

255
-continued
<Compound 4>
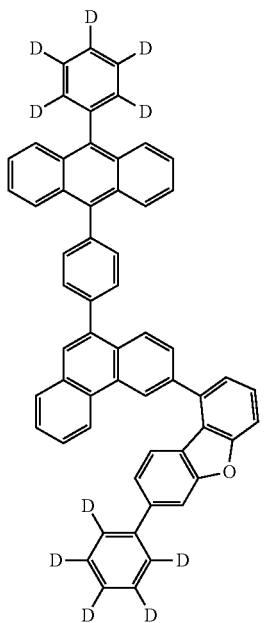
<Compound 5>
256
-continued
<Compound 6>
<Compound 7>
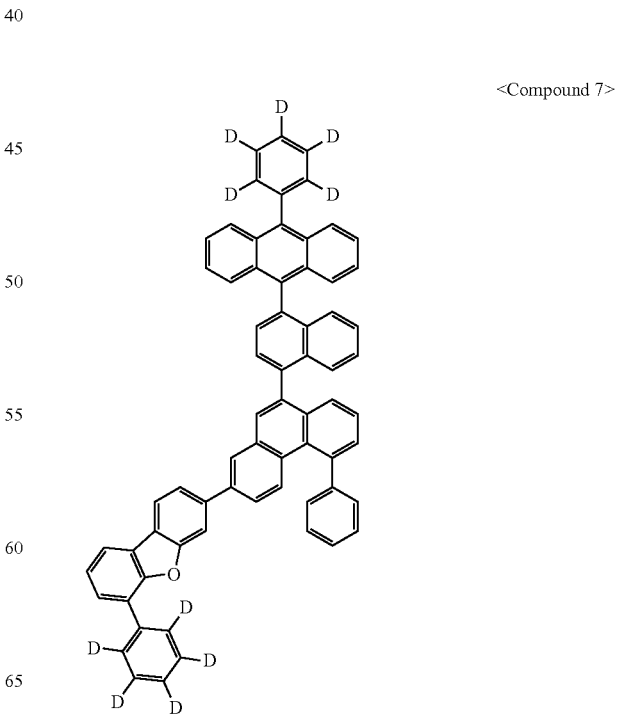
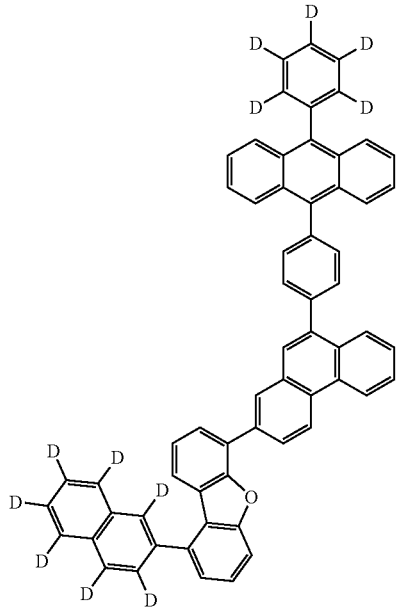

<Compound 8>
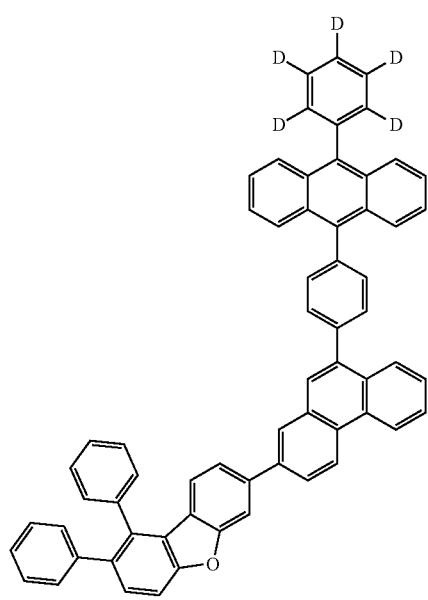
<Compound 10>
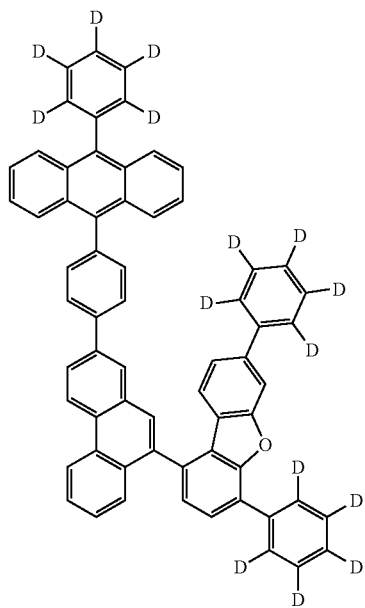
<Compound 9>
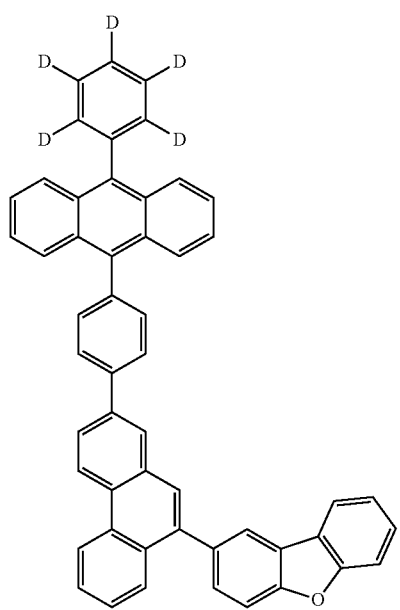
<Compound 11>
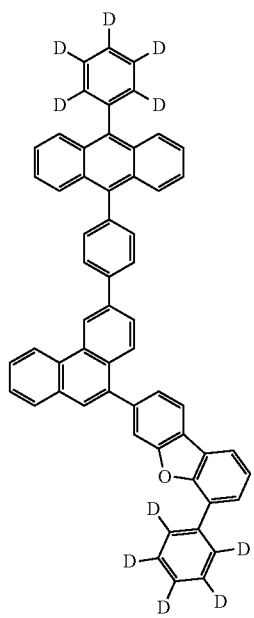

<Compound 12>
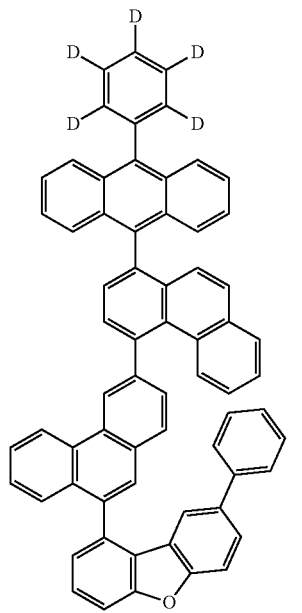
<Compound 13>
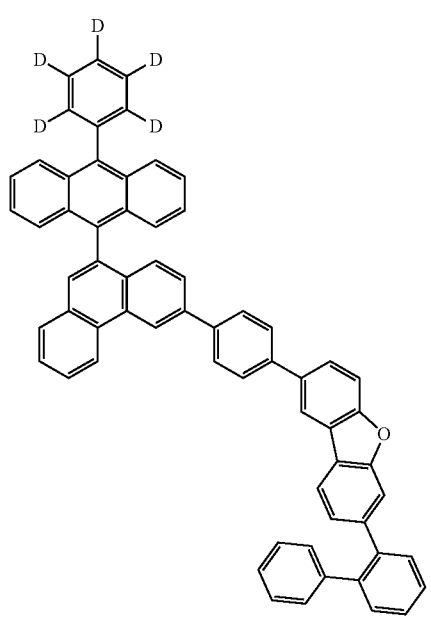
<Compound 14>
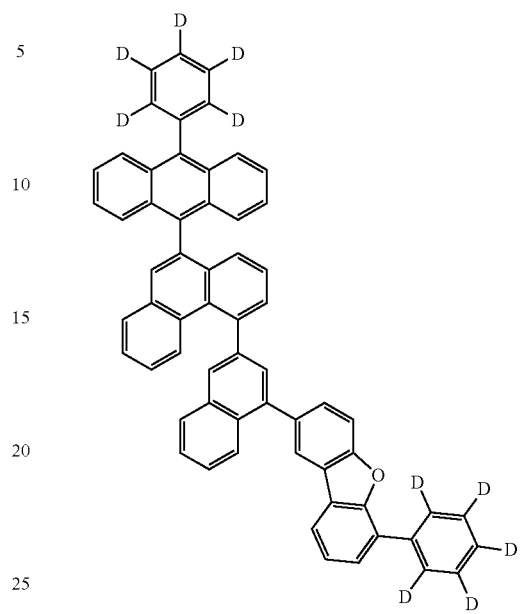
<Compound 15>
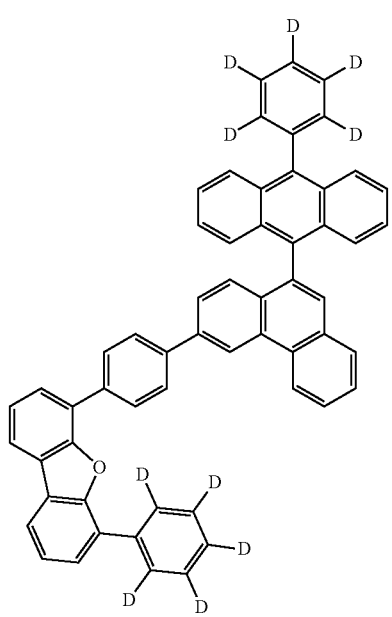

<Compound 16>
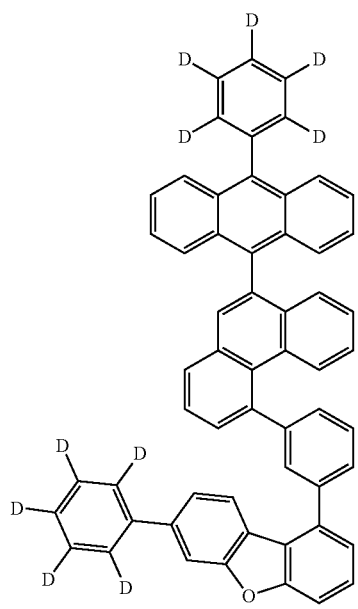
<Compund 17>
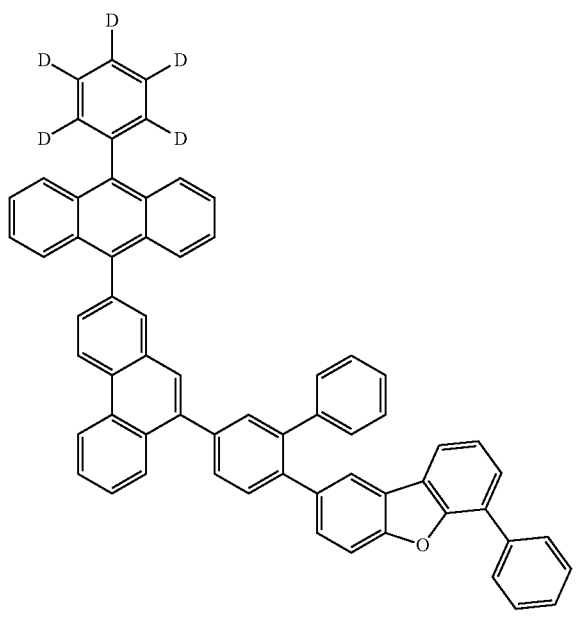
<Compound 18>
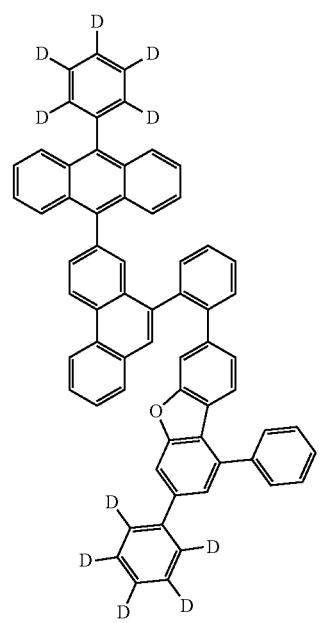
<Compound 19>
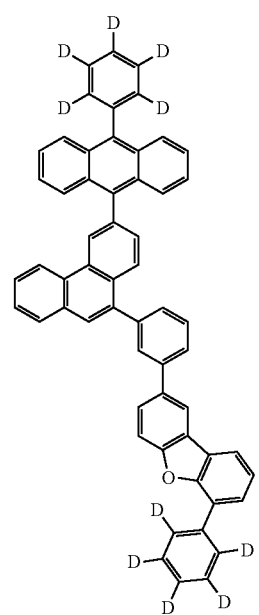

<Compound 20>
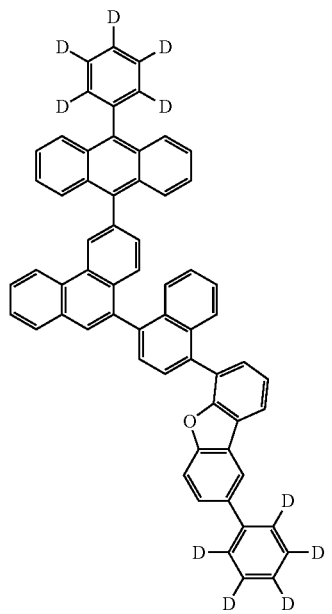
<Compound 21>
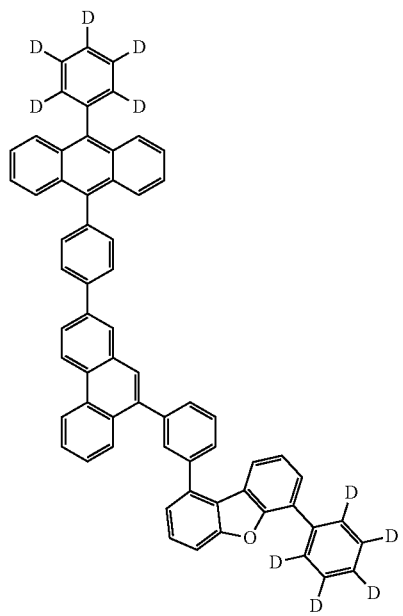
<Compound 22>
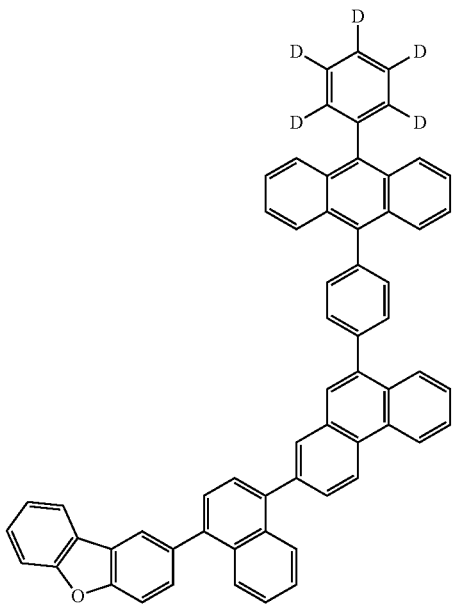
<Compound 23>
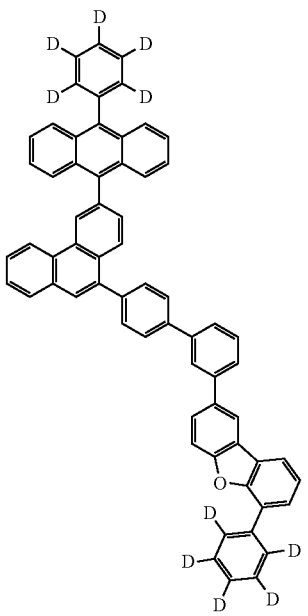

-continued

<Compound 24>

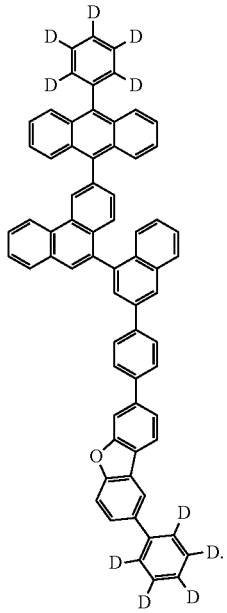

18. An organic light emitting diode, comprising:
a first electrode;
a second electrode facing the first electrode; and
an organic layer interposed between the first electrode and the second electrode, wherein the organic layer contains at least one type of the organic light emitting compounds of claim 1.

19. The organic light emitting diode of claim 18, wherein the organic layer comprises at least one of a hole injection layer, a hole transport layer, a light emitting layer, a functional layer capable of both hole injection and hole transport, an electron transport layer, and an electron injection layer.

20. The organic light emitting diode of claim 18, wherein the organic layer interposed between the first electrode and the second electrode in the organic light emitting diode comprises a light emitting layer, wherein the light emitting layer contains a host and a dopant, the organic light emitting compound serving as the host.

21. The organic light emitting diode of claim 18, wherein the organic light-emitting diode is used for a device selected from among a flat display device, a flexible display device, a monochrome or grayscale flat illumination device, and a monochrome or grayscale flexible illumination device.

22. The organic light emitting diode of claim 20, wherein the dopant comprises at least one selected from compounds represented by the following [Chemical Formula D1] to [Chemical Formula D7]:

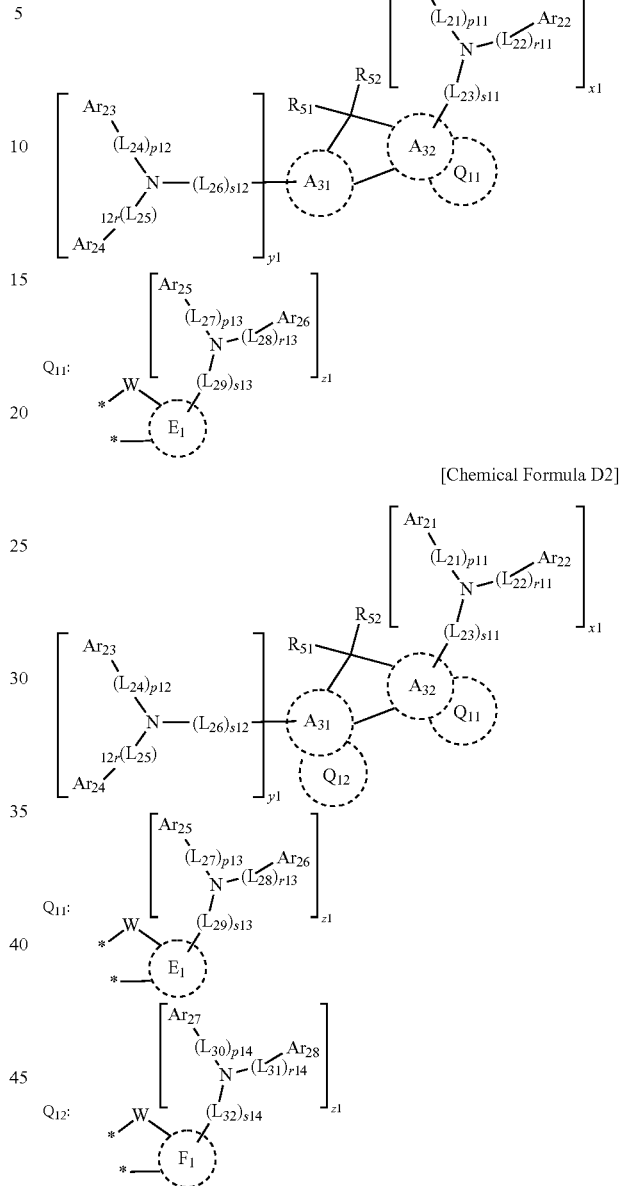

wherein,
$A_{31}$, $A_{32}$, $E_1$, and $F_1$ are same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_{31}$ and two adjacent carbon atoms of the aromatic ring $A_{32}$ form a 5-membered fused ring together with a carbon atom to which substitutents $R_{51}$ and $R_{52}$ are bonded;
linkers $L_{21}$ to $L_{32}$ are same or different, and are each independently selected from among a singlet bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms W is any one selected from among N—$R_{53}$, $CR_{54}R_{55}$, $SiR_{56}R_{57}$, $GeR_{58}R_{59}$, O, S, and Se;

$R_{51}$ to $R_{59}$, and $Ar_{21}$ to $Ar_{28}$ are same or different and are each independently a hydrogen atom, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted arylgermanium of 1 to 30 carbon atoms, a cyano, a nitro, and a halogen, wherein that $R_{51}$ and $R_{52}$ together may form a mono- or polycyclic aliphatic or aromatic ring that is a heterocyclic ring bearing a heteroatom selected from among N, O, P, Si, S, Ge, Se, and Te as a ring member;

p11 to p14, r11 to r14, and s11 to s14 are each independently an integer of 1 to 3, wherein when any of them is 2 or greater, the corresponding $L_{21}$ to $L_{32}$ are same or different, x1 is an integer of 1 or 2, and y1 and z1 are same or different and are each independently an integer of 0 to 3; and $Ar_{21}$ may form a ring with $Ar_{22}$, $Ar_{23}$ may form a ring with $Ar_{24}$, $Ar_{25}$ may form a ring with $Ar_{26}$, and $Ar_{27}$ may form a ring with $Ar_{28}$, two adjacent carbon atoms of the $A_{32}$ ring moiety of Chemical Formula D1 may occupy respective positions * of Structural Formula $Q_{11}$ to form a fused ring, two adjacent carbon atoms of the $A_{31}$ ring moiety of Chemical Formula D2 may occupy respective positions * of structural Formula $Q_{12}$ to form a fused ring, and two adjacent carbon atoms of the $A_{32}$ ring moiety may occupy respective positions * of Structural Formula $Q_{11}$ to form a fuse ring;

wherein, $X_1$ is any one selected from among B, P, and P=O,

T1 to T3 are same or different and are each independently a substituted or unsubstituted aromatic hydrocarbon ring of 6 to 50 carbon atoms, or a substituted or unsubstituted heteroaromatic ring of 2 to 40 carbon atoms;

$Y_1$ is any one selected from among N—R61, $CR_{62}R63$, O, S, and SiR64R65; and $Y_2$ is any one selected from among N—R66, CR67R68, O, S, and SiR69R70;

wherein R61 to R70 are same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen, and R61 to R70 may each be connected to at least one ring of T1 to T3 to further form a mono- or polycyclic aliphatic or aromatic ring;

[Chemical Formula D4]

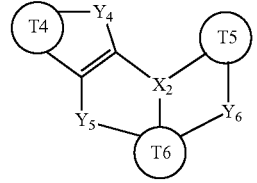

[Chemical Formula D5]

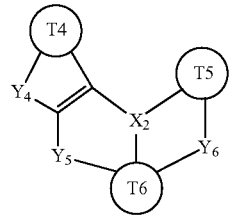

wherein, $X_2$ is any one selected from among B, P, and P=O;

$T_4$ to $T_6$ are as defined for $T_1$ to $T_3$ in [Chemical Formula D3]; and $Y_4$ to $Y_6$ are as defined for $Y_1$ to $Y_2$ in [Chemical Formula D3];

[Chemical Formula D3]

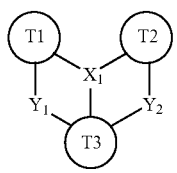

[Chemical Formula D6]

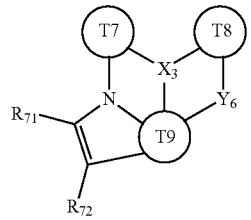

[Chemical Formula D7]

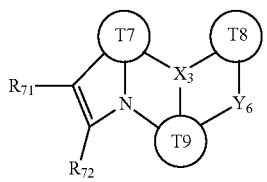

wherein,

X$_3$ is any one selected from among B, P, and P=O,

T$_7$ to T$_9$ are as defined for T$_1$ to T$_3$ in [Chemical Formula D3];

Y$_6$ is as defined for Y$_1$ to Y$_2$ in [Chemical Formula D3]; and

R$_{71}$ to R$_{72}$ are same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a nitro, a cyano, and a halogen, wherein R$_{71}$ and R$_{72}$ are bonded to each other to further form a mono- or polycyclic aliphatic or aromatic ring or are connected to the Q1 ring or Q3 ring to further form a mono- or polycyclic aliphatic or aromatic ring, wherein, the term "substituted" in the expression "substituted or unsubstituted" used for [Chemical Formula D1] to [Chemical Formula D7] means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

\* \* \* \* \*